E

(12) United States Patent
Bruenker et al.

(10) Patent No.: US 12,275,794 B2
(45) Date of Patent: *Apr. 15, 2025

(54) BISPECIFIC ANTIGEN BINDING MOLECULES COMPRISING ANTI-FAP CLONE 212

(71) Applicant: Hoffmann-La Roche Inc., Little Falls, NJ (US)

(72) Inventors: Peter Bruenker, Hittanu (CH); Harald Duerr, Starnberg (DE); Christian Klein, Bonstetten (CH); Pablo Umana, Wollerau (CH); Alexander Bujotzek, Munich (DE); Joerg Zielonka, Bulach (CH); Christine Trumpfheller, Zurich (CH); Moritz Rapp, Zurich (CH); Marine Le Clech, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/557,647

(22) Filed: Dec. 21, 2021

(65) Prior Publication Data

US 2022/0227878 A1 Jul. 21, 2022

Related U.S. Application Data

(62) Division of application No. 16/588,780, filed on Sep. 30, 2019, now Pat. No. 11,242,396.

(30) Foreign Application Priority Data

Oct. 1, 2018 (EP) .................................... 18197866

(51) Int. Cl.
| | |
|---|---|
| *C07K 16/28* | (2006.01) |
| *A61K 39/00* | (2006.01) |
| *A61K 39/395* | (2006.01) |
| *A61P 35/00* | (2006.01) |
| *C07K 1/16* | (2006.01) |
| *C07K 16/40* | (2006.01) |

(52) U.S. Cl.
CPC ...... *C07K 16/2878* (2013.01); *A61K 39/3955* (2013.01); *A61P 35/00* (2018.01); *C07K 1/16* (2013.01); *C07K 16/40* (2013.01); *A61K 2039/505* (2013.01); *C07K 2317/24* (2013.01); *C07K 2317/31* (2013.01); *C07K 2317/565* (2013.01); *C07K 2317/94* (2013.01)

(58) Field of Classification Search
CPC ...... C07K 16/2878; C07K 1/16; C07K 16/40; A61P 35/00; A61K 39/3955
See application file for complete search history.

(56) References Cited

U.S. PATENT DOCUMENTS

| | | | |
|---|---|---|---|
| 6,737,056 B1 | 5/2004 | Presta et al. | |
| 7,332,581 B2 | 2/2008 | Presta et al. | |
| 8,551,485 B2 | 10/2013 | Bernett et al. | |
| 9,011,847 B2 | 4/2015 | Bacac et al. | |
| 10,253,110 B2 | 4/2019 | Bacac et al. | |
| 10,392,445 B2 | 8/2019 | Amann et al. | |
| 10,464,981 B2 | 11/2019 | Amann et al. | |
| 10,526,413 B2 | 1/2020 | Amann et al. | |
| 10,577,429 B2 | 3/2020 | Bacac et al. | |
| 11,149,083 B2 | 10/2021 | Amann et al. | |
| 11,242,396 B2 | 2/2022 | Bruenker et al. | |
| 11,267,903 B2 | 3/2022 | Amann et al. | |
| 11,286,300 B2 | 3/2022 | Ferrara Koller et al. | |
| 2013/0058937 A1 | 3/2013 | Auer et al. | |
| 2014/0099340 A1 | 4/2014 | June et al. | |
| 2014/0242080 A1 | 8/2014 | Jaeger et al. | |
| 2016/0046678 A1* | 2/2016 | Roschke ................ | A61K 45/06 435/375 |
| 2017/0174786 A1 | 6/2017 | Bacac et al. | |
| 2017/0247467 A1 | 8/2017 | Amann et al. | |
| 2017/0342169 A1 | 11/2017 | Akamatsu et al. | |
| 2018/0064808 A1 | 3/2018 | Friess et al. | |
| 2018/0230215 A1 | 8/2018 | Hofer et al. | |
| 2018/0282409 A1 | 10/2018 | Koller et al. | |
| 2018/0340030 A1 | 11/2018 | Bruenker et al. | |
| 2019/0016771 A1 | 1/2019 | Amann et al. | |

(Continued)

FOREIGN PATENT DOCUMENTS

| | | |
|---|---|---|
| CL | 2019002542 A1 | 1/2020 |
| CN | 101237882 A | 8/2008 |

(Continued)

OTHER PUBLICATIONS

The Merck Manuals Online Medical Library, [online]. Whitehouse Station, NJ: Merck Research Laboratories, 2006-2007. [retrieved on Oct. 19, 2020].https://www.merckmanuals.com/professional/hematology-and-oncology/overview-of-cancer/cellular-and-molecular-basis-of-cancer (Year: 2020).*
Fidler et al. "Biological heterogeneity of cancer", Human Vaccines & Immunotherapeutics 8:8, 1141-1142 (Year: 2012).*
U.S. Appl. No. 15/941,519, filed Mar. 30, 2018, Abandoned, US 2018/0230215.
U.S. Appl. No. 16/689,880, filed Nov. 20, 2019, Published, US 2020/0317774.
U.S. Appl. No. 15/281,493, filed Sep. 30, 2016, Abandoned, US 2017/0174786.
U.S. Appl. No. 16/877,150, filed May 18, 2020, Published, US 2021/0070882.

(Continued)

*Primary Examiner* — Amy E Juedes
*Assistant Examiner* — Peter Johansen
(74) *Attorney, Agent, or Firm* — GENENTECH, INC.

(57) ABSTRACT

The invention relates to novel bispecific antigen binding molecules, comprising (a) at least one antigen binding domain capable of specific binding to Fibroblast Activation Protein (FAP) comprising FAP clone 212 or variants thereof, and (b) at least one antigen binding domain capable of specific binding to CD40, and to methods of producing these molecules and to methods of using the same.

27 Claims, 17 Drawing Sheets

Specification includes a Sequence Listing.

(56) References Cited

U.S. PATENT DOCUMENTS

| | | |
|---|---|---|
| 2019/0185566 A1 | 6/2019 | Koller et al. |
| 2019/0194291 A1 | 6/2019 | Bruenker et al. |
| 2019/0211113 A1 | 7/2019 | Amann et al. |
| 2019/0248877 A1 | 8/2019 | Amann et al. |
| 2019/0382507 A1 | 12/2019 | Amann et al. |
| 2020/0071411 A1 | 3/2020 | Amann et al. |
| 2020/0079873 A1 | 3/2020 | Bacac et al. |
| 2020/0190206 A1 | 6/2020 | Koller et al. |
| 2020/0231691 A1 | 7/2020 | Grau-Richards et al. |
| 2020/0247904 A1 | 8/2020 | Amann et al. |
| 2020/0270321 A1 | 8/2020 | Amann et al. |
| 2020/0277392 A1 | 9/2020 | Amann et al. |
| 2020/0317774 A1 | 10/2020 | Hofer et al. |
| 2020/0325225 A1 | 10/2020 | Bacac et al. |
| 2020/0325238 A1 | 10/2020 | Bacac et al. |
| 2020/0347115 A1 | 11/2020 | Duerr et al. |
| 2020/0392237 A1 | 12/2020 | Bacac et al. |
| 2021/0009656 A1 | 1/2021 | Bruenker et al. |
| 2021/0024610 A1 | 1/2021 | Koller et al. |
| 2021/0070882 A1 | 3/2021 | Bacac et al. |
| 2021/0095002 A1 | 4/2021 | Claus et al. |
| 2021/0163617 A1 | 6/2021 | Ferrara et al. |
| 2021/0188992 A1 | 6/2021 | Bruenker et al. |
| 2021/0253724 A1 | 8/2021 | Claus et al. |
| 2021/0292426 A1 | 9/2021 | Duerr et al. |
| 2021/0324108 A1 | 10/2021 | Amann et al. |
| 2022/0025046 A1 | 1/2022 | Amann et al. |
| 2022/0025069 A1 | 1/2022 | Claus et al. |
| 2022/0073646 A1 | 3/2022 | Amann et al. |

FOREIGN PATENT DOCUMENTS

| | | |
|---|---|---|
| CN | 103261418 A | 8/2013 |
| CN | 104936985 A | 9/2015 |
| CN | 103764681 B | 6/2018 |
| CN | 108271377 A | 7/2018 |
| EP | 1806365 A1 | 7/2007 |
| JP | 2009-522329 A1 | 6/2009 |
| JP | 2013-542714 A | 11/2013 |
| JP | 2014-519807 A | 8/2014 |
| JP | 2020-515276 A | 5/2020 |
| JP | 2022-511396 A | 1/2022 |
| RU | 2017-116020 A1 | 11/2018 |
| TW | 201806972 A | 3/2018 |
| TW | 201829469 A | 8/2018 |
| WO | 00/75348 | 12/2000 |
| WO | 2004/056312 A2 | 7/2004 |
| WO | 2006/128103 A2 | 11/2006 |
| WO | 2009/080252 A1 | 7/2009 |
| WO | 2009/089004 A1 | 7/2009 |
| WO | 2009/094391 A1 | 7/2009 |
| WO | 2011/040972 A1 | 4/2011 |
| WO | 2012/020006 A2 | 2/2012 |
| WO | 2012/076190 A1 | 6/2012 |
| WO | 2012/130831 A1 | 10/2012 |
| WO | 2013/026831 A1 | 2/2013 |
| WO | 2014/131711 A1 | 9/2014 |
| WO | 2015/091655 A1 | 6/2015 |
| WO | 2016/055432 A2 | 4/2016 |
| WO | 2016/062734 A1 | 4/2016 |
| WO | 2016/110598 A1 | 7/2016 |
| WO | 2017/060144 A1 | 4/2017 |
| WO | 2017/165464 A1 | 9/2017 |
| WO | 2017/205738 A1 | 11/2017 |
| WO | 2018/017763 A1 | 1/2018 |
| WO | 2018/127473 A1 | 7/2018 |
| WO | 2018/144955 A1 | 8/2018 |
| WO | 2018/185045 A1 | 10/2018 |
| WO | 2018/189220 A1 | 10/2018 |
| WO | 2019/086500 A2 | 5/2019 |
| WO | 2020/007817 A1 | 1/2020 |
| WO | 2020/070035 A1 | 4/2020 |
| WO | 2020/208049 A1 | 10/2020 |
| WO | 2020/260329 A1 | 12/2020 |
| WO | 2021/140130 A1 | 7/2021 |
| WO | 2021/198335 A1 | 10/2021 |

OTHER PUBLICATIONS

U.S. Appl. No. 15/087,405, filed Mar. 31, 2016, Granted, U.S. Pat. No. 10,464,981.
U.S. Appl. No. 16/653,652, filed Oct. 15, 2019, Abandoned, US 2020/0270321.
U.S. Appl. No. 17/455,617, filed Nov. 18, 2021, Un Published.
U.S. Appl. No. 16/184,147, filed Nov. 8, 2018, Abandoned, US 2019/0194291.
U.S. Appl. No. 17/030,251, filed Sep. 23, 2020, Published, US 2021/0009656.
U.S. Appl. No. 15/763,868, filed Mar. 28, 2018, Granted, U.S. Pat. No. 11,286,300.
U.S. Appl. No. 17/578,655, filed Jan. 19, 2022, Un Published.
U.S. Appl. No. 16/446,4861 filed Jun. 19, 2019, Published, US 2020/0190206.
U.S. Appl. No. 17/125,533, filed Dec. 17, 2020, Published, US 2021/0253724, WO 2020/007817.
U.S. Appl. No. 16/446,478, filed Jun. 19, 2019, Un Published.
U.S. Appl. No. 16/820,504, filed Mar. 16, 2020, Published, US 2020/0325238.
U.S. Appl. No. 17/017,576, filed Sep. 23, 2020, Published, US 2021/0163617, WO 2019/175071.
U.S. Appl. No. 14/940,400, filed Nov. 13, 2015, Un Published, WO 2016/075278.
U.S. Appl. No. 15/067,024, filed Mar. 10, 2016, Granted, U.S. Pat. No. 10,392,445.
U.S. Appl. No. 16/522,391, filed Jul. 25, 2019, Published, US 2020/0247904.
U.S. Appl. No. 16/522,412, filed Jul. 25, 2019, Granted, U.S. Pat. No. 11,267,903.
U.S. Appl. No. 17/580,970, filed Jan. 21, 2022, Un Published.
U.S. Appl. No. 17/580,980, filed Jan. 21, 2022, Un Published.
U.S. Appl. No. 15/280,379, filed Sep. 29, 2016, Granted, U.S. Pat. No. 10,526,413.
U.S. Appl. No. 16/684,258, filed Nov. 14, 2019, Published, US 2020/0071411.
U.S. Appl. No. 15/280,386, filed Sep. 29, 2016, Abandoned, US 2017/0247467.
U.S. Appl. No. 16/218,266, filed Dec. 12, 2018, Published, US 2019/0211113.
U.S. Appl. No. 17/347,257, filed Jun. 14, 2021, Published, US 2022/0073646.
U.S. Appl. No. 16/760,820, filed Apr. 30, 2020, Published, US 2021/0324108, WO 2019/086500.
U.S. Appl. No. 17/498,515, filed Oct. 11, 2021, Published, US 2022/0025069, WO 2020/208049.
U.S. Appl. No. 16/144,687, filed Sep. 27, 2018, Abandoned, US 2019/0016771.
U.S. Appl. No. 16/861,801, filed Apr. 29, 2020, Published, US 2020/0347115.
U.S. Appl. No. 16/446,484, filed Jun. 19, 2019, Abandoned.
U.S. Appl. No. 16/825,773, filed Mar. 20, 2020, Published, US 2020/0325225.
U.S. Appl. No. 17/017,942, filed Sep. 19, 2020, Published, US 2021/0095002.
U.S. Appl. No. 17/066,711, filed Oct. 9, 2020, Published, US 2021/0024610, WO 2019/197600.
U.S. Appl. No. 17/644,903, filed Dec. 17, 2021, Un-Published, WO 2020/260329.
U.S. Appl. No. 16/186,443, filed Nov. 9, 2018, Granted, U.S. Pat. No. 11,149,083, WO 2017/194442.
U.S. Appl. No. 16/584,931, filed Sep. 26, 2019, Published, US 2020/0277392, WO 2018/178076.
U.S. Appl. No. 16/581,756, filed Sep. 25, 2019, Published, US 2020/0231691, WO 2018/178055.
U.S. Appl. No. 16/189,041, filed Nov. 13, 2018, Published, US 2019/0185566, WO 2017/194641.

(56) References Cited

OTHER PUBLICATIONS

U.S. Appl. No. 17/649,321, filed Jan. 28, 2022, Un Published.
U.S. Appl. No. 13/205,743, filed Aug. 9, 2011, Granted, U.S. Pat. No. 9,011,847, WO 2012/020006.
U.S. Appl. No. 14/661,839, filed Mar. 18, 2015, Granted, U.S. Pat. No. 10,253,110.
U.S. Appl. No. 14/661,833, filed Mar. 18, 2015, Granted, U.S. Pat. No. 10,577,429.
U.S. Appl. No. 16/378,320, filed Apr. 8, 2019, Published, US 2020/0079873.
U.S. Appl. No. 16/860,552, filed Apr. 28, 2020, Published, US 2020/0392237, WO 2019/086497.
U.S. Appl. No. 17/218,948, filed Mar. 31, 2021, Published, US 2022/0025046.
U.S. Appl. No. 15/943,821, filed Apr. 3, 2018, Abandoned, US 2018/0340030, WO 2018/185045.
U.S. Appl. No. 17/179,223, filed Feb. 18, 2021, Published, US 2021/0188992.
U.S. Appl. No. 16/588,780, filed Sep. 30, 2019, Granted, U.S. Pat. No. 11,242,396, WO 2020/070041.
U.S. Appl. No. 17/218,752, filed Mar. 31, 2021, Published, US 2021/0292426, WO 2020/070035.
Bevan et al., "Helping the CD8+ T-Cell Response" Nat.Rev. Immunol. 4(8):595-602 ( 2004).
Bjorck et al., "The CD40 agonistic monoclonal antibody APX005M has potent immune stimulatory capabilities" J. Immunother Cancer 3:p. 198 ( 2015).
Brocks, B., et al., "Species-Crossreactive scFv Against the Tumor Stroma Marker 'Fibroblast Activation Protein' Selected by Phage Display From an Immunized FAP$^{-/-}$ Knock-Out Mouse" Mol Med 7(7):164-469 (Apr. 10, 2001).
Carbone et al., "A New Mechanism of NK Cell Cytotoxicity Activation: The CD40-CD40 Ligand Interaction" J. Exp. Med. 185(12):2053-2060 ( 1997).
Carter, P., et al., "Bispecific human IgG by design" J Immunol Methods 248(1-2):7-15 (Feb. 1, 2001).
Chowdhury et al., "Ex Vivo Assays of Dendritic Cell Activation and Cytokine Profiles as Predictors of In Vivo Effects in an Anti-Human CD40 Monoclonal Antibody ChiLob 7/4 Phase I Trial" Cancer Immunol Res. 2(3):229-240 ( 2013).
Dahan et al., "Therapeutic Activity of Agonistic, Human Anti-CD40 Monoclonal Antibodies Requires Selective FcgR Engagement" Cancer Cell 29(6):820-831 ( 2016).
Dahlen, E., et al., "Therapeutic Advances in Vaccines and Immunotherapy Bispecific antibodies in cancer immunotherapy" Ther Adv Vacc Immuno 6(1):3-17 (Feb. 28, 2018).
Elgueta et al., Immunological_Reviews 229(1),152-72.
Eliopoulos et al., Mol Cell Biol 20(15),5503-15.
Gale, R., et al. Merck Manuals Online Medical Library "Cellular and Molecular Basis of Cancer" Merck Research Laboratories 2006-2007,:1-8 (Nov. 2020) https://www.merckmanuals.com/professional/hematology-and-oncology/overview-of-cancer/cellular-and-molecular-basis-of-cancer.
Gardai et al., "SEA-CD40, a sugar engineered non-fucosylated anti-CD40 antibody with improve immune avtivating capabilities" AACR 106th Annual Meeting Abstract 2472 (Apr. 2015).
"International Search Report—PCT/EP2019/076375":pp. 1-25 (Jan. 3, 2020).
Khubchandani et al., "Dacetuzumab, a humanized mAb against CD40 for the treatment of hematological malignancies" Curr. Opin. Invest. Dr. 10(6):579-587 ( 2009).
Luheshi, N., et al., "Transformation of the tumour microenvironment by a CD40 agonist antibody correlates with improved responses to PD-L1 blockade in a mouse orthotopic pancreatic tumour model" Oncotarget 7(14):18508-18520 (Apr. 5, 2016).
Mangsbo et al., "The Human Agonistic CD40 Antibody ADC-1013 Eradicates Bladder Tumors and Generates T-cell-Dependent Tumor Immunity" Clin Cancer Res. 21:1115-1126 ( 2014).
Schaefer, W., et al., "Immunoglobulin domain crossover as a generic approach for the production of bispecific IgG antibodies" PNAS USA 108(27):11187-11192 (Jul. 5, 2011).
Shields et al., "High resolution mapping of the binding site on human IgG1 for Fc gamma RI, Fc gamma RII, Fc gamma RIII, and FcRn and design of IgG1 variants with improved binding to the Fc gamma R" J Biol Chem. 276(9):6591-6604 ( 2001).
Teng, M., et al., "CD1d-Based Combination Therapy Eradicates Established Tumors in Mice" J Immunol 183(3):1911-1920 (Aug. 1, 2009).
Vonderheide et al., "Agonistic CD40 Antibodies and Cancer Therapy" Clin. Cancer Res. 19(5):1035-1043 ( 2013).
Vonderheide et al., "Clinical Activity and Immune Modulation in Cancer Patients Treated With CP-870,893, a Novel CD40 Agonist Monoclonal Antibody" J. Clin. Oncol. 25(7):876-883 ( 2007).
Watts, T., "TNF/TNFR family members in costimulation of T cell responses" Annu Rev Immunol 23:23-68 (Sep. 2005).
Zippelius, A. et al., "Induced PD-L1 Expression Mediates Acquired Resistance to Agonistic Anti-CD40 Treatment" Cancer Immunol Res 3(3):236-244 (Mar. 1, 2015).
Bostrom, J., et al., "Improving antibody binding affinity and specificity for therapeutic development" Methods Mol Biol 525:353-376 (Dec. 10, 2009).
Gonzales, N. et al., "Minimizing the Immunogenicity of Antibodies for Clinical Application" Tumour Biol. 26(1):31-43 (2005).
Kunik, V. et al., "Structural Consensus among Antibodies Defines the Antigen Binding Site" PLOS Computational Biology 8(2):1-12 ( 2012).
Sela-Culang, I., et al., "The Structural Basis of Antibody-Antigen Recognition" Front Immunol 4(302):1-13 (Oct. 8, 2013).
Wark, K., et al., "Latest technologies for the enhancement of antibody affinity" Adv Drug Deliv Rev 58(5-6):657-670 (Aug. 7, 2006).
Wu, H., et al., "Humanization of a Murine Monoclonal Antibody by Simultaneous Optimization of Framework and CDR Residues" J Mol Biol 294(1):151-162 (Nov. 19, 1999).
Wyzgol, A., et al., "Trimer Stabilization, Oligomerization, and Antibody-Mediated Cell Surface Immobilization Improve the Activity of Soluble Trimers of CD27L, CD40L, 41BBL, and Glucocorticoid-Induced TNF Receptor Ligand1" J Immunol 183(3):1851-1861 (Aug. 1, 2009).

\* cited by examiner

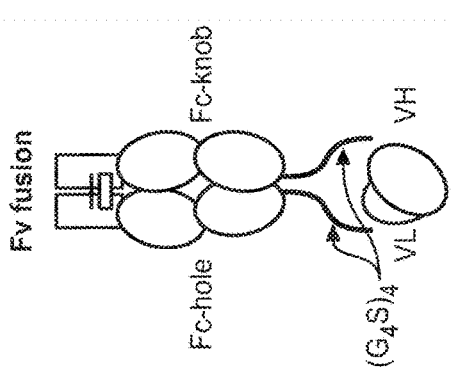
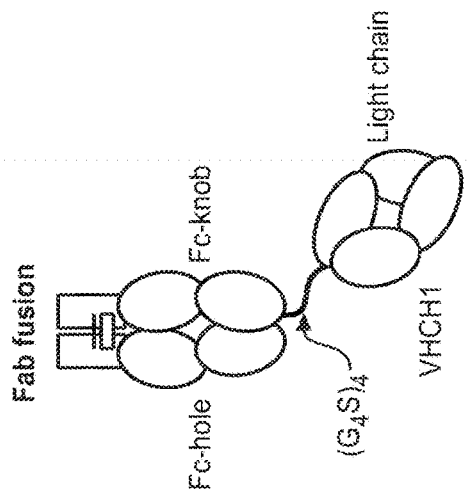
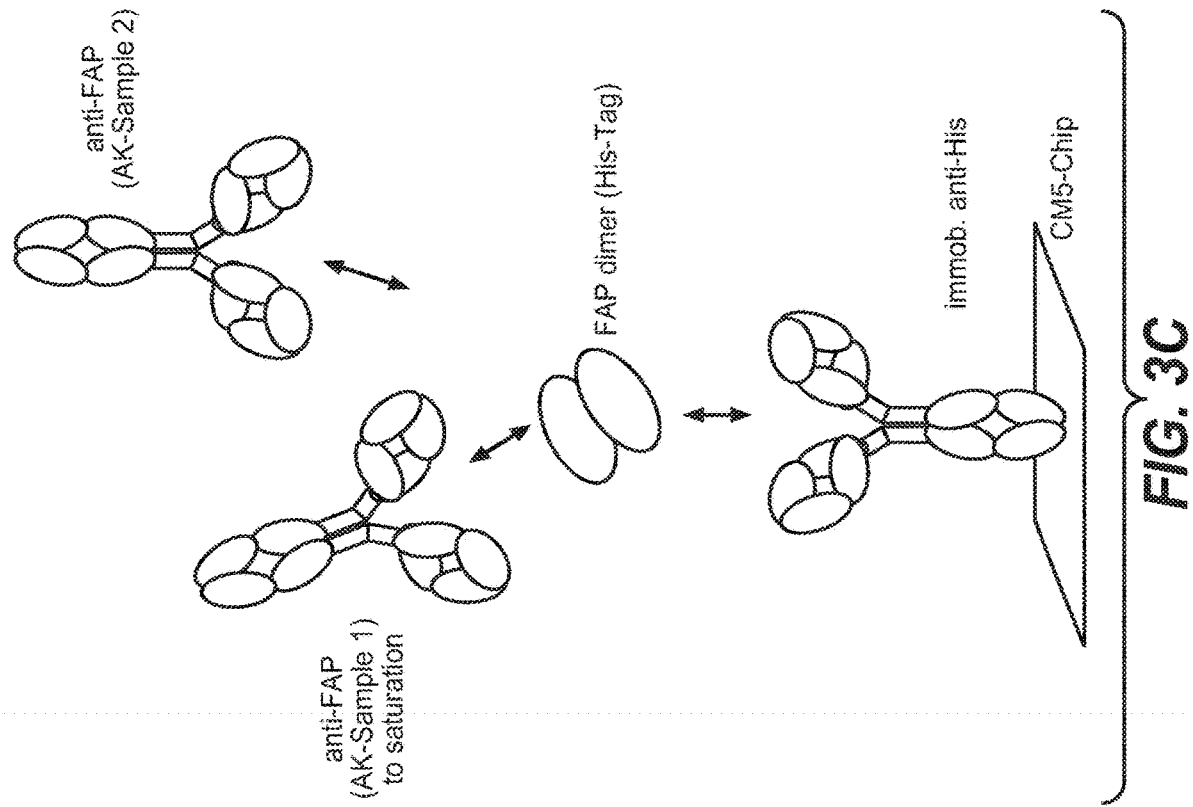

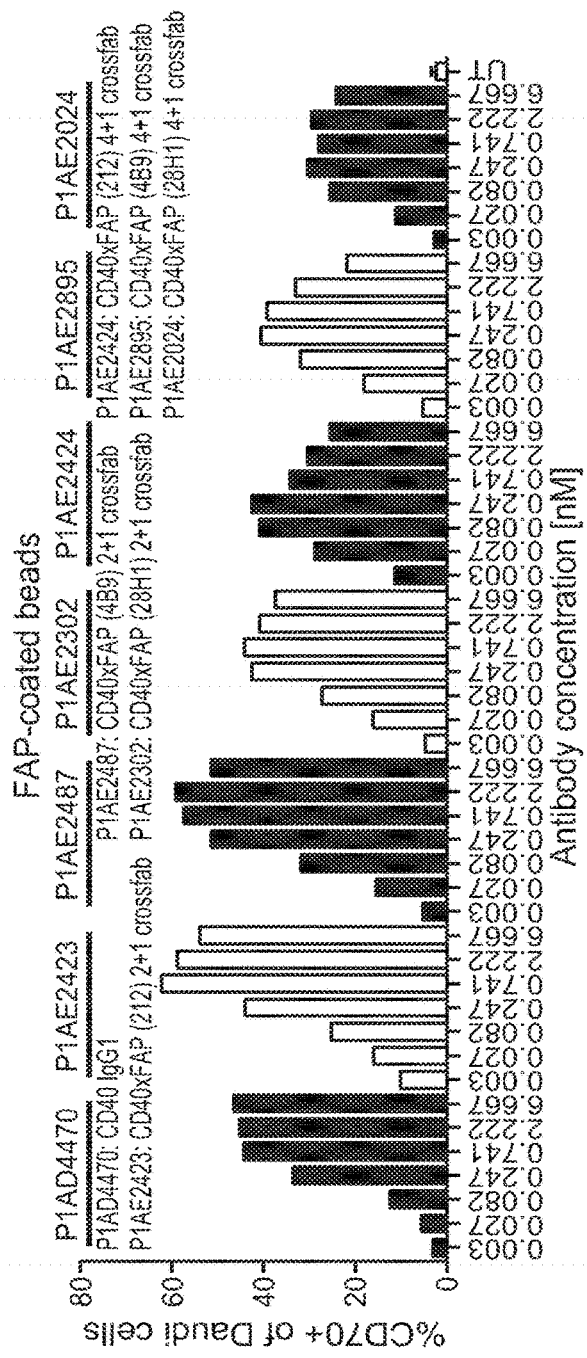
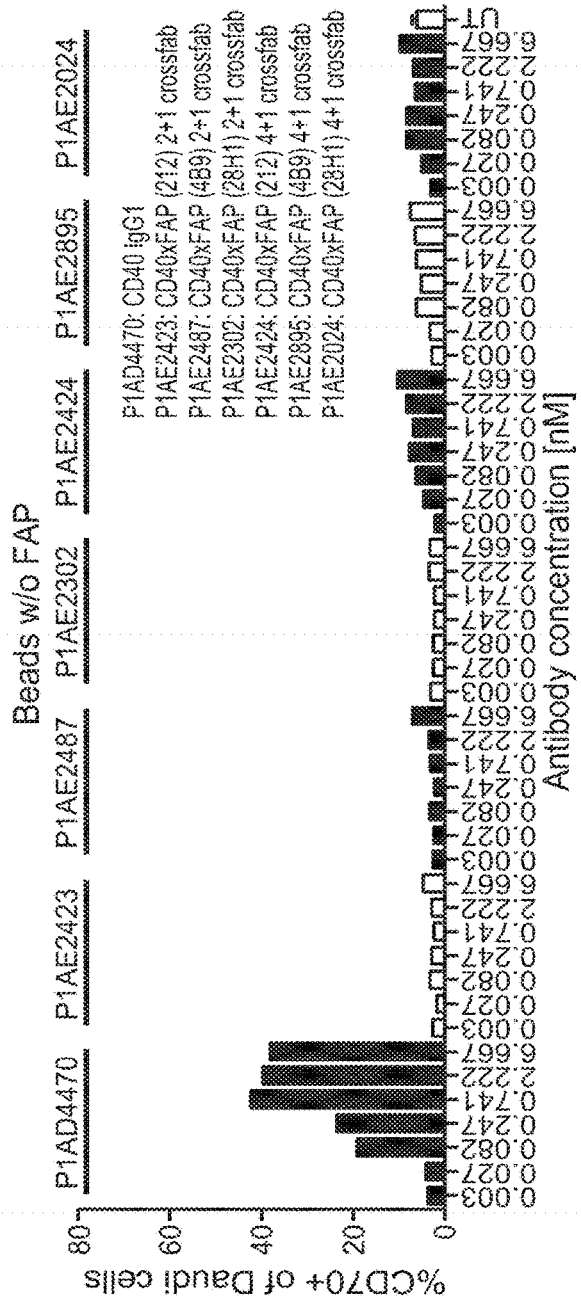
FIG. 6A
FIG. 6B

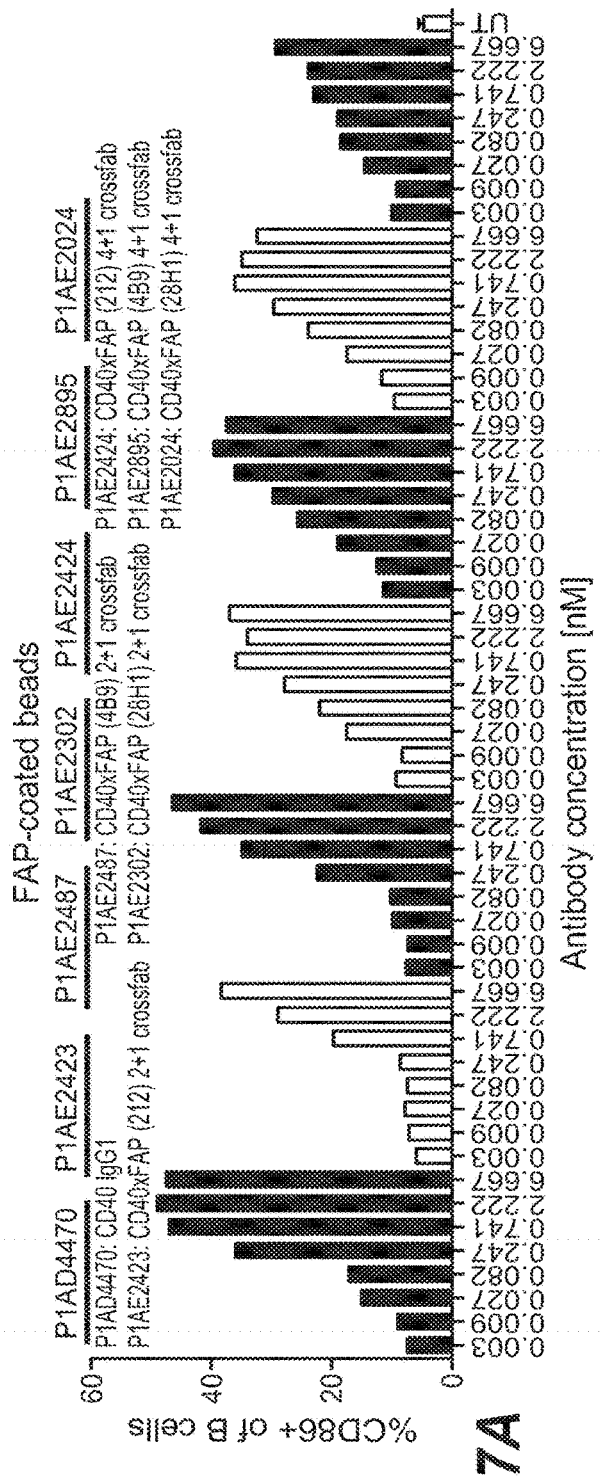
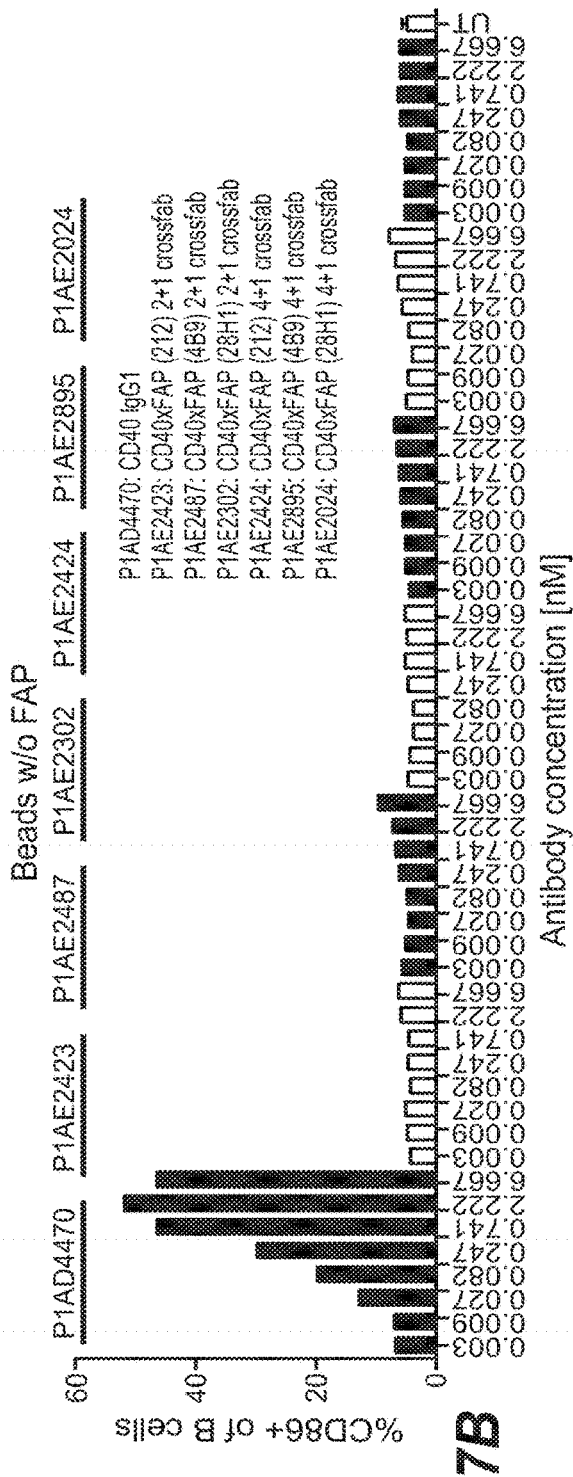
FIG. 7A
FIG. 7B

| Level | - Level | Difference | Std Err Dif | Lower CL | Upper CL | p-Value |
|---|---|---|---|---|---|---|
| Vehicle | FAP-CD40 2+1 | 375.2659 | 86.97106 | 102.307 | 648.2245 | 0.0015* |
| Vehicle | FAP-CD40 2+1 + PD-L1 | 363.6771 | 86.97106 | 90.718 | 636.6358 | 0.0023* |
| Vehicle | FAP-CD40 4+1 + PD-L1 | 278.2715 | 86.97106 | 5.313 | 551.2302 | 0.0426* |
| Vehicle | FAP-CD40 4+1 | 265.6836 | 86.97106 | -7.265 | 538.6523 | 0.0619 |
| PD-L1 | FAP-CD40 2+1 | 259.9493 | 86.97106 | -13.009 | 532.9079 | 0.0729 |
| PD-L1 | FAP-CD40 2+1 + PD-L1 | 248.3605 | 86.97106 | -24.598 | 521.3192 | 0.1003 |
| CD40 | FAP-CD40 2+1 | 228.9741 | 92.97597 | -62.831 | 520.7792 | 0.2312 |
| CD40 | FAP-CD40 2+1 + PD-L1 | 217.3854 | 92.97597 | -74.420 | 509.1905 | 0.2906 |
| CD40 + PD-L1 | FAP-CD40 2+1 | 203.7975 | 89.64772 | -77.562 | 485.1568 | 0.3249 |
| CD40 + PD-L1 | FAP-CD40 2+1 + PD-L1 | 192.2087 | 89.64772 | -89.151 | 473.5681 | 0.3995 |
| Vehicle | CD40 + PD-L1 | 171.4684 | 89.64772 | -109.891 | 452.8277 | 0.5478 |
| PD-L1 | FAP-CD40 4+1 + PD-L1 | 162.9549 | 86.97106 | -110.004 | 435.9136 | 0.5737 |
| PD-L1 | FAP-CD40 4+1 | 150.3770 | 86.97106 | -122.582 | 423.3357 | 0.6687 |
| Vehicle | CD40 | 146.2917 | 92.97597 | -145.513 | 438.0968 | 0.7639 |
| CD40 | FAP-CD40 4+1 + PD-L1 | 131.9798 | 92.97597 | -159.825 | 423.7849 | 0.8447 |
| CD40 | FAP-CD40 4+1 | 119.4019 | 92.97597 | -172.403 | 411.2070 | 0.9012 |
| Vehicle | PD-L1 | 115.3166 | 86.97106 | -157.642 | 388.2753 | 0.8854 |
| FAP-CD40 4+1 | CD40 + PD-L1 | 109.5722 | 86.97106 | -163.386 | 382.5309 | 0.9098 |
| CD40 + PD-L1 | FAP-CD40 4+1 + PD-L1 | 106.8031 | 89.64772 | -174.556 | 388.1625 | 0.9314 |
| FAP-CD40 4+1 | FAP-CD40 2+1 | 97.9835 | 86.97106 | -174.975 | 370.9421 | 0.9484 |
| FAP-CD40 4+1 + PD-L1 | FAP-CD40 2+1 | 96.9943 | 86.97106 | -175.964 | 369.9530 | 0.9510 |
| CD40 + PD-L1 | FAP-CD40 4+1 | 94.2252 | 89.64772 | -187.134 | 375.5846 | 0.9642 |
| FAP-CD40 4+1 + PD-L1 | FAP-CD40 2+1 + PD-L1 | 85.4056 | 86.97106 | -187.553 | 358.3642 | 0.9753 |
| PD-L1 | CD40 + PD-L1 | 56.1518 | 89.64772 | -225.208 | 337.5111 | 0.9984 |
| PD-L1 | CD40 | 30.9751 | 92.97597 | -260.830 | 322.7802 | 1.0000 |
| CD40 | CD40 + PD-L1 | 25.1767 | 95.48445 | -274.501 | 324.8546 | 1.0000 |
| FAP-CD40 4+1 | FAP-CD40 4+1 + PD-L1 | 12.5779 | 86.97106 | -260.381 | 285.5365 | 1.0000 |
| FAP-CD40 2+1 + PD-L1 | FAP-CD40 2+1 | 11.5888 | 86.97106 | -261.370 | 284.5474 | 1.0000 |

FIG. 13A

| Level | -Level | Difference | Std Err Dif | Lower CL | UpperCL | p-Value |
|---|---|---|---|---|---|---|
| CD40 | FAP-CD40 2+1 | 406.4652 | 100.9955 | 89.306 | 723.6240 | 0.0038* |
| CD40 | FAP-CD40 2+1 + PD-L1 | 406.4280 | 100.9955 | 89.269 | 723.5868 | 0.0038* |
| PD-L1 | FAP-CD40 2+1 | 387.1015 | 94.4727 | 90.427 | 683.7764 | 0.0030* |
| PD-L1 | FAP-CD40 2+1 + PD-L1 | 387.0642 | 94.4727 | 90.389 | 683.7391 | 0.0030* |
| CD40 | FAP-CD40 4+1 + PD-L1 | 377.9195 | 100.9955 | 60.761 | 695.0783 | 0.0092* |
| Vehicle | FAP-CD40 2+1 | 361.5613 | 97.3802 | 55.756 | 667.3668 | 0.0100* |
| Vehicle | FAP-CD40 2+1 + PD-L1 | 361.5240 | 97.3802 | 55.719 | 667.3295 | 0.0100* |
| PD-L1 | FAP-CD40 4+1 + PD-L1 | 358.5557 | 94.4727 | 61.881 | 655.2306 | 0.0078* |
| Vehicle | FAP-CD40 4+1 | 333.0155 | 97.3802 | 27.210 | 638.8210 | 0.0235* |
| CD40 | FAP-CD40 4+1 | 330.0047 | 100.9955 | 12.846 | 647.1636 | 0.0358* |
| PD-L1 | FAP-CD40 4+1 | 310.6410 | 94.4727 | 13.966 | 607.3159 | 0.0338* |
| Vehicle | CD40+PD-L1 | 285.1008 | 97.3802 | -20.705 | 590.9063 | 0.0849 |
| CD40 + PD-L1 | FAP-CD40 2+1 | 284.2873 | 97.3802 | -21.518 | 590.0929 | 0.0866 |
| CD40 + PD-L1 | FAP-CD40 2+1 + PD-L1 | 284.2501 | 97.3802 | -21.555 | 590.0556 | 0.0867 |
| CD40 + PD-L1 | FAP-CD40 4+1 + PD-L1 | 255.7416 | 97.3802 | -50.064 | 561.5471 | 0.1670 |
| CD40 + PD-L1 | FAP-CD40 4+1 | 207.8269 | 97.3802 | -97.979 | 513.6324 | 0.4057 |
| CD40 | CD40+PD-L1 | 122.1778 | 103.7204 | -203.538 | 447.8936 | 0.9351 |
| PD-L1 | CD40+PD-L1 | 102.8141 | 97.3802 | -202.991 | 408.6196 | 0.9633 |
| Vehicle | CD40+PD-L1 | 77.2739 | 100.2034 | -237.397 | 391.9452 | 0.9940 |
| FAP-CD40 4+1 + PD-L1 | FAP-CD40 2+1 | 76.4604 | 94.4727 | -220.214 | 373.1354 | 0.9920 |
| FAP-CD40 4+1 + PD-L1 | FAP-CD40 2+1 + PD-L1 | 76.4232 | 94.4727 | -220.252 | 373.0981 | 0.9920 |
| PD-L1 | FAP-CD40 4+1 + PD-L1 | 47.9147 | 94.4727 | -248.760 | 344.5896 | 0.9996 |
| CD40 | Vehicle | 44.9039 | 103.7204 | -280.812 | 370.6196 | 0.9999 |
| FAP-CD40 4+1 + PD-L1 | FAP-CD40 2+1 | 28.5457 | 94.4727 | -268.129 | 325.2207 | 1.0000 |
| FAP-CD40 4+1 + PD-L1 | FAP-CD40 2+1 + PD-L1 | 28.5085 | 94.4727 | -268.166 | 325.1834 | 1.0000 |
| PD-L1 | Vehicle | 25.5402 | 97.3802 | -280.265 | 331.3457 | 1.0000 |
| CD40 | PD-L1 | 19.3637 | 100.9955 | -297.795 | 336.5226 | 1.0000 |
| FAP-CD40 2+1 | FAP-CD40 2+1 + PD-L1 | 0.0372 | 94.4727 | -296.638 | 296.7122 | 1.0000 |

FIG. 13B

Tumors of mice treated with the 4+1 antibody were too small to obtain reliable results Tumors of mice treated with the 4+1 antibody were too small to obtain reliable results Tumors of mice treated with the 4+1 antibody were too small to obtain reliable results

SEQUENCE LISTING

<160> NUMBER OF SEQ ID NOS: 110

<210> SEQ ID NO 1
<211> LENGTH: 277
<212> TYPE: PRT
<213> ORGANISM: Homo sapiens

<400> SEQUENCE: 1

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95
```

```
Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
        130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
            275

<210> SEQ ID NO 2
<211> LENGTH: 760
<212> TYPE: PRT
<213> ORGANISM: Homo sapiens

<400> SEQUENCE: 2

Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
            20                  25                  30

Asn Ser Glu Glu Asn Thr Met Arg Ala Leu Thr Leu Lys Asp Ile Leu
        35                  40                  45

Asn Gly Thr Phe Ser Tyr Lys Thr Phe Phe Pro Asn Trp Ile Ser Gly
    50                  55                  60

Gln Glu Tyr Leu His Gln Ser Ala Asp Asn Asn Ile Val Leu Tyr Asn
65              70                  75                  80

Ile Glu Thr Gly Gln Ser Tyr Thr Ile Leu Ser Asn Arg Thr Met Lys
                85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Ser Asn Gly Glu Phe Val Arg Gly Asn
    130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
```

```
              180              185              190
Phe Asn Gly Ile Pro Asp Trp Val Tyr Glu Glu Met Leu Ala Thr
            195              200              205
Lys Tyr Ala Leu Trp Trp Ser Pro Asn Gly Lys Phe Leu Ala Tyr
        210              215              220
Glu Phe Asn Asp Thr Asp Ile Pro Val Ile Ala Tyr Ser Tyr Tyr Gly
225              230              235              240
Asp Glu Gln Tyr Pro Arg Thr Ile Asn Ile Pro Tyr Pro Lys Ala Gly
                245              250              255
Ala Lys Asn Pro Val Val Arg Ile Phe Ile Ile Asp Thr Thr Tyr Pro
            260              265              270
Ala Tyr Val Gly Pro Gln Glu Val Pro Val Pro Ala Met Ile Ala Ser
            275              280              285
Ser Asp Tyr Tyr Phe Ser Trp Leu Thr Trp Val Thr Asp Glu Arg Val
290              295              300
Cys Leu Gln Trp Leu Lys Arg Val Gln Asn Val Ser Val Leu Ser Ile
305              310              315              320
Cys Asp Phe Arg Glu Asp Trp Gln Thr Trp Asp Cys Pro Lys Thr Gln
                325              330              335
Glu His Ile Glu Glu Ser Arg Thr Gly Trp Ala Gly Phe Phe Val
                340              345              350
Ser Thr Pro Val Phe Ser Tyr Asp Ala Ile Ser Tyr Tyr Lys Ile Phe
            355              360              365
Ser Asp Lys Asp Gly Tyr Lys His Ile His Tyr Ile Lys Asp Thr Val
            370              375              380
Glu Asn Ala Ile Gln Ile Thr Ser Gly Lys Trp Glu Ala Ile Asn Ile
385              390              395              400
Phe Arg Val Thr Gln Asp Ser Leu Phe Tyr Ser Ser Asn Glu Phe Glu
                405              410              415
Glu Tyr Pro Gly Arg Arg Asn Ile Tyr Arg Ile Ser Ile Gly Ser Tyr
                420              425              430
Pro Pro Ser Lys Lys Cys Val Thr Cys His Leu Arg Lys Glu Arg Cys
            435              440              445
Gln Tyr Tyr Thr Ala Ser Phe Ser Asp Tyr Ala Lys Tyr Tyr Ala Leu
            450              455              460
Val Cys Tyr Gly Pro Gly Ile Pro Ile Ser Thr Leu His Asp Gly Arg
465              470              475              480
Thr Asp Gln Glu Ile Lys Ile Leu Glu Glu Asn Lys Glu Leu Glu Asn
                485              490              495
Ala Leu Lys Asn Ile Gln Leu Pro Lys Glu Ile Lys Lys Leu Glu
            500              505              510
Val Asp Glu Ile Thr Leu Trp Tyr Lys Met Ile Leu Pro Pro Gln Phe
            515              520              525
Asp Arg Ser Lys Lys Tyr Pro Leu Leu Ile Gln Val Tyr Gly Gly Pro
            530              535              540
Cys Ser Gln Ser Val Arg Ser Val Phe Ala Val Asn Trp Ile Ser Tyr
545              550              555              560
Leu Ala Ser Lys Glu Gly Met Val Ile Ala Leu Val Asp Gly Arg Gly
                565              570              575
Thr Ala Phe Gln Gly Asp Lys Leu Leu Tyr Ala Val Tyr Arg Lys Leu
            580              585              590
Gly Val Tyr Glu Val Glu Asp Gln Ile Thr Ala Val Arg Lys Phe Ile
            595              600              605
```

```
                Glu Met Gly Phe Ile Asp Glu Lys Arg Ile Ala Ile Trp Gly Trp Ser
                    610                 615                 620

Tyr Gly Gly Tyr Val Ser Ser Leu Ala Leu Ala Ser Gly Thr Gly Leu
                625                 630                 635                 640

Phe Lys Cys Gly Ile Ala Val Ala Pro Val Ser Ser Trp Glu Tyr Tyr
                                645                 650                 655

Ala Ser Val Tyr Thr Glu Arg Phe Met Gly Leu Pro Thr Lys Asp Asp
                                660                 665                 670

Asn Leu Glu His Tyr Lys Asn Ser Thr Val Met Ala Arg Ala Glu Tyr
                                675                 680                 685

Phe Arg Asn Val Asp Tyr Leu Leu Ile His Gly Thr Ala Asp Asp Asn
                    690                 695                 700

Val His Phe Gln Asn Ser Ala Gln Ile Ala Lys Ala Leu Val Asn Ala
                705                 710                 715                 720

Gln Val Asp Phe Gln Ala Met Trp Tyr Ser Asp Gln Asn His Gly Leu
                                725                 730                 735

Ser Gly Leu Ser Thr Asn His Leu Tyr Thr His Met Thr His Phe Leu
                                740                 745                 750

Lys Gln Cys Phe Ser Leu Ser Asp
                                755                 760

<210> SEQ ID NO 3
<211> LENGTH: 5
<212> TYPE: PRT
<213> ORGANISM: Artificial Sequence
<220> FEATURE:
<223> OTHER INFORMATION: FAP (212) CDR-H1

<400> SEQUENCE: 3

Asp Tyr Asn Met Asp
1               5

<210> SEQ ID NO 4
<211> LENGTH: 17
<212> TYPE: PRT
<213> ORGANISM: Artificial Sequence
<220> FEATURE:
<223> OTHER INFORMATION: FAP (212) CDR-H2

<400> SEQUENCE: 4

Asp Ile Tyr Pro Asn Thr Gly Gly Thr Ile Tyr Asn Gln Lys Phe Lys
1               5                   10                  15

Gly

<210> SEQ ID NO 5
<211> LENGTH: 10
<212> TYPE: PRT
<213> ORGANISM: Artificial Sequence
<220> FEATURE:
<223> OTHER INFORMATION: FAP (212) CDR-H3

<400> SEQUENCE: 5

Phe Arg Gly Ile His Tyr Ala Met Asp Tyr
1               5                   10

<210> SEQ ID NO 6
<211> LENGTH: 15
<212> TYPE: PRT
<213> ORGANISM: Artificial Sequence
<220> FEATURE:
<223> OTHER INFORMATION: FAP (212) CDR-L1
```

<400> SEQUENCE: 6

Arg Ala Ser Glu Ser Val Asp Asn Tyr Gly Leu Ser Phe Ile Asn
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: FAP (212) CDR-L2

<400> SEQUENCE: 7

Gly Thr Ser Asn Arg Gly Ser
1               5

<210> SEQ ID NO 8
<211> LENGTH: 9
<212> TYPE: PRT
<213> ORGANISM: Artificial Sequence
<220> FEATURE:
<223> OTHER INFORMATION: FAP (212) CDR-L3

<400> SEQUENCE: 8

Gln Gln Ser Asn Glu Val Pro Tyr Thr
1               5

<210> SEQ ID NO 9
<211> LENGTH: 119
<212> TYPE: PRT
<213> ORGANISM: Artificial Sequence
<220> FEATURE:
<223> OTHER INFORMATION: FAP (212) VH

<400> SEQUENCE: 9

Glu Val Leu Leu Gln Gln Ser Gly Pro Glu Leu Val Lys Pro Gly Ala
1               5                   10                  15

Ser Val Lys Ile Ala Cys Lys Ala Ser Gly Tyr Thr Leu Thr Asp Tyr
            20                  25                  30

Asn Met Asp Trp Val Arg Gln Ser His Gly Lys Ser Leu Glu Trp Ile
        35                  40                  45

Gly Asp Ile Tyr Pro Asn Thr Gly Gly Thr Ile Tyr Asn Gln Lys Phe
    50                  55                  60

Lys Gly Lys Ala Thr Leu Thr Ile Asp Lys Ser Ser Ser Thr Ala Tyr
65                  70                  75                  80

Met Asp Leu Arg Ser Leu Thr Ser Glu Asp Thr Ala Val Tyr Tyr Cys
                85                  90                  95

Thr Arg Phe Arg Gly Ile His Tyr Ala Met Asp Tyr Trp Gly Gln Gly
            100                 105                 110

Thr Ser Val Thr Val Ser Ser
        115

<210> SEQ ID NO 10
<211> LENGTH: 111
<212> TYPE: PRT
<213> ORGANISM: Artificial Sequence
<220> FEATURE:
<223> OTHER INFORMATION: FAP (212) VL

<400> SEQUENCE: 10

Asp Ile Val Leu Thr Gln Ser Pro Val Ser Leu Ala Val Ser Leu Gly
1               5                   10                  15

```
Gln Arg Ala Thr Ile Ser Cys Arg Ala Ser Glu Ser Val Asp Asn Tyr
             20                  25                  30

Gly Leu Ser Phe Ile Asn Trp Phe Gln Gln Lys Pro Gly Gln Pro Pro
         35                  40                  45

Lys Leu Leu Ile Tyr Gly Thr Ser Asn Arg Gly Ser Gly Val Pro Ala
 50                  55                  60

Arg Phe Ser Gly Ser Gly Ser Gly Thr Asp Phe Ser Leu Asn Ile His
 65                  70                  75                  80

Pro Met Glu Glu Asp Asp Thr Ala Met Tyr Phe Cys Gln Gln Ser Asn
                 85                  90                  95

Glu Val Pro Tyr Thr Phe Gly Gly Gly Thr Asn Leu Glu Ile Lys
            100                 105                 110

<210> SEQ ID NO 11
<211> LENGTH: 17
<212> TYPE: PRT
<213> ORGANISM: Artificial Sequence
<220> FEATURE:
<223> OTHER INFORMATION: FAP (VH1G3a) CDR-H2

<400> SEQUENCE: 11

Asp Ile Tyr Pro Asn Thr Gly Gly Thr Ile Tyr Ala Gln Lys Phe Gln
 1               5                  10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: FAP (VH2G3a) CDR-H2

<400> SEQUENCE: 12

Asp Ile Tyr Pro Asn Thr Gly Gly Thr Ile Tyr Ala Asp Ser Val Lys
 1               5                  10                  15

Gly

<210> SEQ ID NO 13
<211> LENGTH: 15
<212> TYPE: PRT
<213> ORGANISM: Artificial Sequence
<220> FEATURE:
<223> OTHER INFORMATION: FAP (VL1G3a) CDR-L1

<400> SEQUENCE: 13

Arg Ala Ser Glu Ser Val Asp Asn Tyr Gly Leu Ser Phe Leu Ala
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: FAP (VL2G3a) CDR-L1

<400> SEQUENCE: 14

Arg Ala Ser Glu Ser Ile Asp Asn Tyr Gly Leu Ser Phe Leu Asn
 1               5                  10                  15

<210> SEQ ID NO 15
<211> LENGTH: 119
<212> TYPE: PRT
<213> ORGANISM: Artificial Sequence
```

```
<220> FEATURE:
<223> OTHER INFORMATION: FAP (VH1G1a)

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
            20                  25                  30

Asn Met Asp Trp Val Arg Gln Ala Pro Gly Gln Gly Leu Glu Trp Ile
        35                  40                  45

Gly Asp Ile Tyr Pro Asn Thr Gly Gly Thr Ile Tyr Asn Gln Lys Phe
    50                  55                  60

Lys Gly Arg Val Thr Met Thr Ile Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Thr Arg Phe Arg Gly Ile His Tyr Ala Met Asp Tyr Trp Gly Gln Gly
            100                 105                 110

Thr Thr Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: FAP (VH1G2a)

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
            20                  25                  30

Asn Met Asp Trp Val Arg Gln Ala Pro Gly Lys Ser Leu Glu Trp Ile
        35                  40                  45

Gly Asp Ile Tyr Pro Asn Thr Gly Gly Thr Ile Tyr Asn Gln Lys Phe
    50                  55                  60

Lys Gly Arg Val Thr Met Thr Ile Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Phe Arg Gly Ile His Tyr Ala Met Asp Tyr Trp Gly Gln Gly
            100                 105                 110

Thr Thr Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: FAP (VH1G3a)

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
            20                  25                  30
```

-continued

Asn Met Asp Trp Val Arg Gln Ala Pro Gly Gln Gly Leu Glu Trp Ile
         35                  40                  45

Gly Asp Ile Tyr Pro Asn Thr Gly Gly Thr Ile Tyr Ala Gln Lys Phe
 50                      55                  60

Gln Gly Arg Val Thr Met Thr Ile Asp Thr Ser Thr Ser Thr Val Tyr
 65                  70                  75                  80

Met Glu Leu Ser Ser Leu Arg Ser Glu Asp Thr Ala Val Tyr Tyr Cys
             85                  90                  95

Thr Arg Phe Arg Gly Ile His Tyr Ala Met Asp Tyr Trp Gly Gln Gly
            100                 105                 110

Thr Thr Val Thr Val Ser Ser
            115

<210> SEQ ID NO 18
<211> LENGTH: 119
<212> TYPE: PRT
<213> ORGANISM: Artificial Sequence
<220> FEATURE:
<223> OTHER INFORMATION: FAP (VH2G1a)

<400> SEQUENCE: 18

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Thr Leu Thr Asp Tyr
             20                  25                  30

Asn Met Asp Trp Val Arg Gln Ala Pro Gly Lys Gly Leu Glu Trp Val
         35                  40                  45

Gly Asp Ile Tyr Pro Asn Thr Gly Gly Thr Ile Tyr Asn Gln Lys Phe
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Thr Arg Phe Arg Gly Ile His Tyr Ala Met Asp Tyr Trp Gly Gln Gly
            100                 105                 110

Thr Thr Val Thr Val Ser Ser
            115

<210> SEQ ID NO 19
<211> LENGTH: 119
<212> TYPE: PRT
<213> ORGANISM: Artificial Sequence
<220> FEATURE:
<223> OTHER INFORMATION: FAP (VH2G2a)

<400> SEQUENCE: 19

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Thr Leu Thr Asp Tyr
             20                  25                  30

Asn Met Asp Trp Val Arg Gln Ala Pro Gly Lys Gly Leu Glu Trp Val
         35                  40                  45

Gly Asp Ile Tyr Pro Asn Thr Gly Gly Thr Ile Tyr Asn Gln Lys Phe
 50                      55                  60

Lys Gly Arg Phe Thr Ile Ser Ile Asp Lys Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

-continued

Thr Arg Phe Arg Gly Ile His Tyr Ala Met Asp Tyr Trp Gln Gly
                100                 105                 110

Thr Thr Val Thr Val Ser Ser
        115

<210> SEQ ID NO 20
<211> LENGTH: 119
<212> TYPE: PRT
<213> ORGANISM: Artificial Sequence
<220> FEATURE:
<223> OTHER INFORMATION: FAP (VH2G3a)

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Leu Thr Asp Tyr
                20                  25                  30

Asn Met Asp Trp Val Arg Gln Ala Pro Gly Lys Gly Leu Glu Trp Val
            35                  40                  45

Gly Asp Ile Tyr Pro Asn Thr Gly Gly Thr Ile Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Phe Arg Gly Ile His Tyr Ala Met Asp Tyr Trp Gln Gly
                100                 105                 110

Thr Thr Val Thr Val Ser Ser
        115

<210> SEQ ID NO 21
<211> LENGTH: 111
<212> TYPE: PRT
<213> ORGANISM: Artificial Sequence
<220> FEATURE:
<223> OTHER INFORMATION: FAP (VL1G1a)

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
                20                  25                  30

Gly Leu Ser Phe Ile Asn Trp Phe Gln Gln Lys Pro Gly Gln Ala Pro
            35                  40                  45

Arg Leu Leu Ile Tyr Gly Thr Ser Asn Arg Gly Ser Gly Ile Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Asn
                85                  90                  95

Glu Val Pro Tyr Thr Phe Gly Gly Gly Thr Lys Val Glu Ile Lys
                100                 105                 110

<210> SEQ ID NO 22
<211> LENGTH: 111
<212> TYPE: PRT
<213> ORGANISM: Artificial Sequence
<220> FEATURE:
<223> OTHER INFORMATION: FAP (VL1G2a)

```
<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Ile Asn Trp Phe Gln Gln Lys Pro Gly Gln Pro Pro
        35                  40                  45

Arg Leu Leu Ile Tyr Gly Thr Ser Asn Arg Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Asn
                85                  90                  95

Glu Val Pro Tyr Thr Phe Gly Gly Gly Thr Lys Val Glu Ile Lys
            100                 105                 110

<210> SEQ ID NO 23
<211> LENGTH: 111
<212> TYPE: PRT
<213> ORGANISM: Artificial Sequence
<220> FEATURE:
<223> OTHER INFORMATION: FAP (VL1G3a)

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Leu Ala Trp Phe Gln Gln Lys Pro Gly Gln Ala Pro
        35                  40                  45

Arg Leu Leu Ile Tyr Gly Thr Ser Asn Arg Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Asn
                85                  90                  95

Glu Val Pro Tyr Thr Phe Gly Gly Gly Thr Lys Val Glu Ile Lys
            100                 105                 110

<210> SEQ ID NO 24
<211> LENGTH: 111
<212> TYPE: PRT
<213> ORGANISM: Artificial Sequence
<220> FEATURE:
<223> OTHER INFORMATION: FAP (VL2G1a)

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Leu Ser Phe Ile Asn Trp Phe Gln Gln Lys Pro Gly Lys Ala Pro
        35                  40                  45

Lys Leu Leu Ile Tyr Gly Thr Ser Asn Arg Gly Ser Gly Val Pro Ser
    50                  55                  60

Arg Phe Ser Gly Ser Gly Ser Gly Thr Asp Phe Thr Leu Thr Ile Ser
65                  70                  75                  80
```

```
Ser Leu Gln Pro Glu Asp Phe Ala Thr Tyr Phe Cys Gln Gln Ser Asn
                85                  90                  95

Glu Val Pro Tyr Thr Phe Gly Gly Gly Thr Lys Val Glu Ile Lys
            100                 105                 110

<210> SEQ ID NO 25
<211> LENGTH: 111
<212> TYPE: PRT
<213> ORGANISM: Artificial Sequence
<220> FEATURE:
<223> OTHER INFORMATION: FAP (VL2G2a)

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Leu Ser Phe Ile Asn Trp Phe Gln Gln Lys Pro Gly Gln Pro Pro
        35                  40                  45

Lys Leu Leu Ile Tyr Gly Thr Ser Asn Arg Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Met Tyr Phe Cys Gln Gln Ser Asn
                85                  90                  95

Glu Val Pro Tyr Thr Phe Gly Gly Gly Thr Lys Val Glu Ile Lys
            100                 105                 110

<210> SEQ ID NO 26
<211> LENGTH: 111
<212> TYPE: PRT
<213> ORGANISM: Artificial Sequence
<220> FEATURE:
<223> OTHER INFORMATION: FAP (VL2G3a)

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Asp Asn Tyr
            20                  25                  30

Gly Leu Ser Phe Leu Asn Trp Phe Gln Gln Lys Pro Gly Lys Ala Pro
        35                  40                  45

Lys Leu Leu Ile Tyr Gly Thr Ser Asn Arg Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Phe Cys Gln Gln Ser Asn
                85                  90                  95

Glu Val Pro Tyr Thr Phe Gly Gly Gly Thr Lys Val Glu Ile Lys
            100                 105                 110

<210> SEQ ID NO 27
<211> LENGTH: 5
<212> TYPE: PRT
<213> ORGANISM: Artificial Sequence
<220> FEATURE:
<223> OTHER INFORMATION: hu CD40  CDR-H1

<400> SEQUENCE: 27
```

```
Gly Tyr Tyr Ile His
1               5

<210> SEQ ID NO 28
<211> LENGTH: 17
<212> TYPE: PRT
<213> ORGANISM: Artificial Sequence
<220> FEATURE:
<223> OTHER INFORMATION: hu CD40  CDR-H2

<400> SEQUENCE: 28

Arg Val Ile Pro Asn Ala Gly Gly Thr Ser Tyr Asn Gln Lys Phe Lys
1               5                   10                  15

Gly

<210> SEQ ID NO 29
<211> LENGTH: 5
<212> TYPE: PRT
<213> ORGANISM: Artificial Sequence
<220> FEATURE:
<223> OTHER INFORMATION: hu CD40  CDR-H3

<400> SEQUENCE: 29

Glu Gly Ile Tyr Trp
1               5

<210> SEQ ID NO 30
<211> LENGTH: 16
<212> TYPE: PRT
<213> ORGANISM: Artificial Sequence
<220> FEATURE:
<223> OTHER INFORMATION: hu CD40  CDR-L1

<400> SEQUENCE: 30

Arg Ser Ser Gln Ser Leu Val His Ser Asn Gly Asn Thr Phe Leu His
1               5                   10                  15

<210> SEQ ID NO 31
<211> LENGTH: 7
<212> TYPE: PRT
<213> ORGANISM: Artificial Sequence
<220> FEATURE:
<223> OTHER INFORMATION: hu CD40  CDR-L2

<400> SEQUENCE: 31

Thr Val Ser Asn Arg Phe Ser
1               5

<210> SEQ ID NO 32
<211> LENGTH: 9
<212> TYPE: PRT
<213> ORGANISM: Artificial Sequence
<220> FEATURE:
<223> OTHER INFORMATION: hu CD40  CDR-L3

<400> SEQUENCE: 32

Ser Gln Thr Thr His Val Pro Trp Thr
1               5

<210> SEQ ID NO 33
<211> LENGTH: 114
<212> TYPE: PRT
<213> ORGANISM: Artificial Sequence
<220> FEATURE:
<223> OTHER INFORMATION: hu CD40 VH

<400> SEQUENCE: 33
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Ala Arg Val Ile Pro Asn Ala Gly Gly Thr Ser Tyr Asn Gln Lys Phe
    50                  55                  60

Lys Gly Arg Phe Thr Leu Ser Val Asp Asn Ser Lys Asn Thr Ala Tyr
65              70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Leu Val Thr Val
            100                 105                 110

Ser Ser

<210> SEQ ID NO 34
<211> LENGTH: 112
<212> TYPE: PRT
<213> ORGANISM: Artificial Sequence
<220> FEATURE:
<223> OTHER INFORMATION: hu CD40 VL

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65              70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gln Gly Thr Lys Val Glu Ile Lys
            100                 105                 110

<210> SEQ ID NO 35
<211> LENGTH: 114
<212> TYPE: PRT
<213> ORGANISM: Artificial Sequence
<220> FEATURE:
<223> OTHER INFORMATION: CD40 (S2C6) VH

<400> SEQUENCE: 35

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Ile His Trp Val Lys Gln Ser His Gly Lys Ser Leu Glu Trp Ile
        35                  40                  45

Gly Arg Val Ile Pro Asn Asn Gly Gly Thr Ser Tyr Asn Gln Lys Phe
    50                  55                  60

Lys Gly Lys Ala Ile Leu Thr Val Asp Lys Ser Ser Ser Thr Ala Tyr
65              70                  75                  80
```

```
Met Glu Leu Arg Ser Leu Thr Ser Glu Asp Ser Ala Val Tyr Tyr Cys
                85                  90                  95

Ala Arg Glu Gly Ile Tyr Trp Trp Gly His Gly Thr Thr Leu Thr Val
            100                 105                 110

Ser Ser

<210> SEQ ID NO 36
<211> LENGTH: 112
<212> TYPE: PRT
<213> ORGANISM: Artificial Sequence
<220> FEATURE:
<223> OTHER INFORMATION: CD40 (S2C6) VL

<400> SEQUENCE: 36

Asp Val Val Thr Gln Thr Pro Leu Ser Leu Pro Val Ser Leu Gly
1               5                   10                  15

Ala Gln Ala Ser Ile Ser Cys Arg Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Trp Thr Phe Gly Gly Gly Thr Lys Leu Glu Ile Gln
            100                 105                 110

<210> SEQ ID NO 37
<211> LENGTH: 114
<212> TYPE: PRT
<213> ORGANISM: Artificial Sequence
<220> FEATURE:
<223> OTHER INFORMATION: VH1a (CD40)

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Ser Leu Glu Trp Met
        35                  40                  45

Gly Arg Val Ile Pro Asn Ala Gly Gly Thr Ser Tyr Asn Gln Lys Phe
    50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser

<210> SEQ ID NO 38
<211> LENGTH: 114
<212> TYPE: PRT
<213> ORGANISM: Artificial Sequence
<220> FEATURE:
```

<223> OTHER INFORMATION: VH1b (CD40)

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Lys Ser Leu Glu Trp Met
        35                  40                  45

Gly Arg Val Ile Pro Asn Ala Gly Gly Thr Ser Tyr Asn Gln Lys Phe
    50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Ile Tyr Trp Trp Gly Gln Gly Thr Thr Val Thr Val
                100                 105                 110

Ser Ser

<210> SEQ ID NO 39
<211> LENGTH: 114
<212> TYPE: PRT
<213> ORGANISM: Artificial Sequence
<220> FEATURE:
<223> OTHER INFORMATION: VH1c (CD40)

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Ser Leu Glu Trp Met
        35                  40                  45

Gly Arg Val Ile Pro Asn Ala Gly Gly Thr Ser Tyr Asn Gln Lys Phe
    50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Ile Tyr Trp Trp Gly His Gly Thr Thr Val Thr Val
                100                 105                 110

Ser Ser

<210> SEQ ID NO 40
<211> LENGTH: 114
<212> TYPE: PRT
<213> ORGANISM: Artificial Sequence
<220> FEATURE:
<223> OTHER INFORMATION: VH1d (CD40)

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Ser Leu Glu Trp Met
        35                  40                  45

```
Gly Arg Val Ile Pro Asn Ala Gly Gly Thr Ser Tyr Asn Gln Lys Phe
        50                  55                  60

Lys Gly Arg Val Thr Leu Ser Val Asp Lys Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Gly Ile Tyr Trp Trp Gly Gln Gly Thr Thr Val Thr Val
                100                 105                 110

Ser Ser

<210> SEQ ID NO 41
<211> LENGTH: 112
<212> TYPE: PRT
<213> ORGANISM: Artificial Sequence
<220> FEATURE:
<223> OTHER INFORMATION: VL1a (CD40)

<400> SEQUENCE: 41

Asp Ile Val Met Thr Gln Thr Pro Leu Ser Leu Ser Val Thr Pro Gly
  1               5                  10                  15

Gln Pro Ala Ser Ile Ser Cys Arg Ser Ser Gln Ser Leu Val His Ser
                 20                  25                  30

Asn Gly Asn Thr Phe Leu His Trp Tyr Leu Gln Lys Pro Gly Gln Ser
             35                  40                  45

Pro Gln Leu Leu Ile Tyr Thr Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Thr
                 85                  90                  95

Thr His Val Pro Trp Thr Phe Gly Gly Gly Thr Lys Val Glu Ile Lys
                100                 105                 110

<210> SEQ ID NO 42
<211> LENGTH: 112
<212> TYPE: PRT
<213> ORGANISM: Artificial Sequence
<220> FEATURE:
<223> OTHER INFORMATION: VL1b (CD40)

<400> SEQUENCE: 42

Asp Ile Val Val Thr Gln Thr Pro Leu Ser Leu Ser Val Thr Pro Gly
  1               5                  10                  15

Gln Pro Ala Ser Ile Ser Cys Arg Ser Ser Gln Ser Leu Val His Ser
                 20                  25                  30

Asn Gly Asn Thr Phe Leu His Trp Tyr Leu Gln Lys Pro Gly Gln Ser
             35                  40                  45

Pro Gln Leu Leu Ile Tyr Thr Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Thr
                 85                  90                  95

Thr His Val Pro Trp Thr Phe Gly Gly Gly Thr Lys Val Glu Ile Lys
                100                 105                 110

<210> SEQ ID NO 43
<211> LENGTH: 112
```

```
<212> TYPE: PRT
<213> ORGANISM: Artificial Sequence
<220> FEATURE:
<223> OTHER INFORMATION: VL1c (CD40)

<400> SEQUENCE: 43

Asp Val Val Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Thr His Val Pro Trp Thr Phe Gly Gly Gly Thr Lys Val Glu Ile Lys
            100                 105                 110

<210> SEQ ID NO 44
<211> LENGTH: 112
<212> TYPE: PRT
<213> ORGANISM: Artificial Sequence
<220> FEATURE:
<223> OTHER INFORMATION: VL1d (CD40)

<400> SEQUENCE: 44

Asp Val Val Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Thr His Val Pro Trp Thr Phe Gly Gly Gly Thr Lys Leu Glu Ile Lys
            100                 105                 110

<210> SEQ ID NO 45
<211> LENGTH: 114
<212> TYPE: PRT
<213> ORGANISM: Artificial Sequence
<220> FEATURE:
<223> OTHER INFORMATION: VH2a (CD40)

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Gly Arg Val Ile Pro Asn Ala Gly Gly Thr Ser Tyr Asn Gln Lys Phe
```

```
                50                  55                  60
Lys Gly Arg Phe Thr Ile Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Tyr Trp Trp Gly Gln Gly Thr Thr Val Thr Val
                100                 105                 110

Ser Ser

<210> SEQ ID NO 46
<211> LENGTH: 114
<212> TYPE: PRT
<213> ORGANISM: Artificial Sequence
<220> FEATURE:
<223> OTHER INFORMATION: VH2b (CD40)

<400> SEQUENCE: 46

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Ser Phe Thr Gly Tyr
                20                  25                  30

Tyr Ile His Trp Val Arg Gln Ala Pro Gly Lys Ser Leu Glu Trp Val
             35                  40                  45

Gly Arg Val Ile Pro Asn Ala Gly Gly Thr Ser Tyr Asn Gln Lys Phe
         50                  55                  60

Lys Gly Arg Phe Thr Ile Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Tyr Trp Trp Gly Gln Gly Thr Thr Val Thr Val
                100                 105                 110

Ser Ser

<210> SEQ ID NO 47
<211> LENGTH: 114
<212> TYPE: PRT
<213> ORGANISM: Artificial Sequence
<220> FEATURE:
<223> OTHER INFORMATION: VH2c (CD40)

<400> SEQUENCE: 47

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Ser Phe Thr Gly Tyr
                20                  25                  30

Tyr Ile His Trp Val Arg Gln Ala Pro Gly Lys Gly Leu Glu Trp Val
             35                  40                  45

Gly Arg Val Ile Pro Asn Ala Gly Gly Thr Ser Tyr Asn Gln Lys Phe
         50                  55                  60

Lys Gly Arg Phe Thr Ile Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Tyr Trp Trp Gly His Gly Thr Thr Val Thr Val
                100                 105                 110

Ser Ser
```

<210> SEQ ID NO 48
<211> LENGTH: 114
<212> TYPE: PRT
<213> ORGANISM: Artificial Sequence
<220> FEATURE:
<223> OTHER INFORMATION: VH2d (CD40)

<400> SEQUENCE: 48

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Gly Arg Val Ile Pro Asn Ala Gly Gly Thr Ser Tyr Gly Asp Ser Val
    50                  55                  60

Lys Gly Arg Phe Thr Ile Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser
```

<210> SEQ ID NO 49
<211> LENGTH: 114
<212> TYPE: PRT
<213> ORGANISM: Artificial Sequence
<220> FEATURE:
<223> OTHER INFORMATION: VH2ab (CD40)

<400> SEQUENCE: 49

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Met His Trp Val Arg Gln Ala Pro Gly Lys Gly Leu Glu Trp Val
        35                  40                  45

Gly Arg Val Ile Pro Asn Ala Gly Gly Thr Ser Tyr Asn Gln Lys Phe
    50                  55                  60

Lys Gly Arg Phe Thr Ile Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser
```

<210> SEQ ID NO 50
<211> LENGTH: 114
<212> TYPE: PRT
<213> ORGANISM: Artificial Sequence
<220> FEATURE:
<223> OTHER INFORMATION: VH2ac (CD40)

<400> SEQUENCE: 50

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Gly Arg Val Ile Pro Asn Ala Gly Gly Thr Ser Tyr Asn Gln Lys Val
    50                  55                  60

Lys Gly Arg Phe Thr Ile Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser

<210> SEQ ID NO 51
<211> LENGTH: 112
<212> TYPE: PRT
<213> ORGANISM: Artificial Sequence
<220> FEATURE:
<223> OTHER INFORMATION: VL2a (CD40)

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gly Gly Thr Lys Val Glu Ile Lys
            100                 105                 110

<210> SEQ ID NO 52
<211> LENGTH: 112
<212> TYPE: PRT
<213> ORGANISM: Artificial Sequence
<220> FEATURE:
<223> OTHER INFORMATION: VL2b (CD40)

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Gln Ser
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95
```

```
Thr His Val Pro Trp Thr Phe Gly Gly Gly Thr Lys Val Glu Ile Lys
        100                 105                 110

<210> SEQ ID NO 53
<211> LENGTH: 112
<212> TYPE: PRT
<213> ORGANISM: Artificial Sequence
<220> FEATURE:
<223> OTHER INFORMATION: VL2ab (CD40)

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gly Gly Thr Lys Val Glu Ile Lys
        100                 105                 110

<210> SEQ ID NO 54
<211> LENGTH: 112
<212> TYPE: PRT
<213> ORGANISM: Artificial Sequence
<220> FEATURE:
<223> OTHER INFORMATION: VL2ac (CD40)

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gly Gly Thr Lys Val Glu Ile Lys
        100                 105                 110

<210> SEQ ID NO 55
<211> LENGTH: 443
<212> TYPE: PRT
<213> ORGANISM: Artificial Sequence
<220> FEATURE:
<223> OTHER INFORMATION: P1AE0400 Heavy chain

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
```

```
                20                  25                  30
Tyr Ile His Trp Val Arg Gln Ala Pro Gly Lys Gly Leu Glu Trp Val
            35                  40                  45
Gly Arg Val Ile Pro Asn Ala Gly Gly Thr Ser Tyr Asn Gln Lys Phe
50                  55                  60
Lys Gly Arg Phe Thr Ile Ser Val Asp Asn Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Glu Gly Ile Tyr Trp Trp Gly Gln Gly Thr Thr Val Thr Val
            100                 105                 110
Ser Ser Ala Ser Thr Lys Gly Pro Ser Val Phe Pro Leu Ala Pro Ser
            115                 120                 125
Ser Lys Ser Thr Ser Gly Gly Thr Ala Ala Leu Gly Cys Leu Val Lys
            130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
            180                 185                 190
Gln Thr Tyr Ile Cys Asn Val Asn His Lys Pro Ser Asn Thr Lys Val
            195                 200                 205
Asp Lys Lys Val Glu Pro Lys Ser Cys Asp Lys Thr His Thr Cys Pro
            210                 215                 220
Pro Cys Pro Ala Pro Glu Ala Ala Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
            260                 265                 270
Asn Trp Tyr Val Asp Gly Val Glu Val His Asn Ala Lys Thr Lys Pro
            275                 280                 285
Arg Glu Glu Gln Tyr Asn Ser Thr Tyr Arg Val Val Ser Val Leu Thr
            290                 295                 300
Val Leu His Gln Asp Trp Leu Asn Gly Lys Glu Tyr Lys Cys Lys Val
305                 310                 315                 320
Ser Asn Lys Ala Leu Gly Ala Pro Ile Glu Lys Thr Ile Ser Lys Ala
                325                 330                 335
Lys Gly Gln Pro Arg Glu Pro Gln Val Tyr Thr Leu Pro Pro Ser Arg
            340                 345                 350
Asp Glu Leu Thr Lys Asn Gln Val Ser Leu Thr Cys Leu Val Lys Gly
            355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly
            435                 440
```

<210> SEQ ID NO 56
<211> LENGTH: 219
<212> TYPE: PRT
<213> ORGANISM: Artificial Sequence
<220> FEATURE:
<223> OTHER INFORMATION: P1AE0400 light chain

<400> SEQUENCE: 56

```
Asp Ile Gln Met Thr Gln Ser Pro Ser Ser Leu Ser Ala Ser Val Gly
1               5                   10                  15

Asp Arg Val Thr Ile Thr Cys Arg Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 57
<211> LENGTH: 443
<212> TYPE: PRT
<213> ORGANISM: Artificial Sequence
<220> FEATURE:
<223> OTHER INFORMATION: P1AE0403 heavy chain

<400> SEQUENCE: 57

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Gly Arg Val Ile Pro Asn Ala Gly Gly Thr Ser Tyr Gly Asp Ser Val
    50                  55                  60

Lys Gly Arg Phe Thr Ile Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
```

```
                    85                  90                  95
Ala Arg Glu Gly Ile Tyr Trp Trp Gly Gln Gly Thr Thr Val Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Gly Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 58
<211> LENGTH: 219
<212> TYPE: PRT
<213> ORGANISM: Artificial Sequence
<220> FEATURE:
<223> OTHER INFORMATION: P1AE0403 light chain

<400> SEQUENCE: 58

Asp Ile Gln Met Thr Gln Ser Pro Ser Ser Leu Ser Ala Ser Val Gly
```

```
            1               5                   10                  15
        Asp Arg Val Thr Ile Thr Cys Arg Ser Ser Gln Ser Leu Val His Ser
                        20                  25                  30

Asn Gly Asn Thr Phe Leu His Trp Tyr Gln Gln Lys Pro Gly Lys Ala
                    35                  40                  45

Pro Lys Leu Leu Ile Tyr Thr Val Ser Asn Arg Phe Ser Gly Val Pro
                50                  55                  60

Ser Arg Phe Ser Gly Ser Gly Ser Gly Thr Asp Phe Thr Leu Thr Ile
        65                  70                  75                  80

Ser Ser Leu Gln Pro Glu Asp Phe Ala Thr Tyr Phe Cys Ser Gln Thr
                            85                  90                  95

Thr His Val Pro Trp Thr Phe Gly Gly Gly Thr Lys Val Glu Ile Lys
                        100                 105                 110

Arg Thr Val Ala Ala Pro Ser Val Phe Ile Phe Pro Pro Ser Asp Glu
                    115                 120                 125

Gln Leu Lys Ser Gly Thr Ala Ser Val Val Cys Leu Leu Asn Asn Phe
                130                 135                 140

Tyr Pro Arg Glu Ala Lys Val Gln Trp Lys Val Asp Asn Ala Leu Gln
        145                 150                 155                 160

Ser Gly Asn Ser Gln Glu Ser Val Thr Glu Gln Asp Ser Lys Asp Ser
                            165                 170                 175

Thr Tyr Ser Leu Ser Ser Thr Leu Thr Leu Ser Lys Ala Asp Tyr Glu
                        180                 185                 190

Lys His Lys Val Tyr Ala Cys Glu Val Thr His Gln Gly Leu Ser Ser
                    195                 200                 205

Pro Val Thr Lys Ser Phe Asn Arg Gly Glu Cys
                210                 215

<210> SEQ ID NO 59
<211> LENGTH: 443
<212> TYPE: PRT
<213> ORGANISM: Artificial Sequence
<220> FEATURE:
<223> OTHER INFORMATION: P1AE0817 heavy chain

<400> SEQUENCE: 59

Gln Val Gln Leu Val Gln Ser Gly Ala Glu Val Lys Lys Pro Gly Ala
        1               5                   10                  15

Ser Val Lys Val Ser Cys Lys Ala Ser Gly Tyr Ser Phe Thr Gly Tyr
                        20                  25                  30

Tyr Ile His Trp Val Arg Gln Ala Pro Gly Gln Ser Leu Glu Trp Met
                    35                  40                  45

Gly Arg Val Ile Pro Asn Ala Gly Gly Thr Ser Tyr Asn Gln Lys Phe
                50                  55                  60

Lys Gly Arg Val Thr Leu Thr Val Asp Lys Ser Ile Ser Thr Ala Tyr
        65                  70                  75                  80

Met Glu Leu Ser Arg Leu Arg Ser Asp Asp Thr Ala Val Tyr Tyr Cys
                            85                  90                  95

Ala Arg Glu Gly Ile Tyr Trp Trp Gly Gln Gly Thr Thr Val Thr Val
                        100                 105                 110

Ser Ser Ala Ser Thr Lys Gly Pro Ser Val Phe Pro Leu Ala Pro Ser
                    115                 120                 125

Ser Lys Ser Thr Ser Gly Gly Thr Ala Ala Leu Gly Cys Leu Val Lys
                130                 135                 140

Asp Tyr Phe Pro Glu Pro Val Thr Val Ser Trp Asn Ser Gly Ala Leu
```

```
            145                 150                 155                 160
        Thr Ser Gly Val His Thr Phe Pro Ala Val Leu Gln Ser Ser Gly Leu
                        165                 170                 175

Tyr Ser Leu Ser Ser Val Val Thr Val Pro Ser Ser Leu Gly Thr
                        180                 185                 190

Gln Thr Tyr Ile Cys Asn Val Asn His Lys Pro Ser Asn Thr Lys Val
                        195                 200                 205

Asp Lys Lys Val Glu Pro Lys Ser Cys Asp Lys Thr His Thr Cys Pro
                    210                 215                 220

Pro Cys Pro Ala Pro Glu Ala Ala Gly Gly Pro Ser Val Phe Leu Phe
        225                 230                 235                 240

Pro Pro Lys Pro Lys Asp Thr Leu Met Ile Ser Arg Thr Pro Glu Val
                        245                 250                 255

Thr Cys Val Val Val Asp Val Ser His Glu Asp Pro Glu Val Lys Phe
                        260                 265                 270

Asn Trp Tyr Val Asp Gly Val Glu Val His Asn Ala Lys Thr Lys Pro
                    275                 280                 285

Arg Glu Glu Gln Tyr Asn Ser Thr Tyr Arg Val Val Ser Val Leu Thr
                    290                 295                 300

Val Leu His Gln Asp Trp Leu Asn Gly Lys Glu Tyr Lys Cys Lys Val
        305                 310                 315                 320

Ser Asn Lys Ala Leu Gly Ala Pro Ile Glu Lys Thr Ile Ser Lys Ala
                        325                 330                 335

Lys Gly Gln Pro Arg Glu Pro Gln Val Tyr Thr Leu Pro Pro Ser Arg
                        340                 345                 350

Asp Glu Leu Thr Lys Asn Gln Val Ser Leu Thr Cys Leu Val Lys Gly
                    355                 360                 365

Phe Tyr Pro Ser Asp Ile Ala Val Glu Trp Ser Asn Gly Gln Pro
                    370                 375                 380

Glu Asn Asn Tyr Lys Thr Thr Pro Pro Val Leu Asp Ser Asp Gly Ser
        385                 390                 395                 400

Phe Phe Leu Tyr Ser Lys Leu Thr Val Asp Lys Ser Arg Trp Gln Gln
                        405                 410                 415

Gly Asn Val Phe Ser Cys Ser Val Met His Glu Ala Leu His Asn His
                        420                 425                 430

Tyr Thr Gln Lys Ser Leu Ser Leu Ser Pro Gly
                        435                 440

<210> SEQ ID NO 60
<211> LENGTH: 219
<212> TYPE: PRT
<213> ORGANISM: Artificial Sequence
<220> FEATURE:
<223> OTHER INFORMATION: P1AE0817 light chain

<400> SEQUENCE: 60

Asp Ile Val Met Thr Gln Thr Pro Leu Ser Leu Ser Val Thr Pro Gly
        1               5                   10                  15

Gln Pro Ala Ser Ile Ser Cys Arg Ser Ser Gln Ser Leu Val His Ser
                        20                  25                  30

Asn Gly Asn Thr Phe Leu His Trp Tyr Leu Gln Lys Pro Gly Gln Ser
                    35                  40                  45

Pro Gln Leu Leu Ile Tyr Thr Val Ser Asn Arg Phe Ser Gly Val Pro
                50                  55                  60

Asp Arg Phe Ser Gly Ser Gly Ser Gly Thr Asp Phe Thr Leu Lys Ile
```

```
                65                  70                  75                  80
        Ser Arg Val Glu Ala Glu Asp Val Gly Val Tyr Phe Cys Ser Gln Thr
                            85                  90                  95

Thr His Val Pro Trp Thr Phe Gly Gly Gly Thr Lys Val Glu Ile Lys
                            100                 105                 110

Arg Thr Val Ala Ala Pro Ser Val Phe Ile Phe Pro Pro Ser Asp Glu
                            115                 120                 125

Gln Leu Lys Ser Gly Thr Ala Ser Val Val Cys Leu Leu Asn Asn Phe
                    130                 135                 140

Tyr Pro Arg Glu Ala Lys Val Gln Trp Lys Val Asp Asn Ala Leu Gln
        145                 150                 155                 160

Ser Gly Asn Ser Gln Glu Ser Val Thr Glu Gln Asp Ser Lys Asp Ser
                            165                 170                 175

Thr Tyr Ser Leu Ser Ser Thr Leu Thr Leu Ser Lys Ala Asp Tyr Glu
                            180                 185                 190

Lys His Lys Val Tyr Ala Cys Glu Val Thr His Gln Gly Leu Ser Ser
                            195                 200                 205

Pro Val Thr Lys Ser Phe Asn Arg Gly Glu Cys
                            210                 215

<210> SEQ ID NO 61
<211> LENGTH: 226
<212> TYPE: PRT
<213> ORGANISM: Artificial Sequence
<220> FEATURE:
<223> OTHER INFORMATION: (P1AE1689) light chain cross VH-Ckappa

<400> SEQUENCE: 61

Gln Val Gln Leu Val Gln Ser Gly Ala Glu Val Lys Lys Pro Gly Ala
        1                   5                   10                  15

Ser Val Lys Val Ser Cys Lys Ala Ser Gly Tyr Thr Leu Thr Asp Tyr
                            20                  25                  30

Asn Met Asp Trp Val Arg Gln Ala Pro Gly Gln Gly Leu Glu Trp Ile
                            35                  40                  45

Gly Asp Ile Tyr Pro Asn Thr Gly Gly Thr Ile Tyr Asn Gln Lys Phe
        50                  55                  60

Lys Gly Arg Val Thr Met Thr Ile Asp Thr Ser Thr Ser Thr Val Tyr
        65                  70                  75                  80

Met Glu Leu Ser Ser Leu Arg Ser Glu Asp Thr Ala Val Tyr Tyr Cys
                            85                  90                  95

Thr Arg Phe Arg Gly Ile His Tyr Ala Met Asp Tyr Trp Gly Gln Gly
                            100                 105                 110

Thr Thr Val Thr Val Ser Ser Ala Ser Val Ala Ala Pro Ser Val Phe
                            115                 120                 125

Ile Phe Pro Pro Ser Asp Glu Gln Leu Lys Ser Gly Thr Ala Ser Val
                    130                 135                 140

Val Cys Leu Leu Asn Asn Phe Tyr Pro Arg Glu Ala Lys Val Gln Trp
        145                 150                 155                 160

Lys Val Asp Asn Ala Leu Gln Ser Gly Asn Ser Gln Glu Ser Val Thr
                            165                 170                 175

Glu Gln Asp Ser Lys Asp Ser Thr Tyr Ser Leu Ser Ser Thr Leu Thr
                            180                 185                 190

Leu Ser Lys Ala Asp Tyr Glu Lys His Lys Val Tyr Ala Cys Glu Val
                            195                 200                 205

Thr His Gln Gly Leu Ser Ser Pro Val Thr Lys Ser Phe Asn Arg Gly
```

```
                    210                 215                 220

Glu Cys
225

<210> SEQ ID NO 62
<211> LENGTH: 219
<212> TYPE: PRT
<213> ORGANISM: Artificial Sequence
<220> FEATURE:
<223> OTHER INFORMATION: VL1a (CD40) light chain (charged)

<400> SEQUENCE: 62

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Thr His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 63
<211> LENGTH: 679
<212> TYPE: PRT
<213> ORGANISM: Artificial Sequence
<220> FEATURE:
<223> OTHER INFORMATION: VH1a (CD40) (VHCH1 charged) Fc
      knob_PGLALA_(P1AE1689) (VL-CH1)

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Ser Leu Glu Trp Met
        35                  40                  45

Gly Arg Val Ile Pro Asn Ala Gly Gly Thr Ser Tyr Asn Gln Lys Phe
    50                  55                  60
```

```
Lys Gly Arg Val Thr Leu Thr Val Asp Lys Ser Ile Ser Thr Ala Tyr
 65                  70                  75                  80

Met Glu Leu Ser Arg Leu Arg Ser Asp Asp Thr Ala Val Tyr Tyr Cys
             85                  90                  95

Ala Arg Glu Gly Ile Tyr Trp Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Glu
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Glu Lys Val Glu Pro Lys Ser Cys Asp Lys Thr His Thr Cys Pro
210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Gly Ala Pro Ile Glu Lys Thr Ile Ser Lys Ala
                325                 330                 335

Lys Gly Gln Pro Arg Glu Pro Gln Val Tyr Thr Leu Pro Pro Cys Arg
            340                 345                 350

Asp Glu Leu Thr Lys Asn Gln Val Ser Leu Trp Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Gly Gly Gly Gly Ser
        435                 440                 445

Gly Gly Gly Gly Ser Gly Gly Gly Ser Gly Gly Gly Gly Ser Glu
    450                 455                 460

Ile Val Leu Thr Gln Ser Pro Ala Thr Leu Ser Leu Ser Pro Gly Glu
465                 470                 475                 480
```

Arg Ala Thr Leu Ser Cys Arg Ala Ser Glu Ser Val Asp Asn Tyr Gly
            485             490             495

Leu Ser Phe Ile Asn Trp Phe Gln Gln Lys Pro Gly Gln Ala Pro Arg
        500             505             510

Leu Leu Ile Tyr Gly Thr Ser Asn Arg Gly Ser Gly Ile Pro Ala Arg
        515             520             525

Phe Ser Gly Ser Gly Ser Gly Thr Asp Phe Thr Leu Thr Ile Ser Ser
        530             535             540

Leu Glu Pro Glu Asp Phe Ala Val Tyr Phe Cys Gln Gln Ser Asn Glu
545             550             555             560

Val Pro Tyr Thr Phe Gly Gly Gly Thr Lys Val Glu Ile Lys Ser Ser
            565             570             575

Ala Ser Thr Lys Gly Pro Ser Val Phe Pro Leu Ala Pro Ser Ser Lys
            580             585             590

Ser Thr Ser Gly Gly Thr Ala Ala Leu Gly Cys Leu Val Lys Asp Tyr
            595             600             605

Phe Pro Glu Pro Val Thr Val Ser Trp Asn Ser Gly Ala Leu Thr Ser
        610             615             620

Gly Val His Thr Phe Pro Ala Val Leu Gln Ser Ser Gly Leu Tyr Ser
625             630             635             640

Leu Ser Ser Val Val Thr Val Pro Ser Ser Ser Leu Gly Thr Gln Thr
            645             650             655

Tyr Ile Cys Asn Val Asn His Lys Pro Ser Asn Thr Lys Val Asp Lys
            660             665             670

Lys Val Glu Pro Lys Ser Cys
            675

<210> SEQ ID NO 64
<211> LENGTH: 443
<212> TYPE: PRT
<213> ORGANISM: Artificial Sequence
<220> FEATURE:
<223> OTHER INFORMATION: VH1a (CD40) (VHCH1 charged) Fc hole_PGLALA

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Ser Leu Glu Trp Met
        35                  40                  45

Gly Arg Val Ile Pro Asn Ala Gly Gly Thr Ser Tyr Asn Gln Lys Phe
    50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Glu
        130                 135                 140

Asp Tyr Phe Pro Glu Pro Val Thr Val Ser Trp Asn Ser Gly Ala Leu
145                 150                 155                 160

```
Thr Ser Gly Val His Thr Phe Pro Ala Val Leu Gln Ser Ser Gly Leu
            165                 170                 175
Tyr Ser Leu Ser Ser Val Val Thr Val Pro Ser Ser Ser Leu Gly Thr
            180                 185                 190
Gln Thr Tyr Ile Cys Asn Val Asn His Lys Pro Ser Asn Thr Lys Val
            195                 200                 205
Asp Glu Lys Val Glu Pro Lys Ser Cys Asp Lys Thr His Thr Cys Pro
            210                 215                 220
Pro Cys Pro Ala Pro Glu Ala Ala Gly Gly Pro Ser Val Phe Leu Phe
225                 230                 235                 240
Pro Pro Lys Pro Lys Asp Thr Leu Met Ile Ser Arg Thr Pro Glu Val
            245                 250                 255
Thr Cys Val Val Val Asp Val Ser His Glu Asp Pro Glu Val Lys Phe
            260                 265                 270
Asn Trp Tyr Val Asp Gly Val Glu Val His Asn Ala Lys Thr Lys Pro
            275                 280                 285
Arg Glu Glu Gln Tyr Asn Ser Thr Tyr Arg Val Val Ser Val Leu Thr
            290                 295                 300
Val Leu His Gln Asp Trp Leu Asn Gly Lys Glu Tyr Lys Cys Lys Val
305                 310                 315                 320
Ser Asn Lys Ala Leu Gly Ala Pro Ile Glu Lys Thr Ile Ser Lys Ala
            325                 330                 335
Lys Gly Gln Pro Arg Glu Pro Gln Val Cys Thr Leu Pro Pro Ser Arg
            340                 345                 350
Asp Glu Leu Thr Lys Asn Gln Val Ser Leu Ser Cys Ala Val Lys Gly
            355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Val Ser Lys Leu Thr Val Asp Lys Ser Arg Trp Gln Gln
            405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly
            435                 440

<210> SEQ ID NO 65
<211> LENGTH: 216
<212> TYPE: PRT
<213> ORGANISM: Artificial Sequence
<220> FEATURE:
<223> OTHER INFORMATION: (P1AE1689) light chain cross VL-CH1

<400> SEQUENCE: 65

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Glu Ser Val Asp Asn Tyr
            20                  25                  30
Gly Leu Ser Phe Ile Asn Trp Phe Gln Gln Lys Pro Gly Gln Ala Pro
            35                  40                  45
Arg Leu Leu Ile Tyr Gly Thr Ser Asn Arg Gly Ser Gly Ile Pro Ala
            50                  55                  60
Arg Phe Ser Gly Ser Gly Ser Gly Thr Asp Phe Thr Leu Thr Ile Ser
65                  70                  75                  80
```

Ser Leu Glu Pro Glu Asp Phe Ala Val Tyr Phe Cys Gln Gln Ser Asn
            85                  90                  95

Glu Val Pro Tyr Thr Phe Gly Gly Thr Lys Val Glu Ile Lys Ser
        100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Lys Val Glu Pro Lys Ser Cys
210                 215

<210> SEQ ID NO 66
<211> LENGTH: 219
<212> TYPE: PRT
<213> ORGANISM: Artificial Sequence
<220> FEATURE:
<223> OTHER INFORMATION: VL1a (CD40) light chain

<400> SEQUENCE: 66

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Thr His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215

-continued

<210> SEQ ID NO 67
<211> LENGTH: 689
<212> TYPE: PRT
<213> ORGANISM: Artificial Sequence
<220> FEATURE:
<223> OTHER INFORMATION: VH1a (CD40) (VHCH1) Fc knob_PGLALA_(P1AE1689) (VH-Ckappa)

<400> SEQUENCE: 67

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Ser Leu Glu Trp Met
        35                  40                  45

Gly Arg Val Ile Pro Asn Ala Gly Gly Thr Ser Tyr Asn Gln Lys Phe
    50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Gly Ala Pro Ile Glu Lys Thr Ile Ser Lys Ala
                325                 330                 335

Lys Gly Gln Pro Arg Glu Pro Gln Val Tyr Thr Leu Pro Pro Cys Arg
            340                 345                 350

Asp Glu Leu Thr Lys Asn Gln Val Ser Leu Trp Cys Leu Val Lys Gly
        355                 360                 365
```

```
Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Gly Gly Gly Gly Ser
            435                 440                 445

Gly Gly Gly Gly Ser Gly Gly Gly Ser Gly Gly Gly Gly Ser Gln
450                 455                 460

Val Gln Leu Val Gln Ser Gly Ala Glu Val Lys Lys Pro Gly Ala Ser
465                 470                 475                 480

Val Lys Val Ser Cys Lys Ala Ser Gly Tyr Thr Leu Thr Asp Tyr Asn
                485                 490                 495

Met Asp Trp Val Arg Gln Ala Pro Gly Gln Gly Leu Glu Trp Ile Gly
            500                 505                 510

Asp Ile Tyr Pro Asn Thr Gly Gly Thr Ile Tyr Asn Gln Lys Phe Lys
            515                 520                 525

Gly Arg Val Thr Met Thr Ile Asp Thr Ser Thr Ser Thr Val Tyr Met
530                 535                 540

Glu Leu Ser Ser Leu Arg Ser Glu Asp Thr Ala Val Tyr Tyr Cys Thr
545                 550                 555                 560

Arg Phe Arg Gly Ile His Tyr Ala Met Asp Tyr Trp Gly Gln Gly Thr
                565                 570                 575

Thr Val Thr Val Ser Ser Ala Ser Val Ala Ala Pro Ser Val Phe Ile
            580                 585                 590

Phe Pro Pro Ser Asp Glu Gln Leu Lys Ser Gly Thr Ala Ser Val Val
            595                 600                 605

Cys Leu Leu Asn Asn Phe Tyr Pro Arg Glu Ala Lys Val Gln Trp Lys
            610                 615                 620

Val Asp Asn Ala Leu Gln Ser Gly Asn Ser Gln Glu Ser Val Thr Glu
625                 630                 635                 640

Gln Asp Ser Lys Asp Ser Thr Tyr Ser Leu Ser Ser Thr Leu Thr Leu
                645                 650                 655

Ser Lys Ala Asp Tyr Glu Lys His Lys Val Tyr Ala Cys Glu Val Thr
            660                 665                 670

His Gln Gly Leu Ser Ser Pro Val Thr Lys Ser Phe Asn Arg Gly Glu
            675                 680                 685

Cys

<210> SEQ ID NO 68
<211> LENGTH: 443
<212> TYPE: PRT
<213> ORGANISM: Artificial Sequence
<220> FEATURE:
<223> OTHER INFORMATION: VH1a (CD40) (VHCH1) Fc hole_PGLALA

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30
```

```
Tyr Ile His Trp Val Arg Gln Ala Pro Gly Gln Ser Leu Glu Trp Met
         35                  40                  45
Gly Arg Val Ile Pro Asn Ala Gly Gly Thr Ser Tyr Asn Gln Lys Phe
 50                  55                  60
Lys Gly Arg Val Thr Leu Thr Val Asp Lys Ser Ile Ser Thr Ala Tyr
 65                  70                  75                  80
Met Glu Leu Ser Arg Leu Arg Ser Asp Asp Thr Ala Val Tyr Tyr Cys
             85                  90                  95
Ala Arg Glu Gly Ile Tyr Trp Trp Gly Gln Gly Thr Thr Val Thr Val
                100                 105                 110
Ser Ser Ala Ser Thr Lys Gly Pro Ser Val Phe Pro Leu Ala Pro Ser
        115                 120                 125
Ser Lys Ser Thr Ser Gly Gly Thr Ala Ala Leu Gly Cys Leu Val Lys
    130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
            180                 185                 190
Gln Thr Tyr Ile Cys Asn Val Asn His Lys Pro Ser Asn Thr Lys Val
        195                 200                 205
Asp Lys Lys Val Glu Pro Lys Ser Cys Asp Lys Thr His Thr Cys Pro
    210                 215                 220
Pro Cys Pro Ala Pro Glu Ala Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
            260                 265                 270
Asn Trp Tyr Val Asp Gly Val Glu Val His Asn Ala Lys Thr Lys Pro
        275                 280                 285
Arg Glu Glu Gln Tyr Asn Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Ala Leu Gly Ala Pro Ile Glu Lys Thr Ile Ser Lys Ala
                325                 330                 335
Lys Gly Gln Pro Arg Glu Pro Gln Val Cys Thr Leu Pro Pro Ser Arg
            340                 345                 350
Asp Glu Leu Thr Lys Asn Gln Val Ser Leu Ser Cys Ala Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Val Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly
        435                 440
```

```
<210> SEQ ID NO 69
<211> LENGTH: 907
<212> TYPE: PRT
<213> ORGANISM: Artificial Sequence
<220> FEATURE:
<223> OTHER INFORMATION: VH1a (CD40) (VHCH1 charged_VH1a (CD40) (VHCH1
      charged)-Fc knob_PGLALA_(P1AE1689) (VL-CH1)

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Ser Leu Glu Trp Met
        35                  40                  45

Gly Arg Val Ile Pro Asn Ala Gly Gly Thr Ser Tyr Asn Gln Lys Phe
    50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Glu
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Glu Lys Val Glu Pro Lys Ser Cys Asp Gly Gly Gly Gly Ser Gly
    210                 215                 220

Gly Gly Ser Gln Val Gln Leu Val Gln Ser Gly Ala Glu Val Lys Lys
225                 230                 235                 240

Lys Pro Gly Ala Ser Val Lys Val Ser Cys Lys Ala Ser Gly Tyr Ser
                245                 250                 255

Phe Thr Gly Tyr Tyr Ile His Trp Val Arg Gln Ala Pro Gly Gln Ser
            260                 265                 270

Leu Glu Trp Met Gly Arg Val Ile Pro Asn Ala Gly Gly Thr Ser Tyr
        275                 280                 285

Asn Gln Lys Phe Lys Gly Arg Val Thr Leu Thr Val Asp Lys Ser Ile
    290                 295                 300

Ser Thr Ala Tyr Met Glu Leu Ser Arg Leu Arg Ser Asp Asp Thr Ala
305                 310                 315                 320

Val Tyr Tyr Cys Ala Arg Glu Gly Ile Tyr Trp Trp Gly Gln Gly Thr
                325                 330                 335

Thr Val Thr Val Ser Ser Ala Ser Thr Lys Gly Pro Ser Val Phe Pro
            340                 345                 350

Leu Ala Pro Ser Ser Lys Ser Thr Ser Gly Gly Thr Ala Ala Leu Gly
        355                 360                 365
```

```
Cys Leu Val Glu Asp Tyr Phe Pro Glu Pro Val Thr Val Ser Trp Asn
370                 375                 380

Ser Gly Ala Leu Thr Ser Gly Val His Thr Phe Pro Ala Val Leu Gln
385                 390                 395                 400

Ser Ser Gly Leu Tyr Ser Leu Ser Ser Val Val Thr Val Pro Ser Ser
                405                 410                 415

Ser Leu Gly Thr Gln Thr Tyr Ile Cys Asn Val Asn His Lys Pro Ser
            420                 425                 430

Asn Thr Lys Val Asp Glu Lys Val Glu Pro Lys Ser Cys Asp Lys Thr
        435                 440                 445

His Thr Cys Pro Pro Cys Pro Ala Pro Glu Ala Ala Gly Gly Pro Ser
450                 455                 460

Val Phe Leu Phe Pro Pro Lys Pro Lys Asp Thr Leu Met Ile Ser Arg
465                 470                 475                 480

Thr Pro Glu Val Thr Cys Val Val Val Asp Val Ser His Glu Asp Pro
                485                 490                 495

Glu Val Lys Phe Asn Trp Tyr Val Asp Gly Val Glu Val His Asn Ala
            500                 505                 510

Lys Thr Lys Pro Arg Glu Glu Gln Tyr Asn Ser Thr Tyr Arg Val Val
        515                 520                 525

Ser Val Leu Thr Val Leu His Gln Asp Trp Leu Asn Gly Lys Glu Tyr
530                 535                 540

Lys Cys Lys Val Ser Asn Lys Ala Leu Gly Ala Pro Ile Glu Lys Thr
545                 550                 555                 560

Ile Ser Lys Ala Lys Gly Gln Pro Arg Glu Pro Gln Val Tyr Thr Leu
                565                 570                 575

Pro Pro Cys Arg Asp Glu Leu Thr Lys Asn Gln Val Ser Leu Trp Cys
            580                 585                 590

Leu Val Lys Gly Phe Tyr Pro Ser Asp Ile Ala Val Glu Trp Glu Ser
        595                 600                 605

Asn Gly Gln Pro Glu Asn Asn Tyr Lys Thr Thr Pro Pro Val Leu Asp
610                 615                 620

Ser Asp Gly Ser Phe Phe Leu Tyr Ser Lys Leu Thr Val Asp Lys Ser
625                 630                 635                 640

Arg Trp Gln Gln Gly Asn Val Phe Ser Cys Ser Val Met His Glu Ala
                645                 650                 655

Leu His Asn His Tyr Thr Gln Lys Ser Leu Ser Leu Ser Pro Gly Gly
            660                 665                 670

Gly Gly Gly Ser Gly Gly Gly Ser Gly Gly Gly Gly Ser Gly Gly
        675                 680                 685

Gly Gly Ser Glu Ile Val Leu Thr Gln Ser Pro Ala Thr Leu Ser Leu
690                 695                 700

Ser Pro Gly Glu Arg Ala Thr Leu Ser Cys Arg Ala Ser Glu Ser Val
705                 710                 715                 720

Asp Asn Tyr Gly Leu Ser Phe Ile Asn Trp Phe Gln Gln Lys Pro Gly
                725                 730                 735

Gln Ala Pro Arg Leu Leu Ile Tyr Gly Thr Ser Asn Arg Gly Ser Gly
            740                 745                 750

Ile Pro Ala Arg Phe Ser Gly Ser Gly Ser Gly Thr Asp Phe Thr Leu
        755                 760                 765

Thr Ile Ser Ser Leu Glu Pro Glu Asp Phe Ala Val Tyr Phe Cys Gln
770                 775                 780

Gln Ser Asn Glu Val Pro Tyr Thr Phe Gly Gly Gly Thr Lys Val Glu
```

```
                785                 790                 795                 800
    Ile Lys Ser Ser Ala Ser Thr Lys Gly Pro Ser Val Phe Pro Leu Ala
                    805                 810                 815

Pro Ser Ser Lys Ser Thr Ser Gly Gly Thr Ala Ala Leu Gly Cys Leu
                    820                 825                 830

Val Lys Asp Tyr Phe Pro Glu Pro Val Thr Val Ser Trp Asn Ser Gly
                    835                 840                 845

Ala Leu Thr Ser Gly Val His Thr Phe Pro Ala Val Leu Gln Ser Ser
        850                 855                 860

Gly Leu Tyr Ser Leu Ser Ser Val Val Thr Val Pro Ser Ser Ser Leu
    865                 870                 875                 880

Gly Thr Gln Thr Tyr Ile Cys Asn Val Asn His Lys Pro Ser Asn Thr
                    885                 890                 895

Lys Val Asp Lys Lys Val Glu Pro Lys Ser Cys
                    900                 905

<210> SEQ ID NO 70
<211> LENGTH: 671
<212> TYPE: PRT
<213> ORGANISM: Artificial Sequence
<220> FEATURE:
<223> OTHER INFORMATION: VH1a (CD40) (VHCH1 charged)_VH1a (CD40) (VHCH1
      charged)-Fc hole_PGLALA

<400> SEQUENCE: 70

Gln Val Gln Leu Val Gln Ser Gly Ala Glu Val Lys Lys Pro Gly Ala
    1               5                   10                  15

Ser Val Lys Val Ser Cys Lys Ala Ser Gly Tyr Ser Phe Thr Gly Tyr
                    20                  25                  30

Tyr Ile His Trp Val Arg Gln Ala Pro Gly Gln Ser Leu Glu Trp Met
                    35                  40                  45

Gly Arg Val Ile Pro Asn Ala Gly Gly Thr Ser Tyr Asn Gln Lys Phe
        50                  55                  60

Lys Gly Arg Val Thr Leu Thr Val Asp Lys Ser Ile Ser Thr Ala Tyr
    65                  70                  75                  80

Met Glu Leu Ser Arg Leu Arg Ser Asp Asp Thr Ala Val Tyr Tyr Cys
                    85                  90                  95

Ala Arg Glu Gly Ile Tyr Trp Trp Gly Gln Gly Thr Thr Val Thr Val
                    100                 105                 110

Ser Ser Ala Ser Thr Lys Gly Pro Ser Val Phe Pro Leu Ala Pro Ser
                    115                 120                 125

Ser Lys Ser Thr Ser Gly Gly Thr Ala Ala Leu Gly Cys Leu Val Glu
                    130                 135                 140

Asp Tyr Phe Pro Glu Pro Val Thr Val Ser Trp Asn Ser Gly Ala Leu
    145                 150                 155                 160

Thr Ser Gly Val His Thr Phe Pro Ala Val Leu Gln Ser Ser Gly Leu
                    165                 170                 175

Tyr Ser Leu Ser Ser Val Val Thr Val Pro Ser Ser Ser Leu Gly Thr
                    180                 185                 190

Gln Thr Tyr Ile Cys Asn Val Asn His Lys Pro Ser Asn Thr Lys Val
                    195                 200                 205

Asp Glu Lys Val Glu Pro Lys Ser Cys Asp Gly Gly Gly Ser Gly
                    210                 215                 220

Gly Gly Gly Ser Gln Val Gln Leu Val Gln Ser Gly Ala Glu Val Lys
    225                 230                 235                 240
```

```
Lys Pro Gly Ala Ser Val Lys Val Ser Cys Lys Ala Ser Gly Tyr Ser
                245                 250                 255

Phe Thr Gly Tyr Tyr Ile His Trp Val Arg Gln Ala Pro Gly Gln Ser
            260                 265                 270

Leu Glu Trp Met Gly Arg Val Ile Pro Asn Ala Gly Gly Thr Ser Tyr
        275                 280                 285

Asn Gln Lys Phe Lys Gly Arg Val Thr Leu Thr Val Asp Lys Ser Ile
    290                 295                 300

Ser Thr Ala Tyr Met Glu Leu Ser Arg Leu Arg Ser Asp Asp Thr Ala
305                 310                 315                 320

Val Tyr Tyr Cys Ala Arg Glu Gly Ile Tyr Trp Trp Gly Gln Gly Thr
                325                 330                 335

Thr Val Thr Val Ser Ser Ala Ser Thr Lys Gly Pro Ser Val Phe Pro
            340                 345                 350

Leu Ala Pro Ser Ser Lys Ser Thr Ser Gly Gly Thr Ala Ala Leu Gly
        355                 360                 365

Cys Leu Val Glu Asp Tyr Phe Pro Glu Pro Val Thr Val Ser Trp Asn
    370                 375                 380

Ser Gly Ala Leu Thr Ser Gly Val His Thr Phe Pro Ala Val Leu Gln
385                 390                 395                 400

Ser Ser Gly Leu Tyr Ser Leu Ser Ser Val Val Thr Val Pro Ser Ser
                405                 410                 415

Ser Leu Gly Thr Gln Thr Tyr Ile Cys Asn Val Asn His Lys Pro Ser
            420                 425                 430

Asn Thr Lys Val Asp Glu Lys Val Glu Pro Lys Ser Cys Asp Lys Thr
        435                 440                 445

His Thr Cys Pro Pro Cys Pro Ala Pro Glu Ala Ala Gly Gly Pro Ser
    450                 455                 460

Val Phe Leu Phe Pro Pro Lys Pro Lys Asp Thr Leu Met Ile Ser Arg
465                 470                 475                 480

Thr Pro Glu Val Thr Cys Val Val Val Asp Val Ser His Glu Asp Pro
                485                 490                 495

Glu Val Lys Phe Asn Trp Tyr Val Asp Gly Val Glu Val His Asn Ala
            500                 505                 510

Lys Thr Lys Pro Arg Glu Glu Gln Tyr Asn Ser Thr Tyr Arg Val Val
        515                 520                 525

Ser Val Leu Thr Val Leu His Gln Asp Trp Leu Asn Gly Lys Glu Tyr
    530                 535                 540

Lys Cys Lys Val Ser Asn Lys Ala Leu Gly Ala Pro Ile Glu Lys Thr
545                 550                 555                 560

Ile Ser Lys Ala Lys Gly Gln Pro Arg Glu Pro Gln Val Cys Thr Leu
                565                 570                 575

Pro Pro Ser Arg Asp Glu Leu Thr Lys Asn Gln Val Ser Leu Ser Cys
            580                 585                 590

Ala Val Lys Gly Phe Tyr Pro Ser Asp Ile Ala Val Glu Trp Glu Ser
        595                 600                 605

Asn Gly Gln Pro Glu Asn Asn Tyr Lys Thr Thr Pro Pro Val Leu Asp
    610                 615                 620

Ser Asp Gly Ser Phe Phe Leu Val Ser Lys Leu Thr Val Asp Lys Ser
625                 630                 635                 640

Arg Trp Gln Gln Gly Asn Val Phe Ser Cys Ser Val Met His Glu Ala
                645                 650                 655

Leu His Asn His Tyr Thr Gln Lys Ser Leu Ser Leu Ser Pro Gly
```

<210> SEQ ID NO 71
<211> LENGTH: 213
<212> TYPE: PRT
<213> ORGANISM: Artificial Sequence
<220> FEATURE:
<223> OTHER INFORMATION: 4B9 light chain cross VL-CH1

<400> SEQUENCE: 71

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 72
<211> LENGTH: 687
<212> TYPE: PRT
<213> ORGANISM: Artificial Sequence
<220> FEATURE:
<223> OTHER INFORMATION: VH1a (CD40) (VHCH1) Fc knob_PGLALA_4B9
      (VH-Ckappa)

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Ser Leu Glu Trp Met
        35                  40                  45

Gly Arg Val Ile Pro Asn Ala Gly Gly Thr Ser Tyr Asn Gln Lys Phe
    50                  55                  60

Lys Gly Arg Val Thr Leu Thr Val Asp Lys Ser Ile Ser Thr Ala Tyr
65                  70                  75                  80

-continued

```
Met Glu Leu Ser Arg Leu Arg Ser Asp Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Gly Ala Pro Ile Glu Lys Thr Ile Ser Lys Ala
                325                 330                 335

Lys Gly Gln Pro Arg Glu Pro Gln Val Tyr Thr Leu Pro Pro Cys Arg
            340                 345                 350

Asp Glu Leu Thr Lys Asn Gln Val Ser Leu Trp Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Gly Gly Gly Gly Ser
            435                 440                 445

Gly Gly Gly Gly Ser Gly Gly Gly Ser Gly Gly Gly Gly Ser Glu
450                 455                 460

Val Gln Leu Leu Glu Ser Gly Gly Leu Val Gln Pro Gly Gly Ser
465                 470                 475                 480

Leu Arg Leu Ser Cys Ala Ala Ser Gly Phe Thr Phe Ser Ser Tyr Ala
                485                 490                 495
```

```
Met Ser Trp Val Arg Gln Ala Pro Gly Lys Gly Leu Glu Trp Val Ser
            500                 505                 510

Ala Ile Ile Gly Ser Gly Ala Ser Thr Tyr Tyr Ala Asp Ser Val Lys
            515                 520                 525

Gly Arg Phe Thr Ile Ser Arg Asp Asn Ser Lys Asn Thr Leu Tyr Leu
        530                 535                 540

Gln Met Asn Ser Leu Arg Ala Glu Asp Thr Ala Val Tyr Tyr Cys Ala
545                 550                 555                 560

Lys Gly Trp Phe Gly Gly Phe Asn Tyr Trp Gly Gln Gly Thr Leu Val
                565                 570                 575

Thr Val Ser Ser Ala Ser Val Ala Ala Pro Ser Val Phe Ile Phe Pro
            580                 585                 590

Pro Ser Asp Glu Gln Leu Lys Ser Gly Thr Ala Ser Val Val Cys Leu
            595                 600                 605

Leu Asn Asn Phe Tyr Pro Arg Glu Ala Lys Val Gln Trp Lys Val Asp
        610                 615                 620

Asn Ala Leu Gln Ser Gly Asn Ser Gln Glu Ser Val Thr Glu Gln Asp
625                 630                 635                 640

Ser Lys Asp Ser Thr Tyr Ser Leu Ser Ser Thr Leu Thr Leu Ser Lys
                645                 650                 655

Ala Asp Tyr Glu Lys His Lys Val Tyr Ala Cys Glu Val Thr His Gln
            660                 665                 670

Gly Leu Ser Ser Pro Val Thr Lys Ser Phe Asn Arg Gly Glu Cys
            675                 680                 685

<210> SEQ ID NO 73
<211> LENGTH: 915
<212> TYPE: PRT
<213> ORGANISM: Artificial Sequence
<220> FEATURE:
<223> OTHER INFORMATION: VH1a (CD40) (VHCH1) _VH1a (CD40) (VHCH1)-Fc
      knob_PGLALA_(4B9) (VH-Ckappa)

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Ser Leu Glu Trp Met
        35                  40                  45

Gly Arg Val Ile Pro Asn Ala Gly Gly Thr Ser Tyr Asn Gln Lys Phe
    50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175
```

-continued

```
Tyr Ser Leu Ser Ser Val Val Thr Val Pro Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Gly Gly Gly Ser Gly
210                 215                 220

Gly Gly Gly Ser Gln Val Gln Leu Val Gln Ser Gly Ala Glu Val Lys
225                 230                 235                 240

Lys Pro Gly Ala Ser Val Lys Val Ser Cys Lys Ala Ser Gly Tyr Ser
                245                 250                 255

Phe Thr Gly Tyr Tyr Ile His Trp Val Arg Gln Ala Pro Gly Gln Ser
            260                 265                 270

Leu Glu Trp Met Gly Arg Val Ile Pro Asn Ala Gly Gly Thr Ser Tyr
            275                 280                 285

Asn Gln Lys Phe Lys Gly Arg Val Thr Leu Thr Val Asp Lys Ser Ile
            290                 295                 300

Ser Thr Ala Tyr Met Glu Leu Ser Arg Leu Arg Ser Asp Asp Thr Ala
305                 310                 315                 320

Val Tyr Tyr Cys Ala Arg Glu Gly Ile Tyr Trp Trp Gly Gln Gly Thr
                325                 330                 335

Thr Val Thr Val Ser Ser Ala Ser Thr Lys Gly Pro Ser Val Phe Pro
            340                 345                 350

Leu Ala Pro Ser Ser Lys Ser Thr Ser Gly Gly Thr Ala Ala Leu Gly
            355                 360                 365

Cys Leu Val Lys Asp Tyr Phe Pro Glu Pro Val Thr Val Ser Trp Asn
            370                 375                 380

Ser Gly Ala Leu Thr Ser Gly Val His Thr Phe Pro Ala Val Leu Gln
385                 390                 395                 400

Ser Ser Gly Leu Tyr Ser Leu Ser Ser Val Val Thr Val Pro Ser Ser
                405                 410                 415

Ser Leu Gly Thr Gln Thr Tyr Ile Cys Asn Val Asn His Lys Pro Ser
            420                 425                 430

Asn Thr Lys Val Asp Lys Lys Val Glu Pro Lys Ser Cys Asp Lys Thr
            435                 440                 445

His Thr Cys Pro Pro Cys Pro Ala Pro Glu Ala Ala Gly Gly Pro Ser
            450                 455                 460

Val Phe Leu Phe Pro Pro Lys Pro Lys Asp Thr Leu Met Ile Ser Arg
465                 470                 475                 480

Thr Pro Glu Val Thr Cys Val Val Val Asp Val Ser His Glu Asp Pro
                485                 490                 495

Glu Val Lys Phe Asn Trp Tyr Val Asp Gly Val Glu Val His Asn Ala
            500                 505                 510

Lys Thr Lys Pro Arg Glu Glu Gln Tyr Asn Ser Thr Tyr Arg Val Val
            515                 520                 525

Ser Val Leu Thr Val Leu His Gln Asp Trp Leu Asn Gly Lys Glu Tyr
            530                 535                 540

Lys Cys Lys Val Ser Asn Lys Ala Leu Gly Ala Pro Ile Glu Lys Thr
545                 550                 555                 560

Ile Ser Lys Ala Lys Gly Gln Pro Arg Glu Pro Gln Val Tyr Thr Leu
                565                 570                 575

Pro Pro Cys Arg Asp Glu Leu Thr Lys Asn Gln Val Ser Leu Trp Cys
            580                 585                 590
```

```
Leu Val Lys Gly Phe Tyr Pro Ser Asp Ile Ala Val Glu Trp Glu Ser
            595                 600                 605

Asn Gly Gln Pro Glu Asn Asn Tyr Lys Thr Thr Pro Pro Val Leu Asp
610                 615                 620

Ser Asp Gly Ser Phe Phe Leu Tyr Ser Lys Leu Thr Val Asp Lys Ser
625                 630                 635                 640

Arg Trp Gln Gln Gly Asn Val Phe Ser Cys Ser Val Met His Glu Ala
                645                 650                 655

Leu His Asn His Tyr Thr Gln Lys Ser Leu Ser Leu Ser Pro Gly Gly
            660                 665                 670

Gly Gly Gly Ser Gly Gly Gly Ser Gly Gly Gly Gly Ser Gly Gly
            675                 680                 685

Gly Gly Ser Glu Val Gln Leu Leu Glu Ser Gly Gly Gly Leu Val Gln
690                 695                 700

Pro Gly Gly Ser Leu Arg Leu Ser Cys Ala Ala Ser Gly Phe Thr Phe
705                 710                 715                 720

Ser Ser Tyr Ala Met Ser Trp Val Arg Gln Ala Pro Gly Lys Gly Leu
            725                 730                 735

Glu Trp Val Ser Ala Ile Ile Gly Ser Gly Ala Ser Thr Tyr Tyr Ala
            740                 745                 750

Asp Ser Val Lys Gly Arg Phe Thr Ile Ser Arg Asp Asn Ser Lys Asn
            755                 760                 765

Thr Leu Tyr Leu Gln Met Asn Ser Leu Arg Ala Glu Asp Thr Ala Val
            770                 775                 780

Tyr Tyr Cys Ala Lys Gly Trp Phe Gly Gly Phe Asn Tyr Trp Gly Gln
785                 790                 795                 800

Gly Thr Leu Val Thr Val Ser Ser Ala Ser Val Ala Ala Pro Ser Val
            805                 810                 815

Phe Ile Phe Pro Pro Ser Asp Glu Gln Leu Lys Ser Gly Thr Ala Ser
            820                 825                 830

Val Val Cys Leu Leu Asn Asn Phe Tyr Pro Arg Glu Ala Lys Val Gln
            835                 840                 845

Trp Lys Val Asp Asn Ala Leu Gln Ser Gly Asn Ser Gln Glu Ser Val
850                 855                 860

Thr Glu Gln Asp Ser Lys Asp Ser Thr Tyr Ser Leu Ser Ser Thr Leu
865                 870                 875                 880

Thr Leu Ser Lys Ala Asp Tyr Glu Lys His Lys Val Tyr Ala Cys Glu
                885                 890                 895

Val Thr His Gln Gly Leu Ser Ser Pro Val Thr Lys Ser Phe Asn Arg
            900                 905                 910

Gly Glu Cys
        915

<210> SEQ ID NO 74
<211> LENGTH: 671
<212> TYPE: PRT
<213> ORGANISM: Artificial Sequence
<220> FEATURE:
<223> OTHER INFORMATION: VH1a (CD40) (VHCH1)_VH1a (CD40) (VHCH1)-Fc
      hole_PGLALA

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30
```

```
Tyr Ile His Trp Val Arg Gln Ala Pro Gly Gln Ser Leu Glu Trp Met
        35                  40                  45
Gly Arg Val Ile Pro Asn Ala Gly Gly Thr Ser Tyr Asn Gln Lys Phe
50                  55                  60
Lys Gly Arg Val Thr Leu Thr Val Asp Lys Ser Ile Ser Thr Ala Tyr
65                  70                  75                  80
Met Glu Leu Ser Arg Leu Arg Ser Asp Thr Ala Val Tyr Tyr Cys
                85                  90                  95
Ala Arg Glu Gly Ile Tyr Trp Trp Gly Gln Gly Thr Thr Val Thr Val
                100                 105                 110
Ser Ser Ala Ser Thr Lys Gly Pro Ser Val Phe Pro Leu Ala Pro Ser
        115                 120                 125
Ser Lys Ser Thr Ser Gly Gly Thr Ala Ala Leu Gly Cys Leu Val Lys
        130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
                180                 185                 190
Gln Thr Tyr Ile Cys Asn Val Asn His Lys Pro Ser Asn Thr Lys Val
        195                 200                 205
Asp Lys Lys Val Glu Pro Lys Ser Cys Asp Gly Gly Gly Ser Gly
        210                 215                 220
Gly Gly Gly Ser Gln Val Gln Leu Val Gln Ser Gly Ala Glu Val Lys
225                 230                 235                 240
Lys Pro Gly Ala Ser Val Lys Val Ser Cys Lys Ala Ser Gly Tyr Ser
                245                 250                 255
Phe Thr Gly Tyr Tyr Ile His Trp Val Arg Gln Ala Pro Gly Gln Ser
                260                 265                 270
Leu Glu Trp Met Gly Arg Val Ile Pro Asn Ala Gly Gly Thr Ser Tyr
        275                 280                 285
Asn Gln Lys Phe Lys Gly Arg Val Thr Leu Thr Val Asp Lys Ser Ile
        290                 295                 300
Ser Thr Ala Tyr Met Glu Leu Ser Arg Leu Arg Ser Asp Asp Thr Ala
305                 310                 315                 320
Val Tyr Tyr Cys Ala Arg Glu Gly Ile Tyr Trp Trp Gly Gln Gly Thr
                325                 330                 335
Thr Val Thr Val Ser Ser Ala Ser Thr Lys Gly Pro Ser Val Phe Pro
                340                 345                 350
Leu Ala Pro Ser Ser Lys Ser Thr Ser Gly Gly Thr Ala Ala Leu Gly
        355                 360                 365
Cys Leu Val Lys Asp Tyr Phe Pro Glu Pro Val Thr Val Ser Trp Asn
        370                 375                 380
Ser Gly Ala Leu Thr Ser Gly Val His Thr Phe Pro Ala Val Leu Gln
385                 390                 395                 400
Ser Ser Gly Leu Tyr Ser Leu Ser Ser Val Val Thr Val Pro Ser Ser
                405                 410                 415
Ser Leu Gly Thr Gln Thr Tyr Ile Cys Asn Val Asn His Lys Pro Ser
                420                 425                 430
Asn Thr Lys Val Asp Lys Lys Val Glu Pro Lys Ser Cys Asp Lys Thr
        435                 440                 445
```

His Thr Cys Pro Pro Cys Pro Ala Pro Glu Ala Ala Gly Gly Pro Ser
450                 455                 460

Val Phe Leu Phe Pro Pro Lys Pro Lys Asp Thr Leu Met Ile Ser Arg
465                 470                 475                 480

Thr Pro Glu Val Thr Cys Val Val Val Asp Val Ser His Glu Asp Pro
                485                 490                 495

Glu Val Lys Phe Asn Trp Tyr Val Asp Gly Val Glu Val His Asn Ala
            500                 505                 510

Lys Thr Lys Pro Arg Glu Glu Gln Tyr Asn Ser Thr Tyr Arg Val Val
        515                 520                 525

Ser Val Leu Thr Val Leu His Gln Asp Trp Leu Asn Gly Lys Glu Tyr
530                 535                 540

Lys Cys Lys Val Ser Asn Lys Ala Leu Gly Ala Pro Ile Glu Lys Thr
545                 550                 555                 560

Ile Ser Lys Ala Lys Gly Gln Pro Arg Glu Pro Gln Val Cys Thr Leu
                565                 570                 575

Pro Pro Ser Arg Asp Glu Leu Thr Lys Asn Gln Val Ser Leu Ser Cys
            580                 585                 590

Ala Val Lys Gly Phe Tyr Pro Ser Asp Ile Ala Val Glu Trp Glu Ser
        595                 600                 605

Asn Gly Gln Pro Glu Asn Asn Tyr Lys Thr Thr Pro Pro Val Leu Asp
    610                 615                 620

Ser Asp Gly Ser Phe Phe Leu Val Ser Lys Leu Thr Val Asp Lys Ser
625                 630                 635                 640

Arg Trp Gln Gln Gly Asn Val Phe Ser Cys Ser Val Met His Glu Ala
                645                 650                 655

Leu His Asn His Tyr Thr Gln Lys Ser Leu Ser Leu Ser Pro Gly
            660                 665                 670

<210> SEQ ID NO 75
<211> LENGTH: 223
<212> TYPE: PRT
<213> ORGANISM: Artificial Sequence
<220> FEATURE:
<223> OTHER INFORMATION: 28H1 light chain cross VH-Ckappa

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Val Ala Ala Pro Ser Val Phe Ile Phe Pro
        115                 120                 125

Pro Ser Asp Glu Gln Leu Lys Ser Gly Thr Ala Ser Val Val Cys Leu
    130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
    210                 215                 220

<210> SEQ ID NO 76
<211> LENGTH: 676
<212> TYPE: PRT
<213> ORGANISM: Artificial Sequence
<220> FEATURE:
<223> OTHER INFORMATION: VH1a (CD40) (VHCH1 charged) Fc knob_PGLALA_28H1
      (VL-CH1)

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Ile His Trp Val Arg Gln Ala Pro Gly Gln Ser Leu Glu Trp Met
            35                  40                  45

Gly Arg Val Ile Pro Asn Ala Gly Gly Thr Ser Tyr Asn Gln Lys Phe
        50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Glu
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Glu Lys Val Glu Pro Lys Ser Cys Asp Lys Thr His Thr Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Ala Leu Gly Ala Pro Ile Glu Lys Thr Ile Ser Lys Ala
                325                 330                 335
Lys Gly Gln Pro Arg Glu Pro Gln Val Tyr Thr Leu Pro Pro Cys Arg
                340                 345                 350
Asp Glu Leu Thr Lys Asn Gln Val Ser Leu Trp Cys Leu Val Lys Gly
            355                 360                 365
Phe Tyr Pro Ser Asp Ile Ala Val Glu Trp Glu Ser Asn Gly Gln Pro
370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
                420                 425                 430
Tyr Thr Gln Lys Ser Leu Ser Leu Ser Pro Gly Gly Gly Gly Gly Ser
            435                 440                 445
Gly Gly Gly Gly Ser Gly Gly Gly Ser Gly Gly Gly Gly Ser Glu
450                 455                 460
Ile Val Leu Thr Gln Ser Pro Gly Thr Leu Ser Leu Ser Pro Gly Glu
465                 470                 475                 480
Arg Ala Thr Leu Ser Cys Arg Ala Ser Gln Ser Val Ser Arg Ser Tyr
                485                 490                 495
Leu Ala Trp Tyr Gln Gln Lys Pro Gly Gln Ala Pro Arg Leu Leu Ile
                500                 505                 510
Ile Gly Ala Ser Thr Arg Ala Thr Gly Ile Pro Asp Arg Phe Ser Gly
            515                 520                 525
Ser Gly Ser Gly Thr Asp Phe Thr Leu Thr Ile Ser Arg Leu Glu Pro
            530                 535                 540
Glu Asp Phe Ala Val Tyr Tyr Cys Gln Gln Gly Gln Val Ile Pro Pro
545                 550                 555                 560
Thr Phe Gly Gln Gly Thr Lys Val Glu Ile Lys Ser Ser Ala Ser Thr
                565                 570                 575
Lys Gly Pro Ser Val Phe Pro Leu Ala Pro Ser Ser Lys Ser Thr Ser
                580                 585                 590
Gly Gly Thr Ala Ala Leu Gly Cys Leu Val Lys Asp Tyr Phe Pro Glu
            595                 600                 605
Pro Val Thr Val Ser Trp Asn Ser Gly Ala Leu Thr Ser Gly Val His
610                 615                 620
Thr Phe Pro Ala Val Leu Gln Ser Ser Gly Leu Tyr Ser Leu Ser Ser
625                 630                 635                 640
Val Val Thr Val Pro Ser Ser Ser Leu Gly Thr Gln Thr Tyr Ile Cys
                645                 650                 655
Asn Val Asn His Lys Pro Ser Asn Thr Lys Val Asp Lys Lys Val Glu
                660                 665                 670
Pro Lys Ser Cys
            675

<210> SEQ ID NO 77
<211> LENGTH: 904

<212> TYPE: PRT
<213> ORGANISM: Artificial Sequence
<220> FEATURE:
<223> OTHER INFORMATION: VH1a (CD40) (VHCH1 charged) _VH1a (CD40) (VHCH1 charged) Fc knob_PGLALA_28H1 (VL-CH1)

<400> SEQUENCE: 77

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Ser Leu Glu Trp Met
        35                  40                  45

Gly Arg Val Ile Pro Asn Ala Gly Gly Thr Ser Tyr Asn Gln Lys Phe
50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Glu
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Glu Lys Val Glu Pro Lys Ser Cys Asp Gly Gly Gly Ser Gly
210                 215                 220

Gly Gly Gly Ser Gln Val Gln Leu Val Gln Ser Gly Ala Glu Val Lys
225                 230                 235                 240

Lys Pro Gly Ala Ser Val Lys Val Ser Cys Lys Ala Ser Gly Tyr Ser
                245                 250                 255

Phe Thr Gly Tyr Tyr Ile His Trp Val Arg Gln Ala Pro Gly Gln Ser
            260                 265                 270

Leu Glu Trp Met Gly Arg Val Ile Pro Asn Ala Gly Gly Thr Ser Tyr
        275                 280                 285

Asn Gln Lys Phe Lys Gly Arg Val Thr Leu Thr Val Asp Lys Ser Ile
    290                 295                 300

Ser Thr Ala Tyr Met Glu Leu Ser Arg Leu Arg Ser Asp Asp Thr Ala
305                 310                 315                 320

Val Tyr Tyr Cys Ala Arg Glu Gly Ile Tyr Trp Trp Gly Gln Gly Thr
                325                 330                 335

Thr Val Thr Val Ser Ser Ala Ser Thr Lys Gly Pro Ser Val Phe Pro
            340                 345                 350

Leu Ala Pro Ser Ser Lys Ser Thr Ser Gly Gly Thr Ala Ala Leu Gly
        355                 360                 365

Cys Leu Val Glu Asp Tyr Phe Pro Glu Pro Val Thr Val Ser Trp Asn
    370                 375                 380
```

```
Ser Gly Ala Leu Thr Ser Gly Val His Thr Phe Pro Ala Val Leu Gln
385                 390                 395                 400

Ser Ser Gly Leu Tyr Ser Leu Ser Ser Val Val Thr Val Pro Ser Ser
            405                 410                 415

Ser Leu Gly Thr Gln Thr Tyr Ile Cys Asn Val Asn His Lys Pro Ser
        420                 425                 430

Asn Thr Lys Val Asp Glu Lys Val Glu Pro Lys Ser Cys Asp Lys Thr
    435                 440                 445

His Thr Cys Pro Pro Cys Pro Ala Pro Glu Ala Ala Gly Gly Pro Ser
    450                 455                 460

Val Phe Leu Phe Pro Pro Lys Pro Lys Asp Thr Leu Met Ile Ser Arg
465                 470                 475                 480

Thr Pro Glu Val Thr Cys Val Val Val Asp Val Ser His Glu Asp Pro
                485                 490                 495

Glu Val Lys Phe Asn Trp Tyr Val Asp Gly Val Glu Val His Asn Ala
                500                 505                 510

Lys Thr Lys Pro Arg Glu Glu Gln Tyr Asn Ser Thr Tyr Arg Val Val
            515                 520                 525

Ser Val Leu Thr Val Leu His Gln Asp Trp Leu Asn Gly Lys Glu Tyr
        530                 535                 540

Lys Cys Lys Val Ser Asn Lys Ala Leu Gly Ala Pro Ile Glu Lys Thr
545                 550                 555                 560

Ile Ser Lys Ala Lys Gly Gln Pro Arg Glu Pro Gln Val Tyr Thr Leu
                565                 570                 575

Pro Pro Cys Arg Asp Glu Leu Thr Lys Asn Gln Val Ser Leu Trp Cys
                580                 585                 590

Leu Val Lys Gly Phe Tyr Pro Ser Asp Ile Ala Val Glu Trp Glu Ser
            595                 600                 605

Asn Gly Gln Pro Glu Asn Asn Tyr Lys Thr Thr Pro Pro Val Leu Asp
        610                 615                 620

Ser Asp Gly Ser Phe Phe Leu Tyr Ser Lys Leu Thr Val Asp Lys Ser
625                 630                 635                 640

Arg Trp Gln Gln Gly Asn Val Phe Ser Cys Ser Val Met His Glu Ala
                645                 650                 655

Leu His Asn His Tyr Thr Gln Lys Ser Leu Ser Leu Ser Pro Gly Gly
                660                 665                 670

Gly Gly Gly Ser Gly Gly Gly Ser Gly Gly Gly Ser Gly Gly
            675                 680                 685

Gly Gly Ser Glu Ile Val Leu Thr Gln Ser Pro Gly Thr Leu Ser Leu
        690                 695                 700

Ser Pro Gly Glu Arg Ala Thr Leu Ser Cys Arg Ala Ser Gln Ser Val
705                 710                 715                 720

Ser Arg Ser Tyr Leu Ala Trp Tyr Gln Gln Lys Pro Gly Gln Ala Pro
                725                 730                 735

Arg Leu Leu Ile Ile Gly Ala Ser Thr Arg Ala Thr Gly Ile Pro Asp
                740                 745                 750

Arg Phe Ser Gly Ser Gly Ser Gly Thr Asp Phe Thr Leu Thr Ile Ser
            755                 760                 765

Arg Leu Glu Pro Glu Asp Phe Ala Val Tyr Tyr Cys Gln Gln Gly Gln
        770                 775                 780

Val Ile Pro Pro Thr Phe Gly Gln Gly Thr Lys Val Glu Ile Lys Ser
785                 790                 795                 800
```

```
Ser Ala Ser Thr Lys Gly Pro Ser Val Phe Pro Leu Ala Pro Ser Ser
                805                 810                 815

Lys Ser Thr Ser Gly Gly Thr Ala Ala Leu Gly Cys Leu Val Lys Asp
            820                 825                 830

Tyr Phe Pro Glu Pro Val Thr Val Ser Trp Asn Ser Gly Ala Leu Thr
        835                 840                 845

Ser Gly Val His Thr Phe Pro Ala Val Leu Gln Ser Ser Gly Leu Tyr
    850                 855                 860

Ser Leu Ser Ser Val Val Thr Val Pro Ser Ser Ser Leu Gly Thr Gln
865                 870                 875                 880

Thr Tyr Ile Cys Asn Val Asn His Lys Pro Ser Asn Thr Lys Val Asp
                885                 890                 895

Lys Lys Val Glu Pro Lys Ser Cys
            900

<210> SEQ ID NO 78
<211> LENGTH: 748
<212> TYPE: PRT
<213> ORGANISM: Artificial Sequence
<220> FEATURE:
<223> OTHER INFORMATION: hu FAP ectodomain+poly-lys-tag+his6-tag

<400> SEQUENCE: 78

Arg Pro Ser Arg Val His Asn Ser Glu Glu Asn Thr Met Arg Ala Leu
1               5                   10                  15

Thr Leu Lys Asp Ile Leu Asn Gly Thr Phe Ser Tyr Lys Thr Phe Phe
            20                  25                  30

Pro Asn Trp Ile Ser Gly Gln Glu Tyr Leu His Gln Ser Ala Asp Asn
        35                  40                  45

Asn Ile Val Leu Tyr Asn Ile Glu Thr Gly Gln Ser Tyr Thr Ile Leu
    50                  55                  60

Ser Asn Arg Thr Met Lys Ser Val Asn Ala Ser Asn Tyr Gly Leu Ser
65                  70                  75                  80

Pro Asp Arg Gln Phe Val Tyr Leu Glu Ser Asp Tyr Ser Lys Leu Trp
                85                  90                  95

Arg Tyr Ser Tyr Thr Ala Thr Tyr Tyr Ile Tyr Asp Leu Ser Asn Gly
            100                 105                 110

Glu Phe Val Arg Gly Asn Glu Leu Pro Arg Pro Ile Gln Tyr Leu Cys
        115                 120                 125

Trp Ser Pro Val Gly Ser Lys Leu Ala Tyr Val Tyr Gln Asn Asn Ile
    130                 135                 140

Tyr Leu Lys Gln Arg Pro Gly Asp Pro Pro Phe Gln Ile Thr Phe Asn
145                 150                 155                 160

Gly Arg Glu Asn Lys Ile Phe Asn Gly Ile Pro Asp Trp Val Tyr Glu
                165                 170                 175

Glu Glu Met Leu Ala Thr Lys Tyr Ala Leu Trp Trp Ser Pro Asn Gly
            180                 185                 190

Lys Phe Leu Ala Tyr Ala Glu Phe Asn Asp Thr Asp Ile Pro Val Ile
        195                 200                 205

Ala Tyr Ser Tyr Gly Asp Glu Gln Tyr Pro Arg Thr Ile Asn Ile
    210                 215                 220

Pro Tyr Pro Lys Ala Gly Ala Lys Asn Pro Val Val Arg Ile Phe Ile
225                 230                 235                 240

Ile Asp Thr Thr Tyr Pro Ala Tyr Val Gly Pro Gln Glu Val Pro Val
                245                 250                 255
```

```
Pro Ala Met Ile Ala Ser Ser Asp Tyr Tyr Phe Ser Trp Leu Thr Trp
            260                 265                 270

Val Thr Asp Glu Arg Val Cys Leu Gln Trp Leu Lys Arg Val Gln Asn
    275                 280                 285

Val Ser Val Leu Ser Ile Cys Asp Phe Arg Glu Asp Trp Gln Thr Trp
290                 295                 300

Asp Cys Pro Lys Thr Gln Glu His Ile Glu Glu Ser Arg Thr Gly Trp
305                 310                 315                 320

Ala Gly Gly Phe Phe Val Ser Thr Pro Val Phe Ser Tyr Asp Ala Ile
                325                 330                 335

Ser Tyr Tyr Lys Ile Phe Ser Asp Lys Asp Gly Tyr Lys His Ile His
            340                 345                 350

Tyr Ile Lys Asp Thr Val Glu Asn Ala Ile Gln Ile Thr Ser Gly Lys
            355                 360                 365

Trp Glu Ala Ile Asn Ile Phe Arg Val Thr Gln Asp Ser Leu Phe Tyr
    370                 375                 380

Ser Ser Asn Glu Phe Glu Glu Tyr Pro Gly Arg Arg Asn Ile Tyr Arg
385                 390                 395                 400

Ile Ser Ile Gly Ser Tyr Pro Pro Ser Lys Lys Cys Val Thr Cys His
                405                 410                 415

Leu Arg Lys Glu Arg Cys Gln Tyr Tyr Thr Ala Ser Phe Ser Asp Tyr
            420                 425                 430

Ala Lys Tyr Tyr Ala Leu Val Cys Tyr Gly Pro Gly Ile Pro Ile Ser
            435                 440                 445

Thr Leu His Asp Gly Arg Thr Asp Gln Glu Ile Lys Ile Leu Glu Glu
    450                 455                 460

Asn Lys Glu Leu Glu Asn Ala Leu Lys Asn Ile Gln Leu Pro Lys Glu
465                 470                 475                 480

Glu Ile Lys Lys Leu Glu Val Asp Glu Ile Thr Leu Trp Tyr Lys Met
                485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Arg Ser Val Phe Ala
            515                 520                 525

Val Asn Trp Ile Ser Tyr Leu Ala Ser Lys Glu Gly Met Val Ile Ala
530                 535                 540

Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
                565                 570                 575

Ala Val Arg Lys Phe Ile Glu Met Gly Phe Ile Asp Glu Lys Arg Ile
            580                 585                 590

Ala Ile Trp Gly Trp Ser Tyr Gly Gly Tyr Val Ser Ser Leu Ala Leu
            595                 600                 605

Ala Ser Gly Thr Gly Leu Phe Lys Cys Gly Ile Ala Val Ala Pro Val
    610                 615                 620

Ser Ser Trp Glu Tyr Tyr Ala Ser Val Tyr Thr Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
            660                 665                 670

Gly Thr Ala Asp Asp Asn Val His Phe Gln Asn Ser Ala Gln Ile Ala
```

```
                675                 680                 685
Lys Ala Leu Val Asn Ala Gln Val Asp Phe Gln Ala Met Trp Tyr Ser
            690                 695                 700

Asp Gln Asn His Gly Leu Ser Gly Leu Ser Thr Asn His Leu Tyr Thr
705                 710                 715                 720

His Met Thr His Phe Leu Lys Gln Cys Phe Ser Leu Ser Asp Gly Lys
                725                 730                 735

Lys Lys Lys Lys Gly His His His His His
            740                 745

<210> SEQ ID NO 79
<211> LENGTH: 761
<212> TYPE: PRT
<213> ORGANISM: murine

<400> SEQUENCE: 79

Met Lys Thr Trp Leu Lys Thr Val Phe Gly Val Thr Thr Leu Ala Ala
1               5                   10                  15

Leu Ala Leu Val Val Ile Cys Ile Val Leu Arg Pro Ser Arg Val Tyr
            20                  25                  30

Lys Pro Glu Gly Asn Thr Lys Arg Ala Leu Thr Leu Lys Asp Ile Leu
        35                  40                  45

Asn Gly Thr Phe Ser Tyr Lys Thr Tyr Phe Pro Asn Trp Ile Ser Glu
50                  55                  60

Gln Glu Tyr Leu His Gln Ser Glu Asp Asp Asn Ile Val Phe Tyr Asn
65                  70                  75                  80

Ile Glu Thr Arg Glu Ser Tyr Ile Ile Leu Ser Asn Ser Thr Met Lys
                85                  90                  95

Ser Val Asn Ala Thr Asp Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Gln Asn Gly Glu Phe Val Arg Gly Tyr
130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Tyr Thr Gly Arg Glu Asn Arg Ile
            180                 185                 190

Phe Asn Gly Ile Pro Asp Trp Val Tyr Glu Glu Met Leu Ala Thr
        195                 200                 205

Lys Tyr Ala Leu Trp Trp Ser Pro Asp Gly Lys Phe Leu Ala Tyr Val
210                 215                 220

Glu Phe Asn Asp Ser Asp Ile Pro Ile Ile Ala Tyr Ser Tyr Tyr Gly
225                 230                 235                 240

Asp Gly Gln Tyr Pro Arg Thr Ile Asn Ile Pro Tyr Pro Lys Ala Gly
                245                 250                 255

Ala Lys Asn Pro Val Val Arg Val Phe Ile Val Asp Thr Thr Tyr Pro
            260                 265                 270

His His Val Gly Pro Met Glu Val Pro Val Pro Glu Met Ile Ala Ser
        275                 280                 285

Ser Asp Tyr Tyr Phe Ser Trp Leu Thr Trp Val Ser Ser Glu Arg Val
290                 295                 300
```

```
Cys Leu Gln Trp Leu Lys Arg Val Gln Asn Val Ser Val Leu Ser Ile
305                 310                 315                 320

Cys Asp Phe Arg Glu Asp Trp His Ala Trp Glu Cys Pro Lys Asn Gln
            325                 330                 335

Glu His Val Glu Glu Ser Arg Thr Gly Trp Ala Gly Gly Phe Phe Val
            340                 345                 350

Ser Thr Pro Ala Phe Ser Gln Asp Ala Thr Ser Tyr Lys Ile Phe
        355                 360                 365

Ser Asp Lys Asp Gly Tyr Lys His Ile His Tyr Ile Lys Asp Thr Val
370                 375                 380

Glu Asn Ala Ile Gln Ile Thr Ser Gly Lys Trp Glu Ala Ile Tyr Ile
385                 390                 395                 400

Phe Arg Val Thr Gln Asp Ser Leu Phe Tyr Ser Ser Asn Glu Phe Glu
                405                 410                 415

Gly Tyr Pro Gly Arg Arg Asn Ile Tyr Arg Ile Ser Ile Gly Asn Ser
                420                 425                 430

Pro Pro Ser Lys Lys Cys Val Thr Cys His Leu Arg Lys Glu Arg Cys
            435                 440                 445

Gln Tyr Tyr Thr Ala Ser Phe Ser Tyr Lys Ala Lys Tyr Tyr Ala Leu
        450                 455                 460

Val Cys Tyr Gly Pro Gly Leu Pro Ile Ser Thr Leu His Asp Gly Arg
465                 470                 475                 480

Thr Asp Gln Glu Ile Gln Val Leu Glu Glu Asn Lys Glu Leu Glu Asn
                485                 490                 495

Ser Leu Arg Asn Ile Gln Leu Pro Lys Val Glu Ile Lys Lys Leu Lys
            500                 505                 510

Asp Gly Gly Leu Thr Phe Trp Tyr Lys Met Ile Leu Pro Pro Gln Phe
        515                 520                 525

Asp Arg Ser Lys Lys Tyr Pro Leu Leu Ile Gln Val Tyr Gly Gly Pro
530                 535                 540

Cys Ser Gln Ser Val Lys Ser Val Phe Ala Val Asn Trp Ile Thr Tyr
545                 550                 555                 560

Leu Ala Ser Lys Glu Gly Ile Val Ile Ala Leu Val Asp Gly Arg Gly
                565                 570                 575

Thr Ala Phe Gln Gly Asp Lys Phe Leu His Ala Val Tyr Arg Lys Leu
                580                 585                 590

Gly Val Tyr Glu Val Glu Asp Gln Leu Thr Ala Val Arg Lys Phe Ile
            595                 600                 605

Glu Met Gly Phe Ile Asp Glu Glu Arg Ile Ala Ile Trp Gly Trp Ser
610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Ile Tyr Ser Glu Arg Phe Met Gly Leu Pro Thr Lys Asp Asp
            660                 665                 670

Asn Leu Glu His Tyr Lys Asn Ser Thr Val Met Ala Arg Ala Glu Tyr
        675                 680                 685

Phe Arg Asn Val Asp Tyr Leu Leu Ile His Gly Thr Ala Asp Asp Asn
            690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Ile
```

-continued

```
                        725                 730                 735
Ser Ser Gly Arg Ser Gln Asn His Leu Tyr Thr His Met Thr His Phe
                    740                 745                 750

Leu Lys Gln Cys Phe Ser Leu Ser Asp
            755                 760
```

<210> SEQ ID NO 80
<211> LENGTH: 749
<212> TYPE: PRT
<213> ORGANISM: Artificial Sequence
<220> FEATURE:
<223> OTHER INFORMATION: Murine FAP ectodomain+poly-lys-tag+his6-tag

<400> SEQUENCE: 80

```
Arg Pro Ser Arg Val Tyr Lys Pro Glu Gly Asn Thr Lys Arg Ala Leu
1               5                   10                  15

Thr Leu Lys Asp Ile Leu Asn Gly Thr Phe Ser Tyr Lys Thr Tyr Phe
            20                  25                  30

Pro Asn Trp Ile Ser Glu Gln Glu Tyr Leu His Gln Ser Glu Asp Asp
        35                  40                  45

Asn Ile Val Phe Tyr Asn Ile Glu Thr Arg Glu Ser Tyr Ile Ile Leu
50                  55                  60

Ser Asn Ser Thr Met Lys Ser Val Asn Ala Thr Asp Tyr Gly Leu Ser
65                  70                  75                  80

Pro Asp Arg Gln Phe Val Tyr Leu Glu Ser Asp Tyr Ser Lys Leu Trp
                85                  90                  95

Arg Tyr Ser Tyr Thr Ala Thr Tyr Tyr Ile Tyr Asp Leu Gln Asn Gly
            100                 105                 110

Glu Phe Val Arg Gly Tyr Glu Leu Pro Arg Pro Ile Gln Tyr Leu Cys
        115                 120                 125

Trp Ser Pro Val Gly Ser Lys Leu Ala Tyr Val Tyr Gln Asn Asn Ile
130                 135                 140

Tyr Leu Lys Gln Arg Pro Gly Asp Pro Pro Phe Gln Ile Thr Tyr Thr
145                 150                 155                 160

Gly Arg Glu Asn Arg Ile Phe Asn Gly Ile Pro Asp Trp Val Tyr Glu
                165                 170                 175

Glu Glu Met Leu Ala Thr Lys Tyr Ala Leu Trp Trp Ser Pro Asp Gly
            180                 185                 190

Lys Phe Leu Ala Tyr Val Glu Phe Asn Asp Ser Asp Ile Pro Ile Ile
        195                 200                 205

Ala Tyr Ser Tyr Tyr Gly Asp Gly Gln Tyr Pro Arg Thr Ile Asn Ile
210                 215                 220

Pro Tyr Pro Lys Ala Gly Ala Lys Asn Pro Val Val Arg Val Phe Ile
225                 230                 235                 240

Val Asp Thr Thr Tyr Pro His His Val Gly Pro Met Glu Val Pro Val
                245                 250                 255

Pro Glu Met Ile Ala Ser Ser Asp Tyr Tyr Phe Ser Trp Leu Thr Trp
            260                 265                 270

Val Ser Ser Glu Arg Val Cys Leu Gln Trp Leu Lys Arg Val Gln Asn
        275                 280                 285

Val Ser Val Leu Ser Ile Cys Asp Phe Arg Glu Asp Trp His Ala Trp
290                 295                 300

Glu Cys Pro Lys Asn Gln Glu His Val Glu Glu Ser Arg Thr Gly Trp
305                 310                 315                 320

Ala Gly Gly Phe Phe Val Ser Thr Pro Ala Phe Ser Gln Asp Ala Thr
```

-continued

```
                325                 330                 335
Ser Tyr Tyr Lys Ile Phe Ser Asp Lys Asp Gly Tyr Lys His Ile His
            340                 345                 350
Tyr Ile Lys Asp Thr Val Glu Asn Ala Ile Gln Ile Thr Ser Gly Lys
            355                 360                 365
Trp Glu Ala Ile Tyr Ile Phe Arg Val Thr Gln Asp Ser Leu Phe Tyr
            370                 375                 380
Ser Ser Asn Glu Phe Glu Gly Tyr Pro Gly Arg Arg Asn Ile Tyr Arg
385                 390                 395                 400
Ile Ser Ile Gly Asn Ser Pro Pro Ser Lys Lys Cys Val Thr Cys His
            405                 410                 415
Leu Arg Lys Glu Arg Cys Gln Tyr Tyr Thr Ala Ser Phe Ser Tyr Lys
            420                 425                 430
Ala Lys Tyr Tyr Ala Leu Val Cys Tyr Gly Pro Gly Leu Pro Ile Ser
            435                 440                 445
Thr Leu His Asp Gly Arg Thr Asp Gln Glu Ile Gln Val Leu Glu Glu
            450                 455                 460
Asn Lys Glu Leu Glu Asn Ser Leu Arg Asn Ile Gln Leu Pro Lys Val
465                 470                 475                 480
Glu Ile Lys Lys Leu Lys Asp Gly Gly Leu Thr Phe Trp Tyr Lys Met
            485                 490                 495
Ile Leu Pro Pro Gln Phe Asp Arg Ser Lys Lys Tyr Pro Leu Leu Ile
            500                 505                 510
Gln Val Tyr Gly Gly Pro Cys Ser Gln Ser Val Lys Ser Val Phe Ala
            515                 520                 525
Val Asn Trp Ile Thr Tyr Leu Ala Ser Lys Glu Gly Ile Val Ile Ala
            530                 535                 540
Leu Val Asp Gly Arg Gly Thr Ala Phe Gln Gly Asp Lys Phe Leu His
545                 550                 555                 560
Ala Val Tyr Arg Lys Leu Gly Val Tyr Glu Val Glu Asp Gln Leu Thr
            565                 570                 575
Ala Val Arg Lys Phe Ile Glu Met Gly Phe Ile Asp Glu Glu Arg Ile
            580                 585                 590
Ala Ile Trp Gly Trp Ser Tyr Gly Gly Tyr Val Ser Ser Leu Ala Leu
            595                 600                 605
Ala Ser Gly Thr Gly Leu Phe Lys Cys Gly Ile Ala Val Ala Pro Val
            610                 615                 620
Ser Ser Trp Glu Tyr Tyr Ala Ser Ile Tyr Ser Glu Arg Phe Met Gly
625                 630                 635                 640
Leu Pro Thr Lys Asp Asp Asn Leu Glu His Tyr Lys Asn Ser Thr Val
            645                 650                 655
Met Ala Arg Ala Glu Tyr Phe Arg Asn Val Asp Tyr Leu Leu Ile His
            660                 665                 670
Gly Thr Ala Asp Asp Asn Val His Phe Gln Asn Ser Ala Gln Ile Ala
            675                 680                 685
Lys Ala Leu Val Asn Ala Gln Val Asp Phe Gln Ala Met Trp Tyr Ser
            690                 695                 700
Asp Gln Asn His Gly Ile Leu Ser Gly Arg Ser Gln Asn His Leu Tyr
705                 710                 715                 720
Thr His Met Thr His Phe Leu Lys Gln Cys Phe Ser Leu Ser Asp Gly
            725                 730                 735
Lys Lys Lys Lys Lys Lys Gly His His His His His
            740                 745
```

<210> SEQ ID NO 81
<211> LENGTH: 748
<212> TYPE: PRT
<213> ORGANISM: Artificial Sequence
<220> FEATURE:
<223> OTHER INFORMATION: Cynomolgus FAP ectodomain+poly-lys-tag+his6-tag

<400> SEQUENCE: 81

```
Arg Pro Pro Arg Val His Asn Ser Glu Glu Asn Thr Met Arg Ala Leu
1               5                   10                  15

Thr Leu Lys Asp Ile Leu Asn Gly Thr Phe Ser Tyr Lys Thr Phe Phe
            20                  25                  30

Pro Asn Trp Ile Ser Gly Gln Glu Tyr Leu His Gln Ser Ala Asp Asn
        35                  40                  45

Asn Ile Val Leu Tyr Asn Ile Glu Thr Gly Gln Ser Tyr Thr Ile Leu
    50                  55                  60

Ser Asn Arg Thr Met Lys Ser Val Asn Ala Ser Asn Tyr Gly Leu Ser
65                  70                  75                  80

Pro Asp Arg Gln Phe Val Tyr Leu Glu Ser Asp Tyr Ser Lys Leu Trp
                85                  90                  95

Arg Tyr Ser Tyr Thr Ala Thr Tyr Tyr Ile Tyr Asp Leu Ser Asn Gly
            100                 105                 110

Glu Phe Val Arg Gly Asn Glu Leu Pro Arg Pro Ile Gln Tyr Leu Cys
        115                 120                 125

Trp Ser Pro Val Gly Ser Lys Leu Ala Tyr Val Tyr Gln Asn Asn Ile
    130                 135                 140

Tyr Leu Lys Gln Arg Pro Gly Asp Pro Pro Phe Gln Ile Thr Phe Asn
145                 150                 155                 160

Gly Arg Glu Asn Lys Ile Phe Asn Gly Ile Pro Asp Trp Val Tyr Glu
                165                 170                 175

Glu Glu Met Leu Ala Thr Lys Tyr Ala Leu Trp Trp Ser Pro Asn Gly
            180                 185                 190

Lys Phe Leu Ala Tyr Ala Glu Phe Asn Asp Thr Asp Ile Pro Val Ile
        195                 200                 205

Ala Tyr Ser Tyr Tyr Gly Asp Glu Gln Tyr Pro Arg Thr Ile Asn Ile
    210                 215                 220

Pro Tyr Pro Lys Ala Gly Ala Lys Asn Pro Phe Val Arg Ile Phe Ile
225                 230                 235                 240

Ile Asp Thr Thr Tyr Pro Ala Tyr Val Gly Pro Gln Glu Val Pro Val
                245                 250                 255

Pro Ala Met Ile Ala Ser Ser Asp Tyr Tyr Phe Ser Trp Leu Thr Trp
            260                 265                 270

Val Thr Asp Glu Arg Val Cys Leu Gln Trp Leu Lys Arg Val Gln Asn
        275                 280                 285

Val Ser Val Leu Ser Ile Cys Asp Phe Arg Glu Asp Trp Gln Thr Trp
    290                 295                 300

Asp Cys Pro Lys Thr Gln Glu His Ile Glu Glu Ser Arg Thr Gly Trp
305                 310                 315                 320

Ala Gly Gly Phe Phe Val Ser Thr Pro Val Phe Ser Tyr Asp Ala Ile
                325                 330                 335

Ser Tyr Tyr Lys Ile Phe Ser Asp Lys Asp Gly Tyr Lys His Ile His
            340                 345                 350

Tyr Ile Lys Asp Thr Val Glu Asn Ala Ile Gln Ile Thr Ser Gly Lys
        355                 360                 365
```

```
Trp Glu Ala Ile Asn Ile Phe Arg Val Thr Gln Asp Ser Leu Phe Tyr
        370                 375                 380

Ser Ser Asn Glu Phe Glu Asp Tyr Pro Gly Arg Arg Asn Ile Tyr Arg
385                 390                 395                 400

Ile Ser Ile Gly Ser Tyr Pro Pro Ser Lys Lys Cys Val Thr Cys His
                405                 410                 415

Leu Arg Lys Glu Arg Cys Gln Tyr Tyr Thr Ala Ser Phe Ser Asp Tyr
            420                 425                 430

Ala Lys Tyr Tyr Ala Leu Val Cys Tyr Gly Pro Gly Ile Pro Ile Ser
        435                 440                 445

Thr Leu His Asp Gly Arg Thr Asp Gln Glu Ile Lys Ile Leu Glu Glu
    450                 455                 460

Asn Lys Glu Leu Glu Asn Ala Leu Lys Asn Ile Gln Leu Pro Lys Glu
465                 470                 475                 480

Glu Ile Lys Lys Leu Glu Val Asp Glu Ile Thr Leu Trp Tyr Lys Met
                485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Arg Ser Val Phe Ala
        515                 520                 525

Val Asn Trp Ile Ser Tyr Leu Ala Ser Lys Glu Gly Met Val Ile Ala
530                 535                 540

Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
                565                 570                 575

Ala Val Arg Lys Phe Ile Glu Met Gly Phe Ile Asp Glu Lys Arg Ile
            580                 585                 590

Ala Ile Trp Gly Trp Ser Tyr Gly Gly Tyr Val Ser Ser Leu Ala Leu
        595                 600                 605

Ala Ser Gly Thr Gly Leu Phe Lys Cys Gly Ile Ala Val Ala Pro Val
    610                 615                 620

Ser Ser Trp Glu Tyr Tyr Ala Ser Val Tyr Thr Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
            660                 665                 670

Gly Thr Ala Asp Asp Asn Val His Phe Gln Asn Ser Ala Gln Ile Ala
        675                 680                 685

Lys Ala Leu Val Asn Ala Gln Val Asp Phe Gln Ala Met Trp Tyr Ser
    690                 695                 700

Asp Gln Asn His Gly Leu Ser Gly Leu Ser Thr Asn His Leu Tyr Thr
705                 710                 715                 720

His Met Thr His Phe Leu Lys Gln Cys Phe Ser Leu Ser Asp Gly Lys
                725                 730                 735

Lys Lys Lys Lys Lys Gly His His His His His
            740                 745

<210> SEQ ID NO 82
<211> LENGTH: 5
<212> TYPE: PRT
<213> ORGANISM: Artificial Sequence
<220> FEATURE:
```

<223> OTHER INFORMATION: Peptide linker G4S

<400> SEQUENCE: 82

Gly Gly Gly Gly Ser
1               5

<210> SEQ ID NO 83
<211> LENGTH: 10
<212> TYPE: PRT
<213> ORGANISM: Artificial Sequence
<220> FEATURE:
<223> OTHER INFORMATION: Peptide linker (G4S)2

<400> SEQUENCE: 83

Gly Gly Gly Gly Ser Gly Gly Gly Gly Ser
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Peptide linker (SG4)2

<400> SEQUENCE: 84

Ser Gly Gly Gly Gly Ser Gly Gly Gly Gly
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Peptide linker G4(SG4)2

<400> SEQUENCE: 85

Gly Gly Gly Gly Ser Gly Gly Gly Gly Ser Gly Gly Gly Gly
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Peptide linker

<400> SEQUENCE: 86

Gly Ser Pro Gly Ser Ser Ser Ser Gly Ser
1               5                   10

<210> SEQ ID NO 87
<211> LENGTH: 15
<212> TYPE: PRT
<213> ORGANISM: Artificial Sequence
<220> FEATURE:
<223> OTHER INFORMATION: Peptide linker (G4S)3

<400> SEQUENCE: 87

Gly Gly Gly Gly Ser Gly Gly Gly Gly Ser Gly Gly Gly Gly Ser
1               5                   10                  15

<210> SEQ ID NO 88
<211> LENGTH: 20
<212> TYPE: PRT
<213> ORGANISM: Artificial Sequence
<220> FEATURE:
<223> OTHER INFORMATION: Peptide linker (G4S)4

<400> SEQUENCE: 88

Gly Gly Gly Gly Ser Gly Gly Gly Ser Gly Gly Gly Ser Gly
1               5                   10                  15

Gly Gly Gly Ser
            20

<210> SEQ ID NO 89
<211> LENGTH: 8
<212> TYPE: PRT
<213> ORGANISM: Artificial Sequence
<220> FEATURE:
<223> OTHER INFORMATION: Peptide linker

<400> SEQUENCE: 89

Gly Ser Gly Ser Gly Ser Gly Ser
1               5

<210> SEQ ID NO 90
<211> LENGTH: 8
<212> TYPE: PRT
<213> ORGANISM: Artificial Sequence
<220> FEATURE:
<223> OTHER INFORMATION: Peptide linker

<400> SEQUENCE: 90

Gly Ser Gly Ser Gly Asn Gly Ser
1               5

<210> SEQ ID NO 91
<211> LENGTH: 8
<212> TYPE: PRT
<213> ORGANISM: Artificial Sequence
<220> FEATURE:
<223> OTHER INFORMATION: Peptide linker

<400> SEQUENCE: 91

Gly Gly Ser Gly Ser Gly Ser Gly
1               5

<210> SEQ ID NO 92
<211> LENGTH: 6
<212> TYPE: PRT
<213> ORGANISM: Artificial Sequence
<220> FEATURE:
<223> OTHER INFORMATION: Peptide linker

<400> SEQUENCE: 92

Gly Gly Ser Gly Ser Gly
1               5

<210> SEQ ID NO 93
<211> LENGTH: 4
<212> TYPE: PRT
<213> ORGANISM: Artificial Sequence
<220> FEATURE:
<223> OTHER INFORMATION: Peptide linker

<400> SEQUENCE: 93

Gly Gly Ser Gly
1

<210> SEQ ID NO 94
<211> LENGTH: 8
<212> TYPE: PRT
<213> ORGANISM: Artificial Sequence

```
-continued

<220> FEATURE:
<223> OTHER INFORMATION: Peptide linker

<400> SEQUENCE: 94

Gly Gly Ser Gly Asn Gly Ser Gly
1               5

<210> SEQ ID NO 95
<211> LENGTH: 8
<212> TYPE: PRT
<213> ORGANISM: Artificial Sequence
<220> FEATURE:
<223> OTHER INFORMATION: Peptide linker

<400> SEQUENCE: 95

Gly Gly Asn Gly Ser Gly Ser Gly
1               5

<210> SEQ ID NO 96
<211> LENGTH: 6
<212> TYPE: PRT
<213> ORGANISM: Artificial Sequence
<220> FEATURE:
<223> OTHER INFORMATION: Peptide linker

<400> SEQUENCE: 96

Gly Gly Asn Gly Ser Gly
1               5

<210> SEQ ID NO 97
<211> LENGTH: 227
<212> TYPE: PRT
<213> ORGANISM: Artificial Sequence
<220> FEATURE:
<223> OTHER INFORMATION: Fc knob chain

<400> SEQUENCE: 97

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190
```

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 98
<211> LENGTH: 227
<212> TYPE: PRT
<213> ORGANISM: Artificial Sequence
<220> FEATURE:
<223> OTHER INFORMATION: Fc hole chain

<400> SEQUENCE: 98

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 99
<211> LENGTH: 20
<212> TYPE: PRT
<213> ORGANISM: Homo sapiens

<400> SEQUENCE: 99

Tyr Tyr Tyr Tyr Tyr Gly Met Asp Val Trp Gly Gln Gly Thr Thr Val
1               5                   10                  15

Thr Val Ser Ser
            20

<210> SEQ ID NO 100
<211> LENGTH: 12
<212> TYPE: PRT
<213> ORGANISM: Homo sapiens

<400> SEQUENCE: 100

```
Leu Thr Phe Gly Gly Gly Thr Lys Val Glu Ile Lys
1               5                   10
```

<210> SEQ ID NO 101
<211> LENGTH: 20
<212> TYPE: PRT
<213> ORGANISM: Homo sapiens

<400> SEQUENCE: 101

```
Tyr Tyr Tyr Tyr Tyr Gly Met Asp Val Trp Gly Gln Gly Thr Thr Val
1               5                   10                  15

Thr Val Ser Ser
            20
```

<210> SEQ ID NO 102
<211> LENGTH: 12
<212> TYPE: PRT
<213> ORGANISM: Homo sapiens

<400> SEQUENCE: 102

```
Leu Thr Phe Gly Gly Gly Thr Lys Val Glu Ile Lys
1               5                   10
```

<210> SEQ ID NO 103
<211> LENGTH: 20
<212> TYPE: PRT
<213> ORGANISM: Homo sapiens

<400> SEQUENCE: 103

```
Tyr Tyr Tyr Tyr Tyr Gly Met Asp Val Trp Gly Gln Gly Thr Thr Val
1               5                   10                  15

Thr Val Ser Ser
            20
```

<210> SEQ ID NO 104
<211> LENGTH: 12
<212> TYPE: PRT
<213> ORGANISM: Homo sapiens

<400> SEQUENCE: 104

```
Leu Thr Phe Gly Gly Gly Thr Lys Val Glu Ile Lys
1               5                   10
```

<210> SEQ ID NO 105
<211> LENGTH: 219
<212> TYPE: PRT
<213> ORGANISM: Artificial Sequence
<220> FEATURE:
<223> OTHER INFORMATION: huCD40 light chain (charged)

<400> SEQUENCE: 105

```
Asp Ile Gln Met Thr Gln Ser Pro Ser Ser Leu Ser Ala Ser Val Gly
1               5                   10                  15

Asp Arg Val Thr Ile Thr Cys Arg Ser Gln Ser Leu Val His Ser
            20                  25                  30

Asn Gly Asn Thr Phe Leu His Trp Tyr Gln Gln Lys Pro Gly Lys Ala
        35                  40                  45
```

```
Pro Lys Leu Leu Ile Tyr Thr Val Ser Asn Arg Phe Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Phe Cys Ser Gln Thr
                 85                  90                  95

Thr His Val Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Arg
            115                 120                 125

Lys Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 106
<211> LENGTH: 676
<212> TYPE: PRT
<213> ORGANISM: Artificial Sequence
<220> FEATURE:
<223> OTHER INFORMATION: huCD40 (VHCH1 charged) Fc PGLALA FAP (VL-CH1)

<400> SEQUENCE: 106

Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Ser Phe Thr Gly Tyr
             20                  25                  30

Tyr Ile His Trp Val Arg Gln Ala Pro Gly Lys Gly Leu Glu Trp Val
         35                  40                  45

Ala Arg Val Ile Pro Asn Ala Gly Gly Thr Ser Tyr Asn Gln Lys Phe
 50                  55                  60

Lys Gly Arg Phe Thr Leu Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Tyr Trp Trp Gly Gln Gly Thr Leu Val Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Glu
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190
```

```
Gln Thr Tyr Ile Cys Asn Val Asn His Lys Pro Ser Asn Thr Lys Val
        195                 200                 205

Asp Glu Lys Val Glu Pro Lys Ser Cys Asp Lys Thr His Thr Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Gly Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Gly Gly Gly Gly Ser
        435                 440                 445

Gly Gly Gly Gly Ser Gly Gly Gly Ser Gly Gly Gly Gly Ser Glu
    450                 455                 460

Ile Val Leu Thr Gln Ser Pro Gly Thr Leu Ser Leu Ser Pro Gly Glu
465                 470                 475                 480

Arg Ala Thr Leu Ser Cys Arg Ala Ser Gln Ser Val Ser Arg Ser Tyr
                485                 490                 495

Leu Ala Trp Tyr Gln Gln Lys Pro Gly Gln Ala Pro Arg Leu Leu Ile
            500                 505                 510

Ile Gly Ala Ser Thr Arg Ala Thr Gly Ile Pro Asp Arg Phe Ser Gly
        515                 520                 525

Ser Gly Ser Gly Thr Asp Phe Thr Leu Thr Ile Ser Arg Leu Glu Pro
    530                 535                 540

Glu Asp Phe Ala Val Tyr Tyr Cys Gln Gln Gly Gln Val Ile Pro Pro
545                 550                 555                 560

Thr Phe Gly Gln Gly Thr Lys Val Glu Ile Lys Ser Ser Ala Ser Thr
                565                 570                 575

Lys Gly Pro Ser Val Phe Pro Leu Ala Pro Ser Ser Lys Ser Thr Ser
            580                 585                 590

Gly Gly Thr Ala Ala Leu Gly Cys Leu Val Lys Asp Tyr Phe Pro Glu
        595                 600                 605
```

```
Pro Val Thr Val Ser Trp Asn Ser Gly Ala Leu Thr Ser Gly Val His
    610                 615                 620

Thr Phe Pro Ala Val Leu Gln Ser Ser Gly Leu Tyr Ser Leu Ser Ser
625                 630                 635                 640

Val Val Thr Val Pro Ser Ser Ser Leu Gly Thr Gln Thr Tyr Ile Cys
                645                 650                 655

Asn Val Asn His Lys Pro Ser Asn Thr Lys Val Asp Lys Lys Val Glu
            660                 665                 670

Pro Lys Ser Cys
        675

<210> SEQ ID NO 107
<211> LENGTH: 118
<212> TYPE: PRT
<213> ORGANISM: Artificial Sequence
<220> FEATURE:
<223> OTHER INFORMATION: VH (PD-L1)

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 108
<211> LENGTH: 107
<212> TYPE: PRT
<213> ORGANISM: Artificial Sequence
<220> FEATURE:
<223> OTHER INFORMATION: VL (PD-L1)

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105
```

```
<210> SEQ ID NO 109
<211> LENGTH: 121
<212> TYPE: PRT
<213> ORGANISM: Artificial Sequence
<220> FEATURE:
<223> OTHER INFORMATION: VH (PD-L1)

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 110
<211> LENGTH: 108
<212> TYPE: PRT
<213> ORGANISM: Artificial Sequence
<220> FEATURE:
<223> OTHER INFORMATION: VL (PD-L1)

<400> SEQUENCE: 110

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105
```

BISPECIFIC ANTIGEN BINDING MOLECULES COMPRISING ANTI-FAP CLONE 212

CROSS-REFERENCE TO RELATED APPLICATIONS

This application is a divisional of U.S. patent application Ser. No. 16/588,780 filed Sep. 30, 2019, now U.S. Pat. No. 11,242,396 issued Feb. 8, 2022, which claims priority to European Patent Application No. 18197866.9, filed Oct. 1, 2018, each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 7, 2021, is named P35043-US-1_SeqListing.txt and is 194,764 bytes in size.

FIELD OF THE INVENTION

The invention relates to new bispecific antigen binding molecules, comprising at least one antigen binding domain capable of specific binding to Fibroblast Activation Protein (FAP), at least one antigen binding domain capable of specific binding to CD40, and a Fc domain composed of a first and a second subunit capable of stable association. The invention further relates to a new anti-FAP clone 212. Further aspects of the invention are methods of producing these molecules and methods of using the same.

BACKGROUND

Multiple molecular signals are required during the generation of a potent adaptive immune response. Signal one involves the binding of a T-cell antigen receptor (TCR) to its cognate antigen presented on the surface of antigen-presenting cells (APCs). Signal two consists of the engagement of costimulatory receptors with their respective ligands between T cells and APCs. One of the best studied and most important costimulatory effectors is the tumor necrosis factor receptor (TNFR) family member CD40 and its ligand CD40L (Elgueta R. et al., *Immunol Rev.* 2009; 229(1):152-72). Several members of the TNFR family including CD40 function after initial T cell activation to sustain APC and T cell responses and thus have pivotal roles in the organization and function of the immune system (Watts T. H. (2005) Annu. Rev. Immunol. 23, 23-68). The combination of different costimulatory TNFR family members allows a sequential and transient regulation of APC and T cell activation and survival resulting in increased immune responses while maintaining tight control of APC and T cell function. Depending on the disease condition, stimulation via costimulatory TNF family members can exacerbate or ameliorate diseases. Activation or blockade of TNFR family costimulators shows promise for several therapeutic applications in multiple fields including cancer, infectious disease, transplantation, and autoimmunity.

Among several costimulatory molecules, the TNFR family member CD40 plays a key role in triggering immune responses by inducing maturation, survival, antigen presentation, cytokine production, and expression of costimulatory molecules of APCs, which then drive antigen-specific T cell responses and NK cell activation by proinflammatory cytokines. CD40 regulates immune responses against infections, tumors and self-antigens and its expression has been demonstrated on the surface of APCs such as B cells, dendritic cells (DCs), monocytes, and macrophages as well as platelets, and cells of non-hematopoietic origin such as myofibroblasts, fibroblasts, epithelial, and endothelial cells (Elgueta R. et al., *Immunol Rev.* 2009; 229(1): 152-72). The CD40 ligand CD40L is expressed on activated CD4$^+$ helper T cells, platelets, monocytic cells, natural killer cell, mast cells, and basophils (Carbone E. et. al., *J Exp Med.* 1997; 185(12): 2053-2060, or Elgueta R. et al., *Immunol Rev.* 2009; 229(1):152-72). Expression of CD40 and CD40L is strongly upregulated in response to various immune stimulatory signals and CD40-CD40L interaction between APCs and CD4$^+$ T cells contributes to increased APC activation and antigen-specific CD8$^+$ T cell responses (Bevan M J., *Nat Rev Immunol.* 2014; 4(8):595-602). Similar immune stimulatory results were observed by using CD40 agonistic antibodies (Vonderheide R H and Glennie M J., *Clin Cancer Res.* 2013; 19(5):1035-43).

Engagement of the type I transmembrane receptor CD40 by its natural ligand CD40L, a type II transmembrane protein or by agonistic antibodies promotes CD40 clustering and induces the recruitment of adapter proteins to the cytoplasmic receptor domain. The recruitment of these adapter proteins known as TNF receptor-associated factors (TRAFs) leads to synergistic activation of mitogen-activated protein kinases (MAPKs), phosphoinositide 3-kinase (PI3K) as well as canonical and non-canonical nuclear factor κB (NFκB) signaling pathways (Elgueta R. et al., *Immunol Rev.* 2009; 229(1):152-72). In turn, this results in APC maturation and activation, which then maximizes antigen-specific T cell responses. Recent studies have shown two different modes of action of agonistic CD40 antibodies in harnessing anti-tumor immunity. Beside its indirect mode of action by mediated tumor cell killing through the activation of the adaptive immune system, agonistic CD40 antibodies can induce direct tumor cell killing through inducing apoptosis of CD40-expressing solid tumor cells (Eliopoulos A G. et al., *Mol Cell Biol.* 2000; 20(15):5503-15). The direct CD40 antibody-mediated killing of tumor cells can provide a source of tumor antigens that can be processed and presented by APC simultaneously activated by CD40 engagement via anti-CD40 antibodies which then can induce tumor antigen-specific T cells, a postulated mechanism known as endogenous vaccination. Given that CD40 engagement can mount in an efficient anti-cancer immune response, agonistic CD40 antibodies have been used successfully in a variety of preclinical tumor models, both as a single-agent and in combination with chemotherapy (Vonderheide R H and Glennie M J., *Clin Cancer Res.* 2013; 19(5): 1035-43).

To date, six CD40 mAb are under investigation in clinical trials: Chi Lob 7/4 (CD40 agonistic IgG1 chimeric mAb; Cancer Research UK; Chowdhury F. et al., *Cancer Immunol Res.* 2013; 2:229-40), ADC1013 (fully human, CD40 agonistic IgG1 antibody; Alligator Bioscience and Johnson & Johnson; Mangsbo S M et al., *Clin Cancer Res.* 2015 Mar. 1; 21(5): 1115-26), APX-005 (fully humanized, CD40 agonistic IgG1 mAb; Apexigen; Bjorck P. et al. *J Immunother Cancer.* 2015; 3(Suppl 2): P198), SEA-CD40 (CD40 agonistic IgG1 chimeric mAb; Seattle Genetics; Gardai S J. et al. *AACR 106th Annual Meeting* 2015; April 18-22, abstract 2472), as well as RO7009789 (fully human, CD40 super agonistic IgG2 mAb) are investigated in clinical phase I studies, and dacetuzumab (CD40 partial agonistic IgG1 chimeric mAb; Seattle Genetics; Khubchandani S. et al., *Curr Opin Investig Drugs.* 2009; 10, 579-87) is investigated in a clinical phase II study. Eligible patients for these studies have solid tumors, classical Hodgkin lymphoma (HL), diffuse large B-cell lymphoma (DLBCL), or indolent lymphoma (including follicular lymphoma). Diverse activities ranging from Fc-dependent cytotoxicity of CD40+ tumor cells via complement mediated cytotoxicity (CMC) or antibody dependent cellular cytoxicity (ADCC) to APC activation to induce anti-tumor T cell responses as well as macrophage activation to deplete tumor and tumor stroma have been shown for these CD40 agonistic antibodies. So far there is no conclusive explanation for this observed heterogeneity. However, recent studies indicate that this mode of action diversity can be explained, at least in part, by differences of the anti-CD40 antibodies in epitope specificity, isotype or Fc:FcγR interaction. For example, it appears that CD40 agonistic antibodies in vivo require crosslinking CD40, bound by its Fab fragment on the target cell, to a Fcγ receptor, bound by its Fc fragment on a cell other than the target cell as has been described for agonistic antibodies specific to other apoptosis-inducing or immunomodulatory members of the TNFR-superfamily (Dahan R., *Cancer Cell.* 2016 Jun. 13; 29(6):820-31; Li F. and Ravetch J. V. *Science,* 2011; 333, 1030-1034; Teng M. W. et al., *J. Immunol.* 2009; 183, 1911-1920). The proposed mechanism includes Fcγ receptor mediated clustering of CD40 transmembrane molecules on target cells and subsequent heightened CD40 signaling to achieve potent in vivo efficacy.

The clinical development of agonistic CD40 antibodies has provided promising initial results. In a first clinical trial CP-870,893 has shown clinical efficacy in patients with advanced cancer. Four out of 29 patients with advanced cancer showed partial responses after receiving a single intravenous infusion of CP-870,893 (Vonderheide R H., *J Clin Oncol.* 2007 Mar. 1; 25(7):876-83). One out of these four patients treated with 9 subsequent doses of CP-870,893 over one and a half years remained in complete remission for more than 5 years. However, the most common side effects of CP-870,893 are cytokine release syndromes and thromboembolic events, so that with the dose schedules and routes of administration used the combined data of the phase 1 clinical studies with more than 140 patients only indicates a limited clinical efficacy and a local administration of the antibody was suggested (Vonderheide R H, Glennie M, *Clin Cancer Res.* 2013, 19(5), 1035-1043). The lack of single agent responses occurs in part due to severe on target/off tumor effects caused by broad CD40 expression, which results in dose limiting toxicity (e.g. cytokine release syndrome). The development of an agonistic CD40 antibody that specifically activates APCs when CD40 is cross-linked by a tumor-specific target could reduce side effects and decrease dose limitations, offering new therapeutic options with the potential to generate an efficient long lasting anti-cancer immunity.

The available pre-clinical and clinical data clearly demonstrate that there is a high clinical need for effective agonists of CD40 that are able to induce and enhance effective endogenous immune responses to cancer. However, almost never are the effects limited to a single type of cells or acting via a single mechanism and studies designed to elucidate inter- and intracellular signaling mechanisms have revealed increasing levels of complexity. Known CD40 antibodies can only be administered in relatively low doses due to dose-limiting toxicities such as cytokine release syndrome and thrombocyte/endothelial cell activation, resulting in an insufficient activation of the pathway on target APCs and a narrow therapeutic index. Thus, there is a need of "targeted" agonists that preferably act on a single type of cells.

The invention relates to new bispecific antigen binding molecules capable of specific binding to CD40 and Fibroblast Activation Protein (FAP) and thus combine a moiety capable of binding to FAP with a moiety capable of agonistic binding to CD40, wherein the activation of APCs through CD40 is provided by cross-linking through FAP expressed on tumor stroma cells and potentially also through FAP intermediately expressed in secondary lymphoid tissues. In contrast to bispecific antigen binding molecules capable of specific binding to CD40 and to immune checkpoint receptors on activated T cells, such as CTLA-4 or PD-1, targeting to a tumor target such as FAP enables CD40-mediated APC activation mainly in the tumor stroma and tumor-draining lymph nodes where fibroblasts express increased levels of FAP compared to other tissues. The antigen binding molecules of this invention may thus be able to trigger the CD40 receptor not only effectively, but also very selectively at the desired site while overcoming the need for FcγR cross-linking thereby reducing side effects. The new bispecific antigen binding molecules are further characterized by comprising a new FAP antigen binding domain that does not lose its excellent binding properties when it is fused to the C-terminus of the Fc domain.

SUMMARY OF THE INVENTION

The present invention relates to bispecific antigen binding molecules combining at least one antigen binding domain capable of specific binding to the costimulatory TNF receptor family member CD40, with at least one antigen binding domain targeting Fibroblast Activation Protein (FAP) comprising a new murine anti-human FAP clone 212 and humanized variants thereof. These bispecific antigen binding molecules are advantageous as they will preferably activate costimulatory CD40 receptors at tumor-associated sitee where FAP is expressed because they are able to bind to FAP with high affinity.

In one aspect, the invention provides a bispecific antigen binding molecule, comprising
(a) at least one antigen binding domain capable of specific binding to CD40, and
(b) at least one antigen binding domain capable of specific binding to Fibroblast Activation Protein (FAP) comprising a heavy chain variable region ($V_L$FAP) comprising
(i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8.

In a particular aspect, the bispecific antigen binding molecule comprises (a) at least one antigen binding domain capable of specific binding to CD40, (b) at least one antigen binding domain capable of specific binding to FAP comprising a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and (c) a Fc domain composed of a first and a second subunit capable of stable association. More particularly, the Fc domain composed of a first and a second subunit capable of stable association comprises mutations that reduce effector function.

In one aspect, the at least one antigen binding domain capable of specific binding to FAP comprises a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, (v) CDR-L2 comprising the amino acid sequence of SEQ ID NO:7, and (vi) CDR-L3 comprising the amino acid sequence of SEQ ID NO:8. In one aspect, the antigen binding domain capable of specific binding to FAP comprises a heavy chain variable region ($V_H$FAP) comprising an amino acid sequence that is at least about 90% identical to the amino acid sequence of SEQ ID NO:9, and a light chain variable region ($V_L$FAP) comprising an amino acid sequence that is at least about 90% identical to the amino acid sequence of SEQ ID NO:10. In a particular aspect, the antigen binding domain capable of specific binding to FAP comprises a heavy chain variable region ($V_H$FAP) comprising the amino acid sequence of SEQ ID NO:9, and a light chain variable region ($V_L$FAP) comprising the amino acid sequence of SEQ ID NO:10.

In another aspect, the antigen binding domain capable of specific binding to FAP comprises a heavy chain variable region ($V_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and a light chain variable region ($V_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26. In particular, the antigen binding domain capable of specific binding to FAP comprises (a) a heavy chain variable region ($V_H$FAP) comprising the amino acid sequence of SEQ ID NO:15 and a light chain variable region ($V_L$FAP) comprising the amino acid sequence of SEQ ID NO:21, (b) a heavy chain variable region ($V_H$FAP) comprising the amino acid sequence of SEQ ID NO:16 and a light chain variable region ($V_L$FAP) comprising the amino acid sequence of SEQ ID NO:21, (c) a heavy chain variable region ($V_H$FAP) comprising the amino acid sequence of SEQ ID NO:16 and a light chain variable region ($V_L$FAP) comprising the amino acid sequence of SEQ ID NO:22, or (d) a heavy chain variable region ($V_H$FAP) comprising the amino acid sequence of SEQ ID NO:19 and a light chain variable region ($V_L$FAP) comprising the amino acid sequence of SEQ ID NO:25. Particularly, the antigen binding domain capable of specific binding to FAP comprises (a) a heavy chain variable region ($V_H$FAP) comprising the amino acid sequence of SEQ ID NO:15 and a light chain variable region ($V_L$FAP) comprising the amino acid sequence of SEQ ID NO:21.

In one aspect, the antigen binding domain capable of specific binding to CD40 binds to a polypeptide comprising, or consisting of, the amino acid sequence of SEQ ID NO:1.

In a further aspect, provided is a bispecific antigen binding molecule, wherein the at least one antigen binding domain capable of specific binding to CD40 comprises a heavy chain variable region ($V_H$CD40) comprising (i) CDR-H1 comprising the amino acid sequence of SEQ ID NO:27, (ii) CDR-H2 comprising the amino acid sequence of SEQ ID NO:28, and (iii) CDR-H3 comprising the amino acid sequence of SEQ ID NO:29, and a light chain variable region ($V_L$CD40) comprising (iv) CDR-L1 comprising the amino acid sequence of SEQ ID NO:30, (v) CDR-L2 comprising the amino acid sequence of SEQ ID NO:31, and (vi) CDR-L3 comprising the amino acid sequence of SEQ ID NO:32.

In one aspect, provided is a bispecific antigen binding molecule as defined herein before, wherein the at least one antigen binding domain capable of specific binding to CD40 comprises
  (i) a heavy chain variable region ($V_H$CD40) comprising an amino acid sequence selected from the group consisting of SEQ ID NO:37, SEQ ID NO:38, SEQ ID NO:39 and SEQ ID NO:40, and
  (ii) a light chain variable region ($V_L$CD40) comprising the amino acid sequence selected from the group consisting of SEQ ID NO:41, SEQ ID NO:42, SEQ ID NO:43, and SEQ ID NO:44.

In another aspect, provided is a bispecific antigen binding molecule as defined herein before, wherein the at least one antigen binding domain capable of specific binding to CD40 comprises (i) a heavy chain variable region ($V_H$CD40) comprising an amino acid sequence selected from the group consisting of SEQ ID NO:45, SEQ ID NO:46, SEQ ID NO:47, SEQ ID NO:48, SEQ ID NO:49 and SEQ ID NO:50, and
  (ii) a light chain variable region ($V_L$CD40) comprising the amino acid sequence selected from the group consisting of SEQ ID NO:51, SEQ ID NO:52, SEQ ID NO:53, and SEQ ID NO:54.

Furthermore, provided is a bispecific antigen binding molecule as defined herein before, wherein the at least one antigen binding domain capable of specific binding to CD40 comprises
  (a) a VH comprising the amino acid sequence of SEQ ID NO:37 and a VL comprising the amino acid sequence of SEQ ID NO:41, or
  (b) a VH comprising the amino acid sequence of SEQ ID NO:37 and a VL comprising the amino acid sequence of SEQ ID NO:42, or
  (c) a VH comprising the amino acid sequence of SEQ ID NO:37 and a VL comprising the amino acid sequence of SEQ ID NO:43, or
  (d) a VH comprising the amino acid sequence of SEQ ID NO:37 and a VL comprising the amino acid sequence of SEQ ID NO:44, or
  (e) a VH comprising the amino acid sequence of SEQ ID NO:38 and a VL comprising the amino acid sequence of SEQ ID NO:41, or
  (f) a VH comprising the amino acid sequence of SEQ ID NO:38 and a VL comprising the amino acid sequence of SEQ ID NO:42, or
  (g) a VH comprising the amino acid sequence of SEQ ID NO:38 and a VL comprising the amino acid sequence of SEQ ID NO:43, or (h) a VH comprising the amino acid sequence of SEQ ID NO:38 and a VL comprising the amino acid sequence of SEQ ID NO:44, or
(i) a VH comprising the amino acid sequence of SEQ ID NO:39 and a VL comprising the amino acid sequence of SEQ ID NO:41, or
(j) a VH comprising the amino acid sequence of SEQ ID NO:39 and a VL comprising the amino acid sequence of SEQ ID NO:42, or
(k) a VH comprising the amino acid sequence of SEQ ID NO:39 and a VL comprising the amino acid sequence of SEQ ID NO:43, or
(l) a VH comprising the amino acid sequence of SEQ ID NO:39 and a VL comprising the amino acid sequence of SEQ ID NO:44, or
(m) a VH comprising the amino acid sequence of SEQ ID NO:40 and a VL comprising the amino acid sequence of SEQ ID NO:41, or
(n) a VH comprising the amino acid sequence of SEQ ID NO:40 and a VL comprising the amino acid sequence of SEQ ID NO:42, or
(o) a VH comprising the amino acid sequence of SEQ ID NO:40 and a VL comprising the amino acid sequence of SEQ ID NO:43, or
(p) a VH comprising the amino acid sequence of SEQ ID NO:40 and a VL comprising the amino acid sequence of SEQ ID NO:44.

In a particular aspect, a bispecific antigen binding molecule is provided, wherein the at least one antigen binding domain capable of specific binding to CD40 comprises a VH comprising the amino acid sequence of SEQ ID NO:37 and a VL comprising the amino acid sequence of SEQ ID NO:41.

In a further aspect, provided is a bispecific antigen binding molecule as defined herein before, wherein the at least one antigen binding domain capable of specific binding to CD40 comprises (a) a VH comprising the amino acid sequence of SEQ ID NO:45 and a VL comprising the amino acid sequence of SEQ ID NO:51, or
(b) a VH comprising the amino acid sequence of SEQ ID NO:46 and a VL comprising the amino acid sequence of SEQ ID NO:51, or
(c) a VH comprising the amino acid sequence of SEQ ID NO:47 and a VL comprising the amino acid sequence of SEQ ID NO:51, or
(d) a VH comprising the amino acid sequence of SEQ ID NO:48 and a VL comprising the amino acid sequence of SEQ ID NO:51, or
(e) a VH comprising the amino acid sequence of SEQ ID NO:45 and a VL comprising the amino acid sequence of SEQ ID NO:52, or
(f) a VH comprising the amino acid sequence of SEQ ID NO:46 and a VL comprising the amino acid sequence of SEQ ID NO:52, or
(g) a VH comprising the amino acid sequence of SEQ ID NO:47 and a VL comprising the amino acid sequence of SEQ ID NO:52, or
(h) a VH comprising the amino acid sequence of SEQ ID NO:48 and a VL comprising the amino acid sequence of SEQ ID NO:52, or
(i) a VH comprising the amino acid sequence of SEQ ID NO:49 and a VL comprising the amino acid sequence of SEQ ID NO:53, or
(j) a VH comprising the amino acid sequence of SEQ ID NO:50 and a VL comprising the amino acid sequence of SEQ ID NO:53, or
(k) a VH comprising the amino acid sequence of SEQ ID NO:49 and a VL comprising the amino acid sequence of SEQ ID NO:54, or
(l) a VH comprising the amino acid sequence of SEQ ID NO:50 and a VL comprising the amino acid sequence of SEQ ID NO:54.

In a further particular aspect, a bispecific antigen binding molecule is provided, wherein the at least one antigen binding domain capable of specific binding to CD40 comprises a VH comprising the amino acid sequence of SEQ ID NO:45 and a VL comprising the amino acid sequence of SEQ ID NO:51 or wherein the antigen binding domain capable of specific binding to CD40 comprises a VH comprising the amino acid sequence of SEQ ID NO:48 and a VL comprising the amino acid sequence of SEQ ID NO:51.

More particularly, provided is a bispecific antigen binding molecule, comprising
(i) at least one antigen binding domain capable of specific binding to CD40, comprising a heavy chain variable region ($V_H$CD40) comprising the amino acid sequence of SEQ ID NO:37 and a light chain variable region ($V_L$CD40) comprising the amino acid sequence of SEQ ID NO:41, and
(ii) at least one antigen binding domain capable of specific binding to FAP, comprising a heavy chain variable region ($V_H$FAP) comprising an amino acid sequence of SEQ ID NO:15 and a light chain variable region ($V_L$FAP) comprising an amino acid sequence of SEQ ID NO:21.

In one aspect, the bispecific antigen binding molecule is a humanized or a chimeric antibody. In a further aspect, the bispecific antigen binding molecule comprises an IgG Fc region, particularly an IgG1 Fc region or an IgG4 Fc region. In particular, the Fc region comprises one or more amino acid substitution that reduces the binding affinity of the antibody to an Fc receptor and/or effector function. In a particular aspect, provided is a bispecific antigen binding molecule, wherein the Fc region is of human IgG1 subclass with the amino acid mutations L234A, L235A and P329G (numbering according to Kabat EU index).

In another aspect, provided is a bispecific antigen binding molecule as defined herein before, wherein the first subunit of the Fc region comprises knobs and the second subunit of the Fc region comprises holes according to the knobs into holes method. In particular, provided is a bispecific antigen binding molecule, wherein (i) the first subunit of the Fc region comprises the amino acid substitutions S354C and T366W (numbering according to Kabat EU index) and the second subunit of the Fc region comprises the amino acid substitutions Y349C, T366S and Y407V (numbering according to Kabat EU index), or (ii) the first subunit of the Fc region comprises the amino acid substitutions K392D and K409D (numbering according to Kabat EU index) and the second subunit of the Fc region comprises the amino acid substitutions E356K and D399K (numbering according to Kabat EU index). More particularly, provided is a bispecific antigen binding molecule, wherein the first subunit of the Fc region comprises the amino acid substitutions S354C and T366W (numbering according to Kabat EU index) and the second subunit of the Fc region comprises the amino acid substitutions Y349C, T366S and Y407V (numbering according to Kabat EU index).

In a further aspect, provided is a bispecific antigen binding molecule, wherein the bispecific antigen binding molecule comprises
(a) at least two Fab fragments capable of specific binding to CD40 connected to a Fc region, and (b) one antigen binding domain capable of specific binding to FAP connected to the C-terminus of the Fc region.

Thus, provided is a bispecific antigen binding molecule that provides bivalent binding towards CD40 and monovalent binding towards FAP.

In another aspect, provided is a bispecific antigen binding molecule, wherein the bispecific antigen binding molecule comprises
(a) at least two Fab fragments capable of specific binding to CD40 fused to a Fc region, and
(b) one antigen binding domain capable of specific binding to FAP fused to the C-terminus of the Fc region.

In a particular aspect, the antigen binding domain capable of specific binding to FAP connected to the C-terminus of the Fc region is a cross-fab fragment. Thus, provided is a bispecific antigen binding molecule, wherein the bispecific antigen binding molecule comprises
(a) at least two Fab fragments capable of specific binding to CD40 fused to a Fc region, and
(b) a cross-fab fragment capable of specific binding to FAP fused to the C-terminus of the Fc region.

In a further aspect, the bispecific antigen binding molecule comprises four Fab fragments capable of specific binding to CD40. Thus, provided is a bispecific antigen binding molecule that provides tetravalent binding towards CD40 and monovalent binding towards FAP.

In one aspect, provided is a bispecific antigen binding molecule comprising
(a) two light chains and two heavy chains of an antibody comprising two Fab fragments capable of specific binding to CD40, and a Fc region, and
(b) a VH and a VL of an antigen binding domain capable specific binding to FAP, wherein the VH is fused to the C-terminus of one of the two heavy chains of (a), and wherein the VL is fused to the C-terminus of the other of the two heavy chains of (a).

In another aspect, provided is a bispecific antigen binding molecule comprising
(a) two light chains and two heavy chains of an antibody comprising two Fab fragments capable of specific binding to CD40, and a Fc region, and
(b) a cross-fab fragment capable specific binding to FAP, wherein the VH-Ckappa chain is fused to the C-terminus of one of the two heavy chains of (a).

In yet another aspect, provided is a bispecific antigen binding molecule comprising
(a) two light chains and two heavy chains of an antibody comprising two Fab fragments capable of specific binding to CD40, and a Fc region, and
(b) a cross-fab fragment capable specific binding to FAP, wherein the VL-CH1 chain is fused to the C-terminus of one of the two heavy chains of (a).

Furthermore, provided is a bispecific antigen binding molecule comprising
(a) two light chains and two heavy chains of an antibody comprising two Fab fragments capable of specific binding to CD40, and a Fc region, and
(b) two Fab fragments capable of specific binding to FAP, wherein one of the Fab fragments is connected to the C-terminus of one of the two heavy chains of (a), and the other of the Fab fragments is connected to the C-terminus of the other of the two heavy chains of (a).

In another aspect, provided is a bispecific antigen binding molecule, wherein the bispecific antigen binding molecule comprises
(a) two heavy chains, each heavy chain comprising a VH and CH1 domain of a Fab fragment capable of specific binding to CD40, and a Fc region subunit,
(b) two light chains, each light chain comprising a VL and CL domain of a Fab fragment capable of specific binding to CD40, and
(c) one Fab fragment capable of specific binding to FAP, wherein the Fab fragments is connected to the C-terminus of one of the two heavy chains of (a).

In another aspect, the Fab fragment capable of specific binding to FAP is a cross-Fab fragment comprising a VL-CH1 chain and a VH-Ckappa chain, and wherein the VH-Ckappa chain or the VL-CH1 chain is connected to the C-terminus of one of the two heavy chains of (a).

In one aspect, provided is a bispecific antigen binding molecule, wherein the bispecific antigen binding molecule comprises four Fab fragments capable of specific binding to CD40. In a particular aspect, provided is a bispecific antigen binding molecule, wherein each of the two heavy chains of (a) as defined herein before comprises two VH-CH1 chains of a Fab fragment capable of specific binding to CD40 that are connected to each other, optionally by a peptide linker.

Thus, in one aspect, the invention provides a bispecific antigen binding molecule comprising
(a) two heavy chains, each heavy chain comprising two VH-CH1 chains of a Fab fragment capable of specific binding to CD40 that are connected to each other, optionally by a peptide linker, and a Fc region subunit,
(b) four light chains, each light chain comprising a VL and Ckappa domain of a Fab fragment capable of specific binding to CD40, and
(c) a cross-Fab fragment capable of specific binding to FAP comprising a VL-CH1 chain and a VH-Ckappa chain, wherein the VH-Ckappa chain or the VL-CH1 chain is connected to the C-terminus of one of the two heavy chains of (a). optionally by a peptide linker.

In another aspect, provided is a bispecific antigen binding molecule comprising
(a) two heavy chains, each heavy chain comprising two VH-CH1 chains of a Fab fragment capable of specific binding to CD40 that are connected to each other, optionally by a peptide linker, and a Fc region subunit,
(b) four light chains, each light chain comprising a VL and CL domain of a Fab fragment capable of specific binding to CD40, and
(c) a cross-fab fragment capable specific binding to FAP, wherein the VH-CL chain of said cross-fab fragment is connected to the C-terminus of one of the two heavy chains of (a).

In yet another aspect, provided is a bispecific antigen binding molecule comprising
(a) two heavy chains, each heavy chain comprising two VH-CH1 chains of a Fab fragment capable of specific binding to CD40 that are connected to each other, optionally by a peptide linker, and a Fc region subunit,
(b) four light chains, each light chain comprising a VL and CL domain of a Fab fragment capable of specific binding to CD40, and
(c) a cross-fab fragment capable specific binding to FAP, wherein the VL-CH1 chain of said cross-fab fragment is connected to the C-terminus of one of the two heavy chains of (a).

In another aspect, provided is an antibody that specifically binds to FAP, wherein said antibody comprises a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8. In a particular aspect, provided is an antibody that specifically binds to FAP, wherein said antibody comprises a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, (v) CDR-L2 comprising the amino acid sequence of SEQ ID NO:7, and (vi) CDR-L3 comprising the amino acid sequence of SEQ ID NO:8.

In a further aspect, provided is an antibody comprising (a) a heavy chain variable region ($V_H$FAP) comprising the amino acid sequence of SEQ ID NO:15 and a light chain variable region ($V_L$FAP) comprising the amino acid sequence of SEQ ID NO:21, (b) a heavy chain variable region ($V_H$FAP) comprising the amino acid sequence of SEQ ID NO:16 and a light chain variable region ($V_L$FAP) comprising the amino acid sequence of SEQ ID NO:21, (c) a heavy chain variable region ($V_H$FAP) comprising the amino acid sequence of SEQ ID NO:16 and a light chain variable region ($V_L$FAP) comprising the amino acid sequence of SEQ ID NO:22, or (d) a heavy chain variable region ($V_H$FAP) comprising the amino acid sequence of SEQ ID NO:19 and a light chain variable region ($V_L$FAP) comprising the amino acid sequence of SEQ ID NO:25.

According to another aspect of the invention, there is provided isolated nucleic acid encoding a bispecific antigen binding molecule as described herein before. Also provided is isolated nucleic acid encoding an antibody as described herein before. The invention further provides a vector, particularly an expression vector, comprising the isolated nucleic acid of the invention and a host cell comprising the isolated nucleic acid or the expression vector of the invention. In some aspects the host cell is a eukaryotic cell, particularly a mammalian cell. In another aspect, provided is a method of producing a bispecific antigen binding molecule or an antibody as described herein before, comprising culturing the host cell as described above under conditions suitable for the expression of the bispecific antigen binding molecule or the antibody, and isolating the bispecific antigen binding molecule or the antibody. The invention also encompasses the bispecific antigen binding molecule that specifically binds to CD40 and to FAP or the antibody that specifically binds to FAP produced by the method of the invention.

The invention further provides a pharmaceutical composition comprising a bispecific antigen binding molecule as described herein before or the antibody as described herein before and a pharmaceutically acceptable carrier. In one aspect, the pharmaceutical composition comprises an additional therapeutic agent.

Also encompassed by the invention is the bispecific antigen binding molecule or the antibody as described herein before, or the pharmaceutical composition comprising the bispecific antigen binding molecule, for use as a medicament.

In one aspect, provided is a bispecific antigen binding molecule as described herein before or the pharmaceutical composition of the invention, for use
 (i) in inducing immune stimulation by CD40 expressing antigen-presenting cells (APCs),
 (ii) in stimulating tumor-specific T cell response,
 (iii) in causing apoptosis of tumor cells,
 (iv) in the treatment of cancer,
 (v) in delaying progression of cancer,
 (vi) in prolonging the survival of a patient suffering from cancer,
 (vii) in the treatment of infections.

In a specific aspect, provided is the bispecific antigen binding molecule as described herein before or the pharmaceutical composition of the invention, for use in the treatment of cancer. In another specific aspect, the invention provides the bispecific antigen binding molecule as described herein before for use in the treatment of cancer, wherein the bispecific antigen binding molecule is administered in combination with a chemotherapeutic agent, radiation and/or other agents for use in cancer immunotherapy. In one aspect, the bispecific antigen binding molecule as described herein is for use in the treatment of cancer, wherein the bispecific antigen binding molecule is for administration in combination with an agent blocking PD-L1/PD-1 interaction. In another aspect, provided is the bispecific antigen binding molecule as described herein before or the pharmaceutical composition of the invention, for use in up-regulating or prolonging cytotoxic T cell activity. In a further aspect, provided is an antibody as described herein before, for use in the treatment of cancer.

In a further aspect, the invention provides a method of inhibiting the growth of tumor cells in an individual comprising administering to the individual an effective amount of the bispecific antigen binding molecule as described herein before, or the pharmaceutical composition of the invention, to inhibit the growth of the tumor cells. In another aspect, the invention provides a method of treating or delaying cancer in an individual comprising administering to the individual an effective amount of the bispecific antigen binding molecule as described herein before, or the pharmaceutical composition of the invention.

Also provided is the use of the bispecific antigen binding molecule as described herein before for the manufacture of a medicament for the treatment of a disease in an individual in need thereof, in particular for the manufacture of a medicament for the treatment of cancer, as well as a method of treating a disease in an individual, comprising administering to said individual a therapeutically effective amount of a composition comprising the bispecific antigen binding molecule of the invention in a pharmaceutically acceptable form. In a specific aspect, the disease is cancer. In any of the above aspects the individual is a mammal, particularly a human.

BRIEF DESCRIPTION OF THE DRAWINGS

FIG. 1A shows a schematic representation of a bispecific FAP-CD40 antibody in a 2+1 format consisting of two CD40 binding moieties combined with one FAP (212) binding moiety as crossover fab fragment, wherein the VL-CH1 chain is fused at the C-terminus of the Fc knob chain (bivalent for CD40 and monovalent for FAP). FIG. 1B shows a schematic representation of a bispecific FAP-CD40 antibody in a 2+1 format consisting of two CD40 binding moieties combined with one FAP (4B9) binding moiety as crossover fab fragment, wherein the VH-Ckappa chain is fused at the C-terminus of the Fc knob chain (bivalent for CD40 and monovalent for FAP). FIG. 1C shows a schematic representation of a bispecific FAP-CD40 antibody in a 2+1 format consisting of two CD40 binding moieties combined with one FAP (28H1) binding moiety as crossover fab fragment, wherein the VL-CH1 chain is fused at the C-terminus of the Fc knob chain (bivalent for CD40 and monovalent for FAP). FIG. 1D shows a schematic representation of a bispecific FAP-CD40 antibody in a 4+1 format consisting of four CD40 binding moieties combined with one FAP (212) binding moiety as crossover fab fragment, wherein the VL-CH1 chain is fused at the C-terminus of the Fc knob chain (tetravalent for CD40 and monovalent for FAP). FIG. 1E shows a schematic representation of a bispecific FAP-CD40 antibody in a 4+1 format consisting of four CD40 binding moieties combined with one FAP (4B9) binding moiety as crossover fab fragment, wherein the VL-CH1 chain is fused at the C-terminus of the Fc knob chain (tetravalent for CD40 and monovalent for FAP). FIG. 1F shows a schematic representation of a bispecific FAP-CD40 antibody in a 4+1 format consisting of four CD40 binding moieties combined with one FAP (28H1) binding moiety as crossover fab fragment, wherein the VL-CH1 chain is fused at the C-terminus of the Fc knob chain (tetravalent for CD40 and monovalent for FAP). The black point symbolizes knob-into-hole mutations. Alternatively, in all molecules the VH-Ckappa chain of the crossfab may be fused at the C-terminus of the Fc knob chain.

FIG. 2A shows that all tested hybridoma-derived murine clones (named 209, 210, 211, 212, 213, 214, 215, 216, 217 and 218) did not compete for binding with anti FAP antibody 4B9 and FIG. 2B shows that the same clones did not compete for binding with anti-FAP antibody 28H1. MFI was measured by flow cytometry. The x-axis shows the concentration of the FAP antibody.

FIG. 3A, FIG. 3B, and FIG. 3C show schematic representations of antibody constructs that were made to determine if the binding properties of the anti-FAP clones are not lost when they are C-terminally fused to an Fc domain. FIG. 3A shows a construct comprising a Fc knob chain and a Fc hole chain wherein the VH domain is fused to the C-terminus of the Fc knob chain and the VL domain is fused to the C-terminus of the Fc hole chain (C-term VH/VL fusion). FIG. 3B shows a construct comprising a Fc knob chain and a Fc hole chain wherein the whole Fab is fused with its VH domain to the C-terminus of the Fc knob chain (C-term Fab fusion). FIG. 3C shows the setup for the epitope binning which was performed using a surface plasmon resonance (SPR) based assay on a Biacore T200 instrument (see Example 1.9).

FIG. 6A and FIG. 6B show the in vitro activation of human Daudi cells by monovalent FAP (212), FAP (4B9) or FAP (28H1)-targeted human anti-CD40 constructs in the presence of FAP-coated (FIG. 6A) or uncoated Dynabeads® (FIG. 6B) after 2 days incubation. With FAP-coated beads all depicted bispecific antibodies monovalent for FAP induced an increase of the B cell activation marker expression CD70. The B cell activation marker upregulation by bispecific FAP-CD40 antibodies in a 2+1 format with a FAP (212) or FAP (4B9) binding domain was higher compared to the upregulation induced by the bispecific FAP-CD40 antibody in a 2+1 format with a FAP (28H1) binding domain, the bispecific FAP-CD40 antibodies in a 4+1 format with a FAP (212), FAP (4B9) or FAP (28H1) binding domain or the FAP-independent positive control antibody. In the absence of FAP (uncoated beads) no increase of CD70 was observed with the depicted FAP-targeted bispecific antibodies bivalent for CD40, while tetravalent CD40 binding molecules induced an upregulation of CD70, but to a lesser extent than in the presence of FAP. Shown is the percentage of CD70-positive vital Daudi cells after 2 days incubation with the indicated titrated antibodies. The x-axis shows the concentration of antibody constructs.

FIG. 7A and FIG. 7B show the in vitro activation of human B cells by monovalent FAP (212), FAP (4B9) or FAP (28H1)-targeted human anti-CD40 constructs in the presence of FAP-coated (FIG. 7A) or uncoated Dynabeads® (FIG. 7B) after 2 days incubation. With FAP-coated beads all depicted bispecific antibodies monovalent for FAP induced an increase of the B cell activation marker expression CD86. Compared to the FAP-independent upregulation of CD86 induced by the cross-linked anti-CD40 antibody (P1AD4470), the CD86 upregulation induced by FAP-dependent bispecific antigen binding molecules was similar or slightly lower. At lower antibody concentrations the B cell activation marker upregulation by bispecific FAP-CD40 antibodies in a 2+1 format with a FAP (212) or FAP (4B9) binding domain was lower compared to the upregulation induced by the bispecific FAP-CD40 antibody in a 2+1 format with a FAP (28H1) binding domain, the bispecific FAP-CD40 antibodies in a 4+1 format with a FAP (212), FAP (4B9) or FAP (28H1) binding domain or the FAP-independent positive control antibody. In the absence of FAP (uncoated beads) no increase of CD86 expression was observed with the bispecific antigen binding molecules, while the positive control antibody induced an upregulation of CD86. Shown is the percentage of CD86-positive vital B cells after 2 days incubation with the indicated titrated antibodies. The x-axis shows the concentration of antibody constructs.

FIG. 13A is a statistical table comparing all treatment groups at day 28 (6 days upon therapy) and FIG. 13B is a statistical table comparing all treatment from day 31 on (9 days upon therapy).

DETAILED DESCRIPTION OF THE INVENTION

Definitions

Figures 1A, 1B, 1C:
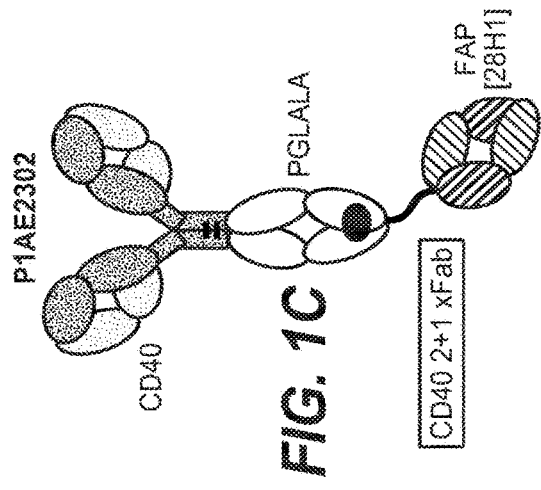
FIG. 1A, FIG. 1B, FIG. 1C, FIG. 1D, FIG. 1E, and FIG. 1F show schematic representations of the bispecific antigen binding molecules which specifically bind to human CD40 and to FAP.

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, antibody fragments and scaffold antigen binding proteins.

As used herein, the term "antigen binding domain capable of specific binding to a target cell antigen" or "moiety capable of specific binding to a target cell antigen" refers to a polypeptide molecule that specifically binds to an antigenic determinant. In one aspect, the antigen binding domain is able to activate signaling through its target cell antigen. In a particular aspect, the antigen binding domain is able to direct the entity to which it is attached (e.g. the CD40 agonist) to a target site, for example to a specific type of tumor cell or tumor stroma bearing the antigenic determinant. Antigen binding domains capable of specific binding to a target cell antigen include antibodies and fragments thereof as further defined herein. In addition, antigen binding domains capable of specific binding to a target cell antigen include scaffold antigen binding proteins as further defined herein, e.g. binding domains which are based on designed repeat proteins or designed repeat domains (see e.g. WO 2002/020565).

In relation to an antibody or fragment thereof, the term "antigen binding domain capable of specific binding to a target cell antigen" refers to the part of the molecule that comprises the area which specifically binds to and is complementary to part or all of an antigen. An antigen binding domain capable of specific antigen binding may be provided, for example, by one or more antibody variable domains (also called antibody variable regions). Particularly, an antigen binding domain capable of specific antigen binding comprises an antibody light chain variable region (VL) and an antibody heavy chain variable region (VH). In another aspect, the "antigen binding domain capable of specific binding to a target cell antigen" can also be a Fab fragment or a cross-Fab fragment.

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells. A bispecific antigen binding molecule as described herein can also form part of a multispecific antibody.

The term "valent" as used within the current application denotes the presence of a specified number of binding sites specific for one distinct antigenic determinant in an antigen binding molecule that are specific for one distinct antigenic determinant. As such, the terms "bivalent", "tetravalent", and "hexavalent" denote the presence of two binding sites, four binding sites, and six binding sites specific for a certain antigenic determinant, respectively, in an antigen binding molecule. In particular aspects of the invention, the bispecific antigen binding molecules according to the invention can be monovalent for a certain antigenic determinant, meaning that they have only one binding site for said antigenic determinant or they can be bivalent or tetravalent for a certain antigenic determinant, meaning that they have two binding sites or four binding sites, respectively, for said antigenic determinant.

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies, triabodies, tetrabodies, cross-Fab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL domain and a constant domain of a light chain (CL), and a VH domain and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments wherein the cysteine residue(s) of the constant domains bear a free thiol group. Pepsin treatment yields an F(ab')$_2$ fragment that has two antigen-combining sites (two Fab fragments) and a part of the Fc region. According to the present invention, the term "Fab fragment" also includes "cross-Fab fragments" or "crossover Fab fragments" as defined below.

The term "cross-Fab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin), a variable domain of antibody light chain or heavy chain (single-domain antibody, sdAb), a variable domain of antibody heavy chain (nanobody, aVH), V$_{NAR}$ fragments, a fibronectin (AdNectin), a C-type lectin domain (Tetranectin); a variable domain of a new antigen receptor beta-lactamase (V$_{NAR}$ fragments), a human gamma-crystallin or ubiquitin (Affilin molecules); a kunitz type domain of human protease inhibitors, microbodies such as the proteins from the knottin family, peptide aptamers and fibronectin (adnectin). CTLA-4 (Cytotoxic T Lymphocyte-associated Antigen 4) is a CD28-family receptor expressed on mainly CD4$^+$ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies (e.g. U.S. Pat. No. 7,166,697B1). Evibodies are around the same size as the isolated variable region of an antibody (e.g. a domain antibody). For further details see Journal of Immunological Methods 248 (1-2), 31-45 (2001). Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633. An affibody is a scaffold derived from Protein A of *Staphylococcus aureus* which can be engineered to bind to antigen. The domain consists of a three-helical bundle of approximately 58 amino acids. Libraries have been generated by randomization of surface residues. For further details see Protein Eng. Des. Sel. 2004, 17, 455-462 and EP 1641818A1. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007). A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999). Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1. A single-domain antibody is an antibody fragment consisting of a single monomeric variable antibody domain. The first single domains were derived from the variable domain of the antibody heavy chain from camelids (nanobodies or $V_HH$ fragments). Furthermore, the term single-domain antibody includes an autonomous human heavy chain variable domain (aVH) or $V_{NAR}$ fragments derived from sharks. Fibronectin is a scaffold which can be engineered to bind to antigen. Adnectins consists of a backbone of the natural amino acid sequence of the 10th domain of the 15 repeating units of human fibronectin type III (FN3). Three loops at one end of the .beta.-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1. Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005). Microbodies are derived from naturally occurring microproteins of 25-50 amino acids in length which contain 3-4 cysteine bridges—examples of microproteins include KalataBI and conotoxin and knottins. The microproteins have a loop which can be engineered to include upto 25 amino acids without affecting the overall fold of the microprotein. For further details of engineered knottin domains, see WO2008098796.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more. An "antigen binding molecule that does not bind to the same epitope" as a reference molecule refers to an antigen binding molecule that does not block binding of the reference molecule to its antigen in a competition assay by 50% or more, and conversely, the reference molecule does not block binding of the antigen binding molecule to its antigen in a competition assay by 50% or more.

The term "antigen binding domain" or "antigen-binding site" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable region (VL) and an antibody heavy chain variable region (VH).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, an molecule that binds to the antigen has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$M to $10^{-13}$M, e.g. from $10^{-9}$M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

A "target cell antigen" as used herein refers to an antigenic determinant presented on the surface of a target cell, in particular a target cell in a tumor such as a cancer cell or a cell of the tumor stroma. Thus, the target cell antigen is a tumor-associated antigen. In particular, the tumor target cell antigen is Fibroblast Activation Protein (FAP).

The term "Fibroblast activation protein (FAP)", also known as Prolyl endopeptidase FAP or Seprase (EC 3.4.21), refers to any native FAP from any vertebrate source, including mammals such as primates (e.g. humans) non-human primates (e.g. cynomolgus monkeys) and rodents (e.g. mice and rats), unless otherwise indicated. The term encompasses "full-length," unprocessed FAP as well as any form of FAP that results from processing in the cell. The term also encompasses naturally occurring variants of FAP, e.g., splice variants or allelic variants. In one embodiment, the antigen binding molecule of the invention is capable of specific binding to human, mouse and/or cynomolgus FAP. The amino acid sequence of human FAP is shown in UniProt (www.uniprot.org) accession no. Q12884 (version 149, SEQ ID NO:2), or NCBI (www.ncbi.nlm.nih.gov/) RefSeq NP 004451.2. The extracellular domain (ECD) of human FAP extends from amino acid position 26 to 760. The amino acid sequence of a His-tagged human FAP ECD is shown in SEQ ID NOs 78. The amino acid sequence of mouse FAP is shown in UniProt accession no. P97321 (version 126, SEQ ID NO:79), or NCBI RefSeq NP_032012.1. The extracellular domain (ECD) of mouse FAP extends from amino acid position 26 to 761. SEQ ID NO:80 shows the amino acid of a His-tagged mouse FAP ECD. SEQ ID NO:81 shows the amino acid of a His-tagged cynomolgus FAP ECD. Preferably, an anti-FAP binding molecule of the invention binds to the extracellular domain of FAP.

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR" as used herein refers to each of the regions of an antibody variable domain which are hypervariable in sequence and which determine antigen binding specificity, for example "complementarity determining regions" ("CDRs").

Generally, antibodies comprise six CDRs: three in the VH (CDR-H1, CDR-H2, CDR-H3), and three in the VL (CDR-L1, CDR-L2, CDR-L3). Exemplary CDRs herein include:
  (a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));
  (b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991)); and
  (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system.

"Framework" or "FR" refers to variable domain residues other than complementary determining regions (CDRs). The FR of a variable domain generally consists of four FR domains: FR1, FR2, FR3, and FR4. Accordingly, the CDR and FR sequences generally appear in the following sequence in VH (or VL): FR1-CDR-H1(CDR-L1)-FR2-CDR-H2(CDR-L2)-FR3-CDR-H3(CDR-L3)-FR4.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)).

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector function" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991) 457-492, Capel, P. J., et al., Immunomethods 4 (1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

Fc□RI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

Fc□RII (CD32) binds complexed IgG with medium to low affinity and is widely expressed. This receptor can be divided into two sub-types, Fc□RIIA and Fc□RIIB Fc□RIIA is found on many cells involved in killing (e.g. macrophages, monocytes, neutrophils) and seems able to activate the killing process. FcγRIIB seems to play a role in inhibitory processes and is found on B cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

Fc□RIII (CD16) binds IgG with medium to low affinity and exists as two types. Fc□RIIIA is found on NK cells, macrophages, eosinophils and some monocytes and T cells and mediates ADCC. FcγRIIIB is highly expressed on neutrophils. Reduced binding to Fc□RIIIA is found e.g. for antibodies comprising an IgG Fc-region with mutation at least at one of the amino acid residues E233-G236, P238, D265, N297, A327, P329, D270, Q295, A327, 5239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

The term "ADCC" or "antibody-dependent cellular cytotoxicity" is a function mediated by Fc receptor binding and refers to lysis of target cells by an antibody as reported herein in the presence of effector cells. The capacity of the antibody to induce the initial steps mediating ADCC is investigated by measuring their binding to Fcγ receptors expressing cells, such as cells, recombinantly expressing FcγRI and/or FcγRIIA or NK cells (expressing essentially FcγRIIIA) In particular, binding to FcγR on NK cells is measured.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

The term "CD40", as used herein, refers to any native CD40 from any vertebrate source, including mammals such as primates (e.g. humans) and rodents (e.g., mice and rats), unless otherwise indicated. The term encompasses "full-length," unprocessed CD40 as well as any form of CD40 that results from processing in the cell. The term also encompasses naturally occurring variants of CD40, e.g., splice variants or allelic variants. The amino acid sequence of an exemplary human CD40 is shown in SEQ ID NO:1 (Uniprot P25942, version 200) and the amino acid sequence of an exemplary mouse CD40 is shown in SEQ ID NO: 146 (Uniprot P27512, version 160). The CD40 antigen is a 50 kDa cell surface glycoprotein which belongs to the Tumor Necrosis Factor Receptor (TNF-R) family. (Stamenkovic et al. (1989), EMBO J. 8: 1403-10). CD40 is expressed in many normal and tumor cell types, including B lymphocytes, dendritic cells, monocytes, macrophages, thymus epithelium, endothelial cells, fibroblasts, and smooth muscle cells. CD40 is expressed in all B-lymphomas and in 70% of all solid tumors and is up-regulated in antigen presenting cells (APCs) by maturation signals, such as IFN-gamma and GM-CSF. CD40 activation also induces differentiation of monocytes into functional dendritic cells (DCs) and enhances cytolytic activity of NK cells through APC-CD40 induced cytokines. Thus CD40 plays an essential role in the initiation and enhancement of immune responses by inducing maturation of APCs, secretion of helper cytokines, upregulation of costimulatory molecules, and enhancement of effector functions.

The term "CD40 agonist" as used herein includes any moiety that agonizes the CD40/CD40L interaction. CD40 as used in this context refers preferably to human CD40, thus the CD40 agonist is preferably an agonist of human CD40. Typically, the moiety will be an agonistic CD40 antibody or antibody fragment.

The terms "anti-CD40 antibody", "anti-CD40", "CD40 antibody and "an antibody that specifically binds to CD40" refer to an antibody that is capable of binding CD40 with sufficient affinity such that the antibody is useful as a diagnostic and/or therapeutic agent in targeting CD40. In one aspect, the extent of binding of an anti-CD40 antibody to an unrelated, non-CD40 protein is less than about 10% of the binding of the antibody to CD40 as measured, e.g., by a radioimmunoassay (RIA) or flow cytometry (FACS). In certain embodiments, an antibody that binds to CD40 has a dissociation constant ($K_D$) of ≤1 μM, ≤100 nM, ≤10 nM, ≤1 nM, ≤0.1 nM, ≤0.01 nM, or ≤0.001 nM (e.g. $10^{-6}$M or less, e.g. from $10^{-6}$M to $10^{-13}$M, e.g., from $10^{-8}$M to $10^{-10}$ M).

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$, $(SG_4)_n$ or $G_4(SG_4)_n$ peptide linkers, wherein "n" is generally a number between 1 and 10, typically between 2 and 4, in particular 2, i.e. the peptides selected from the group consisting of GGGGS (SEQ ID NO:82), GGGGSGGGGS (SEQ ID NO:83), SGGGGSGGGG (SEQ ID NO:84) and GGGGSGGGGSGGGG (SEQ ID NO:85), but also include the sequences GSPGSSSSGS (SEQ ID NO:86), $(G4S)_3$ (SEQ ID NO:87), $(G45)_4$ (SEQ ID NO:88), GSGSGSGS (SEQ ID NO:89), GSGSGNGS (SEQ ID NO:90), GGSGSGSG (SEQ ID NO:91), GGSGSG (SEQ ID NO:92), GGSG (SEQ ID NO:93), GGSGNGSG (SEQ ID NO:94), GGNGSGSG (SEQ ID NO:95) and GGNGSG (SEQ ID NO:96). Peptide linkers of particular interest are (G45) (SEQ ID NO:82), $(G45)_2$ or GGGGSGGGGS (SEQ ID NO:83), $(G45)_3$ (SEQ ID NO:87) and $(G45)_4$ (SEQ ID NO:88).

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

By "fused" or "connected" is meant that the components (e.g. a heavy chain of an antibody and a Fab fragment) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, amino acid sequence variants of the bispecific antigen binding molecules provided herein are contemplated. For example, it may be desirable to improve the binding affinity and/or other biological properties of the TNF ligand trimer-containing antigen binding molecules. Amino acid sequence variants of the TNF ligand trimer-containing antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table B under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |

TABLE A-continued

| Original Residue | Exemplary Substitutions | Preferred Substitutions |
|---|---|---|
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more HVR residues are mutated and the variant antigen binding molecules displayed on phage and screened for a particular biological activity (e.g. binding affinity). In certain embodiments, substitutions, insertions, or deletions may occur within one or more HVRs so long as such alterations do not substantially reduce the ability of the antigen binding molecule to bind antigen. For example, conservative alterations (e.g., conservative substitutions as provided herein) that do not substantially reduce binding affinity may be made in HVRs. A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include bispecific antigen binding molecules of the invention with an N-terminal methionyl residue. Other insertional variants of the molecule include the fusion to the N- or C-terminus to a polypeptide which increases the serum half-life of the bispecific antigen binding molecules.

In certain embodiments, the bispecific antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the TNF ligand trimer-containing antigen binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in TNF family ligand trimer-containing antigen binding molecule may be made in order to create variants with certain improved properties. In one aspect, variants of bispecific antigen binding molecules or antibodies of the invention are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). In another aspect, variants of the bispecific antigen binding molecules or antibodies of the invention are provided with bisected oligosaccharides, e.g., in which a biantennary oligosaccharide attached to the Fc region is bisected by GlcNAc. Such variants may have reduced fucosylation and/or improved ADCC function., see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain aspects, it may be desirable to create cysteine engineered variants of the bispecific antigen binding molecules of the invention, e.g., "thioMAbs," in which one or more residues of the molecule are substituted with cysteine residues. In particular aspects, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain aspects, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

The term "nucleic acid" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler ert al, Nature Medicine 2017, published online 12 Jun. 2017, doi:10.1038/nm.4356 or EP 2 101 823 B1).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding a bispecific antigen binding molecule or antibody" refers to one or more nucleic acid molecules encoding the heavy and light chains (or fragments thereof) of the bispecific antigen binding molecule or antibody, including such nucleic acid molecule(s) in a single vector or separate vectors, and such nucleic acid molecule(s) present at one or more locations in a host cell.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the pharmaceutical composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

The term "chemotherapeutic agent" as used herein refers to a chemical compound useful in the treatment of cancer. In one aspect, the chemotherapeutic agent is an antimetabolite. In one aspect, the antimetabolite is selected from the group consisting of Aminopterin, Methotrexate, Pemetrexed, Raltitrexed, Cladribine, Clofarabine, Fludarabine, Mercaptopurine, Pentostatin, Thioguanine, Capecitabine, Cytarabine, Fluorouracil, Floxuridine, and Gemcitabine. In one particular aspect, the antimetabolite is capecitabine or gemcitabine. In another aspect, the antimetabolite is fluorouracil. In one aspect, the chemotherapeutic agent is an agent that affects microtubule formation. In one aspect, the agent that affects microtubule formation is selected from the group consisting of: paclitaxel, docetaxel, vincristine, vinblastine, vindesine, vinorelbin, taxotere, etoposide, and teniposide. In another aspect, the chemotherapeutic agent is an alkylating agent such as cyclophosphamide. In one aspect, the chemotherapeutic agent is a cytotoxic antibiotic such as a topoisomerase II inhibitor. In one aspect, the topoisomerase II inhibitor is doxorubicin.

Bispecific Antibodies of the Invention

The invention provides novel bispecific antigen binding molecules comprising a new anti-FAP antibody (clone 212). The bispecific antigen binding molecules comprising this new anti-FAP antibody possess particularly advantageous properties such as producibility, stability, binding affinity, biological activity, targeting efficiency, reduced internalization, superior pharmacokinetic (PK) properties, reduced toxicity, an extended dosage range that can be given to a patient and thereby a possibly enhanced efficacy.

Exemplary Bispecific Antigen Binding Molecules

In one aspect, the invention provides bispecific antigen binding molecules that are characterized by targeted agonistic binding to CD40. In particular, the bispecific antigen binding molecule is a CD40 agonist that is targeted against FAP. In another particular aspect, the bispecific antigen binding molecules of the invention comprise a Fc region composed of a first and a second subunit capable of stable association which comprises mutations that reduce effector function. The use of a Fc region comprising mutations that reduce or abolish effector function will prevent unspecific agonism by crosslinking via Fc receptors and will prevent ADCC of CD40$^+$ cells. The bispecific antigen binding molecules as described herein possess the advantage over conventional antibodies capable of specific binding to CD40 in that they selectively induce immune response at the target cells, which are typically cancer cells or tumor stroma.

The bispecific antigen binding molecules are thus characterized by FAP-targeted agonistic binding to CD40. In the presence of FAP-expressing cells the bispecific antigen binding molecules are able to activate antigen presenting cells (APCs), to activate human B cells (Example 5.1.2), human Daudi cells (Example 5.1.1) and human monocyte-derived dendritic cells (moDCs).

In one aspect, provided is a bispecific antigen binding molecule comprising
 (a) at least one antigen binding domain capable of specific binding to CD40, and
 (b) at least one antigen binding domain capable of specific binding to Fibroblast Activation Protein (FAP) comprising a heavy chain variable region ($V_L$FAP) comprising
  (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8.

In a particular aspect, provided is a bispecific antigen binding molecules, comprising a) at least one antigen binding domain capable of specific binding to CD40, and (b) at least one antigen binding domain capable of specific binding to Fibroblast Activation Protein (FAP) comprising a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, (v) CDR-L2 comprising the amino acid sequence of SEQ ID NO:7, and (vi) CDR-L3 comprising the amino acid sequence of SEQ ID NO:8.

In one aspect, provided is a bispecific antigen binding molecule, wherein the antigen binding domain capable of specific binding to FAP comprises a heavy chain variable region ($V_H$FAP) comprising an amino acid sequence that is at least about 90% identical to the amino acid sequence of SEQ ID NO:9, and a light chain variable region ($V_L$FAP) comprising an amino acid sequence that is at least about 90% identical to the amino acid sequence of SEQ ID NO:10.

In another aspect, provided is a bispecific antigen binding molecule, wherein the antigen binding domain capable of specific binding to FAP comprises a heavy chain variable region ($V_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and a light chain variable region ($V_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26.

In one aspect, the bispecific antigen binding molecule comprises
 (a) a heavy chain variable region ($V_H$FAP) comprising the amino acid sequence of SEQ ID NO:15 and a light chain variable region ($V_L$FAP) comprising the amino acid sequence of SEQ ID NO:21,
 (b) a heavy chain variable region ($V_H$FAP) comprising the amino acid sequence of SEQ ID NO:16 and a light chain variable region ($V_L$FAP) comprising the amino acid sequence of SEQ ID NO:21,
 (c) a heavy chain variable region ($V_H$FAP) comprising the amino acid sequence of SEQ ID NO:16 and a light chain variable region ($V_L$FAP) comprising the amino acid sequence of SEQ ID NO:22, or
 (d) a heavy chain variable region ($V_H$FAP) comprising the amino acid sequence of SEQ ID NO:19 and a light chain variable region ($V_L$FAP) comprising the amino acid sequence of SEQ ID NO:25.

In a particular aspect, the bispecific antigen binding molecule comprises a heavy chain variable region ($V_H$FAP) comprising the amino acid sequence of SEQ ID NO:15 and a light chain variable region ($V_L$FAP) comprising the amino acid sequence of SEQ ID NO:21.

In another aspect, provided is a bispecific antigen binding molecule, wherein the antigen binding domain capable of specific binding to CD40 comprises a heavy chain variable region ($V_H$CD40) comprising (i) CDR-H1 comprising the amino acid sequence of SEQ ID NO:27, (ii) CDR-H2 comprising the amino acid sequence of SEQ ID NO:28, and (iii) CDR-H3 comprising the amino acid sequence of SEQ ID NO:29, and a light chain variable region ($V_L$CD40) comprising (iv) CDR-L1 comprising the amino acid sequence of SEQ ID NO:30, (v) CDR-L2 comprising the amino acid sequence of SEQ ID NO:31, and (vi) CDR-L3 comprising the amino acid sequence of SEQ ID NO:32.

In a further aspect, provided is a bispecific antigen binding molecule, wherein the antigen binding domain capable of specific binding to CD40 comprises
- (i) a heavy chain variable region (V$_H$CD40) comprising an amino acid sequence selected from the group consisting of SEQ ID NO:37, SEQ ID NO:38, SEQ ID NO:39 and SEQ ID NO:40, and
- (ii) a light chain variable region (V$_L$CD40) comprising the amino acid sequence selected from the group consisting of SEQ ID NO:41, SEQ ID NO:42, SEQ ID NO:43, and SEQ ID NO:44.

In one aspect, provided is a bispecific antigen binding molecule, wherein the antigen binding domain capable of specific binding to CD40 comprises
- (a) a VH comprising the amino acid sequence of SEQ ID NO:37 and a VL comprising the amino acid sequence of SEQ ID NO:41, or
- (b) a VH comprising the amino acid sequence of SEQ ID NO:37 and a VL comprising the amino acid sequence of SEQ ID NO:42, or
- (c) a VH comprising the amino acid sequence of SEQ ID NO:37 and a VL comprising the amino acid sequence of SEQ ID NO:43, or
- (d) a VH comprising the amino acid sequence of SEQ ID NO:37 and a VL comprising the amino acid sequence of SEQ ID NO:44, or
- (e) a VH comprising the amino acid sequence of SEQ ID NO:38 and a VL comprising the amino acid sequence of SEQ ID NO:41, or
- (f) a VH comprising the amino acid sequence of SEQ ID NO:38 and a VL comprising the amino acid sequence of SEQ ID NO:42, or
- (g) a VH comprising the amino acid sequence of SEQ ID NO:38 and a VL comprising the amino acid sequence of SEQ ID NO:43, or
- (h) a VH comprising the amino acid sequence of SEQ ID NO:38 and a VL comprising the amino acid sequence of SEQ ID NO:44, or
- (i) a VH comprising the amino acid sequence of SEQ ID NO:39 and a VL comprising the amino acid sequence of SEQ ID NO:41, or
- (j) a VH comprising the amino acid sequence of SEQ ID NO:39 and a VL comprising the amino acid sequence of SEQ ID NO:42, or
- (k) a VH comprising the amino acid sequence of SEQ ID NO:39 and a VL comprising the amino acid sequence of SEQ ID NO:43, or
- (l) a VH comprising the amino acid sequence of SEQ ID NO:39 and a VL comprising the amino acid sequence of SEQ ID NO:44, or
- (m) a VH comprising the amino acid sequence of SEQ ID NO:40 and a VL comprising the amino acid sequence of SEQ ID NO:41, or
- (n) a VH comprising the amino acid sequence of SEQ ID NO:40 and a VL comprising the amino acid sequence of SEQ ID NO:42, or
- (o) a VH comprising the amino acid sequence of SEQ ID NO:40 and a VL comprising the amino acid sequence of SEQ ID NO:43, or
- (p) a VH comprising the amino acid sequence of SEQ ID NO:40 and a VL comprising the amino acid sequence of SEQ ID NO:44.

In a particular aspect, the bispecific antigen binding molecule comprises an antigen binding domain capable of specific binding to CD40 comprises a VH comprising the amino acid sequence of SEQ ID NO:37 and a VL comprising the amino acid sequence of SEQ ID NO:41.

In a further aspect, provided is a bispecific antigen binding molecule, wherein the antigen binding domain capable of specific binding to CD40 comprises
- (i) a heavy chain variable region (V$_H$CD40) comprising an amino acid sequence selected from the group consisting of SEQ ID NO:45, SEQ ID NO:46, SEQ ID NO:47, SEQ ID NO:48, SEQ ID NO:49 and SEQ ID NO:50, and
- (ii) a light chain variable region (V$_L$CD40) comprising the amino acid sequence selected from the group consisting of SEQ ID NO:51, SEQ ID NO:52, SEQ ID NO:53, and SEQ ID NO:54.

In one aspect, provided is a bispecific antigen binding molecule, wherein the antigen binding domain capable of specific binding to CD40 comprises
- (a) a VH comprising the amino acid sequence of SEQ ID NO:45 and a VL comprising the amino acid sequence of SEQ ID NO:51, or
- (b) a VH comprising the amino acid sequence of SEQ ID NO:46 and a VL comprising the amino acid sequence of SEQ ID NO:51, or
- (c) a VH comprising the amino acid sequence of SEQ ID NO:47 and a VL comprising the amino acid sequence of SEQ ID NO:51, or
- (d) a VH comprising the amino acid sequence of SEQ ID NO:48 and a VL comprising the amino acid sequence of SEQ ID NO:51, or
- (e) a VH comprising the amino acid sequence of SEQ ID NO:45 and a VL comprising the amino acid sequence of SEQ ID NO:52, or
- (f) a VH comprising the amino acid sequence of SEQ ID NO:46 and a VL comprising the amino acid sequence of SEQ ID NO:52, or
- (g) a VH comprising the amino acid sequence of SEQ ID NO:47 and a VL comprising the amino acid sequence of SEQ ID NO:52, or
- (h) a VH comprising the amino acid sequence of SEQ ID NO:48 and a VL comprising the amino acid sequence of SEQ ID NO:52, or
- (i) a VH comprising the amino acid sequence of SEQ ID NO:49 and a VL comprising the amino acid sequence of SEQ ID NO:53, or
- (j) a VH comprising the amino acid sequence of SEQ ID NO:50 and a VL comprising the amino acid sequence of SEQ ID NO:53, or
- (k) a VH comprising the amino acid sequence of SEQ ID NO:49 and a VL comprising the amino acid sequence of SEQ ID NO:54, or
- (l) a VH comprising the amino acid sequence of SEQ ID NO:50 and a VL comprising the amino acid sequence of SEQ ID NO:54.

In a particular aspect, provided is a bispecific antigen binding molecule which comprises (i) at least one antigen binding domain capable of specific binding to CD40, comprising a heavy chain variable region (V$_H$CD40) comprising the amino acid sequence of SEQ ID NO:37 and a light chain variable region (V$_L$CD40) comprising the amino acid sequence of SEQ ID NO:41, and (ii) at least one antigen binding domain capable of specific binding to FAP, comprising a heavy chain variable region (V$_H$FAP) comprising an amino acid sequence of SEQ ID NO:15 and a light chain variable region (V$_L$FAP) comprising an amino acid sequence of SEQ ID NO:21.

Bispecific Antigen Binding Molecules Binding to CD40 and FAP

In another aspect, provided is a bispecific antigen binding molecule, comprising
- (i) at least one antigen binding domain capable of specific binding to CD40, comprising a heavy chain variable region ($V_H$CD40) comprising an amino acid sequence selected from the group consisting of SEQ ID NO:37, SEQ ID NO:38, SEQ ID NO:39 and SEQ ID NO:40, and a light chain variable region ($V_L$CD40) comprising the amino acid sequence selected from the group consisting of SEQ ID NO:41, SEQ ID NO:42, SEQ ID NO:43, and SEQ ID NO:44., and
- (ii) at least one antigen binding domain capable of specific binding to FAP, comprising a heavy chain variable region ($V_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and a light chain variable region ($V_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26.

In a further aspect, provided is a bispecific antigen binding molecule, comprising
- (i) at least one antigen binding domain capable of specific binding to CD40, comprising a heavy chain variable region ($V_H$CD40) comprising an amino acid sequence selected from the group consisting of SEQ ID NO:45, SEQ ID NO:46, SEQ ID NO:47, SEQ ID NO:48, SEQ ID NO:49 and SEQ ID NO:50, and a light chain variable region ($V_L$CD40) comprising the amino acid sequence selected from the group consisting of SEQ ID NO:51, SEQ ID NO:52, SEQ ID NO:53, and SEQ ID NO:54, and
- (ii) at least one antigen binding domain capable of specific binding to FAP, comprising a heavy chain variable region ($V_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and a light chain variable region ($V_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26.

In a particular aspect, provided is a bispecific antigen binding molecule, comprising
- (i) at least one antigen binding domain capable of specific binding to CD40, comprising a heavy chain variable region ($V_H$CD40) comprising an amino acid sequence of SEQ ID NO:37 and a light chain variable region ($V_L$CD40) comprising an amino acid sequence of SEQ ID NO:41, and
- (ii) at least one antigen binding domain capable of specific binding to FAP, comprising a heavy chain variable region ($V_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and a light chain variable region ($V_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26.

In another particular aspect, provided is a bispecific antigen binding molecule, comprising
- (i) at least one antigen binding domain capable of specific binding to CD40, comprising a heavy chain variable region ($V_H$CD40) comprising an amino acid of SEQ ID NO:45 or SEQ ID NO:48 and a light chain variable region ($V_L$CD40) comprising an amino acid sequence of SEQ ID NO:51, and
- (ii) at least one antigen binding domain capable of specific binding to FAP, comprising a heavy chain variable region ($V_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and a light chain variable region ($V_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26.

In a further aspect, provided is a bispecific antigen binding molecule, wherein
- (i) the antigen binding domain capable of specific binding to CD40 comprises a heavy chain variable region ($V_H$CD40) comprising an amino acid sequence selected from the group consisting of SEQ ID NO:37, SEQ ID NO:38, SEQ ID NO:39 and SEQ ID NO:40, and a light chain variable region ($V_L$CD40) comprising the amino acid sequence selected from the group consisting of SEQ ID NO:41, SEQ ID NO:42, SEQ ID NO:43, and SEQ ID NO:44, and
- (ii) the antigen binding domain capable of specific binding to FAP comprises a heavy chain variable region VH comprising an amino acid sequence of SEQ ID NO:15 and a light chain variable region comprising an amino acid sequence of SEQ ID NO:21.

Furthermore, provided is a bispecific antigen binding molecule, wherein
- (i) the antigen binding domain capable of specific binding to CD40 comprises a heavy chain variable region ($V_H$CD40) comprising an amino acid sequence selected from the group consisting of SEQ ID NO:45, SEQ ID NO:46, SEQ ID NO:47, SEQ ID NO:48, SEQ ID NO:49 and SEQ ID NO:50, and a light chain variable region ($V_L$CD40) comprising the amino acid sequence selected from the group consisting of SEQ ID NO:51, SEQ ID NO:52, SEQ ID NO:53, and SEQ ID NO:54, and
- (ii) the antigen binding domain capable of specific binding to FAP comprises a heavy chain variable region VH comprising an amino acid sequence of SEQ ID NO:15 and a light chain variable region comprising an amino acid sequence of SEQ ID NO:21.

In a particular aspect, provided is a bispecific antigen binding molecule which comprises (i) at least one antigen binding domain capable of specific binding to CD40, comprising a heavy chain variable region ($V_H$CD40) comprising the amino acid sequence of SEQ ID NO:37 and a light chain variable region ($V_L$CD40) comprising the amino acid sequence of SEQ ID NO:41, and (ii) at least one antigen binding domain capable of specific binding to FAP, comprising a heavy chain variable region ($V_H$FAP) comprising an amino acid sequence of SEQ ID NO:15 and a light chain variable region ($V_L$FAP) comprising an amino acid sequence of SEQ ID NO:21.

Bispecific, Monovalent Antigen Binding Molecules (1+1 Format)

In one aspect, the invention relates to bispecific antigen binding molecules comprising
- (a) one antigen binding domain capable of specific binding to CD40,
- (b) one antigen binding domain capable of specific binding to Fibroblast Activation Protein (FAP) comprising a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8 and (c) a Fc domain composed of a first and a second subunit capable of stable association.

In one particular aspect, provided is a bispecific antigen binding molecule, wherein said molecule comprises (a) a first Fab fragment capable of specific binding to CD40, (b) a second Fab fragment capable of specific binding to FAP comprising a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and (c) a Fc domain composed of a first and a second subunit capable of stable association.

In one particular aspect, the invention provides a bispecific antigen binding molecule comprising (a) a first heavy chain comprising the amino acid sequence of SEQ ID NO:63, a second heavy chain comprising the amino acid sequence of SEQ ID NO:98, a first light chain comprising the amino acid sequence of SEQ ID NO:61, a second light chain comprising the amino acid sequence of SEQ ID NO:62.

Bispecific Antigen Binding Molecules Bivalent for Binding to CD40 and Monovalent for Binding to the Target Cell Antigen (2+1 Format)

In another aspect, the invention provides a bispecific antigen binding molecule comprising
- (a) two antigen binding domains capable of specific binding to CD40,
- (b) one antigen binding domain capable of specific binding to FAP comprising a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and
- (c) a Fc domain composed of a first and a second subunit capable of stable association.

Thus, provided is a bispecific antigen binding molecule, wherein the bispecific antigen binding molecule binds bivalently to CD40 and monovalently to FAP.

In one aspect, the bispecific antigen binding molecule comprises

- (a) two light chains and two heavy chains of an antibody comprising two Fab fragments capable of specific binding to CD40 and the Fc domain, and
- (b) a VH and VL domain capable of specific binding to a target cell antigen, wherein the VH domain and the VL domain are each connected via a peptide linker to one of the C-termini of the two heavy chains.

In a further aspect, provided is a bispecific antigen binding molecule, comprising
- (a) two heavy chains, each heavy chain comprising a VH and CH1 domain of a Fab fragment capable of specific binding to CD40 and a Fc region subunit,
- (b) two light chains, each light chain comprising a VL and CL domain of a Fab fragment capable of specific binding to CD40, and
- (c) a cross-fab fragment capable of specific binding to FAP comprising a VL-CH1 chain and a VH-CL chain, wherein the VH-CL chain is connected to the C-terminus of one of the two heavy chains of (a).

In one aspect, the VH-CL (VH-Ckappa) chain is connected to the C-terminus of the Fc knob heavy chain.

In another aspect, provided is a bispecific antigen binding molecule, comprising
- (a) two heavy chains, each heavy chain comprising a VH and CH1 domain of a Fab fragment capable of specific binding to CD40 and a Fc region subunit,
- (b) two light chains, each light chain comprising a VL and CL domain of a Fab fragment capable of specific binding to CD40, and
- (c) a cross-fab fragment capable of specific binding to FAP comprising a VL-CH1 chain and a VH-CL chain, wherein the VL-CH1 chain is connected to the C-terminus of one of the two heavy chains of (a).

In one aspect, the VL-CH1 chain is connected to the C-terminus of the Fc knob heavy chain.

In one particular aspect, the invention provides a bispecific antigen binding molecule comprising
- (a) two light chains, each comprising the amino acid sequence of SEQ ID NO:62, one light chain comprising the amino acid sequence of SEQ ID NO:61, a first heavy chain comprising the amino acid sequence of SEQ ID NO:63, and a second heavy chain comprising the amino acid sequence of SEQ ID NO:64, or
- (b) two light chains, each comprising the amino acid sequence of SEQ ID NO:66, one light chain comprising the amino acid sequence of SEQ ID NO:65, a first heavy chain comprising the amino acid sequence of SEQ ID NO:67, and a second heavy chain comprising the amino acid sequence of SEQ ID NO:68.

In one particular aspect, the invention provides a bispecific antigen binding molecule comprising
- (a) two light chains, each comprising the amino acid sequence of SEQ ID NO:62, one light chain comprising the amino acid sequence of SEQ ID NO:61, a first heavy chain comprising the amino acid sequence of SEQ ID NO:63, and a second heavy chain comprising the amino acid sequence of SEQ ID NO:64.

Bispecific Antigen Binding Molecules in Head-to-Tail Format (2+1)

In another aspect, provided is a bispecific antigen binding molecule, comprising
- (a) a heavy chain comprising the VH and CH1 domain of a Fab fragment capable of specific binding to CD40 and a Fc region subunit,
- (b) a heavy chain comprising a VH and CH1 domain of a Fab fragment capable of specific binding to CD40, a VL and CH1 domain of a Fab fragment capable of specific binding to FAP and a Fc region subunit,
(c) two light chains, each light chain comprising a VL and CL domain of a Fab fragment capable of specific binding to CD40, and
(d) a light chain comprising a VH and CL domain of a Fab fragment capable of specific binding to FAP.

Bispecific antigen binding molecules bivalent for binding to CD40 and bivalent for binding to the target cell antigen (2+2 format)

In another aspect, the invention provides a bispecific antigen binding molecule comprising
(a) two antigen binding domains capable of specific binding to CD40,
(b) two antigen binding domains capable of specific binding to FAP comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and
(c) a Fc domain composed of a first and a second subunit capable of stable association.

Thus, provided is a bispecific antigen binding molecule, wherein the bispecific antigen binding molecule binds bivalently to CD40 and bivalently to FAP.

In one aspect, provided is a bispecific antigen binding molecule, wherein the bispecific antigen binding molecule comprises
(a) two heavy chains, each heavy chain comprising a VH and CH1 domain of a Fab fragment capable of specific binding to CD40, and a Fc region subunit,
(b) two light chains, each light chain comprising a VL and CL domain of a Fab fragment capable of specific binding to CD40, and
(c) two Fab fragments capable of specific binding to FAP, wherein one of the Fab fragments is connected to the C-terminus of one of the two heavy chains of (a), and the other of the Fab fragments is connected to the C-terminus of the other of the two heavy chains of (a).

Bispecific Antigen Binding Molecules Tetravalent for Binding to CD40 and Monovalent for Binding to the Target Cell Antigen (4+1 Format)

In another aspect, the invention provides a bispecific antigen binding molecule comprising
(a) four antigen binding domains capable of specific binding to CD40,
(b) one antigen binding domain capable of specific binding to FAP comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and
(c) a Fc domain composed of a first and a second subunit capable of stable association.

Thus, provided is a bispecific antigen binding molecule, wherein the bispecific antigen binding molecule binds tetravalently to CD40 and monovalently to FAP.

In one aspect, provided is a bispecific antigen binding molecule, wherein the four antigen binding domains capable of specific binding to CD40 are Fab fragments and each two thereof are fused to each other at the heavy chain, optionally via a peptide linker. In a particular aspect, the peptide linker comprises the amino acid sequence of SEQ ID NO:83. More particularly, the antigen binding molecule comprises two heavy chains comprising each a VHCH1-peptide linker-VHCH1 fragment. In a particular aspect, the peptide linker has the amino acid sequence of SEQ ID NO:83.

In a particular aspect, the bispecific antigen binding molecule comprises
(a) four light chains, each light chain comprising a VL and CL domain of a Fab fragment capable of specific binding to CD40,
(b) two heavy chains, wherein each of the heavy chain comprises a VH and CH1 domain of a Fab fragment capable of specific binding to CD40 fused to a VH and CH1 domain of a second Fab fragment capable of specific binding to CD40, and a Fc region subunit, and
(c) a cross-fab fragment capable of specific binding to FAP, wherein the VH domain is connected via a peptide linker to the C-terminus of one of the heavy chains.

In another aspect, the bispecific antigen binding molecule comprises
(a) four light chains, each light chain comprising a VL and CL domain of a Fab fragment capable of specific binding to CD40,
(b) two heavy chains, wherein each of the heavy chain comprises a VH and CH1 domain of a Fab fragment capable of specific binding to CD40 fused to a VH and CH1 domain of a second Fab fragment capable of specific binding to CD40, and a Fc region subunit, and
(c) a cross-fab fragment capable of specific binding to FAP, wherein the VL domain is connected via a peptide linker to the C-terminus of one of the heavy chains.

In a particular aspect, the peptide linker comprises an amino acid sequence selected from SEQ ID NO:82, SEQ ID NO:83, SEQ ID NO:87 and SEQ ID NO:88. More particularly, the peptide linker comprises the SEQ ID NO:83.

In a particular aspect, the invention provides a bispecific antigen binding molecule comprising
(a) four light chains, each comprising the amino acid sequence of SEQ ID NO:62, one light chain comprising the amino acid sequence of SEQ ID NO:61, a first heavy chain comprising the amino acid sequence of SEQ ID NO:69, and a second heavy chain comprising the amino acid sequence of SEQ ID NO:70.

Bispecific Antigen Binding Molecules Tetravalent for Binding to CD40 and Bivalent for Binding to the Target Cell Antigen (4+2 Format)

In another aspect, the invention provides a bispecific antigen binding molecule comprising
(a) four antigen binding domains capable of specific binding to CD40,
(b) two antigen binding domains capable of specific binding to FAP comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region (V$_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and (c) a Fc domain composed of a first and a second subunit capable of stable association:

Thus, provided is a bispecific antigen binding molecule, wherein the bispecific antigen binding molecule binds tetravalently to CD40 and bivalently to FAP.

In one aspect, provided is a bispecific antigen binding molecule, wherein the four antigen binding domains capable of specific binding to CD40 are Fab fragments and each two thereof are fused to each other, optionally via a peptide linker. In a particular aspect, the peptide linker comprises the amino acid sequence of SEQ ID NO:83. More particularly, the antigen binding molecule comprises two heavy chains comprising each a VHCH1-peptide linker-VHCH1 fragment. In a particular aspect, the peptide linker has the amino acid sequence of SEQ ID NO:83.

In another aspect, a bispecific antigen binding molecule is provided, wherein the antigen binding domains capable of specific binding to a target cell antigen are Fab fragments and wherein the first Fab fragment is connected via a peptide linker to the C-terminus of the first subunit of the Fc domain and the second Fab fragment is connected via a peptide linker to the C-terminus of the second subunit of the Fc domain. In one aspect, the two Fab fragments capable of specific binding to the target cell antigen are crossover Fab fragments each comprising a VL-CH1 chain and a VH-CL chain, and wherein the VL-CH1 chain is connected to the C-terminus of one of the two heavy chains.

Fc Domain Modifications Reducing Fc Receptor Binding and/or Effector Function

The bispecific antigen binding molecules of the invention further comprise a Fc domain composed of a first and a second subunit capable of stable association.

In certain aspects, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

The Fc domain confers favorable pharmacokinetic properties to the bispecific antibodies of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular embodiments the Fc domain of the bispecific antibodies of the invention exhibits reduced binding affinity to an Fc receptor and/or reduced effector function, as compared to a native IgG Fc domain, in particular an IgG1 Fc domain or an IgG4 Fc domain. More particularly, the Fc domain is an IgG1 Fc domain.

In one such aspect the Fc domain (or the bispecific antigen binding molecule of the invention comprising said Fc domain) exhibits less than 50%, preferably less than 20%, more preferably less than 10% and most preferably less than 5% of the binding affinity to an Fc receptor, as compared to a native IgG1 Fc domain (or the bispecific antigen binding molecule of the invention comprising a native IgG1 Fc domain), and/or less than 50%, preferably less than 20%, more preferably less than 10% and most preferably less than 5% of the effector function, as compared to a native IgG1 Fc domain (or the bispecific antigen binding molecule of the invention comprising a native IgG1 Fc domain). In one aspect, the Fc domain (or the bispecific antigen binding molecule of the invention comprising said Fc domain) does not substantially bind to an Fc receptor and/or induce effector function. In a particular aspect the Fc receptor is an Fcγ receptor. In one aspect, the Fc receptor is a human Fc receptor. In one aspect, the Fc receptor is an activating Fc receptor. In a specific aspect, the Fc receptor is an activating human Fcγ receptor, more specifically human FcγRIIIa, FcγRI or FcγRIIa, most specifically human FcγRIIIa. In one aspect, the Fc receptor is an inhibitory Fc receptor. In a specific aspect, the Fc receptor is an inhibitory human Fcγ receptor, more specifically human Fc☐RIIB. In one aspect the effector function is one or more of CDC, ADCC, ADCP, and cytokine secretion. In a particular aspect, the effector function is ADCC. In one aspect, the Fc domain domain exhibits substantially similar binding affinity to neonatal Fc receptor (FcRn), as compared to a native IgG1 Fc domain. Substantially similar binding to FcRn is achieved when the Fc domain (or the the bispecific antigen binding molecule of the invention comprising said Fc domain) exhibits greater than about 70%, particularly greater than about 80%, more particularly greater than about 90% of the binding affinity of a native IgG1 Fc domain (or the bispecific antigen binding molecule of the invention comprising a native IgG1 Fc domain) to FcRn.

In a particular aspect, the Fc domain is engineered to have reduced binding affinity to an Fc receptor and/or reduced effector function, as compared to a non-engineered Fc domain. In a particular aspect, the Fc domain of the bispecific antigen binding molecule of the invention comprises one or more amino acid mutation that reduces the binding affinity of the Fc domain to an Fc receptor and/or effector function. Typically, the same one or more amino acid mutation is present in each of the two subunits of the Fc domain. In one aspect, the amino acid mutation reduces the binding affinity of the Fc domain to an Fc receptor. In another aspect, the amino acid mutation reduces the binding affinity of the Fc domain to an Fc receptor by at least 2-fold, at least 5-fold, or at least 10-fold. In one aspect, the bispecific antigen binding molecule of the invention comprising an engineered Fc domain exhibits less than 20%, particularly less than 10%, more particularly less than 5% of the binding affinity to an Fc receptor as compared to bispecific antibodies of the invention comprising a non-engineered Fc domain. In a particular aspect, the Fc receptor is an Fcγ receptor. In other aspects, the Fc receptor is a human Fc receptor. In one aspect, the Fc receptor is an inhibitory Fc receptor. In a specific aspect, the Fc receptor is an inhibitory human Fcγ receptor, more specifically human Fc☐RIIB. In some aspects the Fc receptor is an activating Fc receptor. In a specific aspect, the Fc receptor is an activating human Fcγ receptor, more specifically human FcγRIIIa, FcγRI or FcγRIIa, most specifically human FcγRIIIa. Preferably, binding to each of these receptors is reduced. In some aspects, binding affinity to a complement component, specifically binding affinity to C1q, is also reduced. In one aspect, binding affinity to neonatal Fc receptor (FcRn) is not reduced. Substantially similar binding to FcRn, i.e. preservation of the binding affinity of the Fc domain to said receptor, is achieved when the Fc domain (or the bispecific antigen binding molecule of the invention comprising said Fc domain) exhibits greater than about 70% of the binding affinity of a non-engineered form of the Fc domain (or the bispecific antigen binding molecule of the invention comprising said non-engineered form of the Fc domain) to FcRn. The Fc domain, or the bispecific antigen binding molecule of the invention comprising said Fc domain, may exhibit greater than about 80% and even greater than about 90% of such affinity. In certain embodiments the Fc domain of the bispecific antigen binding molecule of the invention is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). Certain antibody variants with improved or diminished binding to FcRs are described. (e.g. U.S. Pat. No. 6,737,056; WO 2004/056312, and Shields, R. L. et al., J. Biol. Chem. 276 (2001) 6591-6604).

In one aspect of the invention, the Fc domain comprises an amino acid substitution at a position of E233, L234, L235, N297, P331 and P329. In some aspects, the Fc domain comprises the amino acid substitutions L234A and L235A ("LALA"). In one such embodiment, the Fc domain is an IgG1 Fc domain, particularly a human IgG1 Fc domain. In one aspect, the Fc domain comprises an amino acid substitution at position P329. In a more specific aspect, the amino acid substitution is P329A or P329G, particularly P329G. In one embodiment the Fc domain comprises an amino acid substitution at position P329 and a further amino acid substitution selected from the group consisting of E233P, L234A, L235A, L235E, N297A, N297D or P331S. In more particular embodiments the Fc domain comprises the amino acid mutations L234A, L235A and P329G ("P329G LALA"). The "P329G LALA" combination of amino acid substitutions almost completely abolishes Fcγ receptor binding of a human IgG1 Fc domain, as described in PCT Patent Application No. WO 2012/130831 A1. Said document also describes methods of preparing such mutant Fc domains and methods for determining its properties such as Fc receptor binding or effector functions. Such antibody is an IgG1 with mutations L234A and L235A or with mutations L234A, L235A and P329G (numbering according to EU index of Kabat et al, Kabat et al., Sequences of Proteins of Immunological Interest, 5th Ed. Public Health Service, National Institutes of Health, Bethesda, MD, 1991).

In one aspect, the Fc domain is an IgG4 Fc domain. In a more specific embodiment, the Fc domain is an IgG4 Fc domain comprising an amino acid substitution at position S228 (Kabat numbering), particularly the amino acid substitution S228P. In a more specific embodiment, the Fc domain is an IgG4 Fc domain comprising amino acid substitutions L235E and S228P and P329G. This amino acid substitution reduces in vivo Fab arm exchange of IgG4 antibodies (see Stubenrauch et al., Drug Metabolism and Disposition 38, 84-91 (2010)).

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan, A. R. and Winter, G., Nature 322 (1988) 738-740; U.S. Pat. Nos. 5,648,260; 5,624,821; and WO 94/29351 concerning other examples of Fc region variants.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor. Effector function of an Fc domain, or bispecific antigen binding molecules of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in an animal model such as that disclosed in Clynes et al., Proc Natl Acad Sci USA 95, 652-656 (1998).

The following section describes preferred aspects of the bispecific antigen binding molecules of the invention comprising Fc domain modifications reducing Fc receptor binding and/or effector function. In one aspect, the invention relates to the bispecific antigen binding molecule (a) at least one antigen binding domain capable of specific binding to CD40, (b) at least one antigen binding domain capable of specific binding to FAP, and (c) a Fc domain composed of a first and a second subunit capable of stable association, wherein the Fc domain comprises one or more amino acid substitution that reduces the binding affinity of the antibody to an Fc receptor, in particular towards Fc☐ receptor. In another aspect, the invention relates to the bispecific antigen binding molecule comprising (a) at least one antigen binding domain capable of specific binding to CD40, (b) at least one antigen binding domain capable of specific binding to a target cell antigen, and (c) a Fc domain composed of a first and a second subunit capable of stable association, wherein the Fc domain comprises one or more amino acid substitution that reduces effector function. In particular aspect, the Fc domain is of human IgG1 subclass with the amino acid mutations L234A, L235A and P329G (numbering according to Kabat EU index).

Fc Domain Modifications Promoting Heterodimerization

The bispecific antigen binding molecules of the invention comprise different antigen-binding sites, fused to one or the other of the two subunits of the Fc domain, thus the two subunits of the Fc domain may be comprised in two non-identical polypeptide chains. Recombinant co-expression of these polypeptides and subsequent dimerization leads to several possible combinations of the two polypeptides. To improve the yield and purity of the bispecific antigen binding molecules of the invention in recombinant production, it will thus be advantageous to introduce in the Fc domain of the bispecific antigen binding molecules of the invention a modification promoting the association of the desired polypeptides.

Accordingly, in particular aspects the invention relates to the bispecific antigen binding molecule comprising (a) at least one antigen binding domain capable of specific binding to CD40, (b) at least one antigen binding domain capable of specific binding to FAP, and (c) a Fc domain composed of a first and a second subunit capable of stable association, wherein the Fc domain comprises a modification promoting the association of the first and second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

In a specific aspect said modification is a so-called "knob-into-hole" modification, comprising a "knob" modification in one of the two subunits of the Fc domain and a "hole" modification in the other one of the two subunits of the Fc domain. Thus, the invention relates to the bispecific antigen binding molecule comprising (a) at least one antigen binding domain capable of specific binding to CD40, (b) at least one antigen binding domain capable of specific binding to a target cell antigen, and (c) a Fc domain composed of a first and a second subunit capable of stable association, wherein the first subunit of the Fc domain comprises knobs and the second subunit of the Fc domain comprises holes according to the knobs into holes method. In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in one aspect, in the CH3 domain of the first subunit of the Fc domain of the bispecific antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable. The protuberance and cavity can be made by altering the nucleic acid encoding the polypeptides, e.g. by site-specific mutagenesis, or by peptide synthesis. In a specific aspect, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A).

In yet a further aspect, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter (2001), J Immunol Methods 248, 7-15). In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

The C-terminus of the heavy chain of the bispecific antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG. In one aspect of all aspects as reported herein, a bispecific antibody comprising a heavy chain including a C-terminal CH3 domain as specified herein, comprises the C-terminal glycine-lysine dipeptide (G446 and K447, numbering according to Kabat EU index). In one embodiment of all aspects as reported herein, a bispecific antibody comprising a heavy chain including a C-terminal CH3 domain, as specified herein, comprises a C-terminal glycine residue (G446, numbering according to Kabat EU index).

Modifications in the Fab Domains

In one aspect, the invention relates to a bispecific antigen binding molecule comprising (a) a first Fab fragment capable of specific binding to CD40, (b) a second Fab fragment capable of specific binding to FAP, and (c) a Fc domain composed of a first and a second subunit capable of stable association, wherein in one of the Fab fragments either the variable domains VH and VL or the constant domains CH1 and CL are exchanged. The bispecific antibodies are prepared according to the Crossmab technology.

Multispecific antibodies with a domain replacement/exchange in one binding arm (CrossMabVH-VL or CrossMabCH-CL) are described in detail in WO2009/080252 and Schaefer, W. et al, PNAS, 108 (2011) 11187-1191. They clearly reduce the byproducts caused by the mismatch of a light chain against a first antigen with the wrong heavy chain against the second antigen (compared to approaches without such domain exchange).

In one aspect, the invention relates to a bispecific antigen binding molecule comprising (a) a first Fab fragment capable of specific binding to CD40, (b) a second Fab fragment capable of specific binding to FAP, and (c) a Fc domain composed of a first and a second subunit capable of stable association, wherein in one of the Fab fragments the constant domains CL and CH1 are replaced by each other so that the CH1 domain is part of the light chain and the CL domain is part of the heavy chain. More particularly, in the second Fab fragment capable of specific binding to a target cell antigen the constant domains CL and CH1 are replaced by each other so that the CH1 domain is part of the light chain and the CL domain is part of the heavy chain.

In a particular aspect, the invention relates a bispecific antigen binding molecule comprising (a) a first Fab fragment capable of specific binding to CD40, (b) a second Fab fragment capable of specific binding to FAP, wherein the constant domains CL and CH1 are replaced by each other so that the CH1 domain is part of the light chain and the CL domain is part of the heavy chain. Such a molecule binds monovalently to both CD40 and FAP.

In another aspect, the invention relates to a bispecific antigen binding molecule, comprising (a) two light chains and two heavy chains of an antibody comprising two Fab fragments capable of specific binding to CD40 and the Fc domain, and (b) two additional Fab fragments capable of specific binding to FAP, wherein said additional Fab fragments are each connected via a peptide linker to the C-terminus of the heavy chains of (a). In a particular aspect, the additional Fab fragments are Fab fragments, wherein the variable domains VL and VH are replaced by each other so that the VH domain is part of the light chain and the VL domain is part of the heavy chain.

Thus, in a particular aspect, the invention comprises a bispecific antigen binding molecule, comprising (a) two light chains and two heavy chains of an antibody comprising two Fab fragments capable of specific binding to CD40 and the Fc domain, and (b) two additional Fab fragments capable of specific binding to FAP, wherein said two additional Fab fragments capable of specific binding to a target cell antigen are crossover Fab fragments wherein the variable domains VL and VH are replaced by each other and the VL-CH chains are each connected via a peptide linker to the C-terminus of the heavy chains of (a).

In another aspect, and to further improve correct pairing, the bispecific antigen binding molecule comprising (a) a first Fab fragment capable of specific binding to CD40, (b) a second Fab fragment capable of specific binding to FAP, and (c) a Fc domain composed of a first and a second subunit capable of stable association, can contain different charged amino acid substitutions (so-called "charged residues"). These modifications are introduced in the crossed or non-crossed CH1 and CL domains. In a particular aspect, the invention relates to a bispecific antigen binding molecule, wherein in one of CL domains the amino acid at position 123 (EU numbering) has been replaced by arginine (R) and/or wherein the amino acid at position 124 (EU numbering) has been substituted by lysine (K) and wherein in one of the CH1 domains the amino acids at position 147 (EU numbering) and/or at position 213 (EU numbering) have been substituted by glutamic acid (E).

Exemplary Antibodies of the Invention

In one aspect, the invention provides new antibodies and antibody fragments that specifically bind to FAP. These antibodies bind to a different epitope than the known FAP antibodies 4B) or 28H1 that make them especially suitable for the incorporation into bispecific antigen binding molecules that can be used in combination with other FAP-targeted molecules. The new antibodies are further characterized in that they are producable in high amounts and with high titers, that they show high thermal stability (as measured by the aggregation temperature $T_{agg}$), that they are supposed to possess excellent PK properties and that they bind with high affinity to human FAP as measured by Biacore assay.

In one aspect, provided is an antibody that specifically binds to FAP (clone 212), wherein said antibody comprises a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8.

In one aspect, provided is a humanized antibody that specifically binds to FAP, wherein said antibody comprises a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8.

In another aspect, provided is an antibody that competes for binding with an antibody that specifically binds to FAP, wherein said antibody comprises any of the heavy chain variable regions ($V_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and any of the light chain variable regions ($V_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26.

In one aspect, provided is an antibody that competes for binding with an antibody that specifically binds to FAP, wherein said antibody comprises a heavy chain variable region VH comprising an amino acid sequence of SEQ ID NO:15 and a light chain variable region VL comprising an amino acid sequence of SEQ ID NO:21.

In a further aspect, provided is an antibody that specifically binds to FAP, wherein said antibody comprises (a) a heavy chain variable region ($V_H$FAP) comprising the amino acid sequence of SEQ ID NO:15 and a light chain variable region ($V_L$FAP) comprising the amino acid sequence of SEQ ID NO:21, (b) a heavy chain variable region ($V_H$FAP) comprising the amino acid sequence of SEQ ID NO:16 and a light chain variable region ($V_L$FAP) comprising the amino acid sequence of SEQ ID NO:21, (c) a heavy chain variable region ($V_H$FAP) comprising the amino acid sequence of SEQ ID NO:16 and a light chain variable region ($V_L$FAP) comprising the amino acid sequence of SEQ ID NO:22, or (d) a heavy chain variable region ($V_H$FAP) comprising the amino acid sequence of SEQ ID NO:19 and a light chain variable region ($V_L$FAP) comprising the amino acid sequence of SEQ ID NO:25.

In a further aspect, provided is an antibody that specifically binds to FAP comprising a heavy chain variable region ($V_H$FAP) comprising the amino acid sequence of SEQ ID NO:15 and a light chain variable region ($V_L$FAP) comprising the amino acid sequence of SEQ ID NO:21.

Polynucleotides

The invention further provides isolated nucleic acid encoding a bispecific antigen binding molecule as described herein or a fragment thereof or isolated nucleic acid encoding an antibody as described herein.

The isolated polynucleotides encoding bispecific antigen binding molecules of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin.

In some aspects, the isolated polynucleotide encodes a polypeptide comprised in the bispecific molecule according to the invention as described herein.

In one aspect, the present invention is directed to an isolated polynucleotide encoding a bispecific antigen binding molecule, comprising (a) at least one antigen binding domain capable of specific binding to CD40, (b) at least one antigen binding domain capable of specific binding to a FAP comprising a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and (c) a Fc domain composed of a first and a second subunit capable of stable association In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Bispecific antigen binding molecules of the invention may be obtained, for example, by recombinant production. For recombinant production one or more polynucleotide encoding the bispecific antigen binding molecule or polypeptide fragments thereof are provided. The one or more polynucleotide encoding the bispecific antigen binding molecule are isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the bispecific antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the bispecific antigen binding molecule or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the bispecific antigen binding molecule of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the bispecific antigen binding molecule or polypeptide fragments thereof is desired, DNA encoding a signal sequence may be placed upstream of the nucleic acid encoding the bispecific antigen binding molecule of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the fusion protein may be included within or at the ends of the polynucleotide encoding a bispecific antigen binding molecule of the invention or polypeptide fragments thereof.

In a further aspect of the invention, a host cell comprising one or more polynucleotides of the invention is provided. In certain aspects, a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) a bispecific antigen binding molecule of the invention of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr-CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell). Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one aspect, a method of producing a bispecific antigen binding molecule of the invention or polypeptide fragments thereof is provided, wherein the method comprises culturing a host cell comprising polynucleotides encoding the bispecific antigen binding molecule of the invention or polypeptide fragments thereof, as provided herein, under conditions suitable for expression of the bispecific antigen binding molecule of the invention or polypeptide fragments thereof, and recovering the bispecific antigen binding molecule of the invention or polypeptide fragments thereof from the host cell (or host cell culture medium).

Bispecific molecules of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the bispecific antigen binding molecule binds. For example, for affinity chromatography purification of fusion proteins of the invention, a matrix with protein A or protein G may be used. Sequential Protein A or G affinity chromatography and size exclusion chromatography can be used to isolate an antigen binding molecule essentially as described in the examples. The purity of the bispecific antigen binding molecule or fragments thereof can be determined by any of a variety of well-known analytical methods including gel electrophoresis, high pressure liquid chromatography, and the like. For example, the bispecific antigen binding molecules expressed as described in the Examples were shown to be intact and properly assembled as demonstrated by reducing and non-reducing SDS-PAGE.

Assays

The antigen binding molecules provided herein may be characterized for their binding properties and/or biological activity by various assays known in the art. In particular, they are characterized by the assays described in more detail in the examples.

1. Binding Assay

Binding of the bispecific antigen binding molecule provided herein to the corresponding target expressing cells may be evaluated for example by using a murine fibroblast cell line expressing human Fibroblast Activation Protein (FAP) and flow cytometry (FACS) analysis. Binding of the bispecific antigen binding molecules provided herein to CD40 may be determined by using primary B cells as described in Example 4.2.

2. Activity Assays

Bispecific antigen binding molecules of the invention are tested for biological activity. Biological activity may include efficacy and specificity of the bispecific antigen binding molecules. Efficacy and specificity are demonstrated by assays showing agonistic signaling through the CD40 receptor upon binding of the target antigen. Furthermore, in vitro T cell priming assays are conducted using dendritic cells (DCs) that have been incubated with the bispecific antigen binding molecules.

Pharmaceutical Compositions, Formulations and Routes of Administration

In a further aspect, the invention provides pharmaceutical compositions comprising any of the bispecific antigen binding molecules provided herein, e.g., for use in any of the below therapeutic methods. In one embodiment, a pharmaceutical composition comprises any of the bispecific antigen binding molecules provided herein and at least one pharmaceutically acceptable excipient. In another embodiment, a pharmaceutical composition comprises any of the bispecific antigen binding molecules provided herein and at least one additional therapeutic agent, e.g., as described below.

Pharmaceutical compositions of the present invention comprise a therapeutically effective amount of one or more bispecific antigen binding molecules dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one bispecific antigen binding molecule according to the invention and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intra-lesional, intravenous, intra-arterial, intramuscular, intrathecal or intraperitoneal injection. For injection, the bispecific antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the bispecific antigen binding molecules may be in powder form for constitution with a suitable vehicle, e.g., sterile pyrogen-free water, before use. Sterile injectable solutions are prepared by incorporating the antigen binding molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

In addition to the compositions described previously, the antigen binding molecules may also be formulated as a depot preparation. Such long acting formulations may be administered by implantation (for example subcutaneously or intramuscularly) or by intramuscular injection. Thus, for example, the fusion proteins may be formulated with suitable polymeric or hydrophobic materials (for example as emulsion in an acceptable oil) or ion exchange resins, or as sparingly soluble derivatives, for example, as a sparingly soluble salt.

Pharmaceutical compositions comprising the bispecific antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The bispecific antigen binding molecules may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The composition herein may also contain more than one active ingredients as necessary for the particular indication being treated, preferably those with complementary activities that do not adversely affect each other. Such active ingredients are suitably present in combination in amounts that are effective for the purpose intended.

The formulations to be used for in vivo administration are generally sterile. Sterility may be readily accomplished, e.g., by filtration through sterile filtration membranes.

Therapeutic Methods and Compositions

Any of the bispecific antigen binding molecules provided herein may be used in therapeutic methods. For use in therapeutic methods, bispecific antigen binding molecules of the invention can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, bispecific antigen binding molecules of the invention for use as a medicament are provided.

In further aspects, bispecific antigen binding molecules of the invention for use (i) in inducing immune stimulation by CD40+ antigen-presenting cells (APCs), (ii) in stimulating tumor-specific T cell response, (iii) in causing apoptosis of tumor cells, (iv) in the treatment of cancer, (v) in delaying progression of cancer, (vi) in prolonging the survival of a patient suffering from cancer, (vii) in the treatment of infections are provided. In a particular aspect, bispecific antigen binding molecules of the invention for use in treating a disease, in particular for use in the treatment of cancer, are provided.

In certain aspects, bispecific antigen binding molecules of the invention for use in a method of treatment are provided. In one aspect, the invention provides a bispecific antigen binding molecule as described herein for use in the treatment of a disease in an individual in need thereof. In certain aspects, the invention provides a bispecific antigen binding molecule for use in a method of treating an individual having a disease comprising administering to the individual a therapeutically effective amount of the bispecific antigen binding molecule. In certain aspects the disease to be treated is cancer. The subject, patient, or "individual" in need of treatment is typically a mammal, more specifically a human.

In one aspect, provided is a method for i) inducing immune stimulation by CD40+ antigen-presenting cells (APCs), (ii) stimulating tumor-specific T cell response, (iii) causing apoptosis of tumor cells, (iv) treating of cancer, (v) delaying progression of cancer, (vi) prolonging the survival of a patient suffering from cancer, or (vii) treating of infections, wherein the method comprises administering a therapeutically effective amount of the bispecific antigen binding molecule of the invention to an individual in need thereof.

In a further aspect, the invention provides for the use of the bispecific antigen binding molecule of the invention in the manufacture or preparation of a medicament for the treatment of a disease in an individual in need thereof. In one aspect, the medicament is for use in a method of treating a disease comprising administering to an individual having the disease a therapeutically effective amount of the medicament. In certain aspects, the disease to be treated is a proliferative disorder, particularly cancer. Examples of cancers include, but are not limited to, bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other examples of cancer include carcinoma, lymphoma (e.g., Hodgkin's and non-Hodgkin's lymphoma), blastoma, sarcoma, and leukemia. Other cell proliferation disorders that can be treated using the bispecific antigen binding molecule or antibody of the invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan readily recognizes that in many cases the bispecific antigen binding molecule or antibody of the invention may not provide a cure but may provide a benefit. In some aspects, a physiological change having some benefit is also considered therapeutically beneficial. Thus, in some aspects, an amount of the bispecific antigen binding molecule or antibody of the invention that provides a physiological change is considered an "effective amount" or a "therapeutically effective amount".

For the prevention or treatment of disease, the appropriate dosage of a bispecific antigen binding molecule of the invention (when used alone or in combination with one or more other additional therapeutic agents) will depend on the type of disease to be treated, the route of administration, the body weight of the patient, the specific molecule, the severity and course of the disease, whether the bispecific antigen binding molecule of the invention is administered for preventive or therapeutic purposes, previous or concurrent therapeutic interventions, the patient's clinical history and response to the bispecific antigen binding molecule, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The bispecific antigen binding molecule of the invention is suitably administered to the patient at one time or over a series of treatments. Depending on the type and severity of the disease, about 1 µg/kg to 15 mg/kg (e.g. 0.1 mg/kg-10 mg/kg) of the bispecific antigen binding molecule can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the bispecific antigen binding molecule of the invention would be in the range from about 0.005 mg/kg to about 10 mg/kg. In other examples, a dose may also comprise from about 1 µg/kg body weight, about 5 µg/kg body weight, about 10 µg/kg body weight, about 50 µg/kg body weight, about 100 µg/kg body weight, about 200 µg/kg body weight, about 350 µg/kg body weight, about 500 µg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In examples of a derivable range from the numbers listed herein, a range of about 0.1 mg/kg body weight to about 20 mg/kg body weight, about 5 µg/kg body weight to about 1 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion protein). In a particular aspect, the bispecific antigen binding molecule will be administered every three weeks. An initial higher loading dose, followed by one or more lower doses may be administered. However, other dosage regimens may be useful. The progress of this therapy is easily monitored by conventional techniques and assays.

The bispecific antigen binding molecule of the invention will generally be used in an amount effective to achieve the intended purpose. For use to treat or prevent a disease condition, the bispecific antigen binding molecule of the invention, or pharmaceutical compositions thereof, are administered or applied in a therapeutically effective amount. Determination of a therapeutically effective amount is well within the capabilities of those skilled in the art, especially in light of the detailed disclosure provided herein. For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the bispecific antigen binding molecule of the invention which are sufficient to maintain therapeutic effect. Usual patient dosages for administration by injection range from about 0.1 to 50 mg/kg/day, typically from about 0.1 to 1 mg/kg/day. Therapeutically effective plasma levels may be achieved by administering multiple doses each day. Levels in plasma may be measured, for example, by HPLC. In cases of local administration or selective uptake, the effective local concentration of the bispecific antigen binding molecule or antibody of the invention may not be related to plasma concentration. One skilled in the art will be able to optimize therapeutically effective local dosages without undue experimentation.

A therapeutically effective dose of the bispecific antigen binding molecule of the invention described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Bispecific antigen binding molecules that exhibit large therapeutic indices are preferred. In one aspect, the bispecific antigen binding molecule or antibody of the invention exhibits a high therapeutic index. The data obtained from cell culture assays and animal studies can be used in formulating a range of dosages suitable for use in humans. The dosage lies preferably within a range of circulating concentrations that include the ED50 with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with fusion proteins of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The bispecific antigen binding molecule of the invention may be administered in combination with one or more other agents in therapy. For instance, the bispecific antigen binding molecule or antibody of the invention of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent. In certain aspects, an additional therapeutic agent is an immunomodulatory agent, a cytostatic agent, an inhibitor of cell adhesion, a cytotoxic or cytostatic agent, an activator of cell apoptosis, or an agent that increases the sensitivity of cells to apoptotic inducers.

Thus, provided are bispecific antigen binding molecules of the invention or pharmaceutical compositions comprising them for use in the treatment of cancer, wherein the bispecific antigen binding molecule is administered in combination with a chemotherapeutic agent, radiation and/or other agents for use in cancer immunotherapy.

Such other agents are suitably present in combination in amounts that are effective for the purpose intended. The effective amount of such other agents depends on the amount of fusion protein used, the type of disorder or treatment, and other factors discussed above. The bispecific antigen binding molecule or antibody of the invention are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the bispecific antigen binding molecule or antibody of the invention can occur prior to, simultaneously, and/or following, administration of the additional therapeutic agent and/or adjuvant.

In a further aspect, provided is the bispecific antigen binding molecule as described herein before for use in the treatment of cancer, wherein the bispecific antigen binding molecule is administered in combination with another immunomodulator.

The term "immunomodulator" refers to any substance including a monoclonal antibody that effects the immune system. The molecules of the inventions can be considered immunomodulators. Immunomodulators can be used as antineoplastic agents for the treatment of cancer. In one aspect, immunomodulators include, but are not limited to anti-CTLA4 antibodies (e.g. ipilimumab), anti-PD1 antibodies (e.g. nivolumab or pembrolizumab), PD-L1 antibodies (e.g. atezolizumab, avelumab or durvalumab), OX-40 antibodies, 4-1BB antibodies and GITR antibodies. In a further aspect, provided is the bispecific antigen binding molecule as described herein before for use in the treatment of cancer, wherein the bispecific antigen binding molecule is administered in combination with an agent blocking PD-L1/PD-1 interaction. In one aspect, the agent blocking PD-L1/PD-1 interaction is an anti-PD-L1 antibody or an anti-PD1 antibody. More particularly, the agent blocking PD-L1/PD-1 interaction is an anti-PD-L1 antibody, in particular an anti-PD-L1 antibody selected from the group consisting of atezolizumab, durvalumab, pembrolizumab and nivolumab. In one specific aspect, the agent blocking PD-L1/PD-1 interaction is atezolizumab (MPDL3280A, RG7446). In another aspect, the agent blocking PD-L1/PD-1 interaction is an anti-PD-L1 antibody comprising a heavy chain variable domain VH(PDL-1) of SEQ ID NO:107 and a light chain variable domain VL(PDL-1) of SEQ ID NO:108. In another aspect, the agent blocking PD-L1/PD-1 interaction is an anti-PD-L1 antibody comprising a heavy chain variable domain VH(PDL-1) of SEQ ID NO:109 and a light chain variable domain VL(PDL-1) of SEQ ID NO:110. In another aspect, the agent blocking PD-L1/PD-1 interaction is an anti-PD1 antibody, in particular an anti-PD1 antibody selected from pembrolizumab or nivolumab. Such other agents are suitably present in combination in amounts that are effective for the purpose intended. The effective amount of such other agents depends on the amount of bispecific antigen binding molecule used, the type of disorder or treatment, and other factors discussed above. The bispecific antigen binding molecules as described herein before are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the bispecific antigen binding molecule can occur prior to, simultaneously, and/or following, administration of the additional therapeutic agent and/or adjuvant.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific antigen binding molecule of the invention.

The label or package insert indicates that the composition is used for treating the condition of choice. Moreover, the article of manufacture may comprise (a) a first container with a composition contained therein, wherein the composition comprises a bispecific antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE B (Sequences):

| SEQ ID NO: | Name | Sequence |
|---|---|---|
| 1 | hu CD40 | UniProt no. P25942, version 200<br>MVRLPLQCVL WGCLLTAVHP<br>EPPTACREKQ YLINSQCCSL<br>CQPGQKLVSD CTEFTETECL PCGESEFLDT<br>WNRETHCHQH KYCDPNLGLR<br>VQQKGTSETD TICTCEEGWH<br>CTSEACESCV LHRSCSPGFG<br>VKQIATGVSD TICEPCPVGF FSNVSSAFEK<br>CHPWTSCETK DLVVQQAGTN<br>KTDVVCGPQD RLRALVVIPI IFGILFAILL<br>VLVFIKKVAK KPTNKAPHPK<br>QEPQEINFPD DLPGSNTAAP<br>VQETLHGCQP VTQEDGKESR ISVQERQ |
| 2 | hu FAP | UniProt no. Q12884, version 168<br>MKTWVKIVFG VATSAVLALL<br>VMCIVLRPSR VHNSEENTMR<br>ALTLKDILNG TFSYKTFFPN WISGQEYLHQ |

TABLE B-continued (Sequences):

| SEQ ID NO: | Name | Sequence |
|---|---|---|
| | | SADNNIVLYN IETGQSYTIL SNRTMKSVNA SNYGLSPDRQ FVYLESDYSK LWRYSYTATY YIYDLSNGEF VRGNELPRPI QYLCWSPVGS KLAYVYQNNI YLKQRPGDPP FQITFNGREN KIFNGIPDWV YEEEMLATKY ALWWSPNGKF LAYAEFNDTD IPVIAYSYYG DEQYPRTINI PYPKAGAKNP VVRIFIIDTT YPAYVGPQEV PVPAMIASSD YYFSWLTWVT DERVCLQWLK RVQNVSVLSI CDFREDWQTW DCPKTQEHIE ESRTGWAGGF FVSTPVFSYD AISYYKIFSD KDGYKHIHYI KDTVENAIQI TSGKWEAINI FRVTQDSLFY SSNEFEEYPG RRNIYRISIG SYPPSKKCVT CHLRKERCQY YTASFSDYAK YYALVCYGPG IPISTLHDGR TDQEIKILEE NKELENALKN IQLPKEEIKK LEVDEITLWY KMILPPQFDR SKKYPLLIQV YGGPCSQSVR SVFAVNWISY LASKEGMVIA LVDGRGTAFQ GDKLLYAVYR KLGVYEVEDQ ITAVRKFIEM GFIDEKRIAI WGWSYGGYVS SLALASGTGL FKCGIAVAPV SSWEYYASVY TERFMGLPTK DDNLEHYKNS TVMARAEYFR NVDYLLIFIGT ADDNVHFQNS AQIAKALVNA QVDFQAMWYS DQNHGLSGLS TNHLYTHMTH FLKQCFSLSD |
| 3 | FAP (212) CDR-H1 | DYNMD |
| 4 | FAP (212) CDR-H2 | DIYPNTGGTIYNQKFKG |
| 5 | FAP (212) CDR-H3 | FRGIHYAMDY |
| 6 | FAP (212) CDR-L1 | RASESVDNYGLSFIN |
| 7 | FAP (212) CDR-L2 | GTSNRGS |
| 8 | FAP (212) CDR-L3 | QQSNEVPYT |
| 9 | FAP (212) VH | EVLLQQSGPELVKPGASVKIACKASGYTLT DYNMDWVRQSHGKSLEWIGDIYPNTGGTI YNQKFKGKATLTIDKSSSTAYMDLRSLTSE DTAVYYCTRFRGIHYAMDYWGQGTSVTV SS |
| 10 | FAP (212) VL | DIVLTQSPVSLAVSLGQRATISCRASESVDN YGLSFINWFQQKPGQPPKLLIYGTSNRGSG VPARFSGSGSGTDFSLNIHPMEEDDTAMYF CQQSNEVPYTFGGGTNLEIK |
| 11 | FAP (VH1G3a) CDR-H2 | DIYPNTGGTIYAQKFQG |
| 12 | FAP (VH2G3a) CDR-H2 | DIYPNTGGTIYADSVKG |
| 13 | FAP (VL1G3a) CDR-L1 | RASESVDNYGLSFLA |
| 14 | FAP (VL2G3a) CDR-L1 | RASESIDNYGLSFLN |
| 15 | FAP (VH1G1a) | See Table 10 |
| 16 | FAP (VH1G2a) | See Table 10 |
| 17 | FAP (VH1G3a) | See Table 10 |
| 18 | FAP (VH2G1a) | See Table 10 |
| 19 | FAP (VH2G2a) | See Table 10 |
| 20 | FAP (VH2G3a) | See Table 10 |
| 21 | FAP (VL1G1a) | See Table 10 |

TABLE B-continued (Sequences):

| SEQ ID NO: | Name | Sequence |
|---|---|---|
| 22 | FAP (VL1G2a) | See Table 10 |
| 23 | FAP (VL1G3a) | See Table 10 |
| 24 | FAP (VL2G1a) | See Table 10 |
| 25 | FAP (VL2G2a) | See Table 10 |
| 26 | FAP (VL2G3a) | See Table 10 |
| 27 | hu CD40 CDR-H1 | GYYIH |
| 28 | hu CD40 CDR-H2 | RVIPNAGGTSYNQKFKG |
| 29 | hu CD40 CDR-H3 | EGIYW |
| 30 | hu CD40 CDR-L1 | RSSQSLVHSNGNTFLH |
| 31 | hu CD40 CDR-L2 | TVSNRFS |
| 32 | hu CD40 CDR-L3 | SQTTHVPWT |
| 33 | hu CD40 VH | EVQLVESGGGLVQPGGSLRLSCAASGYSFT GYYIEWVRQAPGKGLEWVARVIPNAGGTS YNQKFKGRFTLSVDNSKNTAYLQMNSLRA EDTAVYYCAREGIYWWGQGTLVTVSS |
| 34 | hu CD40 VL | DIQMTQSPSSLSASVGDRVTITCRSSQSLVH SNGNTFLHWYQQKPGKAPKLLIYTVSNRFS GVPSRFSGSGSGTDFTLTISSLQPEDFATYF CSQTTHVPWTFGQGTKVEIK |
| 35 | CD40 (S2C6) VH | EVQLQQSGPD LVKPGASVKI SCKASGYSFT GYYIHWVKQS HGKSLEWIGR VIPNNGGTSY NQKFKGKAIL TVDKSSSTAY MELRSLTSED SAVYYCAREG IYWWGHGTTL TVSS |
| 36 | CD40 (S2C6) VL | DVVVTQTPLS LPVSLGAQAS ISCRSSQSLV HSNGNTFLHW YLQKPGQSPK LLIYTVSNRF SGVPDRFSGS GSGTDFTLKI SRVEAEDLGV YFCSQTTHVP WTFGGGTKLE IQ |
| 37 | VH1a (CD40) | see Table 17 |
| 38 | VH1b (CD40) | see Table 17 |
| 39 | VH1c (CD40) | see Table 17 |
| 40 | VH1d (CD40) | see Table 17 |
| 41 | VL1a (CD40) | see Table 17 |
| 42 | VL1b (CD40) | see Table 17 |
| 43 | VL1c (CD40) | see Table 17 |
| 44 | VL1d (CD40) | see Table 17 |
| 45 | VH2a (CD40) | see Table 18 |
| 46 | VH2b (CD40) | see Table 18 |
| 47 | VH2c (CD40) | see Table 18 |
| 48 | VH2d (CD40) | see Table 18 |
| 49 | VH2ab (CD40) | see Table 18 |
| 50 | VH2ac (CD40) | see Table 18 |
| 51 | VL2a (CD40) | see Table 18 |

TABLE B-continued (Sequences):

| SEQ ID NO: | Name | Sequence |
|---|---|---|
| 52 | VL2b (CD40) | see Table 18 |
| 53 | VL2ab (CD40) | see Table 18 |
| 54 | VL2ac (CD40) | see Table 18 |
| 55 | P1AE0400 heavy chain | see Table 20 |
| 56 | P1AE0400 light chain | see Table 20 |
| 57 | P1AE0403 heavy chain | see Table 20 |
| 58 | P1AE0403 light chain | see Table 20 |
| 59 | P1AE0817 heavy chain | see Table 20 |
| 60 | P1AE0817 light chain | see Table 20 |
| 61 | (P1AE1689) light chain cross VH-Ckappa | see Table 24 |
| 62 | VL1a (CD40) light chain (charged) | see Table 24 |
| 63 | VH1a (CD40) (VHCH1 charged) Fc knob_PGLALA_(P1AE1689)(VL-CH1) | see Table 24 |
| 64 | VH1a (CD40) (VHCH1 charged) Fc hole_PGLALA | see Table 24 |
| 65 | (P1AE1689) light chain cross VL-CH1 | see Table 24 |
| 66 | VL1a (CD40) light chain | see Table 24 |
| 67 | VH1a (CD40) (VHCH1) Fc knob_PGLALA_(P1AE1689)(VH-Ckappa) | see Table 24 |
| 68 | VH1a (CD40) (VHCH1) Fc hole_PGLALA | see Table 24 |
| 69 | VH1a (CD40) (VHCH1 charged_VH1a (CD40) (VHCH1 charged)-Fc knob_PGLALA_(P1AE1689)(VL-CH1) | see Table 24 |
| 70 | VH1a (CD40) (VHCH1 charged)_VH1a (CD40) (VHCH1 charged)-Fc hole_PGLALA | see Table 24 |
| 71 | 4B9 light chain cross VL-CH1 | see Table 24 |
| 72 | VH1a (CD40) (VHCH1) Fc knob_PGLALA_4B9 (VH-Ckappa) | see Table 24 |
| 73 | VH1a (CD40) (VHCH1)_VH1a (CD40) (VHCH1)-Fc knob_PGLALA_(4B9)(VH-Ckappa) | see Table 24 |
| 74 | VH1a (CD40) (VHCH1)_VH1a (CD40) (VHCH1)-Fc hole_PGLALA | see Table 24 |
| 75 | 28H1 light chain cross VH-Ckappa | see Table 24 |

TABLE B-continued (Sequences):

| SEQ ID NO: | Name | Sequence |
|---|---|---|
| 76 | VH1a (CD40) (VHCH1 charged) Fc knob_PGLALA_28H1 (VL-CH1) | see Table 24 |
| 77 | VH1a (CD40) (VHCH1 charged)_VH1a (CD40) (VHCH1 charged) Fc knob_PGLALA_28H1 (VL-CH1) | see Table 24 |
| 78 | hu FAP ectodomain+poly-lys-tag+hs$_6$-tag | RPSRVHNSEENTMRALTLKDILNGTFSYKT FFPNWISGQEYLHQSADNNIVLYNIETGQS YTILSNRTMKSVNASNYGLSPDRQFVYLES DYSKLWRYSYTATYYIYDLSNGEFVRGNE LPRPIQYLCWSPVGSKLAYVYQNNIYLKQR PGDPPFQITFNGRENKIFNGIPDWVYEEEML ATKYALWWSPNGKFLAYAEFNDTDIPVIA YSYYGDEQYPRTINIPYPKAGAKNPVVRIFI IDTTYPAYVGPQEVPVPAMIASSDYYFSWL TWVTDERVCLQWLKRVQNVSVLSICDFRE DWQTWDCPKTQEHIEESRTGWAGGFFVST PVFSYDAISYYKIFSDKDGYKHIHYIKDTVE NAIQITSGKWEAINIFRVTQDSLFYSSNEFEE YPGRRNIYRISIGSYPPSKKCVTCHLRKERC QYYTASFSDYAKYYALVCYGPGIPISTLHD GRTDQEIKILEENKELENALKNIQLPKEEIK KLEVDEITLWYKMILPPQFDRSKKYPLLIQ VYGGPCSQSVRSVFAVNWISYLASKEGMV IALVDGRGTAFQGDKLLYAVYRKLGVYEV EDQITAVRKFIEMGFIDEKRIAIWGWSYGG YVSSLALASGTGLFKCGIAVAPVSSWEYYA SVYTERFMGLPTKDDNLEHYKNSTVMARA EYFRNVDYLLIHGTADDNVHFQNSAQIAK ALVNAQVDFQAMWYSDQNHGLSGLSTNH LYTHMTHFLKQCFSLSDGKKKKKGHHH HHH |
| 79 | mouse FAP | UniProt no. P97321 |
| 80 | Murine FAP ectodomain+poly-lys-tag+his$_6$-tag | RPSRVYKPEGNTKRALTLKDILNGTFSYKT YFPNWISEQEYLHQSEDDNIVFYNIETRESY IILSNSTMKSVNATDYGLSPDRQFVYLESD YSKLWRYSYTATYYIYDLQNGEFVRGYEL PRPIQYLCWSPVGSKLAYVYQNNIYLKQRP GDPPFQITYTGRENRIFNGIPDWVYEEEML ATKYALWWSPDGKFLAYVEFNDSDIPIIAY SYYGDGQYPRTINIPYPKAGAKNPVVRVFI VDTTYPHHVGPMEVPVPEMIASSDYYFSW LTWVSSERVCLQWLKRVQNVSVLSICDFR EDWHAWECPKNQEHVEESRTGWAGGFFV STPAFSQDATSYYKIFSDKDGYKHIHYIKDT VENAIQITSGKWEAIYIFRVTQDSLFYSSNE FEGYPGRRNIYRISIGNSPPSKKCVTCHLRK ERCQYYTASFSYKAKYYALVCYGPGLPIST LHDGRTDQEIQVLEENKELENSLRNIQLPK VEIKKLKDGGLTFWYKMILPPQFDRSKKYP LLIQVYGGPCSQSVKSVFAVNWITYLASKE GIVIALVDGRGTAFQGDKFLHAVYRKLGV YEVEDQLTAVRKFIEMGFIDEERIAIWGWS YGGYVSSLALASGTGLFKCGIAVAPVSSWE YYASIYSERFMGLPTKDDNLEHYKNSTVM ARAEYFRNVDYLLIHGTADDNVHFQNSAQ IAKALVNAQVDFQAMWYSDQNHGILSGRS QNHLYTHMTHFLKQCFSLSDGKKKKKG HHHHHH |
| 81 | Cynomolgus FAP ectodomain+poly-lys-tag+his$_6$-tag | RPPRVHNSEENTMRALTLKDILNGTFSYKT FFPNWISGQEYLHQSADNNIVLYNIETGQS YTILSNRTMKSVNASNYGLSPDRQFVYLES DYSKLWRYSYTATYYIYDLSNGEFVRGNE LPRPIQYLCWSPVGSKLAYVYQNNIYLKQR PGDPPFQITFNGRENKIFNGIPDWVYEEEML ATKYALWWSPNGKFLAYAEFNDTDIPVIA |

TABLE B-continued (Sequences):

| SEQ ID NO: | Name | Sequence |
|---|---|---|
| | | YSYYGDEQYPRTINIPYPKAGAKNPFVRIFII DTTYPAYVGPQEVPVPAMIASSDYYFSWL TWVTDERVCLQWLKRVQNVSVLSICDFRE DWQTWDCPKTQEHIEESRTGWAGGFFVST PVFSYDAISYYKIFSDKDGYKHIHYIKDTVE NAIQITSGKWEAINIFRVTQDSLFYSSNEFE DYPGRRNIYRISIGSYPPSKKCVTCHLRKER CQYYTASFSDYAKYYALVCYGPGIPISTLH DGRTDQEIKILEENKELENALKNIQLPKEEI KKLEVDEITLWYKMILPPQFDRSKKYPLLI QVYGGPCSQSVRSVFAVNWISYLASKEGM VIALVDGRGTAFQGDKLLYAVYRKLGVYE VEDQITAVRKFIEMGFIDEKRIAIWGWSYG GYVSSLALASGTGLFKCGIAVAPVSSWEYY ASVYTERFMGLPTKDDNLEHYKNSTVMAR AEYFRNVDYLLIHGTADDNVHFQNSAQIA KALVNAQVDFQAMWYSDQNHGLSGLSTN HLYTHMTHFLKQCFSLSDGKKKKKKGHH HHHH |
| 82 | Peptide linker (G45) | GGGGS |
| 83 | Peptide linker (G45)2 | GGGGSGGGGS |
| 84 | Peptide linker (5G4)2 | SGGGGSGGGG |
| 85 | Peptide linker G4(5G4)2 | GGGGSGGGGSGGGG |
| 86 | peptide linker | GSPGSSSSGS |
| 87 | (G4S)$_3$ peptide linker | GGGGSGGGGSGGGGS$_3$ |
| 88 | (G4S)$_4$ peptide linker | GGGGSGGGGSGGGGSGGGGS |
| 89 | peptide linker | GSGSGSGS |
| 90 | peptide linker | GSGSGNGS |
| 91 | peptide linker | GGSGSGSG |
| 92 | peptide linker | GGSGSG |
| 93 | peptide linker | GGSG |
| 94 | peptide linker | GGSGNGSG |
| 95 | peptide linker | GGNGSGSG |
| 96 | peptide linker | GGNGSG |
| 97 | Fc knob chain | DKTHTCPPCPAPELLGGPSVFLFPPKPKDTL MISRTPEVTCVVVDVSHEDPEVKFNWYVD GVEVHNAKTKPREEQYNSTYRVVSVLTVL HQDWLNGKEYKCKVSNKALPAPIEKTISK AKGQPREPQVYTLPPCRDELTKNQVSLWC LVKGFYPSDIAVEWESNGQPENNYKTTPPV LDSDGSFFLYSKLTVDKSRWQQGNVFSCS VMHEALHNHYTQKSLSLSPGK |
| 98 | Fc hole chain | DKTHTCPPCPAPELLGGPSVFLFPPKPKDTL MISRTPEVTCVVVDVSHEDPEVKFNWYVD GVEVHNAKTKPREEQYNSTYRVVSVLTVL HQDWLNGKEYKCKVSNKALPAPIEKTISK AKGQPREPQVCTLPPSRDELTKNQVSLSCA VKGFYPSDIAVEWESNGQPENNYKTTPPVL DSDGSFFLVSKLTVDKSRWQQGNVFSCSV MHEALHNHYTQKSLSLSPGK |
| 99 | Acceptor framework IGHJ6*01/02 (page 106) | YYYYYGMDVWGQGTTVTVSS |
| 100 | Acceptor framework IGKJ4*01/02 (page 106) | LTFGGGTKVEIK |

TABLE B-continued (Sequences):

| SEQ ID NO: | Name | Sequence |
|---|---|---|
| 101 | Acceptor framework 1 IGHJ6*01/02 (page 110) | YYYYYGMDVWGQGTTVTVSS |
| 102 | Acceptor framework 1 IGKJ4*01/02 (page 110) | LTFGGGTKVEIK |
| 103 | Acceptor framework 2 IGHJ6*01/02 (page 111) | YYYYYGMDVWGQGTTVTVSS |
| 104 | Acceptor framework 2 IGKJ4*01/02 (page 111) | LTFGGGTKVEIK |
| 105 | huCD40 light chain (charged) | See Table 24 |
| 106 | huCD40 (VHCH1 charged) Fc PGLALA FAP (VL-CH1) | See Table 24 |
| 107 | VH (PD-L1) | EVQLVESGGGLVQPGGSLRLSCAASGFTFS DSWIHWVRQAPGKGLEWVAWISPYGGST YYADSVKGRFTISADTSKNTAYLQMNSLR AEDTAVYYCARRHWPGGFDYWGQGTLVT VSS |
| 108 | VL (PD-L1) | DIQMTQSPSSLSASVGDRVTITCRASQDVST AVAWYQQKPGKAPKLLIYSASFLYSGVPS RFSGSGSGTDFTLTISSLQPEDFATYYCQQY LYHPATFGQGTKVEIK |
| 109 | VH (PD-L1) | EVQLVESGGGLVQPGGSLRLSCAASGFTFS RYWMSWVRQAPGKGLEWVANIKQDGSEK YYVDSVKGRFTISRDNAKNSLYLQMNSLR AEDTAVYYCAREGGWFGELAFDYWGQGT LVTVSS |
| 110 | VL (PD-L1) | EIVLTQSPGTLSLSPGERATLSCRASQRVSS SYLAWYQQKPGQAPRLLIYDASSRATGIPD RFSGSGSGTDFTLTISRLEPEDFAVYYCQQY GSLPWTFGQGTKVEIK |

The following numbered paragraphs (paras) describe aspects of the present invention:

1. A bispecific antigen binding molecule, comprising
   (a) at least one antigen binding domain capable of specific binding to CD40, and
   (b) at least one antigen binding domain capable of specific binding to Fibroblast Activation Protein (FAP) comprising a heavy chain variable region ($V_L$FAP) comprising
   (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8.

2. The bispecific antigen binding molecule of para 1, additionally comprising (c) a Fc region composed of a first and a second subunit capable of stable association.

3. The bispecific antigen binding molecule of paras 1 or 2, wherein the antigen binding domain capable of specific binding to FAP comprises a heavy chain variable region ($V_H$FAP) comprising an amino acid sequence that is at least about 90% identical to the amino acid sequence of SEQ ID NO:9, and a light chain variable region ($V_L$FAP) comprising an amino acid sequence that is at least about 90% identical to the amino acid sequence of SEQ ID NO:10.

4. The bispecific antigen binding molecule of any one of paras 1 to 3, wherein the antigen binding domain capable of specific binding to FAP comprises a heavy chain variable region ($V_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and a light chain variable region ($V_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26.

5. The bispecific antigen binding molecule of any one of paras 1 to 4, wherein the antigen binding domain capable of specific binding to FAP comprises
   (a) a heavy chain variable region ($V_H$FAP) comprising the amino acid sequence of SEQ ID NO:15 and a light chain variable region ($V_L$FAP) comprising the amino acid sequence of SEQ ID NO:21,
   (b) a heavy chain variable region ($V_H$FAP) comprising the amino acid sequence of SEQ ID NO:16 and a light chain variable region (V_LFAP) comprising the amino acid sequence of SEQ ID NO:21, (c) a heavy chain variable region (V_HFAP) comprising the amino acid sequence of SEQ ID NO:16 and a light chain variable region (V_LFAP) comprising the amino acid sequence of SEQ ID NO:22, or (d) a heavy chain variable region (V_HFAP) comprising the amino acid sequence of SEQ ID NO:19 and a light chain variable region (V_LFAP) comprising the amino acid sequence of SEQ ID NO:25.

6. The bispecific antigen binding molecule of any one of paras 1 to 5, wherein the antigen binding domain capable of specific binding to CD40 comprises a heavy chain variable region (V_HCD40) comprising (i) CDR-H1 comprising the amino acid sequence of SEQ ID NO:27, (ii) CDR-H2 comprising the amino acid sequence of SEQ ID NO:28, and (iii) CDR-H3 comprising the amino acid sequence of SEQ ID NO:29, and a light chain variable region (V_LCD40) comprising (iv) CDR-L1 comprising the amino acid sequence of SEQ ID NO:30, (v) CDR-L2 comprising the amino acid sequence of SEQ ID NO:31, and (vi) CDR-L3 comprising the amino acid sequence of SEQ ID NO:32.

7. The bispecific antigen binding molecule of any one of paras 1 to 6, wherein the antigen binding domain capable of specific binding to CD40 comprises
   (i) a heavy chain variable region (V_HCD40) comprising an amino acid sequence selected from the group consisting of SEQ ID NO:37, SEQ ID NO:38, SEQ ID NO:39 and SEQ ID NO:40, and
   (ii) a light chain variable region (V_LCD40) comprising the amino acid sequence selected from the group consisting of SEQ ID NO:41, SEQ ID NO:42, SEQ ID NO:43, and SEQ ID NO:44.

8. The bispecific antigen binding molecule of any one of paras 1 to 6, wherein the antigen binding domain capable of specific binding to CD40 comprises
   (i) a heavy chain variable region (V_HCD40) comprising an amino acid sequence selected from the group consisting of SEQ ID NO:45, SEQ ID NO:46, SEQ ID NO:47, SEQ ID NO:48, SEQ ID NO:49 and SEQ ID NO:50, and
   (ii) a light chain variable region (V_LCD40) comprising the amino acid sequence selected from the group consisting of SEQ ID NO:51, SEQ ID NO:52, SEQ ID NO:53, and SEQ ID NO:54.

9. The bispecific antigen binding molecule of any one of paras 1 to 5 or 7, wherein the antigen binding domain capable of specific binding to CD40 comprises
   (a) a VH comprising the amino acid sequence of SEQ ID NO:37 and a VL comprising the amino acid sequence of SEQ ID NO:41, or
   (b) a VH comprising the amino acid sequence of SEQ ID NO:37 and a VL comprising the amino acid sequence of SEQ ID NO:42, or
   (c) a VH comprising the amino acid sequence of SEQ ID NO:37 and a VL comprising the amino acid sequence of SEQ ID NO:43, or
   (d) a VH comprising the amino acid sequence of SEQ ID NO:37 and a VL comprising the amino acid sequence of SEQ ID NO:44, or
   (e) a VH comprising the amino acid sequence of SEQ ID NO:38 and a VL comprising the amino acid sequence of SEQ ID NO:41, or
   (f) a VH comprising the amino acid sequence of SEQ ID NO:38 and a VL comprising the amino acid sequence of SEQ ID NO:42, or
   (g) a VH comprising the amino acid sequence of SEQ ID NO:38 and a VL comprising the amino acid sequence of SEQ ID NO:43, or
   (h) a VH comprising the amino acid sequence of SEQ ID NO:38 and a VL comprising the amino acid sequence of SEQ ID NO:44, or
   (i) a VH comprising the amino acid sequence of SEQ ID NO:39 and a VL comprising the amino acid sequence of SEQ ID NO:41, or
   (j) a VH comprising the amino acid sequence of SEQ ID NO:39 and a VL comprising the amino acid sequence of SEQ ID NO:42, or
   (k) a VH comprising the amino acid sequence of SEQ ID NO:39 and a VL comprising the amino acid sequence of SEQ ID NO:43, or
   (l) a VH comprising the amino acid sequence of SEQ ID NO:39 and a VL comprising the amino acid sequence of SEQ ID NO:44, or
   (m) a VH comprising the amino acid sequence of SEQ ID NO:40 and a VL comprising the amino acid sequence of SEQ ID NO:41, or
   (n) a VH comprising the amino acid sequence of SEQ ID NO:40 and a VL comprising the amino acid sequence of SEQ ID NO:42, or
   (o) a VH comprising the amino acid sequence of SEQ ID NO:40 and a VL comprising the amino acid sequence of SEQ ID NO:43, or
   (p) a VH comprising the amino acid sequence of SEQ ID NO:40 and a VL comprising the amino acid sequence of SEQ ID NO:44.

10. The bispecific antigen binding molecule of any one of paras 1 to 5 or 7 or 9, wherein the antigen binding domain capable of specific binding to CD40 comprises a VH comprising the amino acid sequence of SEQ ID NO:37 and a VL comprising the amino acid sequence of SEQ ID NO:41.

11. The bispecific antigen binding molecule of any one of paras 1 to 5 or 8, wherein the antigen binding domain capable of specific binding to CD40 comprises
    (a) a VH comprising the amino acid sequence of SEQ ID NO:45 and a VL comprising the amino acid sequence of SEQ ID NO:51, or
    (b) a VH comprising the amino acid sequence of SEQ ID NO:46 and a VL comprising the amino acid sequence of SEQ ID NO:51, or
    (c) a VH comprising the amino acid sequence of SEQ ID NO:47 and a VL comprising the amino acid sequence of SEQ ID NO:51, or
    (d) a VH comprising the amino acid sequence of SEQ ID NO:48 and a VL comprising the amino acid sequence of SEQ ID NO:51, or
    (e) a VH comprising the amino acid sequence of SEQ ID NO:45 and a VL comprising the amino acid sequence of SEQ ID NO:52, or
    (f) a VH comprising the amino acid sequence of SEQ ID NO:46 and a VL comprising the amino acid sequence of SEQ ID NO:52, or
    (g) a VH comprising the amino acid sequence of SEQ ID NO:47 and a VL comprising the amino acid sequence of SEQ ID NO:52, or
    (h) a VH comprising the amino acid sequence of SEQ ID NO:48 and a VL comprising the amino acid sequence of SEQ ID NO:52, or
    (i) a VH comprising the amino acid sequence of SEQ ID NO:49 and a VL comprising the amino acid sequence of SEQ ID NO:53, or (j) a VH comprising the amino acid sequence of SEQ ID NO:50 and a VL comprising the amino acid sequence of SEQ ID NO:53, or (k) a VH comprising the amino acid sequence of SEQ ID NO:49 and a VL comprising the amino acid sequence of SEQ ID NO:54, or (l) a VH comprising the amino acid sequence of SEQ ID NO:50 and a VL comprising the amino acid sequence of SEQ ID NO:54.

12. The bispecific antigen binding molecule of any one of paras 1 to 5 or 8 or 11, wherein the antigen binding domain capable of specific binding to CD40 comprises a VH comprising the amino acid sequence of SEQ ID NO:45 and a VL comprising the amino acid sequence of SEQ ID NO:51 or wherein the antigen binding domain capable of specific binding to CD40 comprises a VH comprising the amino acid sequence of SEQ ID NO:48 and a VL comprising the amino acid sequence of SEQ ID NO:51.

13. The bispecific antigen binding molecule of any one of paras 1 to 7, comprising
   (i) at least one antigen binding domain capable of specific binding to CD40, comprising a heavy chain variable region ($V_H$CD40) comprising the amino acid sequence of SEQ ID NO:37 and a light chain variable region ($V_L$CD40) comprising the amino acid sequence of SEQ ID NO:41, and
   (ii) at least one antigen binding domain capable of specific binding to FAP, comprising a heavy chain variable region ($V_L$FAP) comprising an amino acid sequence of SEQ ID NO:15 and a light chain variable region ($V_L$FAP) comprising an amino acid sequence of SEQ ID NO:21.

14. The bispecific antigen binding molecule of any one of paras 2 to 13, wherein the Fc region is an IgG, particularly an IgG1 Fc region or an IgG4 Fc region and wherein the Fc region comprises one or more amino acid substitution that reduces the binding affinity of the antibody to an Fc receptor and/or effector function.

15. The bispecific antigen binding molecule of any one of paras 2 to 14, wherein the Fc region is of human IgG1 subclass with the amino acid mutations L234A, L235A and P329G (numbering according to Kabat EU index).

16. The bispecific antigen binding molecule of any one of paras 1 to 15, wherein the bispecific antigen binding molecule comprises
   (a) at least two Fab fragments capable of specific binding to CD40 connected to a Fc region, and
   (b) one antigen binding domain capable of specific binding to FAP connected to the C-terminus of the Fc region.

17. The bispecific antigen binding molecule of any one of paras 1 to 16, wherein the bispecific antigen binding molecule comprises
   (a) at least two Fab fragments capable of specific binding to CD40 fused to a Fc region, and
   (b) a cross-fab fragment capable of specific binding to FAP fused to the C-terminus of the Fc region.

18. The bispecific antigen binding molecule of para 17, wherein the VH-Ckappa chain of the cross-fab fragment capable of specific binding to FAP is fused to the C-terminus of the Fc region.

19. The bispecific antigen binding molecule of any one of paras 1 to 18, wherein the bispecific antigen binding molecule comprises four Fab fragments capable of specific binding to CD40.

20. An antibody that specifically binds to FAP, wherein said antibody comprises a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8.

21. The antibody of para 20, wherein said antibody comprises
   (a) a heavy chain variable region ($V_H$FAP) comprising the amino acid sequence of SEQ ID NO:15 and a light chain variable region ($V_L$FAP) comprising the amino acid sequence of SEQ ID NO:21,
   (b) a heavy chain variable region ($V_H$FAP) comprising the amino acid sequence of SEQ ID NO:16 and a light chain variable region ($V_L$FAP) comprising the amino acid sequence of SEQ ID NO:21,
   (c) a heavy chain variable region ($V_H$FAP) comprising the amino acid sequence of SEQ ID NO:16 and a light chain variable region ($V_L$FAP) comprising the amino acid sequence of SEQ ID NO:22, or
   (d) a heavy chain variable region ($V_H$FAP) comprising the amino acid sequence of SEQ ID NO:19 and a light chain variable region ($V_L$FAP) comprising the amino acid sequence of SEQ ID NO:25.

22. Isolated nucleic acid encoding the bispecific antigen binding molecule of any one of paras 1 to 19 or the antibody of paras 20 or 21.

23. An expression vector comprising the isolated nucleic acid of para 22.

24. A host cell comprising isolated nucleic acid of para 22 or the expression vector of para 23.

25. A method of producing a bispecific antigen binding molecule, comprising culturing the host cell of para 24 under conditions suitable for the expression of the bispecific antigen binding molecule, and isolating the bispecific antigen binding molecule.

26. A pharmaceutical composition comprising the bispecific antigen binding molecule of any one of paras 1 to 19 or the antibody of paras 20 or 21 and a pharmaceutically acceptable carrier.

25. The pharmaceutical composition of para 24, further comprising an additional therapeutic agent.

26. The bispecific antigen binding molecule of any one of paras 1 to 19, or the pharmaceutical composition of para 24, for use as a medicament.

27. The bispecific antigen binding molecule of any one of paras 1 to 19, or the pharmaceutical composition of para 24, for use
   (i) in inducing immune stimulation by CD40 expressing antigen-presenting cells (APCs),
   (ii) in stimulating tumor-specific T cell response,
   (iii) in causing apoptosis of tumor cells,
   (iv) in the treatment of cancer,
   (v) in delaying progression of cancer,
   (vi) in prolonging the survival of a patient suffering from cancer,
   (vii) in the treatment of infections.

28. The bispecific antigen binding molecule of any one of paras 1 to 19, or the pharmaceutical composition of para 24, for use in the treatment of cancer.

29. Use of the bispecific antigen binding molecule of any one of paras 1 to 19, or the pharmaceutical composition of para 24, in the manufacture of a medicament for the treatment of cancer.

30. A method of treating an individual having cancer comprising administering to the individual an effective amount of the bispecific antigen binding molecule of any one of paras 1 to 19, or the pharmaceutical composition of para 24.

31. The bispecific antigen binding molecule according to any one of paras 1 to 19 or the pharmaceutical composition according to para 24 for use in the treatment of cancer, wherein the bispecific antigen binding molecule is administered in combination with a chemotherapeutic agent, radiation and/or other agents for use in cancer immunotherapy.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, New York, 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

CE-SDS

Purity, antibody integrity and molecular weight of bispecific and control antibodies were analyzed by CE-SDS using microfluidic Labchip technology (Caliper Life Science, USA). 5 μl of protein solution was prepared for CE-SDS analysis using the HT Protein Express Reagent Kit according manufacturer's instructions and analysed on LabChip GXII system using a HT Protein Express Chip. Data were analyzed using LabChip GX Software version 3.0.618.0.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/ $K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

This section describes the characterization of the multi-specific antibodies with VH/VL or CH/CL exchange (CrossMabs) with emphasis on their correct assembly. The expected primary structures were analyzed by electrospray ionization mass spectrometry (ESI-MS) of the deglycosylated intact CrossMabs and deglycosylated/FabALACTICA or alternatively deglycosylated/GingisKHAN digested CrossMabs.

The CrossMabs were deglycosylated with N-Glycosidase F in a phosphate or Tris buffer at 37° C. for up to 17 h at a protein concentration of 1 mg/ml. The FabALACTICA or GingisKHAN (Genovis AB; Sweden) digestions were performed in the buffers supplied by the vendor with 100 μs deglycosylated CrossMabs. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Example 1

Generation of New Antibodies Against Fibroblast Activation Protein (FAP)

1.1 Immunization of Mice

Balb/c and NMRI mice were used for immunization. The animals were housed according to the Appendix A "Guidelines for accommodation and care of animals" in an AAALACi accredited animal facility. All animal immunization protocols and experiments were approved by the Government of Upper Bavaria (permit number 55.2-1-54-2531-19-10) and performed according to the German Animal Welfare Act and the Directive 2010/63 of the European Parliament and Council. Balb/c and NMRI mice (n=5), 6-8 week old, received four rounds of immunization with recombinant produced extracellular domain of human fibroblast activation protein alpha (amino acid 27-759; accession number NP_004451) covalently attached to a His tag (SEQ ID NO:78). Before each immunization, mice were anesthetized with a gas mixture of oxygen and isoflurane. For the first immunization, 30 μs protein dissolved in PBS, pH 7.4, were mixed with an equal volume of CFA (BD Difco, #263810) and administered intraperitoneal (i.p.) Another 10 μs of protein emulsified in Abisco adjuvant was administered subcutaneously (s.c.) at week 6. A third dose of 5 μg protein without adjuvant was administered i.p. at week 10. Finally, three days prior to the preparation of splenocytes for antibody development using hybridoma technology, the mice were subjected to intravenous (i.v.) booster immunizations with 50 μg of protein. Serum was tested for antigen-specific total IgG antibody production by ELISA. Three days after the final immunization, mice were euthanized and the spleen was isolated aseptically and prepared for hybridoma generation. The mouse lymphocytes were isolated and fused with a mouse myeloma cell line using PEG based standard protocols to generate hybridomas. The resulting hybridoma cells were plated at approximately $10^4$ in flat bottom 96 well micro titer plate, followed by about two weeks of incubation in selective medium and then screened for the production of antigen-specific antibodies. Once extensive hybridoma growth occurs, the antibody secreting hybridomas are replated. Hybridoma supernatants were screened for specific binding to recombinant human fibroblast activation protein alpha (huFAP) by ELISA, followed by evaluation of kinetic binding parameters to recombinant huFAP using Biacore measurement.

Culture of hybridomas: Generated muMAb hybridomas were cultured in RPMI 1640 (PAN—Catalogue No. (Cat. No.) PO4-17500) supplemented with 2 mM L-glutamine (GIBCO—Cat. No. 35050-038), 1 mM Na-Pyruvat (GIBCO—Cat. No. 11360-039), 1× NEAA (GIBCO—Cat. No. 11140-035), 10% FCS (PAA—Cat. No. A15-649). 1× Pen Strep (Roche—Cat. No. 1074440), 1× Nutridoma CS (Roche—Cat. No. 1363743), 50 μM Mercaptoethanol (GIBCO—Cat. No. 31350-010) and 50 U/ml IL 6 mouse (Roche—Cat. No. 1 444 581) at 37° C. and 5% $CO_2$.

1.2 Competitive Cellular Binding of Anti-huFAP Antibodies to FAP Clone 4B9 and 28H1

The resulting clones were tested for their binding behavior in comparison to FAP clone 4B9. The generation and preparation of FAP clones 4B9 and 28H1 is described in WO 2012/020006 A2, which is incorporated herein by reference. To determine whether the murine FAP clones recognize different epitopes as clones 4B9 and 28H1 a competition binding to human FAP expressed on transfected HEK cells was performed.

Briefly, the target cells were harvested with Cell Dissociation buffer, washed with FACS Buffer (PBS+2% FCS+5 mM EDTA+0.25% sodium acide) and seeded into 96-U bottom plates (1×105 cells/well). Unlabeled primary anti-human FAP antibodies (mu IgG1) were added to the cells (final concentrations 60 μg/ml to 0.2 μg/ml; 1:3 dilutions) and incubated for 20 min at 4° C. before addition of AlexaFluor647-labeled anti FAP antibody 4B9 or 28H1 (end concentration 20 μg/ml). After 30 min incubation at 4° C., cells were washed, fixed and the fluorescent signal intensities of the AF647-labeled clones 4B9 and 28H1 were measured using a Miltenyi MACSQuant.

Figure 2A:
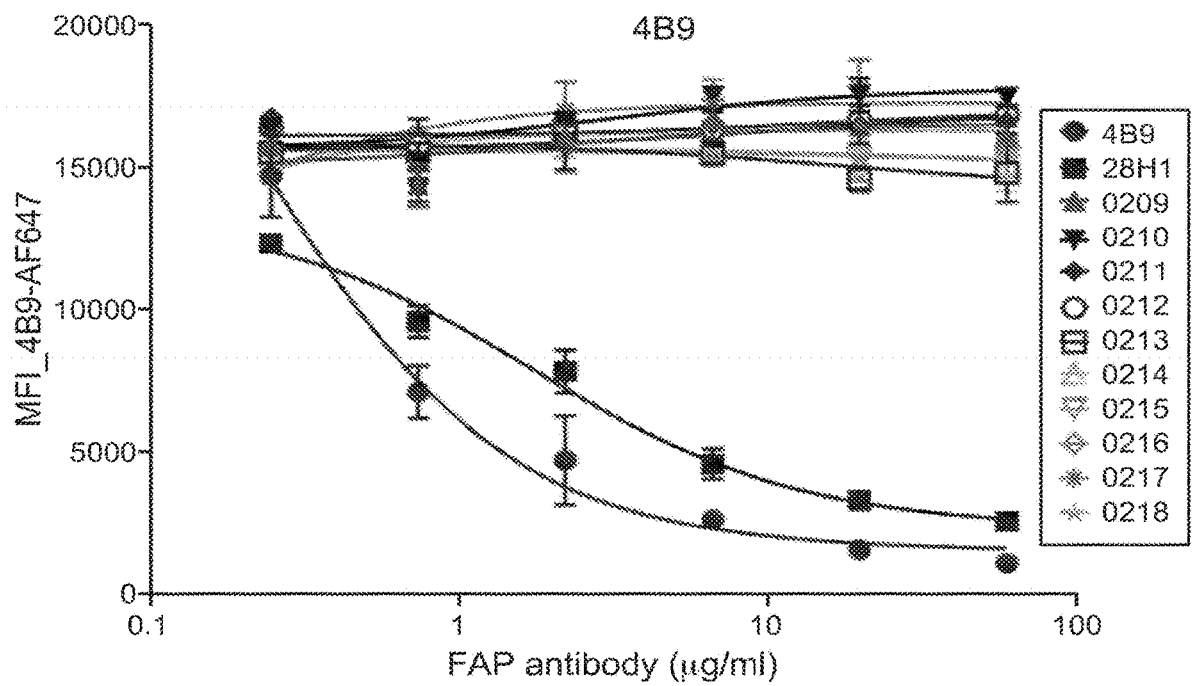
FIG. 2A and FIG. 2B show the cellular binding of immunization derived FAP clones to human FAP expressed on transfected HEK cells in competition to FAP clones 4B9 and 28H1.
Figure 2B:
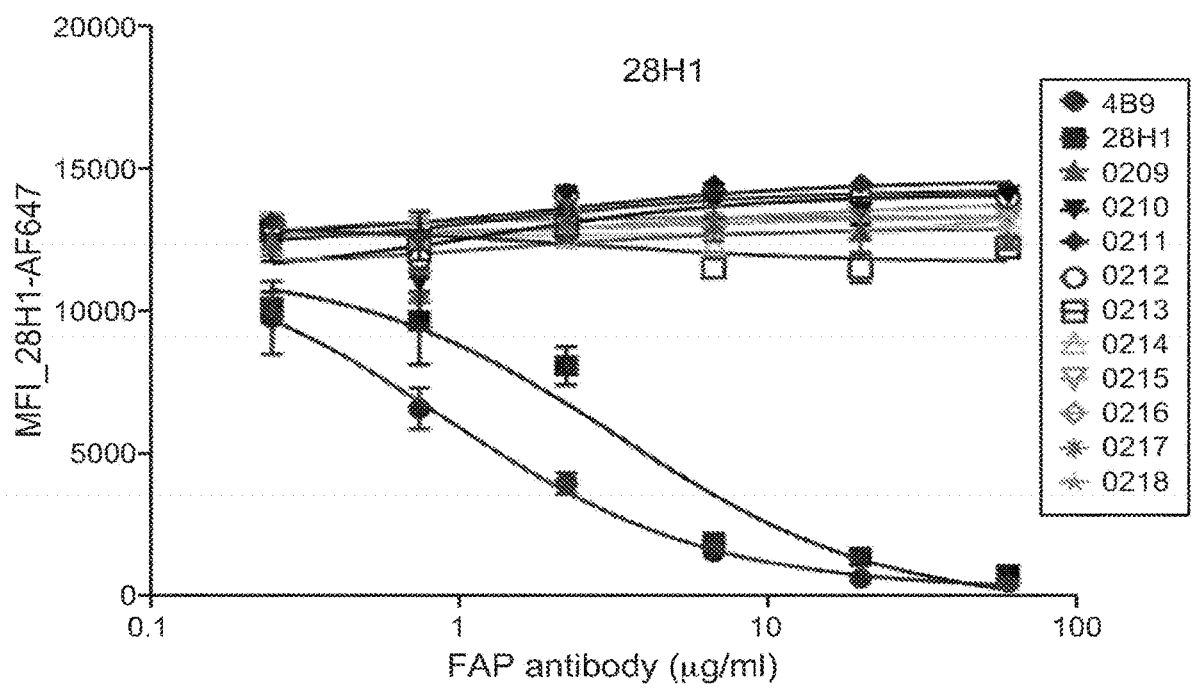
Figure 10:
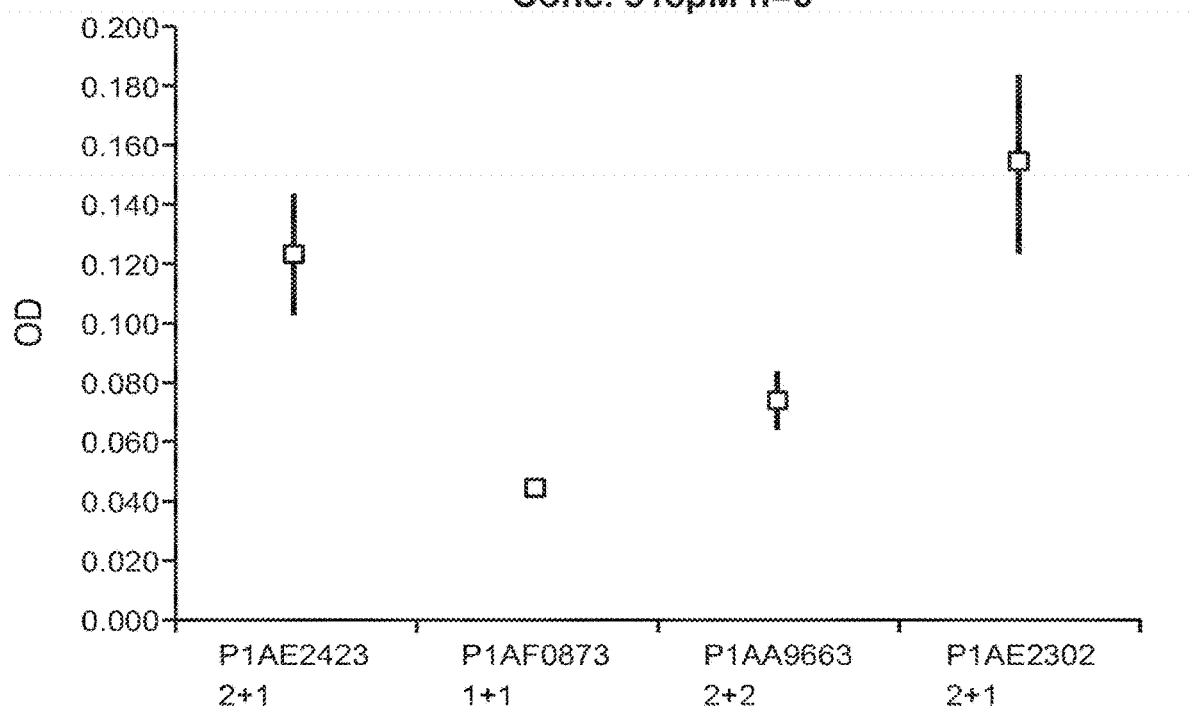
In FIG. 10 the potential of FAP×CD40 antibodies in different formats to activate the CD40 receptor (independent from FAP) is shown. In the reporter cell line assay the signal transduction results in the induction of NF☐B-dependent production of secreted embryonic alkaline phosphatase (SEAP) and the activity of SEAP is measured. The mean of the optical density (OD) of n=6 and the 3×STDEV is plotted against the molecules.

As can be seen in FIG. 2A and FIG. 2B, 10 hybridoma-derived murine antibodies were identified (named clones 209, 210, 211, 212, 213, 214, 215, 216, 217 and 218) that did not compete for binding with anti FAP antibodies 4B9 or 28H1.

1.3 Target Binding Specificity of Anti-huFAP Murine Antibodies

Fibroblast activation protein (FAP, FAP-a, seprase) is a type II transmembrane serine protease, belonging to the prolyl oligopeptidase family. This family comprises serine proteases that cleave peptides preferentially after proline residues. Other important members of this family that are expressed in the human proteome are prolyl oligopeptidase (PREP) and the dipeptidyl peptidases (DPPs). DPP-IV is the closest homolog of FAP. In contrast to FAP, DPP-IV is ubiquitously expressed and plays a role in various biological processes such as T cell co-stimulation, chemokine biology, glucose metabolism, and tumorigenesis and therefore the desired anti-human FAP antibodies should not bind to human DPP-IV.

Binding to human FAP and human DPP-IV was determined by flow cytometry using human FAP or human DPPIV-transfected HEK cells. Briefly, the target cells were harvested with Cell Dissociation buffer, washed with FACS Buffer (PBS+2% FCS+5 mM EDTA+0.25% sodium acide) and seeded into 96-U bottom plates (1×$10^5$ cells/well). Unlabeled primary antibodies were added to the cells (final concentration 10 μg/ml) and incubated for 30 min at 4° C. After washing, cells were incubated with a goat anti-mouse IgG-PE F(ab')2 (Serotec) for 30 min at 4° C. in the dark. Afterwards, cells were washed, fixed and measured using a BD FACS Canto™ II. No unspecific binding to human DPP-IV was detected for any of the 10 hybridoma derived anti-human FAP antibodies.

1.4 Generation of Anti-huFAP Antibodies in huIgG1_LALA_PG Format

The DNA sequences of the new anti-huFAP antibodies were determined with standard sequencing methods. Based on the VH and VL domains new anti-FAP antibodies were expressed as huIgG1 antibodies with an effector silent Fc (P329G; L234, L235A) to abrogate binding to Fc☐ receptors according to the method described in WO 2012/130831 A1. In detail, antibodies were expressed by transient transfection of HEK293-F cells grown in suspension with expression vectors encoding the different peptide chains. Transfection into HEK293-F cells (Invitrogen, USA) was performed according to the cell supplier's instructions using Maxiprep (Qiagen, Germany) preparations of the antibody vectors, F17 based medium (Invitrogen, USA), PEIpro (Polyscience Europe GmbH) and an initial cell density of 1-2 million viable cells/ml in serum free FreeStyle 293 expression medium (Invitrogen). Cell culture supernatants were harvested after 7 days of cultivation in shake flasks or stirred fermenters by centrifugation at 14000 g for 30 minutes and filtered through a 0.22 μm filter.

The antibodies were purified from cell culture supernatants by affinity chromatography using MabSelectSure-Sepharose™ (GE Healthcare, Sweden) chromatography. Briefly, sterile filtered cell culture supernatants were captured on a MabSelect SuRe resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM citrate, pH 3.0. After neutralization with 1 M Tris pH 9.0, aggregated protein was separated from monomeric antibody species by size exclusion chromatography (Superdex 200, GE Healthcare) in 20 mM histidine, 140 mM NaCl, pH 6.0. Monomeric protein fractions were pooled, concentrated if required using e.g. a MILLIPORE Amicon Ultra (30 KD MWCO) centrifugal concentrator and stored at −80° C. Sample aliquots were used for subsequent analytical characterization e.g. by CE-SDS, size exclusion chromatography, mass spectrometry and endotoxin determination.

1.5 Cellular Binding of Anti-huFAP Antibodies

The binding of anti-FAP antibodies with a human IgG1 P329G LALA Fc to human FAP was determined by flow cytometry using human FAP-transfected HEK cells. Briefly, the target cells were harvested with Cell Dissociation buffer, washed with FACS Buffer (PBS+2% FCS+5 mM EDTA+0.25% sodium acide) and seeded into 96-U bottom plates (1×105 cells/well). Unlabeled primary antibodies were added to the cells (final concentrations 10 µg/ml to 0.64 ng/ml; 1:5 dilutions) and incubated for 30 min at 4° C. After washing, cells were incubated with a PE-conjugated AffiPure F(ab)$_2$ Fragment Goat anti-human IgG, Fc□ specific (Jackson Immunoresearch) for 30 min at 4° C. in the dark. Afterwards, cells were washed, fixed and measured using a BD FACS LSR Fortessa™.

All anti-FAP antibodies showed similar binding to human FAP as seen before. The $EC_{50}$ values of selected binders are shown in Table 1 below.

TABLE 1

Cellular binding of anti-FAP antibodies to huFAP expressing cells

| Sample ID | clone | $EC_{50}$ [µg/ml] cellular binding to FAP-transfected HEK cells |
|---|---|---|
|  | 4B9 | 0.089 |
| P1AD9427 | 209 | 0.145 |
| P1AD9436 | 210 | 0.125 |
| P1AD9437 | 211 | 0.198 |
| P1AD9438 | 212 | 0.118 |
| P1AD9440 | 214 | 0.086 |

1.6 Cellular Internalization of Anti-huFAP Antibodies

Internalization of FAP binders was determined using human FAP-transfected HEK cells as targets. Briefly, the target cells were harvested with Cell Dissociation buffer, washed with cold FACS Buffer (PBS+2% FCS+5 mM EDTA+0.25% sodium acide) and resuspended at 1.5×10$^6$ cells/ml in cold FACS Buffer. Cells were distributed in 15 ml tubes (each tube containing 3×10$^6$ cells in 2 ml). 2 ml of anti-human FAP antibody solutions were added to the cells (final concentration 20 µg/ml) and incubated for 45 min at 4° C. Afterwards, cells were washed, resuspended in cold FACS Buffer and cells for time point "0" were seeded immediately into 96-U bottom plates (1.5×10$^5$ cells/well) and kept at 4° C. whereas all other cells were centrifuged, resuspended in warm RPMI1640 medium containing 10% FCS and 1% Glutamax (1.5×10$^6$ cells/ml) and shifted to 37° C. in a humidified incubator (5% $CO_2$). After each indicated time point, 100 µl/tube of cell suspension was transferred to plates, immediately cooled down with cold FACS Buffer and stored in the fridge until all time points have been collected. After collection of all time points, cells were washed with cold FACS Buffer and incubated with PE-labeled secondary antibody for 30 min at 4° C. Afterwards, cells were washed, fixed and measured using a BD FACS Canto™ II.

The signals caused by the labeled secondary antibody stayed nearly constant over time, which means that no loss of antibody was observed over time, none of the tested anti-hu FAP antibodies was internalized.

1.7 Binding Kinetics of Anti-huFAP Antibodies

To evaluate human FAP binding kinetics, biotinylated human FAP was immobilized on a Series S Biacore CAPture Chip (GE Healthcare 28-9202-34) according to the manufacturer's instructions, resulting in a surface density of approximately 20 resonance units (RU). As running and dilution buffer, HBS-P+ (10 mM HEPES, 150 mM NaCl pH 7.4, 0.05% Surfactant P20) was used. A dilution series of anti-huFAP Fabs (3.7-300 nM, 1:3 dilution) was successively injected for 120 s each, dissociation was monitored for 1800 s at a flow rate of 30 µl/min (single cycle kinetics). The surface was regenerated by injecting 6 M guanidine-HCl, 0.25 M NaOH for 120 s. Bulk refractive index differences were corrected by subtracting blank injections and by subtracting the response obtained from the control flow cell without captured human FAP. Curve fitting was performed using the 1:1 Langmuir binding model within the Biacore evaluation software. The affinity data are shown in Table 2 below.

TABLE 2

Affinity of anti-FAP Fabs to human FAP as measured by Biacore

| Sample ID | clone | ka (1/Ms) | kd (1/s) | KD |
|---|---|---|---|---|
|  | 4B9_Fab | 1.82E+06 | 7.80E−04 | 430 pM |
| P1AD9427_Fab | 209 | 3.50E+06 | 1.77E−03 | 510 pM |
| P1AD9436_Fab | 210 | 1.87E+06 | <E−06 | <10 pM |
| P1AD9437_Fab | 211 | 8.13E+05 | 4.61E−05 | 60 pM |
| P1AD9438_Fab | 212 | 1.06E+06 | <E−06 | <10 pM |
| P1AD9440_Fab | 214 | 1.99E+06 | <E−06 | <10 pM |

1.8 Format-Depending Binding of Anti-huFAP Clones

In order to determine if the binding properties of the anti-FAP clones are not lost when they are C-terminally fused to an Fc domain, constructs comprising a Fc knob chain and a Fc hole chain wherein the VH domain is fused to the C-terminus of the Fc knob chain and the VL domain is fused to the C-terminus of the Fc hole chain (FIG. 3A, C-term VH/VL fusion) and constructs comprising a Fc knob chain and a Fc hole chain wherein the whole Fab is fused with its VH domain to the C-terminus of the Fc knob chain (FIG. 3B, C-term Fab fusion). The Fc knob chain has the amino acid sequence of SEQ ID NO:97 and the Fc hole chain has the amino acid sequences of SEQ ID NO:98.

The affinity of the constructs towards biotinylated recombinant human FAP and biotinylated recombinant cynomolgus FAP as compared to the antibodies is shown in Table 3 below.

TABLE 3

Affinity to human FAP and cynomolgus FAP as measured by Biacore

| | Affinity to human FAP KD [nM] | | | Affinity to cynomolgus FAP KD [nM] | | |
|---|---|---|---|---|---|---|
| clone | free Fab | C-term Fab fusion | C-term VH/VL fusion | IgG | C-term Fab fusion | C-term VH/VL fusion |
| 209 | 0.31 | 1.52 | 42.40 | 0.33 | 1.60 | 50.00 |
| 210 | 0.07 | 0.17 | 3.95 | 0.12 | 0.20 | 3.44 |
| 211 | 0.28 | 1.20 | 10.90 | 0.32 | 1.30 | 11.40 |
| 212 | 0.12 | 0.62 | 5.72 | 0.14 | 0.64 | 6.19 |
| 214 | 0.06 | 0.19 | 2.49 | 0.09 | 0.21 | 2.77 |

Cellular binding of the constructs to FAP-transfected HEK cells has also been determined as described herein before. The $EC_{50}$ values are shown in Table 4. The C-terminal fusion constructs of all anti-FAP antibodies were able to bind to human and cynomolgus FAP, however the constructs wherein the whole Fab is fused with its VH domain to the C-terminus of the Fc knob chain were superior to those wherein the VH domain is fused to the C-terminus of the Fc knob chain and the VL domain is fused to the C-terminus of the Fc hole chain.

first and second antibody (FAP-binder) were injected successively, each for 120 seconds at a concentration of 10 µg/ml over both flow cells. After each cycle the surface was regenerated with 10 mM glycine pH1.5 for 60 seconds (GE Healthcare BR-1003-54).

The results are shown in Table 5 below:

TABLE 5

Competitive Binding of anti-FAP antibodies to 4B9

| | 4B9 | 209 | 210 | 211 | 212 | 214 |
|---|---|---|---|---|---|---|
| 4B9 | Competitive Binding | Simultaneous Binding | Simultaneous Binding | Simultaneous Binding | Simultaneous Binding | Simultaneous Binding |
| 209 | Simultaneous Binding | Competitive Binding | Simultaneous Binding | Simultaneous Binding | Simultaneous Binding | Simultaneous Binding |
| 210 | Simultaneous Binding | Simultaneous Binding | Competitive Binding | Competitive Binding | Competitive Binding | Competitive Binding |
| 211 | Simultaneous Binding | Simultaneous Binding | Competitive Binding | Competitive Binding | Competitive Binding | Competitive Binding |
| 212 | Simultaneous Binding | Simultaneous Binding | Competitive Binding | Competitive Binding | Competitive Binding | Competitive Binding |
| 214 | Simultaneous Binding | Simultaneous Binding | Competitive Binding | Competitive Binding | Competitive Binding | Competitive Binding |

TABLE 4

Cellular binding to huFAP expressing cells

| | Cellular binding to human FAP $EC_{50}$ [µg/ml] | | | Cellular binding to cynomolgus FAP $EC_{50}$ [µg/ml] | | |
|---|---|---|---|---|---|---|
| clone | IgG | C-term Fab fusion | C-term VH/VL fusion | IgG | C-term Fab fusion | C-term VH/VL fusion |
| 209 | 0.15 | 1.2 | 5.7 | 0.4 | 1.1 | 7.9 |
| 210 | 0.13 | 1.8 | 9.0 | 0.4 | 1.3 | 7.1 |
| 211 | 0.20 | 3.7 | 9.3 | 0.3 | 2.9 | 6.7 |
| 212 | 0.12 | 2.8 | 8.8 | 0.3 | 2.3 | 11.1 |
| 214 | 0.09 | 1.7 | 9.4 | 0.3 | 1.3 | 3.6 |

1.9 Competitive Binding of Anti-Human FAP Clones as Determined by Biacore

Epitope binning was performed using a surface plasmon resonance (SPR) based assay on a Biacore T200 instrument. FAP antigen was captured by an immobilized anti-His antibody. In a first step the FAP-binder was injected until saturation. A second FAP-binder was injected subsequently. The assay design is schematically shown in FIG. 3C. An increase in binding signal after addition of the second antibody indicates its binding to a different epitope from the first antibody. No additional binding indicated that the first and the second antibody recognize the same epitope region.

An anti-His antibody (GE Healthcare Kit 28-9950-56) with a concentration of 20 µg/ml was immobilized by amine coupling (GE Healthcare Kit BR-1000-50) to the surface of a CM5 sensor chip (GE Healthcare BR-1005-30). Injection time was 600 seconds at a flow rate of 10 µl/min to yield 12000 response units (RU) on two flow cells, one used as reference and one used as active flow cell. Running buffer was HBS-N (GE Healthcare BR-1006-70). For the measurement PBS-P+ (GE Healthcare 28-9950-84) was used as running and dilution buffer. Flow cell temperature was set to 25° C., sample compartment to 12° C. The flow rate was set to 10 µl/min for the whole run.

His-tagged FAP antigen was captured with a concentration of 20 µg/ml for 180 seconds on the active flow cell. The Thus, three epitope bins were identified. As requested, none of the anti-FAP antibodies did compete for binding with antibody 4B9 (Epitope bin 1). Antibodies 210, 211, 212 and 214 competed with each other for binding and thus form one group (Epitope bin 3), whereas antibody 209 did not compete for binding with any other of the antibodies (Epitope bin 2).

1.9 Thermal Stability Evaluation of Anti-FAP Antibodies

Samples are prepared at a concentration of 1 mg/mL in 20 mM Histidine/Histidine chloride, 140 mM NaCl, pH 6.0, transferred into an optical 384-well plate by centrifugation through a 0.4 µm filter plate and covered with paraffine oil. The hydrodynamic radius is measured repeatedly by dynamic light scattering on a DynaPro Plate Reader (Wyatt) while the samples are heated with a rate of 0.05° C./min from 25° C. to 80° C. Alternatively, samples were transferred into a 10 µL micro-cuvette array and static light scattering data as well as fluorescence data upon excitation with a 266 nm laser were recorded with an Optim1000 instrument (Avacta Inc.), while they were heated at a rate of 0.1° C./min from 25° C. to 90° C. The aggregation onset temperature ($T_{agg}$) is defined as the temperature at which the hydrodynamic radius (DLS) or the scattered light intensity (Optim1000) starts to increase. The melting temperature is defined as the inflection point in a graph showing fluorescence intensity vs. wavelength. The aggregation onset temperatures of selected anti-FAP antibodies is shown in Table 6.

TABLE 6

Aggregation onset temperatures of anti-FAP antibodies

| | 4B9 | 209 | 210 | 212 | 214 |
|---|---|---|---|---|---|
| $T_{agg}$ (° C.) | 60 | 66 | 61 | 67 | 61 |

The anti-FAP clone 212 was chosen for humanization as it binds with a comparable high affinity to human FAP as antibody 4B9 and showed favorable properties for the development. In silico analysis of its sequences indicated only one predicted degradation hotspot (Trp at position 401). The sequences of murine clone 212 are shown in Table 7.

TABLE 7

Amino acid sequences of the variable domains of murine anti-FAP clone 212

| Description | Sequence | Seq ID No |
|---|---|---|
| FAP(212) VH | EVLLQQSGPELVKPGASVKIACKASGYTLT DYNMDWVRQSHGKSLEWIGDIYPNTGGTIY NQKFKGKATLTIDKSSSTAYMDLRSLTSED TAVYYCTRFRGIHYAMDYWGQGTSVTVSS | 9 |
| FAP(212) VL | DIVLTQSPVSLAVSLGQRATISCRASESVD NYGLSFINWFQQKPGQPPKLLIYGTSNRGS GVPARFSGSGSGTDFSLNIHPMEEDDTAMY FCQQSNEVPYTFGGGTNLEIK | 10 |

1.10 Humanization of Anti-FAP Clone 212

1.10.1 Methodology

Suitable human acceptor frameworks were identified by querying a BLASTp database of human V- and J-region sequences for the murine input sequences (cropped to the variable part). Selective criteria for the choice of human acceptor framework were sequence homology, same or similar CDR lengths, and the estimated frequency of the human germline, but also the conservation of certain amino acids at the VH-VL domain interface. Following the germline identification step, the CDRs of the murine input sequences were grafted onto the human acceptor framework regions. Each amino acid difference between these initial CDR grafts and the parental antibodies was rated for possible impact on the structural integrity of the respective variable region, and "back mutations" towards the parental sequence were introduced whenever deemed appropriate. The structural assessment was based on Fv region homology models of both the parental antibody and the humanization variants, created with an in-house antibody structure homology modeling protocol implemented using the Biovia Discovery Studio Environment, version 17R2. In some humanization variants, "forward mutations" were included, i.e., amino acid exchanges that change the original amino acid occurring at a given CDR position of the parental binder to the amino acid found at the equivalent position of the human acceptor germline. The aim is to increase the overall human character of the humanization variants (beyond the framework regions) to further reduce the immunogenicity risk.

An in silico tool developed in-house was used to predict the VH-VL domain orientation of the paired VH and VL humanization variants (see WO 2016/062734). The results were compared to the predicted VH-VL domain orientation of the parental binders to select for framework combinations which are close in geometry to the original antibodies. The rationale is to detect possible amino acid exchanges in the VH-VL interface region that might lead to disruptive changes in the pairing of the two domains that in turn might have detrimental effects on the binding properties.

1.10.2 Choice of Acceptor Framework and Adaptations Thereof

The following acceptor frameworks were chosen:

TABLE 8

| Acceptor framework | | | |
|---|---|---|---|
| Murine V-region germline | Graft variant | Choice of human acceptor V-region germline | Identity to human V-region germline after grafting (BLASTp): |
| FAP (212) VH | IGHV1-18*01 | VH1 | IGHV1-46*01 | 87.8% |
| | | VH2 | IGHV3-23*03 | 82.7% |
| FAP (212) VL | IGKV3-2*01 | VL1 | IGKV3-11*01 | 85.1% |
| | | VL2 | IGKV1-39*01 | 82.8% |

Post-CDR3 framework regions were adapted from human IGHJ germline IGHJ6*01/02 (YYYYYGMDV-WGQGTTVTVSS) and human IGKJ germline IGKJ4*01/02 (LTFGGGTKVEIK). The part relevant for the acceptor framework is indicated in bold script.

Based on structural considerations, back mutations from the human acceptor framework to the amino acid in the parental binder were introduced at positions H43 (Q>K), H44 (G>S), H48 (M>I), H71 (R>I), H73 (T>K), H93 (A>T) [VH1], H49 (S>G), H71 (R>I), H73 (N>K), H78 (L>A), H93 (A>T), H94 (K>R) [VH2], L36 (Y>F), L43 (A>P), L87 (Y>F) [VL1] and L36 (Y>F), L42 (K>Q), L43 (A>P), L85 (T>M), L87 (Y>F) [VL2].

Furthermore, the positions H60 (N>A), H64 (K>Q) [VH1], H60 (N>A), H61 (Q>D), H62 (K>S), H63 (F>V) [VH2], L33 (I>L), L34 (N>A) [VL1] and L27b (V>I), L33 (I>L) [VL2] were identified as promising candidates for forward mutations. All positions are given in the Kabat EU numbering scheme.

TABLE 9 list of variants

| Variant name | Back/forward mutations | Identity to human V-region germline (BLASTp) |
|---|---|---|
| VH1G1a | bM48I, bR71I, bA93T | 84.7% |
| VH1G2a | bQ43K, bG44S, bM48I, bR71I, bT73K, bA93T | 81.6% |
| VH1G3a | bM48I, fN60A, fK64Q, bR71I, bA93T | 86.7% |
| VH2G1a | bS49G, bA93T, bK94R | 79.6% |
| VH2G2a | bS49G, bR71I, bN73K, bL78A, bA93T, bK94R | 76.5% |
| VH2G3a | bS49G, fN60A, fQ61D, fK62S, fF63V, bA93T, bK94R | 83.7% |
| VL1G1a | bY36F, bY87F | 83% |
| VL1G2a | bY36F, bA43P, bY87F | 81.9% |
| VL1G3a | fI33L, fN34A, bY36F, bY87F | 85.1% |
| VL2G1a | bY36F, bY87F | 80.8% |
| VL2G2a | bY36F, bK42Q, bA43P, bT85M, bY87F | 77.8% |
| VL2G3a | fV27bI, fI33L, bY36F, bY87F | 82.8% |

Note:
Back mutations are prefixed with b, forward mutations with f, e.g., bM48I refers to a back mutation (human germline amino acid to parental antibody amino acid) from methionine to isoleucine at position 48 (Kabat).

The resulting VH and VL domains of humanized FAP antibodies based on the acceptor framework can be found in Table 10 below.

TABLE 10

Amino acid sequences of the VH and VL domains of humanized FAP antibodies

| Description | Sequence | Seq ID No |
|---|---|---|
| VH1G1a | QVQLVQSGAEVKKPGASVKVSCKASGYTLTDYNM DWVRQAPGQGLEWIGDIYPNTGGTIYNQKFKGRVT MTIDTSTSTVYMELSSLRSEDTAVYYCTRFRGIHYA MDYWGQGTTVTVSS | 15 |
| VH1G2a | QVQLVQSGAEVKKPGASVKVSCKASGYTLTDYNM DWVRQAPGKSLEWIGDIYPNTGGTIYNQKFKGRVT MTIDKSTSTVYMELSSLRSEDTAVYYCTRFRGIHYA MDYWGQGTTVTVSS | 16 |
| VH1G3a | QVQLVQSGAEVKKPGASVKVSCKASGYTLTDYNM DWVRQAPGQGLEWIGDIYPNTGGTIYAQKFQGRVT MTIDTSTSTVYMELSSLRSEDTAVYYCTRFRGIHYA MDYWGQGTTVTVSS | 17 |
| VH2G1a | EVQLLESGGGLVQPGGSLRLSCAASGYTLTDYNMD WVRQAPGKGLEWVGDIYPNTGGTIYNQKFKGRFTIS RDNSKNTLYLQMNSLRAEDTAVYYCTRFRGIHYAM DYWGQGTTVTVSS | 18 |
| VH2G2a | EVQLLESGGGLVQPGGSLRLSCAASGYTLTDYNMD WVRQAPGKGLEWVGDIYPNTGGTIYNQKFKGRFTIS IDKSKNTAYLQMNSLRAEDTAVYYCTRFRGIHYAM DYWGQGTTVTVSS | 19 |
| VH2G3a | EVQLLESGGGLVQPGGSLRLSCAASGYTLTDYNMD WVRQAPGKGLEWVGDIYPNTGGTIYADSVKGRFTIS RDNSKNTLYLQMNSLRAEDTAVYYCTRFRGIHYAM DYWGQGTTVTVSS | 20 |
| VL1G1a | EIVLTQSPATLSLSPGERATLSCRASESVDNYGLSFIN WFQQKPGQAPRLLIYGTSNRGSGIPARFSGSGSGTDF TLTISSLEPEDFAVYFCQQSNEVPYTFGGGTKVEIK | 21 |
| VL1G2a | EIVLTQSPATLSLSPGERATLSCRASESVDNYGLSFIN WFQQKPGQPPRLLIYGTSNRGSGIPARFSGSGSGTDF TLTISSLEPEDFAVYFCQQSNEVPYTFGGGTKVEIK | 22 |
| VL1G3a | EIVLTQSPATLSLSPGERATLSCRASESVDNYGLSFLA WFQQKPGQAPRLLIYGTSNRGSGIPARFSGSGSGTDF TLTISSLEPEDFAVYFCQQSNEVPYTFGGGTKVEIK | 23 |
| VL2G1a | DIQMTQSPSSLSASVGDRVTITCRASESVDNYGLSFI NWFQQKPGKAPKLLIYGTSNRGSGVPSRFSGSGSGT DFTLTISSLQPEDFATYFCQQSNEVPYTFGGGTKVEI K | 24 |
| VL2G2a | DIQMTQSPSSLSASVGDRVTITCRASESVDNYGLSFI NWFQQKPGQPPKLLIYGTSNRGSGVPSRFSGSGSGT DFTLTISSLQPEDFAMYFCQQSNEVPYTFGGGTKVEI K | 25 |
| VL2G3a | DIQMTQSPSSLSASVGDRVTITCRASESIDNYGLSFLN WFQQKPGKAPKLLIYGTSNRGSGVPSRFSGSGSGTD FTLTISSLQPEDFATYFCQQSNEVPYTFGGGTKVEIK | 26 |

1.10.3 New Humanized Anti-FAP Fabs

Based on the new humanization variants of VH and VL new anti-FAP Fabs were expressed.

TABLE 11

Nomenclature for VH/VL combinations expressed as Fabs

| | VL1G1a | VL1G2a | VL1G3a | VL2G1a | VL2G2a | VL2G3a |
|---|---|---|---|---|---|---|
| VH1G1a | P1AE1689 | | | | | |
| VH1G2a | P1AE1690 | P1AE1693 | | | | |
| VH1G3a | | | | | | |
| VH2G1a | | | | | | |

TABLE 11-continued

Nomenclature for VH/VL combinations expressed as Fabs

| | VL1G1a | VL1G2a | VL1G3a | VL2G1a | VL2G2a | VL2G3a |
|---|---|---|---|---|---|---|
| VH2G2a | | | | | P1AE1702 | |
| VH2G3a | | | | | | |

The affinity of the new humanized anti-FAP variants based on clone 212 was analyzed in comparison with anti-FAP antibody 4B9. Furthermore, the humanness of the humanized variants was calculated and its aggregation onset temperature was measured.

TABLE 12

Affinity of humanization variants of clone 212 as measured by Biacore

| Sample ID | ka (1/Ms) | kd (1/s) | KD (pM) | T ½ (min) | Identity to hu V germline | $T_{agg}$ [° C.] |
|---|---|---|---|---|---|---|
| P1AE1689_Fab | 4.43E+05 | 4.21E−05 | 95 | 274 | 83/84.7 | 72.7 |
| P1AE1690_Fab | 5.51E+05 | 6.30E−05 | 114 | 183 | 83/81.7 | 75.4 |
| P1AE1693_Fab | 5.30E+05 | 7.18E−05 | 135 | 161 | 81.9/81.7 | 75.4 |
| P1AE1702_Fab | 5.02E+05 | 1.07E−04 | 213 | 108 | 77.8/76.5 | 71.6 |
| 4B9_Fab | 7.47E+05 | 2.08E−04 | 279 | 55 | | 60 |

1.11 FcRn/Heparin Binding and in Silico Charge Distribution

The charge distribution of antibodies 4B9 and P1AE1689 in PBS, pH 7.4, was calculated in an in-silico model. According to the model, 4B9 has a large positive patch which is sometimes correlated with increased heparin binding. P1AE1689, on the other hand, shows a large negative charge patch which might be indicative for weak heparin interaction.

These predictions were confirmed by chromatography of both antibodies using a FcRn affinity column and pH gradient as well as a heparin affinity column and pH gradient. WO 2015/140126 discloses a method for the prediction of the in vivo half-life of an antibody based on the retention time determined on an FcRn affinity chromatography column, whereas heparin binding correlates with non-specific interactions with cell surface structures.

Example 2

Generation and Production of Humanized Variants of Anti-CD40 Antibody S2C6

2.1 Generation of Humanized Variants of Anti-CD40 Antibody S2C6

2.2.1 Methodology

For the identification of a suitable human acceptor framework during the humanization of the anti-CD40 binder S2C6 a combination of two methodologies was used. On the one hand, a classical approach was taken by searching for an acceptor framework with high sequence homology, grafting of the CDRs on this framework, and evaluating which back-mutations can be envisaged. More explicitly, each amino acid difference of the identified frameworks to the parental antibody was judged for impact on the structural integrity of the binder, and back mutations towards the parental sequence were introduced whenever appropriate. The structural assessment was based on Fv region homology models of both the parental antibody and its humanized versions created with an in-house antibody structure homology modeling tool implemented using the Biovia Discovery Studio Environment, version 4.5.

On the other hand, an in-house developed in silico tool was used to predict the orientation of the VH and VL domains of the humanized versions towards each other (see WO 2016062734 incorporated herein by reference). The results were compared to the predicted VH-VL domain orientation of the parental binder to select for framework combinations which are close in geometry to the starting antibody. The rational is to detect possible amino acid exchange in the VH-VL interface region that might lead to disruptive changes in the pairing of the two domains.

2.2.2 Choice of Acceptor Framework and Adaptations Thereof

Two different acceptor frameworks were chosen as described in Table 16 and Table 18 below.

TABLE 13

Acceptor framework 1: "IGHV1-IGKV2D"

| | Murine V-region germline | Choice of human acceptor V-region germline | Identity to human V-region germline after grafting (BLASTp): |
|---|---|---|---|
| S2C6 VH | IGHV1-26*01 | IGHV1-2*05 | 91.8% |
| S2C6 VL | IGKV1-110*01 | IGKV2D-29*02 | 88.0% |

Post-CDR3 framework regions were adapted from human IGHJ germline IGHJ6*01/02 (YYYYYGMDVWGQGTTVTVSS) and human IGKJ germline IGKJ4*01/02 (LTFGGGTKVEIK). The part relevant for the acceptor framework is indicated in bold script.

Based on structural considerations, back mutations from the human acceptor framework to the amino acid in the parental binder were introduced at positions H43 (Q>K), H44 (G>S), H69 (M>L), H71 (R>V), H73 (T>K), H88 (V>A) and H105 (Q>H) of the VH region and at positions L2 (I>V), L4 (M>V), L87 (Y>F) and L104 (V>L) of the VL region. In one variant, mutation T70S (VH) was included to study the effect of a slightly more hydrophilic residue at this position.

All variants include the N54A mutation (VH) to address a putative developability hotspot (asparagine deamidation). All positions are given in the Kabat EU numbering scheme.

In the following Table 14 the Humanization variant VH-VL pairing matrix is shown:

|  |  | VL1a bY87F | VL1b bM4V, bY87F | VL1c bI2V, bM4V, bY83F | VL1d bI2V, bM4V, bY783F, |
|---|---|---|---|---|---|
| VH1a | bG44S, bM69L, bR71V, bT73K, bV88A | x | x | x | x |
| VH1b | bQ43K, bG44S, bM69L, bR71V, bT73K, bV88A | x | x | x | x |
| VH1c | bG44S, bM69L, bR71V, bT73K, bV88A, bQ105H | x | x | x | x |
| VH1d | bG44S, bM69L, bR71V, bT73K, bV88A, xT70S | x | x | x | x |

Mutation N54A applies to all VH variants and is not explicitly mentioned. Back mutations prefixed with b, forward mutations prefixed with f, and other mutations prefixed with x

TABLE 15

Acceptor framework 2: "IGHV3-IGKV1"

| Murine V-region germline | Choice of human acceptor V-region germline | Identity to human V-region germline after grafting (BLASTp): |
|---|---|---|
| S2C6 VH IGHV1-26*01 | IGHV3-23*02 | 79.6% |
| S2C6 VL IGKV1-110*01 | IGKV1-39*01 | 79.0% |

Post-CDR3 framework regions were adapted from human IGHJ germline IGHJ6*01/02 (YYYYYGMDVW-GQGTTVTVSS) and human IGKJ germline IGKJ4*01/02 (LTFGGGTKVEIK). The part relevant for the acceptor framework is indicated in bold script.

Based on structural considerations, back mutations from the human acceptor framework to the amino acid in the parental binder were introduced at positions H44 (G>S), H49 (S>G), H71 (R>V), H78 (L>A), H94 (K>R) and H105 (Q>H) of the VH region and at positions L42 (K>Q), L43 (A>S) and L87 (Y>F) of the VL region. Furthermore, four positions in CDR-H2 were identified as promising candidates for forward mutations, i.e., amino acid exchanges from parental binder to human acceptor germline in order to increase overall human character, namely H60 (N>G), H61 (Q>D), H62 (K>S) and H63 (F>V).

All variants include the N54A mutation (VH) to address a putative developability hotspot (asparagine deamidation). All positions are given in the Kabat EU numbering scheme.

In the following Table 16 the Humanization variant VH-VL pairing matrix is shown:

|  |  | VL2a bY87F | VL2b bK42Q, bA43S, |
|---|---|---|---|
| VH2a | bS49G, bR71V, bL78A, bK94R | x | x |
| VH2b | bG44S, bS49G, bR71V, bL78A, bK94R | x | x |
| VH2c | bS49G, bR71V, bL78A, bK94R, bQ105H | x | x |
| VH2d | bS49G, fN60G, fQ61D, fK62S, fF63V, bR71V, bL78A, bK94R | x | x |

Back mutations prefixed with b, forward mutations prefixed with f.

2.2.3 VH and VL Domains of the Resulting Humanized CD40 Antibodies

The resulting VH and VL domains of humanized CD40 antibodies based on acceptor framework 1 can be found in Table 17 below and the resulting VH and VL domains of humanized CD40 antibodies based on acceptor framework 2 are listed in Table 18 below.

TABLE 17

Amino acid sequences of the VH and VL domains of humanized CD40 antibodies based on acceptor framework 1

| Description | Sequence | Seq ID No |
|---|---|---|
| VH1a | QVQLVQSGAEVKKPGASVKVSCKASGYSFTGYYIHW VRQAPGQSLEWMGRVIPNAGGTSYNQKFKGRVTLTV DKSISTAYMELSRLRSDDTAVYYCAREGIYWWGQGT TVTVSS | 37 |
| VH1b | QVQLVQSGAEVKKPGASVKVSCKASGYSFTGYYIHW VRQAPGKSLEWMGRVIPNAGGTSYNQKFKGRVTLTV DKSISTAYMELSRLRSDDTAVYYCAREGIYWWGQGT TVTVSS | 38 |
| VH1c | QVQLVQSGAEVKKPGASVKVSCKASGYSFTGYYIHW VRQAPGQSLEWMGRVIPNAGGTSYNQKFKGRVTLTV DKSISTAYMELSRLRSDDTAVYYCAREGIYWWGHGT TVTVSS | 39 |
| VH1d | QVQLVQSGAEVKKPGASVKVSCKASGYSFTGYYIHW VRQAPGQSLEWMGRVIPNAGGTSYNQKFKGRVTLSV DKSISTAYMELSRLRSDDTAVYYCAREGIYWWGQGT TVTVSS | 40 |
| VL1a | DIVMTQTPLSLSVTPGQPASISCRSSQSLVHSNGNTFL HWYLQKPGQSPQLLIYTVSNRFSGVPDRFSGSGSGTD FTLKISRVEAEDVGVYFCSQTTHVPWTFGGGTKVEIK | 41 |
| VL1b | DIVVTQTPLSLSVTPGQPASISCRSSQSLVHSNGNTFLH WYLQKPGQSPQLLIYTVSNRFSGVPDRFSGSGSGTDF TLKISRVEAEDVGVYFCSQTTHVPWTFGGGTKVEIK | 42 |

TABLE 17-continued

Amino acid sequences of the VH and VL domains of humanized CD40 antibodies based on acceptor framework 1

| Description | Sequence | Seq ID No |
|---|---|---|
| VL1c | DVVVTQTPLSLSVTPGQPASISCRSSQSLVHSNGNTFLHWYLQKPGQSPQLLIYTVSNRFSGVPDRFSGSGSGTDFTLKISRVEAEDVGVYFCSQTTHVPWTFGGGTKVEIK | 43 |
| VL1d | DVVVTQTPLSLSVTPGQPASISCRSSQSLVHSNGNTFLHWYLQKPGQSPQLLIYTVSNRFSGVPDRFSGSGSGTDFTLKISRVEAEDVGVYFCSQTTHVPWTFGGGTKLEIK | 44 |

15

TABLE 18

Amino acid sequences of the VH and VL domains of humanized CD40 antibodies based on acceptor framework 2

| Description | Sequence | Seq ID No |
|---|---|---|
| VH2a | EVQLLESGGGLVQPGGSLRLSCAASGYSFTGYYIHWVRQAPGKGLEWVGRVIPNAGGTSYNQKFKGRFTISVDNSKNTAYLQMNSLRAEDTAVYYCAREGIYWWGQGTTVTVSS | 45 |
| VH2b | EVQLLESGGGLVQPGGSLRLSCAASGYSFTGYYIHWVRQAPGKSLEWVGRVIPNAGGTSYNQKFKGRFTISVDNSKNTAYLQMNSLRAEDTAVYYCAREGIYWWGQGTTVTVSS | 46 |
| VH2c | EVQLLESGGGLVQPGGSLRLSCAASGYSFTGYYIHWVRQAPGKGLEWVGRVIPNAGGTSYNQKFKGRFTISVDNSKNTAYLQMNSLRAEDTAVYYCAREGIYWWGHGTTVTVSS | 47 |
| VH2d | EVQLLESGGGLVQPGGSLRLSCAASGYSFTGYYIHWVRQAPGKGLEWVGRVIPNAGGTSYGDSVKGRFTISVDNSKNTAYLQMNSLRAEDTAVYYCAREGIYWWGQGTTVTVSS | 48 |
| VH2ab | EVQLLESGGGLVQPGGSLRLSCAASGYSFTGYYMHWVRQAPGKGLEWVGRVIPNAGGTSYNQKFKGRFTISVDNSKNTAYLQMNSLRAEDTAVYYCAREGIYWWGQGTTVTVSS | 49 |
| VH2ac | EVQLLESGGGLVQPGGSLRLSCAASGYSFTGYYIHWVRQAPGKGLEWVGRVIPNAGGTSYNQKVKGRFTISVDNSKNTAYLQMNSLRAEDTAVYYCAREGIYWWGQGTTVTVSS | 50 |
| VL2a | DIQMTQSPSSLSASVGDRVTITCRSSQSLVHSNGNTFLHWYQQKPGKAPKLLIYTVSNRFSGVPSRFSGSGSGTDFTLTISSLQPEDFATYFCSQTTHVPWTFGGGTKVEIK | 51 |
| VL2b | DIQMTQSPSSLSASVGDRVTITCRSSQSLVHSNGNTFLHWYQQKPGQSPKLLIYTVSNRFSGVPSRFSGSGSGTDFTLTISSLQPEDFATYFCSQTTHVPWTFGGGTKVEIK | 52 |
| VL2ab | DIQMTQSPSSLSASVGDRVTITCRASQSLVHSNGNTFLHWYQQKPGKAPKLLIYTVSNRFSGVPSRFSGSGSGTDFTLTISSLQPEDFATYFCSQTTHVPWTFGGGTKVEIK | 53 |
| VL2ac | DIQMTQSPSSLSASVGDRVTITCRSSQSIVHSNGNTFLHWYQQKPGKAPKLLIYTVSNRFSGVPSRFSGSGSGTDFTLTISSLQPEDFATYFCSQTTHVPWTFGGGTKVEIK | 54 |

2.2.4 New Humanized CD40 Antibodies in huIgG1_LALA_PG Format

Based on the new humanization variants of VH and VL new CD40 antibodies were expressed as huIgG1 antibodies with an effector silent Fc (P329G; L234, L235A) to abrogate binding to Fc□ receptors according to the method described in WO 2012/130831 A1.

TABLE 19

Nomenclature for VH/VL combinations expressed as huIgG1_LALA_PG antibodies

|      | VL1a     | VL1b     | VL1c     | VL1d     | VL2a     | VL2b     | VL2ab    | VL2ac    |
|------|----------|----------|----------|----------|----------|----------|----------|----------|
| VH1a | P1AE0817 | P1AE1001 | P1AE0993 | P1AE0996 |          |          |          |          |
| VH1b | P1AE1002 | P1AE1003 | P1AE1004 | P1AE1005 |          |          |          |          |
| VH1c | P1AE0997 | P1AE1006 | P1AE0818 | P1AE0998 |          |          |          |          |
| VH1d | P1AE0999 | P1AE1007 | P1AE1000 | P1AE0819 |          |          |          |          |
| VH2a |          |          |          |          | P1AE0400 | P1AE0404 |          |          |
| VH2b |          |          |          |          | P1AE0401 | P1AE0405 |          |          |
| VH2c |          |          |          |          | P1AE0402 | P1AE0406 |          |          |
| VH2d |          |          |          |          | P1AE0403 | P1AE0407 |          |          |
| VH2ab |         |          |          |          |          |          | P1AE1125 | P1AE1126 |
| VH2ac |         |          |          |          |          |          | P1AE1134 | P1AE1135 |

Exemplary full-length sequences of humanized CD40 antibodies as human IgG1_LALAPG antibodies can be found in Table 20.

TABLE 20

Amino acid sequences of the humanized CD40 IgG1_LALAPG antibodies

| Antibody | Sequence | Seq ID No |
|----------|----------|-----------|
| P1AE0400 heavy chain | EVQLLESGGGLVQPGGSLRLSCAASGYSFTGYYIHW VRQAPGKGLEWVGRVIPNAGGTSYNQKFKGRFTISV DNSKNTAYLQMNSLRAEDTAVYYCAREGIYWWGQ GTTVTVSSASTKGPSVFPLAPSSKSTSGGTAALGCLV KDYFPEPVTVSWNSGALTSGVHTFPAVLQSSGLYSL SSVVTVPSSSLGTQTYICNVNHKPSNTKVDKKVEPK SCDKTHTCPPCPAPEAAGGPSVFLFPPKPKDTLMISR TPEVTCVVVDVSHEDPEVKFNWYVDGVEVHNAKT KPREEQYNSTYRVVSVLTVLHQDWLNGKEYKCKVS NKALGAPIEKTISKAKGQPREPQVYTLPPSRDELTKN QVSLTCLVKGFYPSDIAVEWESNGQPENNYKTTPPV LDSDGSFFLYSKLTVDKSRWQQGNVFSCSVMHEAL HNHYTQKSLSLSPG | 55 |
| P1AE0400 light chain | DIQMTQSPSSLSASVGDRVTITCRSSQSLVHSNGNTF LHWYQQKPGKAPKLLIYTVSNRFSGVPSRFSGSGSG TDFTLTISSLQPEDFATYFCSQTTHVPWTFGGGTKVE IKRTVAAPSVFIFPPSDEQLKSGTASVVCLLNNFYPRE AKVQWKVDNALQSGNSQESVTEQDSKDSTYSLSST LTLSKADYEKHKVYACEVTHQGLSSPVTKSFNRGEC | 56 |
| P1AE0403 heavy chain | EVQLLESGGGLVQPGGSLRLSCAASGYSFTGYYIHW VRQAPGKGLEWVGRVIPNAGGTSYGDSVKGRFTISV DNSKNTAYLQMNSLRAEDTAVYYCAREGIYWWGQ GTTVTVSSASTKGPSVFPLAPSSKSTSGGTAALGCLV KDYFPEPVTVSWNSGALTSGVHTFPAVLQSSGLYSL SSVVTVPSSSLGTQTYICNVNHKPSNTKVDKKVEPK SCDKTHTCPPCPAPEAAGGPSVFLFPPKPKDTLMISR TPEVTCVVVDVSHEDPEVKFNWYVDGVEVHNAKT KPREEQYNSTYRVVSVLTVLHQDWLNGKEYKCKVS NKALGAPIEKTISKAKGQPREPQVYTLPPSRDELTKN QVSLTCLVKGFYPSDIAVEWESNGQPENNYKTTPPV LDSDGSFFLYSKLTVDKSRWQQGNVFSCSVMHEAL HNHYTQKSLSLSPG | 60 |
| P1AE0403 light chain | DIQMTQSPSSLSASVGDRVTITCRSSQSLVHSNGNTF LHWYQQKPGKAPKLLIYTVSNRFSGVPSRFSGSGSG TDFTLTISSLQPEDFATYFCSQTTHVPWTFGGGTKVE IKRTVAAPSVFIFPPSDEQLKSGTASVVCLLNNFYPRE AKVQWKVDNALQSGNSQESVTEQDSKDSTYSLSST LTLSKADYEKHKVYACEVTHQGLSSPVTKSFNRGEC | 61 |

TABLE 20-continued

Amino acid sequences of the humanized CD40 IgG1_LALAPG antibodies

| Antibody | Sequence | Seq ID No |
|---|---|---|
| P1AE0817 heavy chain | QVQLVQSGAEVKKPGASVKVSCKASGYSFTGYYIH WVRQAPGQSLEWMGRVIPNAGGTSYNQKFKGRVT LTVDKSISTAYMELSRLRSDDTAVYYCAREGIYWW GQGTTVTVSSASTKGPSVFPLAPSSKSTSGGTAALGC LVKDYFPEPVTVSWNSGALTSGVHTFPAVLQSSGLY SLSSVVTVPSSSLGTQTYICNVNHKPSNTKVDKKVEP KSCDKTHTCPPCPAPEAAGGPSVFLFPPKPKDTLMIS RTPEVTCVVVDVSHEDPEVKFNWYVDGVEVHNAK TKPREEQYNSTYRVVSVLTVLHQDWLNGKEYKCKV SNKALGAPIEKTISKAKGQPREPQVYTLPPSRDELTK NQVSLTCLVKGFYPSDIAVEWESNGQPENNYKTTPP VLDSDGSFFLYSKLTVDKSRWQQGNVFSCSVMHEA LHNHYTQKSLSLSPG | 62 |
| P1AE0817 light chain | DIVMTQTPLSLSVTPGQPASISCRSSQSLVHSNGNTFL HWYLQKPGQSPQLLIYTVSNRFSGVPDRFSGSGSGT DFTLKISRVEAEDVGVYFCSQTTHVPWTFGGGTKVE IKRTVAAPSVFIFPPSDEQLKSGTASVVCLLNNFYPRE AKVQWKVDNALQSGNSQESVTEQDSKDSTYSLSST LTLSKADYEKHKVYACEVTHQGLSSPVTKSFNRGEC | 63 |

2.2.5 Production of the New Humanized CD40 Antibodies in huIgG1_LALA_PG Format The antibodies were expressed by transient transfection of HEK293-F cells grown in suspension with expression vectors encoding the different peptide chains. Transfection into HEK293-F cells (Invitrogen, USA) was performed according to the cell supplier's instructions using Maxiprep (Qiagen, Germany) preparations of the antibody vectors, F17 based medium (Invitrogen, USA), PEIpro (Polyscience Europe GmbH) and an initial cell density of 1-2 million viable cells/ml in serum free FreeStyle 293 expression medium (Invitrogen). Cell culture supernatants were harvested after 7 days of cultivation in shake flasks or stirred fermenters by centrifugation at 14000 g for 30 minutes and filtered through a 0.22 µm filter.

The antibodies were purified from cell culture supernatants by affinity chromatography using MabSelectSure-Sepharose™ (GE Healthcare, Sweden) chromatography. Briefly, sterile filtered cell culture supernatants were captured on a MabSelect SuRe resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM citrate, pH 3.0, followed by neutralization with 1 M Tris pH 9.0. Dependent on product quality received after ProteinA purification, a hydrophobic interaction chromatography (HIC) purification step was included using Butyl-Sepharose 4FF (GE Healthcare, Sweden) resin. Prior HIC purification, the protein was dialysed against HIC equilibration buffer. HIC purification was performed using 40 mM acetate, 1.5 M ammonium sulfate, pH 5.5 as equilibration/washing buffer and 40 mM acetate pH 5.5 as elution buffer and a linear gradient was applied for purification. Subsequently, aggregated protein was separated from monomeric antibody species by size exclusion chromatography (Superdex 200, GE Healthcare) in 20 mM histidine, 140 mM NaCl, pH 6.0. Monomeric protein fractions were pooled, concentrated if required using e.g. a MILLIPORE Amicon Ultra (30 KD MWCO) centrifugal concentrator and stored at −80° C. Sample aliquots were used for subsequent analytical characterization e.g. by CE-SDS, size exclusion chromatography, mass spectrometry and endotoxin determination.

The production yield for the different humanized CD40 antibodies is shown in Table 21 as titer values calculated from the yield after preparative affinity chromatography using MabSelectSure-Sepharose™ chromatography.

Purity and molecular weight of the molecule after the final purification step were analyzed by CE-SDS analyses in the presence and absence of a reducing agent. The Caliper LabChip GXII system (Caliper Lifescience) was used according to the manufacturer's instruction.

The aggregate content of the molecule was analyzed using a TSKgel G3000 SW XL analytical size-exclusion column (Tosoh) in 25 mM potassium phosphate, 125 mM sodium chloride, 200 mM L-arginine monohydrocloride, 0.02% (w/v) $NaN_3$, pH 6.7 running buffer at 25° C.

For direct comparison of all antibodies the thermal stability was monitored by Static Light Scattering (SLS) and by measuring the intrinsic protein fluorescence in response to applied temperature stress. 30 µg of filtered protein sample with a protein concentration of 1 mg/ml was applied in duplicate to an Optim 2 instrument (Avacta Analytical Ltd). The temperature was ramped from 25 to 85° C. at 0.1° C./min, with the radius and total scattering intensity being collected. For determination of intrinsic protein fluorescence the sample was excited at 266 nm and emission was collected between 275 nm and 460 nm. For all antibodies the aggregation temperature (Tagg) was between 64° C. and 69° C. and is provided in Table 21 or Table 22 below.

The production yield for the humanized CD40 antibodies with the different frameworks is shown in Table 21 or Table 22 below.

TABLE 21

Production titer, humanness and aggregation temperature of humanized CD40 antibodies based on acceptor framework 2

| Antibody | VH/VL | Titer [µg/ml] | humanness (VH/VL in %) | $T_{agg}$ |
|---|---|---|---|---|
| P1AD4470 | control | 140 | 77.6/78 | 68 |
| P1AE0400 | VL2a/VH2a | 219 | 77.6/78 | 69 |
| P1AE0401 | VL2a/VH2b | 162 | 76.5/78 | 69 |

TABLE 21-continued

Production titer, humanness and aggregation temperature of humanized CD40 antibodies based on acceptor framework 2

| Antibody | VH/VL | Titer [µg/ml] | humanness (VH/VL in %) | $T_{agg}$ |
|---|---|---|---|---|
| P1AE0402 | VL2a/VH2c | 196 | 77.6/78 | 69 |
| P1AE0403 | VL2a/VH2d | 137 | 80.6/78 | 67 |
| P1AE0404 | VL2b/VH2a | 165 | 77.6/76 | 69 |
| P1AE0405 | VL2b/VH2b | 128 | 76.5/76 | 69 |
| P1AE0406 | VL2b/VH2c | 154 | 77.6/76 | 69 |
| P1AE0407 | VL2b/VH2d | 102 | 80.6/76 | 67 |

TABLE 22

Production titer, humanness and aggregation temperature of humanized CD40 antibodies based on acceptor framework 1

| Antibody | VH/VL | Titer [µg/ml] | humanness (VH/VL in %) | $T_{agg}$ |
|---|---|---|---|---|
| P1AE0816 | control | 8.5 | 84.7/84 | 64 |
| P1AE0817 | VH1a/VL1a | 62 | 86.7/87 | 67 |
| P1AE0818 | VH1c/VL1c | 47 | 86.7/85 | 66 |
| P1AE0819 | VH1d/VL1d | 90 | 85.7/85 | 67 |
| P1AE0993 | VH1a/VL1c | 34 | 86.7/85 | 67 |
| P1AE0996 | VH1a/VL1d | 16 | 86.7/85 | 67 |
| P1AE0997 | VH1c/VL1a | 44 | 86.7/87 | 66 |
| P1AE0998 | VH1c/VL1d | 24 | 86.7/85 | 66 |
| P1AE0999 | VH1d/VL1a | 34 | 85.7/87 | 67 |
| P1AE1000 | VH1d/VL1c | 16 | 85.7/85 | 66 |
| P1AE1001 | VH1a/VL1b | 34 | 86.7/86 | 65 |
| P1AE1002 | VH1b/VL1a | 46 | 85.7/87 | 67 |
| P1AE1003 | VH1b/VL1b | 49 | 85.7/86 | 66 |
| P1AE1004 | VH1b/VL1c | 60 | 85.7/85 | 67 |
| P1AE1005 | VH1b/VL1d | 7 | 85.7/85 | 65 |
| P1AE1006 | VH1c/VL1b | 24 | 86.7/86 | 65 |
| P1AE1007 | VH1d/VL1b | 34 | 85.7/86 | 67 |

2.2.6 Generation of Recombinant Human and Cynomolgus Monkey CD40 Extracellular Domain Protein Following constructs were cloned and expressed by transient expression in HEK293 cells:

1) Human CD40 extracellular domain (amino acids 21-193 of SEQ ID NO:1, NCBI accession number NP_001241) with C-terminal His-AviTag™ tag (SEQ ID NO:266)
2) Cynomolgus monkey (*Macaca fascicularis*) CD40 extracellular domain (amino acids 21-193, cynomolgus CD40 extracellular domain sequence was taken from Roche cynomolgus cDNA database, unpublished data) with C-terminal His-AviTag™ tag (SEQ ID NO:267)

CD40 extracellular domain antigens for binding analysis were generated by gene synthesis (Eurofins Genomics GmbH service, Germany), cloned via unique restriction sites into Roche's in house expression vector using standard cloning procedures. Cloning of all constructs was verified by sequencing. All antigens were expressed under the control of the CMV-promoter. For transient expression of the CD40 extracellular domain constructs, suspension-adapted HEK293-F cells (Life Technologies, USA) were transfected with the respective plasmids: In general, 1 L of HEK293-F cells at about $2 \times 10^6$ cells/ml were transfected with a total of 500 µg plasmid DNA complexed by the PEIpro Transfection Reagent (Polysciences Europe GmbH, Germany) according to manufacturer's instructions. After transfection, HEK293-F cells were incubated for 6 days. The cells were subsequently harvested by centrifugation and the protein-containing supernatant was filtered using a 0.22 µm vacuum filtration system (Millipore). The His-AviTag™ tagged proteins were purified by IMAC affinity chromatography using complete-His-Tag resin (Roche Diagnostics). After washing with 50 mM $Na_2PO_4$, 300 mM NaCl, pH 8.0, His-AviTag™ fusion proteins were eluted using washing buffer supplemented with 500 mM Imidazol at pH 7.0. Aggregated protein was separated from monomeric fusion proteins by size exclusion chromatography (Superdex 75, GE Healthcare) in 20 mM Tris, 150 mM NaCl, pH 7.4. Monomeric protein fractions were pooled, concentrated if required using e.g. a MILLIPORE Amicon Ultra (10 KD MWCO) centrifugal concentrator and stored at −80° C. Sample aliquots were used for subsequent analytical characterization e.g. by CE-SDS, size exclusion chromatography and mass spectrometry.

Biotinylation of CD40 Extracellular Domain:

Enzymatic site specific biotinylation of human or cynomolgus CD40 extracellular domain constructs containing a C-terminal AviTag™ was performed by using the BirA biotin-protein ligase kit (Avidity LLC, USA) according to manufactures instruction. Briefly, ¹/₁₀ volume of BiomixA (10× concentration: 0.5M bicine buffer, pH 8.3) and BiomixB (10× concentration: 100 mM ATP, 100 mM MgOAc, 500 µM d-biotin) was added to AviTag™ containing protein followed by addition of 2.5 µs BirA ligase per 10 nmol protein. The reaction mixture was incubated at 30° C. for 1 h and purified by size exclusion chromatography on a Superdex75 prep grade prepacked HiLoad column (GE Healthcare, Sweden).

2.2.7 Human/Cynomolgus CD40 Binding Surface Plasmon Resonance Spectroscopy Assay Around 12000 resonance units (RU) of the capturing system (10 µg/ml goat anti human F(ab)'₂; Order Code: 28958325; GE Healthcare Bio-Sciences AB, Sweden) were coupled on a CMS chip (GE Healthcare BR-1005-30) at pH 5.0 by using an amine coupling kit supplied by the GE Healthcare. The sample and system buffer was PBS-T (10 mM phosphate buffered saline including 0.05% Tween20) pH 7.4. The flow cell was set to 25° C.—and the sample block set to 12° C.—and primed with running buffer twice. The antibody was captured by injecting a 50 nM solution for 30 sec at a flow of 5 µl/min. Association was measured by injection of human CD40 extra cellular domain or cynomolgus monkey CD40 extracellular domain in various concentrations in solution for 300 sec at a flow of 30 µl/min starting with 300 nM in 1:3 dilutions. The dissociation phase was monitored for up to 1200 sec and triggered by switching from the sample solution to running buffer. The surface was regenerated by 60 sec washing with a Glycine pH 2.1 solution at a flow rate of 30 µl/min. Bulk refractive index differences were corrected by subtracting the response obtained from a goat anti human F(ab')₂ surface. Blank injections are also subtracted (=double referencing). For calculation of apparent $K_D$ and other kinetic parameters the Langmuir 1:1 model was used. The apparent Kd was calculated using the Biacore™ B4000 evaluation software (version 1.1).

2.2.8 Cellular Binding Assay for Characterisation of CD40-Specific Humanized Antibodies CD40 positive cells (Raji cells) were detached from the culture bottle using Trypsin and were counted using a Casy cell counter. After pelleting at 4° C., the cells were resuspended in FACS Buffer (2.5% FCS in PBS), adjusted to 2.0E+06 cells/mL, and dispensed to 96-well PP V-bottom-plates (25 µL/well=5.0E+04Zellen/well).

The CD40 specific antibodies were adjusted to 20 µg/mL in FACS buffer, resulting in a final concentration of 10 µg/mL. 20 µl were added to 25 µl cell suspension and incubated for 1 h at 4° C. The cells were then washed twice in FACS buffer. After washing, the cells were resuspended in 50 µL FACS-buffer containing secondary antibody (<huIgG>-Alexa488, c=10 µg/mL) and incubated 1 h bei 4° C. The cells were then washed twice in FACS buffer and resuspended in 70 μl/well FACS buffer for measurement using a FACS Canto (BD, Pharmingen).

In Table 23 the affinity of the humanized CD40 antibodies (measured by Biacore) and the cellular binding to CD40 expressing cells (Raji cells) is shown.

TABLE 23

Affinity and cellular binding of humanized CD40 antibodies to CD40 expressing cells

| ID | VH/VL | Affinity [nM] | Ka (1/Ms) | Kd (1/s) | $EC_{50}$ [μg/ml] cellular binding (Raji) |
|---|---|---|---|---|---|
| P1AD4470 | control | 4.6 | 1.69E+06 | 7.81E-03 | 0.09 |
| P1AE0400 | VL2a/VH2a | 4.2 | 1.68E+06 | 6.99E-03 | 0.12 |
| P1AE0401 | VL2a/VH2b | 4.6 | 1.69E+06 | 7.87E-03 | 0.13 |
| P1AE0402 | VL2a/VH2c | 4.2 | 1.67E+06 | 7.09E-03 | 0.13 |
| P1AE0403 | VL2a/VH2d | 29 | 1.40E+06 | 4.07E-02 | 0.12 |
| P1AE0404 | VL2b/VH2a | 4.2 | 1.63E+06 | 6.93E-03 | 0.11 |
| P1AE0405 | VL2b/VH2b | 5.1 | 1.61E+06 | 8.14E-03 | 0.09 |
| P1AE0406 | VL2b/VH2c | 4.2 | 1.67E+06 | 7.09E-03 | 0.09 |
| P1AE0407 | VL2b/VH2d | 30 | 1.19E+06 | 3.55E-02 | 0.12 |
| P1AE0816 | control | 8.7 | 2.53E+06 | 2.19E-02 | 0.09 |
| P1AE0817 | VH1a/VL1a | 2.5 | 2.40E+06 | 5.93E-03 | 0.09 |
| P1AE0818 | VH1c/VL1c | 3.2 | 2.63E+06 | 8.47E-03 | 0.14 |
| P1AE0819 | VH1d/VL1d | 3.4 | 2.59E+06 | 8.77E-03 | 0.11 |
| P1AE0993 | VH1a/VL1c | 3.4 | 2.68E+06 | 8.98E-03 | 0.13 |
| P1AE0996 | VH1a/VL1d | 3.5 | 2.59E+06 | 9.08E-03 | 0.12 |
| P1AE0997 | VH1c/VL1a | 2.3 | 2.59E+06 | 6.03E-03 | 0.12 |
| P1AE0998 | VH1c/VL1d | 3.3 | 2.70E+06 | 8.96E-03 | 0.12 |
| P1AE0999 | VH1d/VL1a | 2.4 | 2.45E+06 | 5.92E-03 | 0.15 |
| P1AE1000 | VH1d/VL1c | 3.2 | 2.68E+06 | 8.62E-03 | 0.14 |
| P1AE1001 | VH1a/VL1b | 2.7 | 2.56E+06 | 6.81E-03 | 0.08 |
| P1AE1002 | VH1b/VL1a | 2.2 | 2.54E+06 | 5.57E-03 | 0.13 |
| P1AE1003 | VH1b/VL1b | 2.5 | 2.46E+06 | 6.06E-03 | 0.13 |
| P1AE1004 | VH1b/VL1c | 3 | 2.63E+06 | 7.95E-03 | 0.14 |
| P1AE1005 | VH1b/VL1d | 3.2 | 2.58E+06 | 8.16E-03 | 0.11 |
| P1AE1006 | VH1c/VL1b | 2.6 | 2.53E+06 | 6.51E-03 | 0.14 |
| P1AE1007 | VH1d/VL1b | 2.7 | 2.50E+06 | 6.62E-03 | 0.12 |

2.2.9 Antibody Characterisation by UHR-ESI-QTOF Mass Spectrometry

The samples were desalted by HPLC on a Sephadex G25 5×250 mm column (Amersham Biosciences, Freiburg, Germany) using 40% acetonitrile with 2% formic acid (v/v). The total mass was determined by UHR-ESI-QTOF MS on a maXis 4G UHR-QTOF MS system (Bruker Daltonik, Bremen, Germany) equipped with a TriVersa NanoMate source (Advion, Ithaca, NY). Data acquisition was done at 900-4000 m/z (ISCID: 0.0 eV). The raw mass spectra were evaluated and transformed into individual relative molar masses using an in-house developed software tool.

2.2.10 Thermal Stability Evaluation of Antibodies

Samples are prepared at a concentration of 1 mg/mL in 20 mM Histidine/Histidine chloride, 140 mM NaCl, pH 6.0, transferred into an optical 384-well plate by centrifugation through a 0.4 μm filter plate and covered with paraffine oil. The hydrodynamic radius is measured repeatedly by dynamic light scattering on a DynaPro Plate Reader (Wyatt) while the samples are heated with a rate of 0.05° C./min from 25° C. to 80° C. Alternatively, samples were transferred into a 10 μL micro-cuvette array and static light scattering data as well as fluorescence data upon excitation with a 266 nm laser were recorded with an Optim1000 instrument (Avacta Inc.), while they were heated at a rate of 0.1° C./min from 25° C. to 90° C. The aggregation onset temperature is defined as the temperature at which the hydrodynamic radius (DLS) or the scattered light intensity (Optim1000) starts to increase. The melting temperature is defined as the inflection point in a graph showing fluorescence intensity vs. wavelength.

Example 3

Generation and Production of Bispecific Constructs with New Anti-FAP Clone 212 and its Humanized Variants 3.1 Generation of Bispecific Antigen Binding Molecules Targeting Fibroblast Activation Protein (FAP) and CD40

Figures 1D, 1E, 1F:
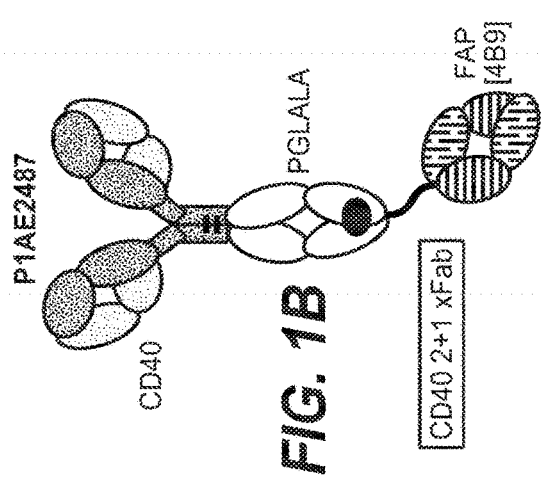

Bispecific CD40-FAP antibodies were prepared in 2+1 format consisting of two CD40 binding moieties combined with one FAP binding moiety at the C-terminus of an Fc (FIG. 1A to FIG. 1C) or in 4+1 format consisting of four CD40 binding moieties combined with one FAP binding moiety at the C-terminus of an Fc (FIG. 1D to FIG. 1F). The bispecific CD40-FAP antibodies included new anti-FAP clone 212 (FIG. 1A and FIG. 1D), however for comparison corresponding molecules with FAP clones 4B9 (FIG. 1B and FIG. 1E) and 28H1 (FIG. 1C and FIG. 1F) were prepared. The generation and preparation of FAP binders 28H1 and 4B9 has been described in WO 2012/020006 A2, which is incorporated herein by reference. To generate the 4+1 and the 2+1 molecules the knob-into-hole technology was used to achieve heterodimerization. The S354C/T366W mutations were introduced in the first heavy chain HC1 (Fc knob heavy chain) and the Y349C/T366S/L368A/Y407V mutations were introduced in the second heavy chain HC2 (Fc hole heavy chain). Independent of the bispecific format, in all cases an effector silent Fc (P329G; L234, 234A) was used to abrogate binding to Fc☐ receptors according to the method described in WO 2012/130831 A1. Sequences of the bispecific molecules are shown in Table 24.

All genes are transiently expressed under control of a chimeric MPSV promoter consisting of the MPSV core promoter combined with the CMV promoter enhancer fragment. The expression cassette also contains a synthetic polyA signal at the 3' end of the cDNAs. The expression vector also contains the oriP region for episomal replication in EBNA (Epstein Barr Virus Nuclear Antigen) containing host cells.

TABLE 24

Amino acid sequences of the bispecific antigen binding molecules

| Construct | Sequence | Seq ID No |
|---|---|---|
| | P1AE2423 | |
| CD40 (P1AE0817) x FAP (P1AE1689) (2 + 1) C-terminal crossfab fusion | | |
| (P1AE1689) light chain cross VH-Ckappa | QVQLVQSGAEVKKPGASVKVSCKASGYTLTDYNM DWVRQAPGQGLEWIGDIYPNTGGTIYNQKFKGRV TMTIDTSTSTVYMELSSLRSEDTAVYYCTRFRGIHY AMDYWGQGTTVTVSSASVAAPSVFIFPPSDEQLKS GTASVVCLLNNFYPREAKVQWKVDNALQSGNSQE | 61 |

TABLE 24-continued

Amino acid sequences of the bispecific antigen binding molecules

| Construct | Sequence | Seq ID No |
|---|---|---|
| | SVTEQDSKDSTYSLSSTLTLSKADYEKHKVYACEV<br>THQGLSSPVTKSFNRGEC | |
| VL1a (CD40) light chain (charged) | DIVMTQTPLSLSVTPGQPASISCRSSQSLVHSNGNTF<br>LHWYLQKPGQSPQLLIYTVSNRFSGVPDRFSGSGS<br>GTDFTLKISRVEAEDVGVYFCSQTTHVPWTFGGGT<br>KVEIKRTVAAPSVFIFPPSDRKLKSGTASVVCLLNN<br>FYPREAKVQWKVDNALQSGNSQESVTEQDSKDST<br>YSLSSTLTLSKADYEKHKVYACEVTHQGLSSPVTK<br>SFNRGEC | 62 |
| VH1 a (CD40) (VHCH1 charged) Fc knob_PGLALA_(P1AE1689) (VL-CH1) | QVQLVQSGAEVKKPGASVKVSCKASGYSFTGYYI<br>HWVRQAPGQSLEWMGRVIPNAGGTSYNQKFKGR<br>VTLTVDKSISTAYMELSRLRSDDTAVYYCAREGIY<br>WWGQGTTVTVSSASTKGPSVFPLAPSSKSTSGGTA<br>ALGCLVEDYFPEPVTVSWNSGALTSGVHTFPAVLQ<br>SSGLYSLSSVVTVPSSSLGTQTYICNVNHKPSNTKV<br>DEKVEPKSCDKTHTCPPCPAPEAAGGPSVFLFPPKP<br>KDTLMISRTPEVTCVVVDVSHEDPEVKFNWYVDG<br>VEVHNAKTKPREEQYNSTYRVVSVLTVLHQDWLN<br>GKEYKCKVSNKALGAPIEKTISKAKGQPREPQVYT<br>LPPCRDELTKNQVSLWCLVKGFYPSDIAVEWESNG<br>QPENNYKTTPPVLDSDGSFFLYSKLTVDKSRWQQG<br>NVFSCSVMHEALHNHYTQKSLSLSPGGGGGSGGG<br>GSGGGGSGGGGSEIVLTQSPATLSLSPGERATLSCR<br>ASESVDNYGLSFINWFQQKPGQAPRLLIYGTSNRGS<br>GIPARFSGSGSGTDFTLTISSLEPEDFAVYFCQQSNE<br>VPYTFGGGTKVEIKSSASTKGPSVFPLAPSSKSTSG<br>GTAALGCLVKDYFPEPVTVSWNSGALTSGVHTFPA<br>VLQSSGLYSLSSVVTVPSSSLGTQTYICNVNHKPSN<br>TKVDKKVEPKSC | 63 |
| VH1a (CD40) (VHCH1 charged) Fc hole_PGLALA | QVQLVQSGAEVKKPGASVKVSCKASGYSFTGYYI<br>HWVRQAPGQSLEWMGRVIPNAGGTSYNQKFKGR<br>VTLTVDKSISTAYMELSRLRSDDTAVYYCAREGIY<br>WWGQGTTVTVSSASTKGPSVFPLAPSSKSTSGGTA<br>ALGCLVEDYFPEPVTVSWNSGALTSGVHTFPAVLQ<br>SSGLYSLSSVVTVPSSSLGTQTYICNVNHKPSNTKV<br>DEKVEPKSCDKTHTCPPCPAPEAAGGPSVFLFPPKP<br>KDTLMISRTPEVTCVVVDVSHEDPEVKFNWYVDG<br>VEVHNAKTKPREEQYNSTYRVVSVLTVLHQDWLN<br>GKEYKCKVSNKALGAPIEKTISKAKGQPREPQVCT<br>LPPSRDELTKNQVSLSCAVKGFYPSDIAVEWESNG<br>QPENNYKTTPPVLDSDGSFFLVSKLTVDKSRWQQG<br>NVFSCSVMHEALHNHYTQKSLSLSPG | 64 |

P1AE2734
CD40 (P1AE0817) × FAP (P1AE1689) (2 + 1) with different
C-terminal crossfab fusion

| | | |
|---|---|---|
| (P1AE1689) light chain cross VL-CH1 | EIVLTQSPATLSLSPGERATLSCRASESVDNYGLSFI<br>NWFQQKPGQAPRLLIYGTSNRGSGIPARFSGSGSGT<br>DFTLTISSLEPEDFAVYFCQQSNEVPYTFGGGTKVEI<br>KSSASTKGPSVFPLAPSSKSTSGGTAALGCLVKDYF<br>PEPVTVSWNSGALTSGVHTFPAVLQSSGLYSLSSV<br>VTVPSSSLGTQTYICNVNHKPSNTKVDKKVEPKSC | 65 |
| VL1a (CD40) light chain | DIVMTQTPLSLSVTPGQPASISCRSSQSLVHSNGNTF<br>LHWYLQKPGQSPQLLIYTVSNRFSGVPDRFSGSGS<br>GTDFTLKISRVEAEDVGVYFCSQTTHVPWTFGGGT<br>KVEIKRTVAAPSVFIFPPSDEQLKSGTASVVCLLNN<br>FYPREAKVQWKVDNALQSGNSQESVTEQDSKDST<br>YSLSSTLTLSKADYEKHKVYACEVTHQGLSSPVTK<br>SFNRGEC | 66 |
| VH1a (CD40) (VHCH1) Fc knob_PGLALA_(P1AE1689) (VH-Ckappa) | QVQLVQSGAEVKKPGASVKVSCKASGYSFTGYYI<br>HWVRQAPGQSLEWMGRVIPNAGGTSYNQKFKGR<br>VTLTVDKSISTAYMELSRLRSDDTAVYYCAREGIY<br>WWGQGTTVTVSSASTKGPSVFPLAPSSKSTSGGTA<br>ALGCLVEDYFPEPVTVSWNSGALTSGVHTFPAVLQ<br>SSGLYSLSSVVTVPSSSLGTQTYICNVNHKPSNTKV<br>DKKVEPKSCDKTHTCPPCPAPEAAGGPSVFLFPPKP<br>KDTLMISRTPEVTCVVVDVSHEDPEVKFNWYVDG<br>VEVHNAKTKPREEQYNSTYRVVSVLTVLHQDWLN<br>GKEYKCKVSNKALGAPIEKTISKAKGQPREPQVYT | 67 |

TABLE 24-continued

Amino acid sequences of the bispecific antigen binding molecules

| Construct | Sequence | Seq ID No |
|---|---|---|
| | LPPCRDELTKNQVSLWCLVKGFYPSDIAVEWESNG QPENNYKTTPPVLDSDGSFFLYSKLTVDKSRWQQG NVFSCSVMHEALHNHYTQKSLSLSPGGGGSGGGG GSGGGGSGGGGSQVQLVQSGAEVKKPGASVKVSC KASGYTLTDYNMDWVRQAPGQGLEWIGDIYPNTG GTIYNQKFKGRVTMTIDTSTSTVYMELSSLRSEDTA VYYCTRFRGIHYAMDYWGQGTTVTVSSASVAAPS VFIFPPSDEQLKSGTASVVCLLNNFYPREAKVQWK VDNALQSGNSQESVTEQDSKDSTYSLSSTLTLSKA DYEKHKVYACEVTHQGLSSPVTKSFNRGEC | |
| VH1a (CD40) (VHCH1) Fc hole_PGLALA | QVQLVQSGAEVKKPGASVKVSCKASGYSFTGYYI HWVRQAPGQSLEWMGRVIPNAGGTSYNQKFKGR VTLTVDKSISTAYMELSRLRSDDTAVYYCAREGIY WWGQGTTVTVSSASTKGPSVFPLAPSSKSTSGGTA ALGCLVKDYFPEPVTVSWNSGALTSGVHTFPAVLQ SSGLYSLSSVVTVPSSSLGTQTYICNVNHKPSNTKV DKKVEPKSCDKTHTCPPCPAPEAAGGPSVFLFPPKP KDTLMISRTPEVTCVVVDVSHEDPEVKFNWYVDG VEVHNAKTKPREEQYNSTYRVVSVLTVLHQDWLN GKEYKCKVSNKALGAPIEKTISKAKGQPREPQVCT LPPSRDELTKNQVSLSCAVKGFYPSDIAVEWESNG QPENNYKTTPPVLDSDGSFFLVSKLTVDKSRWQQG NVFSCSVMHEALHNHYTQKSLSLSPG | 68 |

P1AE2424
CD40 (P1AE0817) x FAP (P1AE1689) (4 + 1) with
C-terminal crossfab fusion

| Construct | Sequence | Seq ID No |
|---|---|---|
| (P1AE1689) light chain cross VH-Ckappa | QVQLVQSGAEVKKPGASVKVSCKASGYTLTDYNM DWVRQAPGQGLEWIGDIYPNTGGTIYNQKFKGRV TMTIDTSTSTVYMELSSLRSEDTAVYYCTRFRGIHY AMDYWGQGTTVTVSSASVAAPSVFIFPPSDEQLKS GTASVVCLLNNFYPREAKVQWKVDNALQSGNSQE SVTEQDSKDSTYSLSSTLTLSKADYEKHKVYACEV THQGLSSPVTKSFNRGEC | 61 |
| VL1a (CD40) light chain (charged) | DIVMTQTPLSLSVTPGQPASISCRSSQSLVHSNGNTF LHWYLQKPGQSPQLLIYTVSNRFSGVPDRFSGSGS GTDFTLKISRVEAEDVGVYFCSQTTHVPWTFGGGT KVEIKRTVAAPSVFIFPPSDRKLKSGTASVVCLLNN FYPREAKVQWKVDNALQSGNSQESVTEQDSKDST YSLSSTLTLSKADYEKHKVYACEVTHQGLSSPVTK SFNRGEC | 62 |
| VH1a (CD40) (VHCH1 charged_VH1a (CD40) (VHCH1 charged)-Fc knob_PGLALA_(P1AE1689) (VL-CH1) | QVQLVQSGAEVKKPGASVKVSCKASGYSFTGYYI HWVRQAPGQSLEWMGRVIPNAGGTSYNQKFKGR VTLTVDKSISTAYMELSRLRSDDTAVYYCAREGIY WWGQGTTVTVSSASTKGPSVFPLAPSSKSTSGGTA ALGCLVEDYFPEPVTVSWNSGALTSGVHTFPAVLQ SSGLYSLSSVVTVPSSSLGTQTYICNVNHKPSNTKV DEKVEPKSCDGGGGSGGGGSQVQLVQSGAEVKKP GASVKVSCKASGYSFTGYYIHWVRQAPGQSLEWM GRVIPNAGGTSYNQKFKGRVTLTVDKSISTAYMEL SRLRSDDTAVYYCAREGIYWWGQGTTVTVSSAST KGPSVFPLAPSSKSTSGGTAALGCLVEDYFPEPVTV SWNSGALTSGVHTFPAVLQSSGLYSLSSVVTVPSSS LGTQTYICNVNHKPSNTKVDEKVEPKSCDKTHTCP PCPAPEAAGGPSVFLFPPKPKDTLMISRTPEVTCVV VDVSHEDPEVKFNWYVDGVEVHNAKTKPREEQY NSTYRVVSVLTVLHQDWLNGKEYKCKVSNKALG APIEKTISKAKGQPREPQVYTLPPCRDELTKNQVSL WCLVKGFYPSDIAVEWESNGQPENNYKTTPPVLDS DGSFFLYSKLTVDKSRWQQGNVFSCSVMHEALHN HYTQKSLSLSPGGGGSGGGGSGGGGSGGGSEIV LTQSPATLSLSPGERATLSCRASESVDNYGLSFINW FQQKPGQAPRLLIYGTSNRGSGIPARFSGSGSGTDF TLTISSLEPEDFAVYFCQQSNEVPYTFGGGTKVEIKS SASTKGPSVFPLAPSSKSTSGGTAALGCLVKDYFPE PVTVSWNSGALTSGVHTFPAVLQSSGLYSLSSVVT VPSSSLGTQTYICNVNHKPSNTKVDKKVEPKSC | 69 |
| VH1a (CD40) (VHCH1 charged)_VH1a | QVQLVQSGAEVKKPGASVKVSCKASGYSFTGYYI HWVRQAPGQSLEWMGRVIPNAGGTSYNQKFKGR VTLTVDKSISTAYMELSRLRSDDTAVYYCAREGIY | 70 |

TABLE 24-continued

Amino acid sequences of the bispecific antigen binding molecules

| Construct | Sequence | Seq ID No |
|---|---|---|
| (CD40) (VHCH1 charged)-Fc hole_PGLALA | WWGQGTTVTVSSASTKGPSVFPLAPSSKSTSGGTA ALGCLVEDYFPEPVTVSWNSGALTSGVHTFPAVLQ SSGLYSLSSVVTVPSSSLGTQTYICNVNHKPSNTKV DEKVEPKSCDGGGGSGGGGSQVQLVQSGAEVKKP GASVKVSCKASGYSFTGYYIHWVRQAPGQSLEWM GRVIPNAGGTSYNQKFKGRVTLTVDKSISTAYMEL SRLRSDDTAVYYCAREGIYWWGQGTTVTVSSAST KGPSVFPLAPSSKSTSGGTAALGCLVEDYFPEPVTV SWNSGALTSGVHTFPAVLQSSGLYSLSSVVTVPSSS LGTQTYICNVNHKPSNTKVDEKVEPKSCDKTHTCP PCPAPEAAGGPSVFLFPPKPKDTLMISRTPEVTCVV VDVSHEDPEVKFNWYVDGVEVHNAKTKPREEQY NSTYRVVSVLTVLHQDWLNGKEYKCKVSNKALG APIEKTISKAKGQPREPQVCTLPPSRDELTKNQVSLS CAVKGFYPSDIAVEWESNGQPENNYKTTPPVLDSD GSFFLVSKLTVDKSRWQQGNVFSCSVMHEALHNH YTQKSLSLSPG | |

P1AE2487
CD40 (P1AE0817) x FAP (4B9) (2 + 1) C-terminal crossfab fusion

| Construct | Sequence | Seq ID No |
|---|---|---|
| 4B9 light chain cross VL-CH1 | EIVLTQSPGTLSLSPGERATLSCRASQSVTSSYLAW YQQKPGQAPRLLINVGSRRATGIPDRFSGSGSGTDF TLTISRLEPEDFAVYYCQQGIMLPPTFGQGTKVEIK SSASTKGPSVFPLAPSSKSTSGGTAALGCLVKDYFP EPVTVSWNSGALTSGVHTFPAVLQSSGLYSLSSVV TVPSSSLGTQTYICNVNHKPSNTKVDKKVEPKSC | 71 |
| VL1a (CD40) light chain | DIVMTQTPLSLSVTPGQPASISCRSSQSLVHSNGNTF LHWYLQKPGQSPQLLIYTVSNRFSGVPDRFSGSGS GTDFTLKISRVEAEDVGVYFCSQTTHVPWTFGGGT KVEIKRTVAAPSVFIFPPSDEQLKSGTASVVCLLNN FYPREAKVQWKVDNALQSGNSQESVTEQDSKDST YSLSSTLTLSKADYEKHKVYACEVTHQGLSSPVTK SFNRGEC | 66 |
| VH1a (CD40) (VHCH1) Fc knob_PGLALA_4B9 (VH-Ckappa) | QVQLVQSGAEVKKPGASVKVSCKASGYSFTGYYI HWVRQAPGQSLEWMGRVIPNAGGTSYNQKFKGR VTLTVDKSISTAYMELSRLRSDDTAVYYCAREGIY WWGQGTTVTVSSASTKGPSVFPLAPSSKSTSGGTA ALGCLVKDYFPEPVTVSWNSGALTSGVHTFPAVLQ SSGLYSLSSVVTVPSSSLGTQTYICNVNHKPSNTKV DKKVEPKSCDKTHTCPPCPAPEAAGGPSVFLFPPKP KDTLMISRTPEVTCVVVDVSHEDPEVKFNWYVDG VEVHNAKTKPREEQYNSTYRVVSVLTVLHQDWLN GKEYKCKVSNKALGAPIEKTISKAKGQPREPQVYT LPPCRDELTKNQVSLWCLVKGFYPSDIAVEWESNG QPENNYKTTPPVLDSDGSFFLYSKLTVDKSRWQQG NVFSCSVMHEALHNHYTQKSLSLSPGGGGGSGGG GSGGGGSGGGGSEVQLLESGGGLVQPGGSLRLSCA ASGFTFSSYAMSWVRQAPGKGLEWVSAIIGSGAST YYADSVKGRFTISRDNSKNTLYLQMNSLRAEDTAV YYCAKGWFGGFNYWGQGTLVTVSSASVAAPSVFI FPPSDEQLKSGTASVVCLLNNFYPREAKVQWKVD NALQSGNSQESVTEQDSKDSTYSLSSTLTLSKADYE KHKVYACEVTHQGLSSPVTKSFNRGEC | 72 |
| VH1a (CD40) (VHCH1) Fc hole_PGLALA | QVQLVQSGAEVKKPGASVKVSCKASGYSFTGYYI HWVRQAPGQSLEWMGRVIPNAGGTSYNQKFKGR VTLTVDKSISTAYMELSRLRSDDTAVYYCAREGIY WWGQGTTVTVSSASTKGPSVFPLAPSSKSTSGGTA ALGCLVKDYFPEPVTVSWNSGALTSGVHTFPAVLQ SSGLYSLSSVVTVPSSSLGTQTYICNVNHKPSNTKV DKKVEPKSCDKTHTCPPCPAPEAAGGPSVFLFPPKP KDTLMISRTPEVTCVVVDVSHEDPEVKFNWYVDG VEVHNAKTKPREEQYNSTYRVVSVLTVLHQDWLN GKEYKCKVSNKALGAPIEKTISKAKGQPREPQVCT LPPSRDELTKNQVSLSCAVKGFYPSDIAVEWESNG QPENNYKTTPPVLDSDGSFFLVSKLTVDKSRWQQG NVFSCSVMHEALHNHYTQKSLSLSPG | 68 |

TABLE 24-continued

Amino acid sequences of the bispecific antigen binding molecules

| Construct | Sequence | Seq ID No |
|---|---|---|
| | P1AE2895 CD40 (P1AE0817) × FAP (4B9) (4 + 1) C-terminal crossfab fusion | |
| 4B9 light chain cross VL-CH1 | EIVLTQSPGTLSLSPGERATLSCRASQSVTSSYLAW YQQKPGQAPRLLINVGSRRATGIPDRFSGSGSGTDF TLTISRLEPEDFAVYYCQQGIMLPPTFGQGTKVEIK SSASTKGPSVFPLAPSSKSTSGGTAALGCLVKDYFP EPVTVSWNSGALTSGVHTFPAVLQSSGLYSLSSVV TVPSSSLGTQTYICNVNHKPSNTKVDKKVEPKSC | 71 |
| VL1a (CD40) light chain | DIVMTQTPLSLSVTPGQPASISCRSSQSLVHSNGNTF LHWYLQKPGQSPQLLIYTVSNRFSGVPDRFSGSGS GTDFTLKISRVEAEDVGVYFCSQTTHVPWTFGGGT KVEIKRTVAAPSVFIFPPSDEQLKSGTASVVCLLNN FYPREAKVQWKVDNALQSGNSQESVTEQDSKDST YSLSSTLTLSKADYEKHKVYACEVTHQGLSSPVTK SFNRGEC | 66 |
| VH1a (CD40) (VHCH1)_VH1a (CD40) (VHCH1)-Fc knob_PGLALA_(4B9) (VH-Ckappa) | QVQLVQSGAEVKKPGASVKVSCKASGYSFTGYYI HWVRQAPGQSLEWMGRVIPNAGGTSYNQKFKGR VTLTVDKSISTAYMELSRLRSDDTAVYYCAREGIY WWGQGTTVTVSSASTKGPSVFPLAPSSKSTSGGTA ALGCLVKDYFPEPVTVSWNSGALTSGVHTFPAVLQ SSGLYSLSSVVTVPSSSLGTQTYICNVNHKPSNTKV DKKVEPKSCDGGGGSGGGGSQVQLVQSGAEVKKP GASVKVSCKASGYSFTGYYIHWVRQAPGQSLEWM GRVIPNAGGTSYNQKFKGRVTLTVDKSISTAYMEL SRLRSDDTAVYYCAREGIYWWGQGTTVTVSSAST KGPSVFPLAPSSKSTSGGTAALGCLVKDYFPEPVTV SWNSGALTSGVHTFPAVLQSSGLYSLSSVVTVPSSS LGTQTYICNVNHKPSNTKVDKKVEPKSCDKTHTCP PCPAPEAAGGPSVFLFPPKPKDTLMISRTPEVTCVV VDVSHEDPEVKFNWYVDGVEVHNAKTKPREEQY NSTYRVVSVLTVLHQDWLNGKEYKCKVSNKALG APIEKTISKAKGQPREPQVYTLPPCRDELTKNQVSL WCLVKGFYPSDIAVEWESNGQPENNYKTTPPVLDS DGSFFLYSKLTVDKSRWQQGNVFSCSVMHEALHN HYTQKSLSLSPGGGGGSGGGGSGGGGSGGGGSEV QLLESGGGLVQPGGSLRLSCAASGFTFSSYAMSWV RQAPGKGLEWVSAIIGSGASTYYADSVKGRFTISRD NSKNTLYLQMNSLRAEDTAVYYCAKGWFGGFNY WGQGTLVTVSSASVAAPSVFIFPPSDEQLKSGTASV VCLLNNFYPREAKVQWKVDNALQSGNSQESVTEQ DSKDSTYSLSSTLTLSKADYEKHKVYACEVTHQGL SSPVTKSFNRGEC | 73 |
| VH1 a (CD40) (VHCH1)_VH1 a (CD40) (VHCH1)-Fc hole_PGLALA | QVQLVQSGAEVKKPGASVKVSCKASGYSFTGYYI HWVRQAPGQSLEWMGRVIPNAGGTSYNQKFKGR VTLTVDKSISTAYMELSRLRSDDTAVYYCAREGIY WWGQGTTVTVSSASTKGPSVFPLAPSSKSTSGGTA ALGCLVKDYFPEPVTVSWNSGALTSGVHTFPAVLQ SSGLYSLSSVVTVPSSSLGTQTYICNVNHKPSNTKV DKKVEPKSCDGGGGSGGGGSQVQLVQSGAEVKKP GASVKVSCKASGYSFTGYYIHWVRQAPGQSLEWM GRVIPNAGGTSYNQKFKGRVTLTVDKSISTAYMEL SRLRSDDTAVYYCAREGIYWWGQGTTVTVSSAST KGPSVFPLAPSSKSTSGGTAALGCLVKDYFPEPVTV SWNSGALTSGVHTFPAVLQSSGLYSLSSVVTVPSSS LGTQTYICNVNHKPSNTKVDKKVEPKSCDKTHTCP PCPAPEAAGGPSVFLFPPKPKDTLMISRTPEVTCVV VDVSHEDPEVKFNWYVDGVEVHNAKTKPREEQY NSTYRVVSVLTVLHQDWLNGKEYKCKVSNKALG APIEKTISKAKGQPREPQVCTLPPSRDELTKNQVSLS CAVKGFYPSDIAVEWESNGQPENNYKTTPPVLDSD GSFFLVSKLTVDKSRWQQGNVFSCSVMHEALHNH YTQKSLSLSPG | 74 |
| | P1AE2302 CD40 (P1AE0817) × FAP (28H1) (2 + 1) C-terminal crossfab fusion | |
| 28H1 light chain cross VH-Ckappa | EVQLLESGGGLVQPGGSLRLSCAASGFTFSSHAMS WVRQAPGKGLEWVSAIWASGEQYYADSVKGRFTI SRDNSKNTLYLQMNSLRAEDTAVYYCAKGWLGN FDYWGQGTLVTVSSASVAAPSVFIFPPSDEQLKSGT | 75 |

TABLE 24-continued

Amino acid sequences of the bispecific antigen binding molecules

| Construct | Sequence | Seq ID No |
|---|---|---|
| | ASVVCLLNNFYPREAKVQWKVDNALQSGNSQESV<br>TEQDSKDSTYSLSSTLTLSKADYEKHKVYACEVTH<br>QGLSSPVTKSFNRGEC | |
| VL1a (CD40)<br>light chain<br>(charged) | DIVMTQTPLSLSVTPGQPASISCRSSQSLVHSNGNTF<br>LHWYLQKPGQSPQLLIYTVSNRFSGVPDRFSGSGS<br>GTDFTLKISRVEAEDVGVYFCSQTTHVPWTFGGGT<br>KVEIKRTVAAPSVFIFPPSDRKLKSGTASVVCLLNN<br>FYPREAKVQWKVDNALQSGNSQESVTEQDSKDST<br>YSLSSTLTLSKADYEKHKVYACEVTHQGLSSPVTK<br>SFNRGEC | 62 |
| VH1a (CD40)<br>(VHCH1<br>charged) Fc<br>knob_PGLALA_28H1<br>(VL-CH1) | QVQLVQSGAEVKKPGASVKVSCKASGYSFTGYYI<br>HWVRQAPGQSLEWMGRVIPNAGGTSYNQKFKGR<br>VTLTVDKSISTAYMELSRLRSDDTAVYYCAREGIY<br>WWGQGTTVTVSSASTKGPSVFPLAPSSKSTSGGTA<br>ALGCLVEDYFPEPVTVSWNSGALTSGVHTFPAVLQ<br>SSGLYSLSSVVTVPSSSLGTQTYICNVNHKPSNTKV<br>DEKVEPKSCDKTHTCPPCPAPEAAGGPSVFLFPPKP<br>KDTLMISRTPEVTCVVVDVSHEDPEVKFNWYVDG<br>VEVHNAKTKPREEQYNSTYRVVSVLTVLHQDWLN<br>GKEYKCKVSNKALGAPIEKTISKAKGQPREPQVYT<br>LPPCRDELTKNQVSLWCLVKGFYPSDIAVEWESNG<br>QPENNYKTTPPVLDSDGSFFLYSKLTVDKSRWQQG<br>NVFSCSVMHEALHNHYTQKSLSLSPGGGGGSGGG<br>GSGGGGSGGGGSEIVLTQSPGTLSLSPGERATLSCR<br>ASQSVSRSYLAWYQQKPGQAPRLLIIGASTRATGIP<br>DRFSGSGSGTDFTLTISRLEPEDFAVYYCQQGQVIP<br>PTFGQGTKVEIKSSASTKGPSVFPLAPSSKSTSGGTA<br>ALGCLVKDYFPEPVTVSWNSGALTSGVHTFPAVLQ<br>SSGLYSLSSVVTVPSSSLGTQTYICNVNHKPSNTKV<br>DKKVEPKSC | 76 |
| VH1a (CD40)<br>(VHCH1<br>charged) Fc<br>hole_PGLALA | QVQLVQSGAEVKKPGASVKVSCKASGYSFTGYYI<br>HWVRQAPGQSLEWMGRVIPNAGGTSYNQKFKGR<br>VTLTVDKSISTAYMELSRLRSDDTAVYYCAREGIY<br>WWGQGTTVTVSSASTKGPSVFPLAPSSKSTSGGTA<br>ALGCLVEDYFPEPVTVSWNSGALTSGVHTFPAVLQ<br>SSGLYSLSSVVTVPSSSLGTQTYICNVNHKPSNTKV<br>DEKVEPKSCDKTHTCPPCPAPEAAGGPSVFLFPPKP<br>KDTLMISRTPEVTCVVVDVSHEDPEVKFNWYVDG<br>VEVHNAKTKPREEQYNSTYRVVSVLTVLHQDWLN<br>GKEYKCKVSNKALGAPIEKTISKAKGQPREPQVCT<br>LPPSRDELTKNQVSLSCAVKGFYPSDIAVEWESNG<br>QPENNYKTTPPVLDSDGSFFLVSKLTVDKSRWQQG<br>NVFSCSVMHEALHNHYTQKSLSLSPG | 64 |

P1AE2024
CD40 (P1AE0817) x FAP (28H1) (4 + 1) C-terminal crossfab fusion

| Construct | Sequence | Seq ID No |
|---|---|---|
| 28H1 light chain<br>cross VH-Ckappa | EVQLLESGGGLVQPGGSLRLSCAASGFTFSSHAMS<br>WVRQAPGKGLEWVSAIWASGEQYYADSVKGRFTI<br>SRDNSKNTLYLQMNSLRAEDTAVYYCAKGWLGN<br>FDYWGQGTLVTVSSASVAAPSVFIFPPSDEQLKSGT<br>ASVVCLLNNFYPREAKVQWKVDNALQSGNSQESV<br>TEQDSKDSTYSLSSTLTLSKADYEKHKVYACEVTH<br>QGLSSPVTKSFNRGEC | 75 |
| VL1a (CD40)<br>light chain<br>(charged) | DIVMTQTPLSLSVTPGQPASISCRSSQSLVHSNGNTF<br>LHWYLQKPGQSPQLLIYTVSNRFSGVPDRFSGSGS<br>GTDFTLKISRVEAEDVGVYFCSQTTHVPWTFGGGT<br>KVEIKRTVAAPSVFIFPPSDRKLKSGTASVVCLLNN<br>FYPREAKVQWKVDNALQSGNSQESVTEQDSKDST<br>YSLSSTLTLSKADYEKHKVYACEVTHQGLSSPVTK<br>SFNRGEC | 62 |
| VH1a (CD40)<br>(VHCH1<br>charged)_VH1a<br>(CD40)<br>(VHCH1<br>charged) Fc<br>knob_PGLALA_28H1<br>(VL-CH1) | QVQLVQSGAEVKKPGASVKVSCKASGYSFTGYYI<br>HWVRQAPGQSLEWMGRVIPNAGGTSYNQKFKGR<br>VTLTVDKSISTAYMELSRLRSDDTAVYYCAREGIY<br>WWGQGTTVTVSSASTKGPSVFPLAPSSKSTSGGTA<br>ALGCLVEDYFPEPVTVSWNSGALTSGVHTFPAVLQ<br>SSGLYSLSSVVTVPSSSLGTQTYICNVNHKPSNTKV<br>DEKVEPKSCDGGGGSGGGGSQVQLVQSGAEVKKP<br>GASVKVSCKASGYSFTGYYIHWVRQAPGQSLEWM<br>GRVIPNAGGTSYNQKFKGRVTLTVDKSISTAYMEL | 77 |

TABLE 24-continued

Amino acid sequences of the bispecific antigen binding molecules

| Construct | Sequence | Seq ID No |
|---|---|---|
| | SRLRSDDTAVYYCAREGIYWWGQGTTVTVSSAST KGPSVFPLAPSSKSTSGGTAALGCLVEDYFPEPVTV SWNSGALTSGVHTFPAVLQSSGLYSLSSVVTVPSSS LGTQTYICNVNHKPSNTKVDEKVEPKSCDKTHTCP PCPAPEAAGGPSVFLFPPKPKDTLMISRTPEVTCVV VDVSHEDPEVKFNWYVDGVEVHNAKTKPREEQY NSTYRVVSVLTVLHQDWLNGKEYKCKVSNKALG APIEKTISKAKGQPREPQVYTLPPCRDELTKNQVSL WCLVKGFYPSDIAVEWESNGQPENNYKTTPPVLDS DGSFFLYSKLTVDKSRWQQGNVFSCSVMHEALHN HYTQKSLSLSPGGGGSGGGGSGGGGSGGGGSEIV LTQSPGTLSLSPGERATLSCRASQSVSRSYLAWYQ QKPGQAPRLLIIGASTRATGIPDRFSGSGSGTDFTLT ISRLEPEDFAVYYCQQGQVIPPTFGQGTKVEIKSSAS TKGPSVFPLAPSSKSTSGGTAALGCLVKDYFPEPVT VSWNSGALTSGVHTFPAVLQSSGLYSLSSVVTVPSS SLGTQTYICNVNHKPSNTKVDKKVEPKSC | |
| VH1a (CD40) (VHCH1 charged)_VH1a (CD40) (VHCH1 charged)-Fc hole_PGLALA | QVQLVQSGAEVKKPGASVKVSCKASGYSFTGYYI HWVRQAPGQSLEWMGRVIPNAGGTSYNQKFKGR VTLTVDKSISTAYMELSRLRSDDTAVYYCAREGIY WWGQGTTVTVSSASTKGPSVFPLAPSSKSTSGGTA ALGCLVEDYFPEPVTVSWNSGALTSGVHTFPAVLQ SSGLYSLSSVVTVPSSSLGTQTYICNVNHKPSNTKV DEKVEPKSCDGGGGSGGGGSQVQLVQSGAEVKKP GASVKVSCKASGYSFTGYYIHWVRQAPGQSLEWM GRVIPNAGGTSYNQKFKGRVTLTVDKSISTAYMEL SRLRSDDTAVYYCAREGIYWWGQGTTVTVSSAST KGPSVFPLAPSSKSTSGGTAALGCLVEDYFPEPVTV SWNSGALTSGVHTFPAVLQSSGLYSLSSVVTVPSSS LGTQTYICNVNHKPSNTKVDEKVEPKSCDKTHTCP PCPAPEAAGGPSVFLFPPKPKDTLMISRTPEVTCVV VDVSHEDPEVKFNWYVDGVEVHNAKTKPREEQY NSTYRVVSVLTVLHQDWLNGKEYKCKVSNKALG APIEKTISKAKGQPREPQVCTLPPSRDELTKNQVSLS CAVKGFYPSDIAVEWESNGQPENNYKTTPPVLDSD GSFFLVSKLTVDKSRWQQGNVFSCSVMHEALHNH YTQKSLSLSPG | 70 |

P1AF0873
CD40 (P1AE0817) × FAP (P1AE1689) (1 + 1) C-terminal crossfab fusion

| Construct | Sequence | Seq ID No |
|---|---|---|
| (P1AE1689) light chain cross VH-Ckappa | QVQLVQSGAEVKKPGASVKVSCKASGYTLTDYNM DWVRQAPGQGLEWIGDIYPNTGGTIYNQKFKGRV TMTIDTSTSTVYMELSSLRSEDTAVYYCTRFRGIHY AMDYWGQGTTVTVSSASVAAPSVFIFPPSDEQLKS GTASVVCLLNNFYPREAKVQWKVDNALQSGNSQE SVTEQDSKDSTYSLSSTLTLSKADYEKHKVYACEV THQGLSSPVTKSFNRGEC | 61 |
| VL1 a (CD40) light chain (charged) | DIVMTQTPLSLSVTPGQPASISCRSSQSLVHSNGNTF LHWYLQKPGQSPQLLIYTVSNRFSGVPDRFSGSGS GTDFTLKISRVEAEDVGVYFCSQTTHVPWTFGGGT KVEIKRTVAAPSVFIFPPSDRKLKSGTASVVCLLNN FYPREAKVQWKVDNALQSGNSQESVTEQDSKDST YSLSSTLTLSKADYEKHKVYACEVTHQGLSSPVTK SFNRGEC | 62 |
| VH1 a (CD40) (VHCH1 charged) Fc knob_PGLALA (P1AE1689) (VL-CH1) | QVQLVQSGAEVKKPGASVKVSCKASGYSFTGYYI HWVRQAPGQSLEWMGRVIPNAGGTSYNQKFKGR VTLTVDKSISTAYMELSRLRSDDTAVYYCAREGIY WWGQGTTVTVSSASTKGPSVFPLAPSSKSTSGGTA ALGCLVEDYFPEPVTVSWNSGALTSGVHTFPAVLQ SSGLYSLSSVVTVPSSSLGTQTYICNVNHKPSNTKV DEKVEPKSCDKTHTCPPCPAPEAAGGPSVFLFPPKP KDTLMISRTPEVTCVVVDVSHEDPEVKFNWYVDG VEVHNAKTKPREEQYNSTYRVVSVLTVLHQDWLN GKEYKCKVSNKALGAPIEKTISKAKGQPREPQVYT LPPCRDELTKNQVSLWCLVKGFYPSDIAVEWESNG QPENNYKTTPPVLDSDGSFFLYSKLTVDKSRWQQG NVFSCSVMHEALHNHYTQKSLSLSPGGGGSGGG GSGGGGSGGGGSEIVLTQSPATLSLSPGERATLSCR ASESVDNYGLSFINWFQQKPGQAPRLLIYGTSNRGS GIPARFSGSGSGTDFTLTISSLEPEDFAVYFCQQSNE VPYTFGGGTKVEIKSSASTKGPSVFPLAPSSKSTSG | 63 |

TABLE 24-continued

Amino acid sequences of the bispecific antigen binding molecules

| Construct | Sequence | Seq ID No |
|---|---|---|
| | GTAALGCLVKDYFPEPVTVSWNSGALTSGVHTFPA VLQSSGLYSLSSVVTVPSSSLGTQTYICNVNHKPSN TKVDKKVEPKSC | |
| Fc hole | DKTHTCPPCPAPEAAGGPSVFLFPPKPKDTLMISRT PEVTCVVVDVSHEDPEVKFNWYVDGVEVHNAKT KPREEQYNSTYRVVSVLTVLHQDWLNGKEYKCKV SNKALGAPIEKTISKAKGQPREPQVCTLPPSRDELT KNQVSLSCAVKGFYPSDIAVEWESNGQPENNYKTT PPVLDSDGSFFLVSKLTVDKSRWQQGNWSCSVMH EALHNHYTQKSLSLSPG | 98 |

P1AA9663
CD40 (huCD40) × FAP (28H1) (2 + 2) C-terminal crossfab fusion

| Construct | Sequence | Seq ID No |
|---|---|---|
| 28H1 light chain cross VH-Ckappa | EVQLLESGGGLVQPGGSLRLSCAASGFTFSSHAMS WVRQAPGKGLEWVSA1WASGEQYYADSVKGRFTI SRDNSKNTLYLQMNSLRAEDTAVYYCAKGWLGN FDYWGQGTLVTVSSASVAAPSVFIFPPSDEQLKSGT ASVVCLLNNFYPREAKVQWKVDNALQSGNSQESV TEQDSKDSTYSLSSTLTLSKADYEKHKVYACEVTH QGLSSPVTKSFNRGEC | 75 |
| CD40 light chain (charged) | DIQMTQSPSSLSASVGDRVTITCRSSQSLVHSNGNT FLHWYQQKPGKAPKLLIYTVSNRFSGVPSRFSGSGS GTDFTLTISSLQPEDFATYFCSQTTHVPWTFGQGTK VEIKRTVAAPSVFIFPPSDRKLKSGTASVVCLLNNF YPREAKVQWKVDNALQSGNSQESVTEQDSKDSTY SLSSTLTLSKADYEKHKVYACEVTHQGLSSPVTKS FNRGEC | 105 |
| CD40 (VHCH1 charged) Fc PGLALA FAP (VL-CH1) | EVQLVESGGGLVQPGGSLRLSCAASGYSFTGYYIH WVRQAPGKGLEWVARVIPNAGGTSYNQKFKGRFT LSVDNSKNTAYLQMNSLRAEDTAVYYCAREGIYW WGQGTLVTVSSASTKGPSVFPLAPSSKSTSGGTAA LGCLVEDYFPEPVTVSWNSGALTSGVHTFPAVLQS SGLYSLSSVVTVPSSSLGTQTYICNVNHKPSNTKVD EKVEPKSCDKTHTCPPCPAPEAAGGPSVFLFPPKPK DTLMISRTPEVTCVVVDVSHEDPEVKFNWYVDGV EVHNAKTKPREEQYNSTYRVVSVLTVLHQDWLNG KEYKCKVSNKALGAPIEKTISKAKGQPREPQVYTL PPSRDELTKNQVSLTCLVKGFYPSDIAVEWESNGQ PENNYKTTPPVLDSDGSFFLYSKLTVDKSRWQQGN VFSCSVMHEALHNHYTQKSLSLSPGGGGGSGGGG SGGGGSGGGGSEIVLTQSPGTLSLSPGERATLSCRA SQSVSRSYLAWYQQKPGQAPRLLIIGASTRATGIPD RFSGSGSGTDFTLTISRLEPEDFAVYYCQQGVIPPT FGQGTKVEIKSSASTKGPSVFPLAPSSKSTSGGTAA LGCLVKDYFPEPVTVSWNSGALTSGVHTFPAVLQS SGLYSLSSVVTVPSSSLGTQTYICNVNHKPSNTKVD KKVEPKSC | 106 |

3.2 Production of Bispecific Antigen Binding Molecules Targeting FAP and CD40

The bispecific antigen binding molecules targeting fibroblast activation protein (FAP) and CD40 were expressed by transient transfection of HEK cells grown in suspension with expression vectors encoding the 4 different peptide chains. Transfection into HEK293-F cells (Invitrogen) was performed according to the cell supplier's instructions using Maxiprep (Qiagen) preparations of the antibody vectors, F17 medium (Invitrogen, USA), Peipro (Polyscience Europe GmbH) and an initial cell density of 1-2 million viable cells/ml in serum free FreeStyle 293 expression medium (Invitrogen). Cell culture supernatants were harvested after 7 days of cultivation in shake flasks or stirred fermenters by centrifugation at 14000 g for 30 minutes and filtered through a 0.22 µm filter.

The bispecific antibodies were purified from cell culture supernatants by Protein A affinity chromatography using MabSelectSure-Sepharose™ (GE Healthcare, Sweden) chromatography. Briefly, sterile filtered cell culture supernatants were captured on a MabSelect SuRe resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM cirate, pH 3.0. After neutralization with 1 M Tris pH 9.0, aggregated protein was separated from monomeric antibody species by size exclusion chromatography (Superdex 200, GE Healthcare) in 20 mM histidine, 140 mM NaCl, pH 6.0. Monomeric protein fractions were pooled, concentrated if required using e.g. a MILLIPORE Amicon Ultra. (30 KD MWCO) centrifugal concentrator and stored at −80° C. Sample aliquots were used for subsequent analytical characterization e.g. by CE-SDS, size exclusion chromatography, mass spectrometry and endotoxin determination.

TABLE 25

Production yield of bispecific CD40-FAP antigen binding molecules

| Sample | Yield after ProtA from 0.9 L transient HEK expression in mg | % monomer by SEC after ProtA | % product peak by CE-SDS after ProtA | Yield after prep. HIC and prep. SEC [mg/L] | % monomer by SEC after prep. HIC and prep. SEC | % product peak by CE-SDS after prep. HIC and prep. SEC |
|---|---|---|---|---|---|---|
| P1AE2423 | 16.5 | 92 | >95 | 11.25 | >95 | >95 |
| P1AE2424 | 10.4 | 93 | >95 | 6.4 | >95 | >95 |
| P1AE2734 | 25 | 89 | 18 | | | |
| P1AE2487 | 14 | 93 | 82 | 4.8 | >95 | >95 |
| P1AE2895 | 14.4 | 94 | 91 | 4.1 | >95 | >95 |
| P1AE2302 | | | | 12 | | |
| P1AE2024 | | | | 6.6 | | |

P1AE2734 is a bispecific antibody wherein the VH-Ckappa chain of the crossfab is fused to the C-terminus of one of the Fc domain heavy chains. This bispecific antibody was much more difficult to produce and to purify than the bispecific antibody P1AE2423, wherein the VL-CH1 chain of the crossfab is fused to the C-terminus of one of the Fc domain heavy chains. Further purification steps had to be applied, i.e. an ion exchange chromatography as well as an additional CE-SDS led to 1 mg of substance.

3.3 Binding Kinetics of Bispecific Anti-huFAP Antibodies

To evaluate human FAP binding kinetics of bispecific FAP-targeted antibodies, the binding kinetics were measured as described in Example 1.7, however with using a HIS-tagged human FAP ectodomain as ligand. The affinity data of the bispecific 2+1 CD40×FAP antibodies with different fusion of the crossfab are shown in Table 25A below.

TABLE 25A

Affinity of 2 + 1 CD40 × FAP bispecific antibodies to human FAP as measured by SPR

| Sample ID | ka (1/Ms) | kd (1/s) | KD [nM] |
|---|---|---|---|
| P1AE2423 VL-CH1 fused to Fc | 3.4E+05 | 3.2E−05 | 9.4E−11 |
| P1AE2734 VH-Ckappa fused to Fc | 2.5E+05 | 5.2E−05 | 2.1E−10 |

FAP binding affinities of bispecific antibodies as C-terminal Fab-fusion are in a similar range between the two crossing variants (measured by SPR).

Example 4

Characterization of Bispecific Constructs Targeting CD40 and FAP 4.1 Binding to Human FAP-Expressing Murine Fibroblast Cells The binding to cell surface FAP was tested using the human fibroblast activating protein (huFAP) expressing NIH/3T3-hFAP clone 19. The NIH/3T3-huFAP clone 19 was generated by the transfection of the mouse embryonic fibroblast NIH/3T3 cell line (ATCC CRL-1658) with the expression vector pETR4921 to express under 1.5 µg/mL Puromycin selection huFAP.

NIH/3T3-huFAP cells were cultured with 1× Dulbecco's Modified Eagle's Medium (DMEM) (gibco, Cat. No. 42430-025) supplemented with 10% Fetal Bovine Serum (FBS) (life technologies, Cat. No. 16140, Lot No. 1797306A). 1.5 µg/mL Puromycin (gibco, Cat. No. A11138-03) was added to the medium for selection of FAP-expressing cells. NIH/3T3-huFAP cells were removed from culture flasks by using enzyme-free Cell Dissociation Buffer (gibco, Cat. No. 13151014). $0.3 \times 10^5$ NIH/3T3-hFAP clone 19 cells were added in 200 µl of 1×DMEM with 10% FBS to each well of a round-bottom 96-well plate (greiner bio-one, cellstar, Cat. No. 650185). Plates were centrifuged 5 minutes at 1700 rpm and supernatants were flicked off. Cells were washed once with 200 µL of 4° C. cold FACS buffer (eBioscience, Cat. No. 00-4222-26). All samples were resuspended in 50 µL/well of 4° C. cold FACS buffer containing the bispecific antigen binding molecules (primary antibody) or the isotype control antibody DP47 at the indicated range of concentrations (in duplicates) and incubated for 120 minutes at 4° C. Afterwards the cells were washed three times with 200 µL 4° C. cold FACS buffer. Cells were further stained with 25 µL/well of 4° C. cold secondary antibody solution (1:50 dilution of secondary antibody) containing the R-Phycoerythrin (PE) conjugated AffiniPure F(ab')₂ Fragment Goat Anti-Human IgG, Fcγ Fragment Specific (Jackson ImmunoResearch, Cat. No. 109-116-098) secondary antibody and incubated for 60 minutes at 4° C. in the dark. Cells were washed with 200 µl FACS buffer and resuspended in 85 µL/well FACS buffer containing 0.2 µg/mL DAPI (Roche, Cat. No. 10236276001) and acquired the same day using a 5-laser LSR-Fortessa (BD Bioscience with DIVA software). Data analysis was performed using the FlowJo version 10 software (FlowJo LLC).

Figure 4:
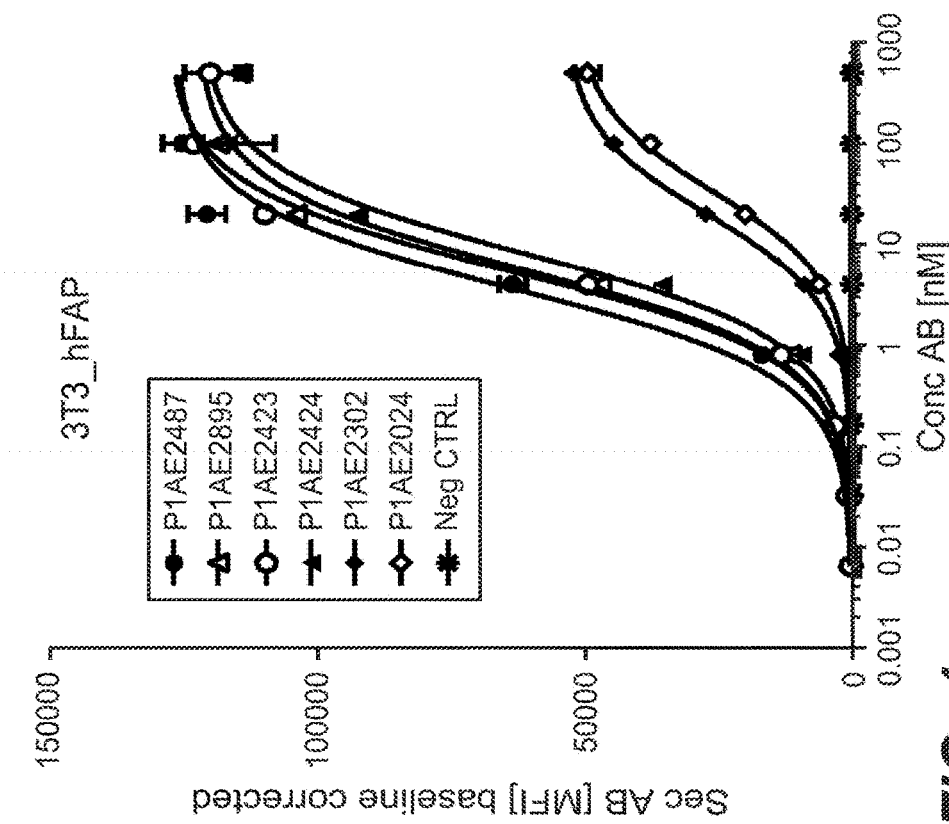
FIG. 4 shows the binding of human tetravalent or bivalent anti-CD40 antibodies in a FAP (212), FAP (4B9) or FAP (28H1)-targeted monovalent format to human FAP-positive NIH/3T3 cells. The transgenic modified mouse embryonic fibroblast NIH/3T3-hFAP cell line expresses high levels of human fibroblast activation protein (huFAP). All depicted anti-CD40 antigen binding molecules with a FAP binding moiety efficiently bind to NIH/3T3-hFAP cells but vary in their binding strength ($EC_{50}$ values as well as signal strength) to NIH/3T3-hFAP cells. The FAP-CD40 constructs with a C-terminal FAP (212) or FAP (4B9) binding domain bind stronger than the FAP-CD40 constructs with a C-terminal FAP (28H1) binding domain. Shown is the binding as median of fluorescence intensity (MFI) of phycoerythrin (PE)-labeled anti-human IgG Fcγ-specific goat IgG F(ab')2 fragment which is used as secondary detection antibody. The MFI was measured by flow cytometry and the baseline was corrected by subtracting the MFI of the blank control. The x-axis shows the concentration of antibody constructs.

As shown in FIG. 4, the bispecific antibodies monovalent for FAP bind to human FAP-expressing target cells. Therefore, the FAP-targeted anti-CD40 antigen binding molecules show direct tumor-targeting properties. The FAP constructs with a C-terminal FAP (212 (P1AE1689)) or FAP (4B9) binding domain bind stronger than the FAP constructs with a C-terminal FAP (28H1) binding domain explained by a higher binding affinity of the FAP (212) and FAP (4B9) binders towards human FAP compared to the FAP (28H1) binder. The strongest FAP binding was observed for the 2+1 construct with a FAP (4B9) binding moiety (P1AE2487). No binding of the isotype control antibody DP47 (human germline control) to the NIH/3T3-hFAP cells was detected. The $EC_{50}$ values as measured for different bispecific antibodies are shown in Table 26 below.

TABLE 26

Human FAP binding characterization of 212 (P1AE1689),
4B9 and 28H1 in different bispecific antibody formats

| Molecule | | EC$_{50}$ [nM] |
|---|---|---|
| P1AE2423 | CD40 × FAP (212) 2 + 1 crossfab | 5.19 |
| P1AE2487 | CD40 × FAP (4B9) 2 + 1 crossfab | 3.70 |
| P1AE2302 | CD40 × FAP (28H1) 2 + 1 crossfab | 20.01 |
| P1AE2424 | CD40 × FAP (212) 4 + 1 crossfab | 7.52 |
| P1AE2895 | CD40 × FAP (4B9) 4 + 1 crossfab | 5.27 |
| P1AE2024 | CD40 × FAP (28H1) 4 + 1 crossfab | 38.67 |

4.2 Binding to Human CD40-Expressing Primary B Cells

The binding to cell surface CD40 was tested using human primary B cells isolated from peripheral blood mononuclear cells (PBMCs). In order to isolate PBMCs a buffy coat was obtained from the Stiftung Zürcher Blutspendedienst SRK. 50 mL of buffy coat were diluted in the same volume of PBS (gibco, Cat. No. 10010023). 50 mL polypropylene centrifuge tubes (TPP, Cat. No. 91050) were supplied with 15 mL of Lymphoprep™ (STEMCELL Technologies, Cat. No. 07851) and 25 mL of the buffy coat/PBS solution per tube were carefully layered above the Lymphoprep™. The tubes were centrifuged at 2000 rpm for 24 minutes at room temperature with low acceleration and without break. Afterwards the PBMCs were collected from the interface, washed three times with PBS, resuspended in 10 mL of PBS and cells were analyzed for cell type and number with a Beckman Coulter cell counter Ac·T™ 5diff OV (Beckman Coulter, Cat. No. 6605580). Prior to the B cell isolation from the PBMCs, the CD14-positive fraction was removed by magnetic labeling of the CD14-positive cells with CD14 microbeads (Miltenyi, Cat. No. 130-050-201) and subsequent isolation with an autoMACS® Pro Separator (Miltenyi, Cat. No. 130-092-545). The CD14-negative fraction was used for subsequent B cell isolation with the Miltenyi B cell isolation kit II (Cat. No. 130-091-151) and autoMACS® separation. 0.3×10$^5$ B cells were added in 200 µl of R10 medium consisting of Roswell Park Memorial Institute medium (RPMI) 1640 (gibco, Cat. No. 31870-025) supplied with 10% (v/v) FBS, 1% (v/v) Penicillin Streptomycin (gibco, Cat. No. 15070-063), 1% (v/v) L-Glutamine (gibco, Cat. No. 25030-024), 1% (v/v) Sodium-Pyruvate (gibco, Cat. No. 11360-039), 1% (v/v) MEM non-essential amino acids (gibco, Cat. No. 11140-035) and 50 µM β-Mercaptoethanol (gibco, Cat. No. 31350-010) to each well of a round-bottom 96-well plate (greiner bio-one, cellstar, Cat. No. 650185). Plates were centrifuged 5 minutes at 1700 rpm and supernatants were flicked off. Cells were washed once with 200 µL of 4° C. cold FACS buffer (eBioscience, Cat. No. 00-4222-26). All samples were resuspended in 50 µL/well of 4° C. cold FACS buffer containing the bispecific antigen binding molecules (primary antibody) or the isotype control antibody DP47 at the indicated range of concentrations (in duplicates) and incubated for 120 minutes at 4° C. Afterwards the cells were washed three times with 200 µL 4° C. cold FACS buffer. Cells were further stained with 25 µL/well of 4° C. cold secondary antibody solution (1:50 dilution of secondary antibody) containing the R-Phycoerythrin (PE) conjugated AffiniPure F(ab')$_2$ Fragment Goat Anti-Human IgG, Fcγ Fragment Specific (Jackson ImmunoResearch, Cat. No. 109-116-098) secondary antibody and incubated for 60 minutes at 4° C. in the dark. Cells were washed with 200 µl FACS buffer and resuspended in 85 µL/well FACS-buffer containing 0.2 µg/mL DAPI (Roche, Cat. No. 10236276001) and acquired the same day using a 5-laser LSR-Fortessa (BD Bioscience with DIVA software). Data analysis was performed using the FlowJo version 10 software (FlowJo LLC).

Figure 5:
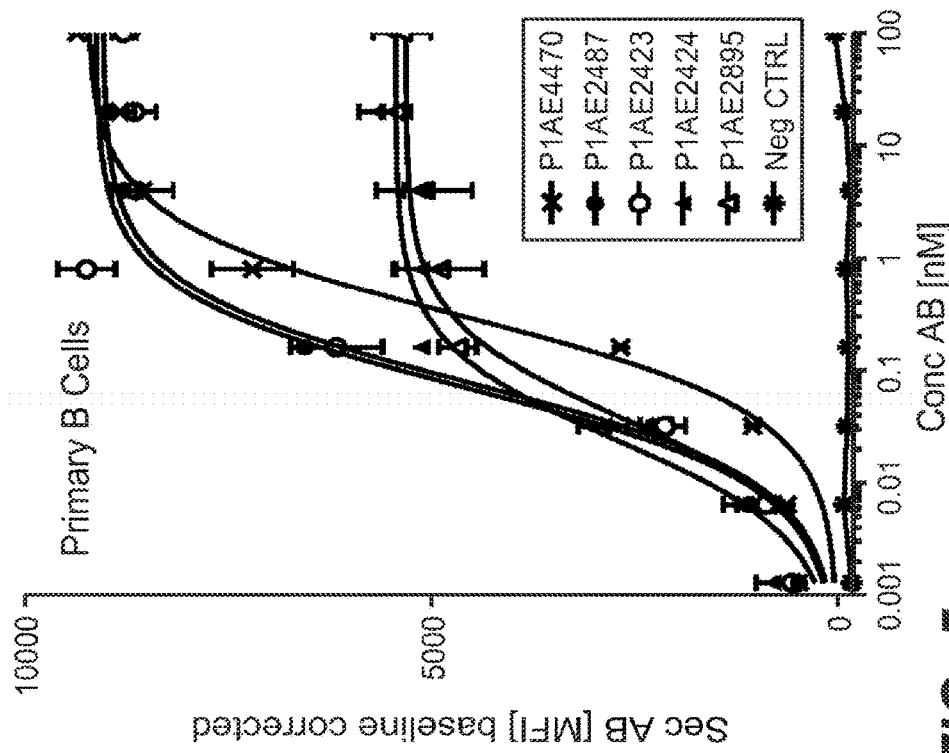
FIG. 5 shows the binding of human tetravalent or bivalent anti-CD40 antibodies in a FAP (212) or FAP (4B9)-targeted monovalent format to primary human B cells with high surface expression levels of human CD40. All depicted constructs bind to CD40 but vary in their binding strength ($EC_{50}$ values as well as signal strength) to CD40-positive B cells. Bivalent anti-CD40 antibodies show higher $EC_{50}$ levels and reach higher binding plateaus compared to tetravalent anti-CD40 antibodies, irrespective of their FAP binding moiety. Binding of anti-CD40 antibodies to cell surface proteins was detected with an anti-human IgG Fcγ-specific goat IgG F(ab')2 fragment conjugated to phycoerythrin (PE) using FACS analysis. The MFI was measured by flow cytometry and baseline corrected by subtracting the MFI of the blank control. The x-axis shows the concentration of antibody constructs.

As shown in FIG. 5, all depicted clones bind to CD40 but vary in their binding strength (EC$_{50}$ values as well as signal strength) to CD40-positive B cells. Irrespective of their FAP binding moiety, bivalent anti-CD40 antibodies show higher EC$_{50}$ levels and reach higher binding plateaus compared to tetravalent anti-CD40 antibodies explained by more occupied CD40 binding sites per antibody and a gain of avidity of the tetravalent relative to the bivalent CD40 formats. No binding of the negative control antibody to B cells was detected. The EC$_{50}$ values as measured for different bispecific antibodies are shown in Table 27 below.

TABLE 27

Human CD40 binding characterization of CD40 antibodies
in different bispecific antibody formats

| Molecule | | EC$_{50}$ [nM] |
|---|---|---|
| P1AD4470 | CD40 IgG1 | 0.333 |
| P1AE2423 | CD40 × FAP (212) 2 + 1 crossfab | 0.095 |
| P1AE2487 | CD40 × FAP (4B9) 2 + 1 crossfab | 0.086 |
| P1AE2424 | CD40 × FAP (212) 4 + 1 crossfab | 0.036 |
| P1AE2895 | CD40 × FAP (4B9) 4 + 1 crossfab | 0.049 |

Example 5

Functional Properties of FAP-Targeted Anti-Human CD40 Binding Molecules 5.1 CD40-Mediated Activation of Human B Cells by FAP-Targeted Anti-Human CD40 Binding Molecules Ligation of CD40 induces B cell and dendritic cell (DC) maturation as well as activation and promotes survival of these cell types. Upon CD40 signaling cytokine production and costimulatory molecule expression on the surface of B cells and DCs is increased (S. Quezada et al., Annu Rev Immunol. 2004, 22, 307-328; S. Danese et al., Gut. 2004, 53, 1035-1043; G. Bishop et al., Adv Exp Med Biol. 2007, 597, 131-151).

In order to test the agonistic properties and the FAP specificity of the different FAP-dependent anti-CD40 antibodies, Daudi cells or primary B cells obtained from human buffy coats were incubated with the FAP-dependent agonistic anti-human CD40 antibodies in the presence of FAP-coated beads and the B cell activation was measured by FACS.

5.1.1. Activation of Human Daudi Cells by FAP-Targeted Anti-Human CD40 Binding Molecules Using FAP-Coated Dynabeads as Source of Antigen 1×10$^5$ Daudi cells, a human B lymphoblast cell line with high expression levels of human CD40 (ATCC CCL-213), were added in 100 µl of 1× Dulbecco's Modified Eagle's Medium (DMEM) (gibco, Cat. No. 42430-025) supplemented with 10% Fetal Bovine Serum (FBS) (life technologies, Cat. No. 16140, Lot No. 1797306A) per well of a 96-well flat-bottom plate. Streptavidin Dynabeads® (ThermoFisher Scientific, Cat. No.: 11205D) were coated with biotinylated human FAP (produced in-house) (binding capacity of 6.5×10$^4$ beads: 0.01 µs of protein) according to the manufacturer's instructions and added to the Daudi cells in a beads to cell ratio of 2:1 in 50 µl of 1×DMEM with 10% FBS. As control, non-coated beads were added to the Daudi cells. FAP-targeted anti-human CD40 antibodies were added in 50 µl of 1×DMEM with 10% FBS medium to the Daudi cells at concentrations ranging from 6.7 nM to 0.003 nM (3× dilution series). As positive control, the FAP-independent agonistic anti-human CD40 antibody SGN-40 (IgG1, INN: Dacetuzumab) was used. The antibody is bivalent for CD40. Since it is described in the literature that the SGN-40 antibody requires Fc receptor cross-linking for biological activity (C. Law et al., Cancer Res 2005, 65, 8331-8338), the antibody was incubated with a cross-linking goat anti-human IgG Fcγ fragment specific F(ab')2 fragment (Jackson ImmunoResearch, Cat. No. 109-006-008) for 30 minutes before the antibody was added to the Daudi cells. After 48 hours, cells were transferred into a 96-well round-bottom plate, washed once with PBS and incubated with 50 µl of 3 µg/mL of Fc receptor blocking Mouse IgG Isotype Control (ThermoFisher Scientific, Cat. No. 10400C) in PBS. After 15 minutes of incubation at 4° C., cells were washed with PBS and 50 µl of a mixture of fluorescently labelled antibodies in PBS were added to the cells. The following fluorescently labelled antibodies were used: anti-human CD83 BV421 (Biolegend, clone HB15e, Cat. No. 305324), anti-human CD80 BV605 (BD Biosciences, clone L307.4, Cat. No. 563315), anti-HLA-ABC FITC (BD Biosciences, clone G46-2.6, Cat. No. 555552), anti-human CD14 PerCP-Cy5.5 (Biolegend, clone HCD14, Cat. No. 325622), anti-human CD3 PerCP-Cy5.5 (Biolegend, clone UCHT1, Cat. No. 300430), anti-human CD70 PE (Biolegend, clone 113-16, Cat. No. 355104), anti-human CD86 PE-CF594 (BD Biosciences, clone FUN-1, Cat. No. 562390), anti-HLA-DR APC (BD Biosciences, clone G46-6, Cat. No. 559866) and anti-human CD19 APC-H7 (BD Biosciences, clone SJ25C1, Cat. No. 560177). In order to distinguish between live and dead cells, the viability dye Zombie Aqua™ (Biolegend, Cat. No. 423102) was added to the antibody mixture. After 30 minutes of incubation at 4° C., cells were washed twice with PBS and resuspended in 200 µl of PBS. Cells were analyzed the same day using a 5-laser LSR-Fortessa (BD Bioscience with DIVA software). Data analysis was performed using the FlowJo version 10 software (FlowJo LLC). Live (aqua negative) cells, negative for CD14 and CD3 and positive for CD19 were analyzed for CD70, CD80, CD83 and CD86 expression.

Daudi cells analyzed after 2 days of incubation with agonistic anti-CD40 antibodies showed an increase in CD70 expression for all depicted antibodies (see FIG. 6A and FIG. 6B). The upregulation of this activation marker was dependent on FAP in case of the different FAP-targeted antibodies. At lower antibody concentrations the increase of expression induced by these FAP-dependent antibodies was higher compared to the increase induced by the cross-linked CD40 antibody (P1AD4470). In addition, the CD70 upregulation by bispecific FAP-CD40 antibodies in a 2+1 format with a FAP (212) or FAP (4B9) binding domain was higher compared to the upregulation induced by the bispecific FAP-CD40 antibody in a 2+1 format with a FAP (28H1) binding domain, the bispecific FAP-CD40 antibodies in a 4+1 format with a FAP (212), FAP (4B9) or FAP (28H1) binding domain or the FAP-independent positive control antibody. In the absence of FAP (uncoated beads) no increase of CD70 was observed with the depicted bispecific antibodies bivalent for CD40, while tetravalent CD40 binding molecules induced an upregulation of CD70, but to a lesser extent than in the presence of FAP indicating a low but detectable FAP-independent CD40 activation of tetravalent CD40 binders in Daudi cells.

5.1.2 Activation of Human B Cells by FAP-Targeted Anti-Human CD40 Binding Molecules Using FAP-Coated Dynabeads as Source of Antigen B cells were isolated from buffy coats as described in Example 4.2 and 1×10$^5$B cells in 100 µl of R10 medium were added per well of a 96-well flat-bottom plate. Streptavidin Dynabeads® (ThermoFisher Scientific, Cat. No.: 11205D) were coated with biotinylated human FAP (produced in-house) (binding capacity of 6.5×10$^4$ beads: 0.01 µs of protein) according to the manufacturer's instructions and added to the B cells in a beads to cell ratio of 2:1 in 50 µl of R10 medium. As control non-coated beads were added to the B cells. The FAP-targeted anti-human CD40 antibodies or positive control antibodies (described in Example 5.1.1) were added in 50 µl of R10 medium to the B cells. After 2 days B cells were analyzed by FACS following the staining and analysis procedures specified in Example 5.1.1.

B cells analyzed after 2 days of incubation with agonistic anti-CD40 antibodies showed an increase in CD86 expression for all depicted antibodies (see FIG. 7A and FIG. 7B). The upregulation of CD86 was dependent on FAP in case of the different FAP-targeted antibodies and the increase of expression induced by these FAP-dependent antibodies was comparable or slightly lower to the increase induced by the cross-linked anti-CD40 antibody P1AD4470. The bispecific antibodies monovalent for FAP with one FAP (212) binding domain induced a similar increase of activation marker expression as the molecules with one FAP (4B9) binding moiety. At lower antibody concentrations the 4+1 formats, irrespective of their FAP binding moiety, induced a higher B cell activation compared to the 2+1 formats with a FAP (212) or FAP (4B9) binding moiety.

5.2 CD40-Mediated Activation of DCs by FAP-Targeted Anti-CD40 Binding Molecules and Subsequent Priming of T Cells In order to demonstrate the ability of DCs activated by the FAP-dependent anti-human CD40 antibodies to efficiently prime T cells, in vitro T cell priming assays were established. For these assays DCs from the spleens of transgenic mice expressing the human CD40 receptor (huCD40tg mice; mice with similar human and murine CD40 receptor expression pattern; C57BL/6 background; generated by Taconic) were isolated, pulsed with either SIINFEKL peptide or with ovalbumin (OVA; DEC-205 receptor-mediated antigen uptake) and incubated with different agonistic anti-human CD40 antibodies. FAP was provided via FAP-coated Dynabeads® in order to show FAP-dependency of the bispecific antigen binding molecules. 24 hours later, CD8-positive T cells were isolated from spleens of OT1 mice (CD8-positive T cells of these mice all possess a transgenic TCR recognizing SIINFEKL in the context of H2-Kb; C57BL/6-Tg (TcraTcrb)1100Mjb/Crl, Charles River), carboxyfluorescein succinimidyl ester (CFSE) labelled and added to the pulsed DCs. On day four of the experiment the T cell proliferation was analyzed by FACS.

5.2.1 T Cell Priming Via OVA-Pulsed DCs Activated by FAP-Targeted Anti-CD40 Binding Molecules DCs were isolated from the spleens of huCD40tg mice. In order to isolate splenic DCs, the spleen from a huCD40tg mouse was put into one well of a 6-well plate containing 2.25 mL Hank's Balanced Salt Solution (HBSS) with Calcium$^{2+}$ (gibco, Cat. No. 14025-05), 250 µl of a 10 mg/mL solution of collagenase D (end concentration 1 mg/mL) (Sigma-Aldrich, Cat. No. 11088866001) and 12.5 µl of a 10 mg/mL DNase solution (end concentration 0.05 mg/mL) (Sigma-Aldrich, D5025-150KU, Lot. No. SLBR0535V). The spleen was ballooned using a 3 mL syringe (BD, Cat.

No. 309658) with a 21G needle (Braun, Cat. No. 4657527) and subsequently, with the help of scissors, torn into small pieces. After a 25 minutes incubation at 37° C., 50 µL of 0.5 M ethylenediaminetetraacetic acid (EDTA) (Applichem, Cat. No. A4892.1000) were added, followed by a second incubation step at 37° C. for five minutes. The solution containing splenocytes and small pieces of splenic tissue was filtered through a 40 µm filter (Corning, Cat. No. 352340) into a 50 mL polypropylene centrifuge tube. Remaining splenic tissue pieces were smashed through the filter with the end of a 3 mL syringe plug. In the next step the 50 mL tube was centrifuged at 1500 rpm for 5 minutes at room temperature, the supernatant was discarded and 1 mL of 1× cell lysis buffer (diluted 1:10 with distilled water) (BD, Cat. No. 555899) was added to the splenocytes in order to lyse the red blood cells. After four minutes of incubation at room temperature, 20 mL of R10 were added followed by a centrifugation step at 1500 rpm for 5 minutes at room temperature. The supernatant was removed, the splenocytes were resuspended in 30 mL of R10 and cell numbers as well as viability were determined with the automated EVE cell counter (VWR, Cat. No. 734-2675). The mouse CD11c UltraPure microbeads (Miltenyi, Cat. No. 130-108-338) were used according to the manufacturer's instruction to isolate DCs by autoMACS® separation. Subsequently 0.25× $10^5$ DCs were seeded in 50 µl of R10 per well of a 96-well flat-bottom plate.

The DCs were then either pulsed with 1 ng/mL SIIN-FEKL (Ovalbumin residues 257-264, Eurogentec, Cat. No. AS-60193-5, Lot. No. 1360618), which requires no uptake and processing by the DCs, as positive control or loaded with OVA protein as antigen. In order to promote the OVA uptake in a Toll-like receptor (TLR) stimulus independent way (additional TLR stimuli might lead to a high overall activation of DCs, making the detection of different activation states due to stimulation with agonistic anti-CD40 antibodies impossible) the OVA Antigen Delivery Reagent (Miltenyi, Cat. No. 130-094-663) in combination with a biotinylated anti-mouse DEC205 antibody (Miltenyi, clone NLDC-145, Cat. No. 130-101-854) was used according to the manufacturer's protocol. In brief, DCs were incubated with a biotinylated antibody that binds to the DEC205 receptor, which is highly expressed on CD8-positive cross-presenting DCs (M. Lahoud et al., Int Immunol. 2000, 12(5), 731-735). Afterwards, the OVA delivery reagent, an anti-biotin antibody coupled to FITC and OVA, was added to the cells leading to DEC205 receptor-mediated uptake of OVA. In order to provide a negative control, DCs were only labelled with the anti-DEC205 antibody without the addition of OVA. In addition, human FAP-coated or non-coated Dynabeads® were added in 50 µL of R10 to the DCs at a 2:1 beads to cell ratio as described in Example 5.1.1. In the next step different agonistic anti-CD40 antibodies were added in 50 µL of R10 at concentrations ranging from 6.7 nM to 0.01 nM (10× dilution series). In this experimental setup, the bispecific 2+1 and 4+1 anti-human CD40 antibodies containing one FAP (212) or FAP (4B9) FAP binding site were compared to the cross-linked SGN-40 antibody.

On the next day, splenic CD8-positive cells from OT1 mice were isolated. In order to do so, the spleen of an OT1 mouse was smashed through a 40 µm filter with the end of a 3 mL syringe plug into a 50 mL tube. The filter was washed with R10 and the splenocytes were centrifuged at 1500 rpm for 5 minutes at room temperature. 1 mL of 1× cell lysis buffer (diluted 1:10 with distilled water) was added to the cells and after four minutes of incubation at room temperature, 20 mL of R10 were added. The tube was centrifuged at 1500 rpm for 5 minutes at room temperature and the supernatant was discarded. The splenocytes were resuspended in 30 mL of R10 and cell counts as well as viability were determined with the automated EVE cell counter. CD8-positive cells were isolated in a negative selection process using the mouse CD8a$^+$ T Cell Isolation Kit (Miltenyi, Cat. No. 130-104-075) and autoMACS® separation according to the manufacturer's instructions. CD8-positive cells that were found in the negative fraction after the separation were then washed with pre-warmed PBS, counted with the EVE cell counter and the cell number was adjusted to $2×10^7$ cells/mL in pre-warmed PBS. 10 mM CFSE solution (CellTrace™ CFSE Cell Proliferation Kit, ThermoFisher, Cat. No. C34554) was 5000-fold diluted in pre-warmed PBS and added to the cells resuspended in PBS in a 1:1 ratio (CFSE end concentration 1 µM). After a short vortex, cells were incubated for five minutes at room temperature. The labelling reaction was stopped by adding 40 mL of pre-warmed R10 medium to the cells. After two washing steps with PBS, CD8-positive cells were resuspended in R10 and $0.5×10^5$ cells were added in 100 µl R10 to the pulsed DCs. On day four of the experiment, the T cell proliferation was analyzed by flow cytometry. Therefore, the cells were transferred from the 96-well flat-bottom plates into 96-well round-bottom plates, washed once with PBS and incubated with 50 µl of 3 µg/mL of Fc receptor blocking Mouse IgG Isotype Control in PBS. After 15 minutes of incubation at 4° C., cells were washed with PBS and 50 µl of a mixture of fluorescently labelled antibodies in PBS were added to the cells. The following antibodies were used: anti-mouse CD4 BV421 (Biolegend, clone GK1.5, Cat. No. 100438), anti-mouse CD86 BV785 (Biolegend, clone GL-1, Cat. No. 105043), anti-I-A/I-E PerCp-Cy5.5 (Biolegend, clone M5/114.15.2, Cat. No. 107626), anti-mouse CD70 PE (eBioscience, clone FR70, Cat. No. 12-0701-82), anti-mouse CD3 PE-CF594 (BD Biosciences, clone 145-2C11, Cat. No. 562286), anti-mouse CD25 PE-Cy7 (eBioscience, clone PC61.5, Cat. No. 25-0251-82), anti-mouse CD11c APC (BD Biosciences, clone HL3, Cat. No. 561119), anti-mouse CD44 Alexa Fluor 700 (BD Biosciences, clone IM7, Cat. No. 560567) and anti-mouse CD8 APC-Cy7 (Biolegend, clone 53-6.7, Cat. No. 100714). In order to distinguish between live and dead cells, the viability dye Zombie Aqua™ was added to the antibody mixture. Cells were incubated for 30 minutes at 4° C. with 50 µl of the staining antibody mix. Afterwards, cells were washed two times with PBS, resuspended in 200 µl of PBS and analyzed using a 5-laser LSR-Fortessa. Data analysis was performed using the FlowJo version 10 software. Viable CD3- and CD8-positive cells were analyzed for CFSE signal as well as CD25 and CD44 expression.

Figure 8A:
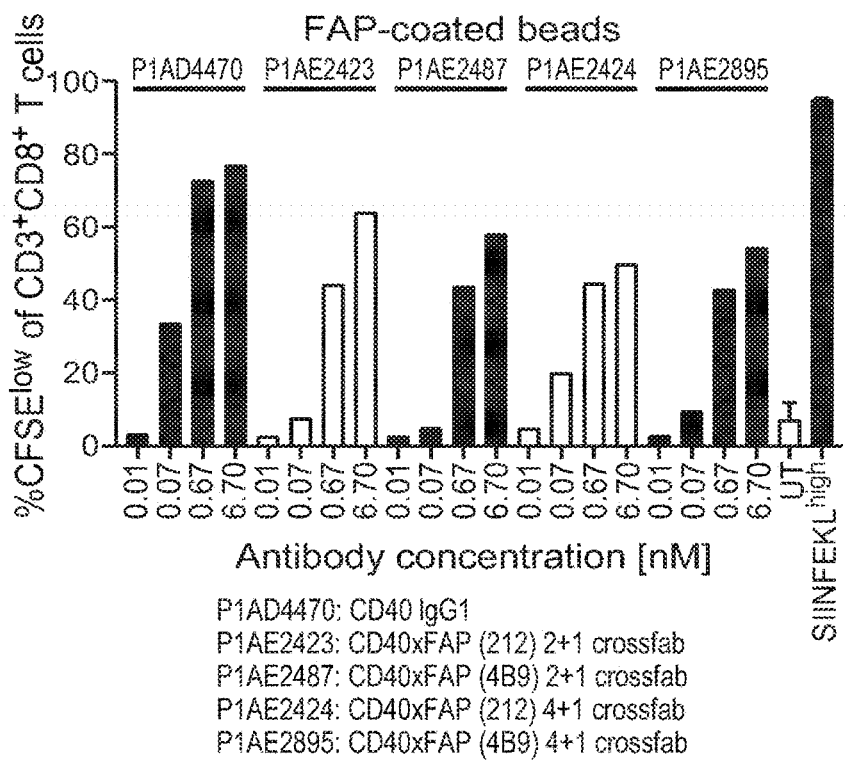
FIG. 8A and FIG. 8B show the T cell priming of OVA-pulsed DCs activated by FAP-targeted anti-CD40 binding molecules in the presence (FIG. 8A) or absence (FIG. 8B) of FAP. DCs isolated from huCD40 transgenic mice, treated with DEC205-OVA conjugate and stimulated with FAP-dependent bispecific anti-CD40 antibodies as well as FAP-coated beads induced a strong proliferation of antigen-specific T cells. In contrast, in the absence of FAP (uncoated beads) no T cell proliferation was induced by DCs stimulated with FAP-targeted anti-CD40 antibodies. The T cell proliferation induced by DCs stimulated with the human bispecific antigen binding molecules with two or four CD40 and one FAP (212) or FAP (4B9) binding moieties was comparable. DCs pulsed with high amounts of SIINFEKL instead of DEC205-OVA conjugate induced a strong T cell proliferation. Shown is the percentage of proliferating (CFSE-low) vital CFSE-labeled murine $CD3^+CD8^+$ OT-1 T cells co-cultured with huCD40 tg DCs pre-incubated with the indicated titrated antibodies in the presence of OVA (FIG. 8A and FIG. 8B). The x-axis shows the concentration of antibody constructs.
Figure 8B:
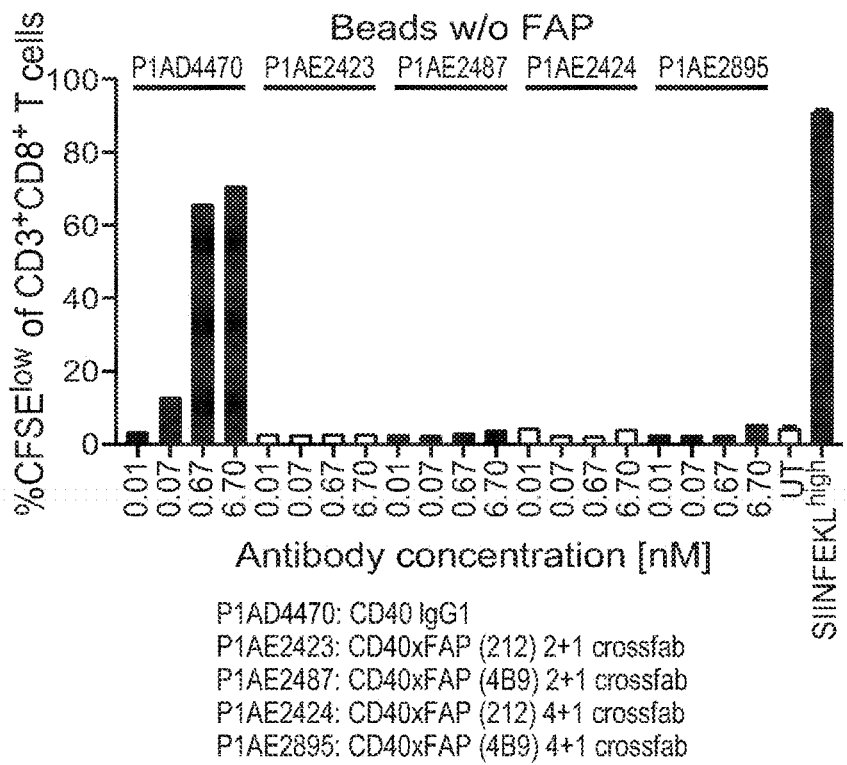

FIG. 8A and FIG. 8B show that DCs incubated with the OVA delivery reagent and stimulated with the bispecific antigen binding molecules targeting human CD40 and FAP highly enhance CD8-positive OT1 T cell proliferation. These effects were FAP-dependent. The increase of T cell proliferation induced by the depicted FAP-dependent antibodies was slightly lower compared to the increase induced by the cross-linked CD40 antibody (P1AD4470). The levels of proliferation induced by DCs stimulated with the 2+1 or 4+1 bispecific anti-CD40 antibodies with one FAP (212) or FAP (4B9) binding moiety were comparable.

5.3 Two Cell Line Bridging Assay for FAP Binding and CD40 Signal Transduction

The mode of action of the bispecific antibodies is reflected in the two cell line bridging assay: the antibodies bind to FAP on the FAP expressing cell line and to CD40 receptor on the reporter gene cell line. In case of clustering of the CD40 receptor the signal transduction results in the induction of NF☐B-dependent production of secreted embryonic alkaline phosphatase In brief: The reporter cell line HEK-Blue™ CD40L (Invivogen, transfected with plasmids encoding human CD40 receptor and a NFkB-inducible secreted embryonic alkaline phosphatase (SEAP)) was detached by Accutase (Life Technologies) and $6.8 \times 10^6$ cells were transferred into a sterile 50 mL centrifuge tube (Greiner) and placed on a roller mixer (Heidolph) until use.

The native target cells (WM-266-4, ATCC) expressing FAP on the surface were used as ready-to-use frozen cells. Each vial contained $2 \times 10^7$ cells/2 mL DMEM, 10% FBS and 5% DMSO. The maintenance culture of the cells should be done in DMEM with high glucose and HEPES (Life Technologies). The target cells were thawed for 2 minutes in a 37° C. pre-warmed water bath. The 2 mL cell suspension was transferred immediately into a 50 mL centrifuge tube with 30 mL DMEM, 10% FBS (Life Technologies). An aliquot of $13.6 \times 10^6$ cells was transferred into a 50 mL centrifuge tube and placed on a roller mixer until use. The thawing of the cells was done after preparation of the antibody dilution series.

The HEK-Blue™ Detection Medium (Invivogen) was used for preparation of cell suspensions and antibody dilutions. Three pouches were solved in 150 mL destilled water (Life Technologies) and filtered through a 0.22 μm membrane (Millipore) into a sterile glass bottle (Schott). 150 μl Gentamicin (50 mg/mL, Life Technologies) was added.

The antibody dilutions were made 2-fold concentrated in HEK-Blue™ Detection Medium. Eight concentrations in a serial dilution series (1:4) resulted in the final assay concentrations from 518 pM to 0.0316 pM. 100 μL of each antibody concentration was transferred into clear 96-well micro titer tissue culture plates (Greiner). Duplicates on 3 plates per molecule were evaluated.

Figure 9:
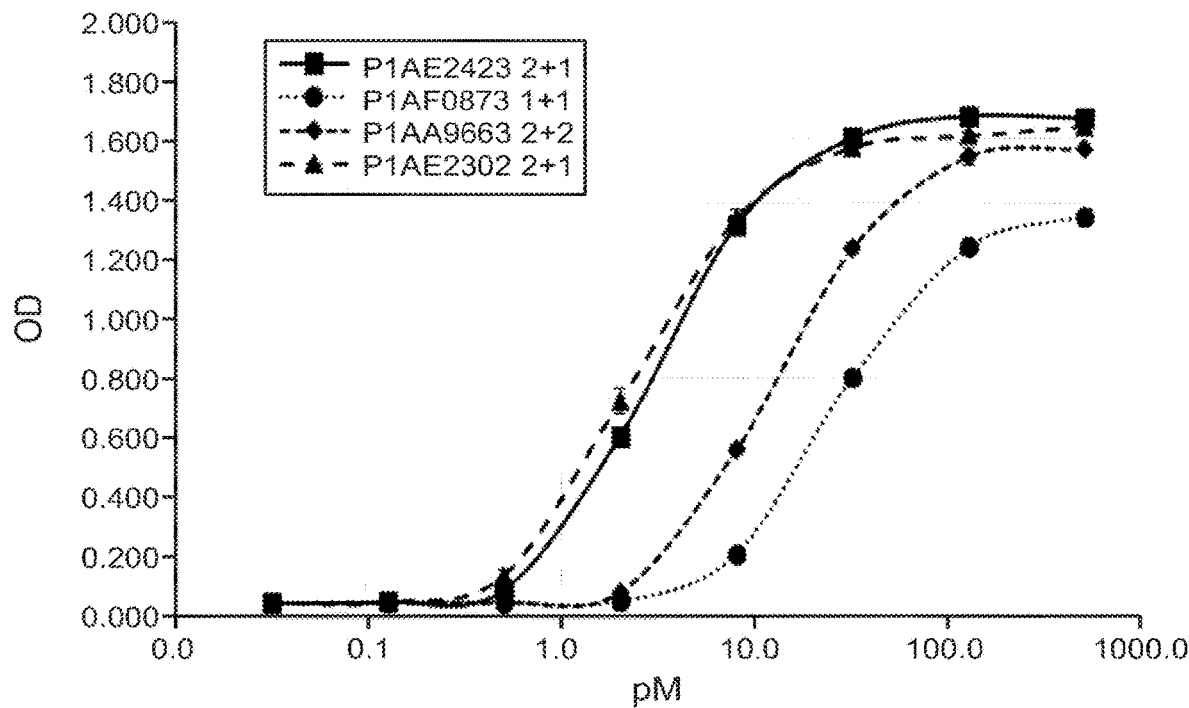
FIG. 9 shows the effect of simultaneous binding of the bispecific FAP×CD40 antibodies in the two cell line bridging assay as described in Example 5.3. Shown is the optical density (OD) against the concentration of the bispecific antibodies in different formats.

Both cell lines (reporter and target cell line) were centrifuged 4 minutes at 180×g at room temperature. The supernatants were removed and each cell line was resuspended in 17 mL HEK-Blue™ Detection Medium. By combining both cell lines, finally the mix contained $2 \times 10^5$ HEK-Blue™ CD40L cells per mL and $4 \times 10^5$ WM-266 4 cells per mL. 100 μL of the cell mixture was added into each well of the assay plates. Finally, 20.000 HEK-Blue™ CD40L cells and 40.000 WM-266-4 cells were present in each well. The plates were pre-incubated for 15 minutes at room temperature to allow cell distribution and settlement and then incubated for 20 hours at 37° C. and 5% $CO_2$ (cell incubator). Activity of SEAP was measured with HEK-Blue™ Detection Medium at 650 nm (Victor X4, Perkin Elmer). The optical density (OD) was plotted against the concentration of the antibodies (see FIG. 9). The $EC_{50}$ values are shown in Table 28 below.

TABLE 28

$EC_{50}$ values as measured in the Two cell line bridging assay

| Molecule | | $EC_{50}$ [pM] |
|---|---|---|
| P1AE2423 | CD40 × FAP (212) 2 + 1 crossfab | 3.2 |
| P1AF0873 | CD40 × FAP (212) 1 + 1 crossfab | 26.5 |
| P1AA9663 | CD40 × FAP (28H1) 2 + 2 crossfab | 13.2 |
| P1AE2302 | CD40 × FAP (28H1) 2 + 1 crossfab | 2.5 |

The $EC_{50}$ values are very similar for the 2+1 molecules P1AE2423 and P1AE2302 comprising two CD40-binding Fab fragment and FAP-binding crossfab fragment. The $EC_{50}$ is significantly higher for the 1+1 crossfab construct P1AF0873 and the 2+2 construct P1AA9663. In addition, the 1+1 construct P1AF0873 shows a significant less pronounced higher asymptote meaning less effectivity.

5.4 FAP-Independent CD40 Specific Assay

The potential activation of the CD40 pathway without the clustering via FAP was evaluated. In case of activation of the CD40 receptor the signal transduction results in the induction of NF☐B-dependent production of secreted embryonic alkaline phosphatase.

In brief, the reporter cell line HEK-Blue™ CD40L (Invivogen, transfected with plasmids encoding human CD40 receptor and a NF☐B-inducible secreted embryonic alkaline phosphatase (SEAP)) was detached by Accutase (Life Technologies) and $3.4 \times 10^6$ cells were transferred into a sterile 50 mL centrifuge tube (Greiner) and placed on a roller mixer (Heidolph) until use. The HEK-Blue™ Detection Medium (Invivogen) was used from the "two cell line bridging assay for FAP binding and CD40 signal transduction". The antibody dilution was made 2-fold concentrated in HEK-Blue™ Detection Medium. The final assay concentration was 518 pM. Of the three independent dilution series of the "two cell line bridging assay for FAP binding and CD40 signal transduction" 100 μL of the highest antibody concentration was transferred in duplicates into a clear 96-well micro titer tissue culture plate (Greiner). This resulted in 6 values per molecule being evaluated on 1 plate.

The reporter cell line was centrifuged 4 minutes at 180×g at room temperature. The supernatant was removed and the cells were resuspended in 17 mL HEK-Blue™ Detection Medium. 100 μL comprising 20.000 HEK-Blue™ CD40L cells were present in the wells. The plates were pre-incubated for 15 minutes at room temperature to allow cell distribution and settlement and then incubated for 20 hours at 37° C. and 5% $CO_2$ (cell incubator). Activity of SEAP was measured with HEK-Blue™ Detection Medium at 650 nm (Victor X4, Perkin Elmer). The mean of the optical density (OD) of n=6 and the 3×STDEV was plotted against the molecules (see FIG. 10).

The highest concentration used in the FAP dependent assay was used to incubate the CD40 specific reporter cells with the molecules. Without clustering via the FAP binding the activation of CD40 receptor and subsequent signal transduction was very low. It was even lower for P1AF0873 (1+1 crossmab) and P1AA9663 (2+2 crossmab) than for the 2+1 molecules P1AE2423 and P1AE2302 (overlapping error bars).

Example 6

Assessment of the Anti-Tumor Efficacy of FAP-Targeted Anti-Human CD40 Binding Molecules in Combination with PD-L1

Figure 11:
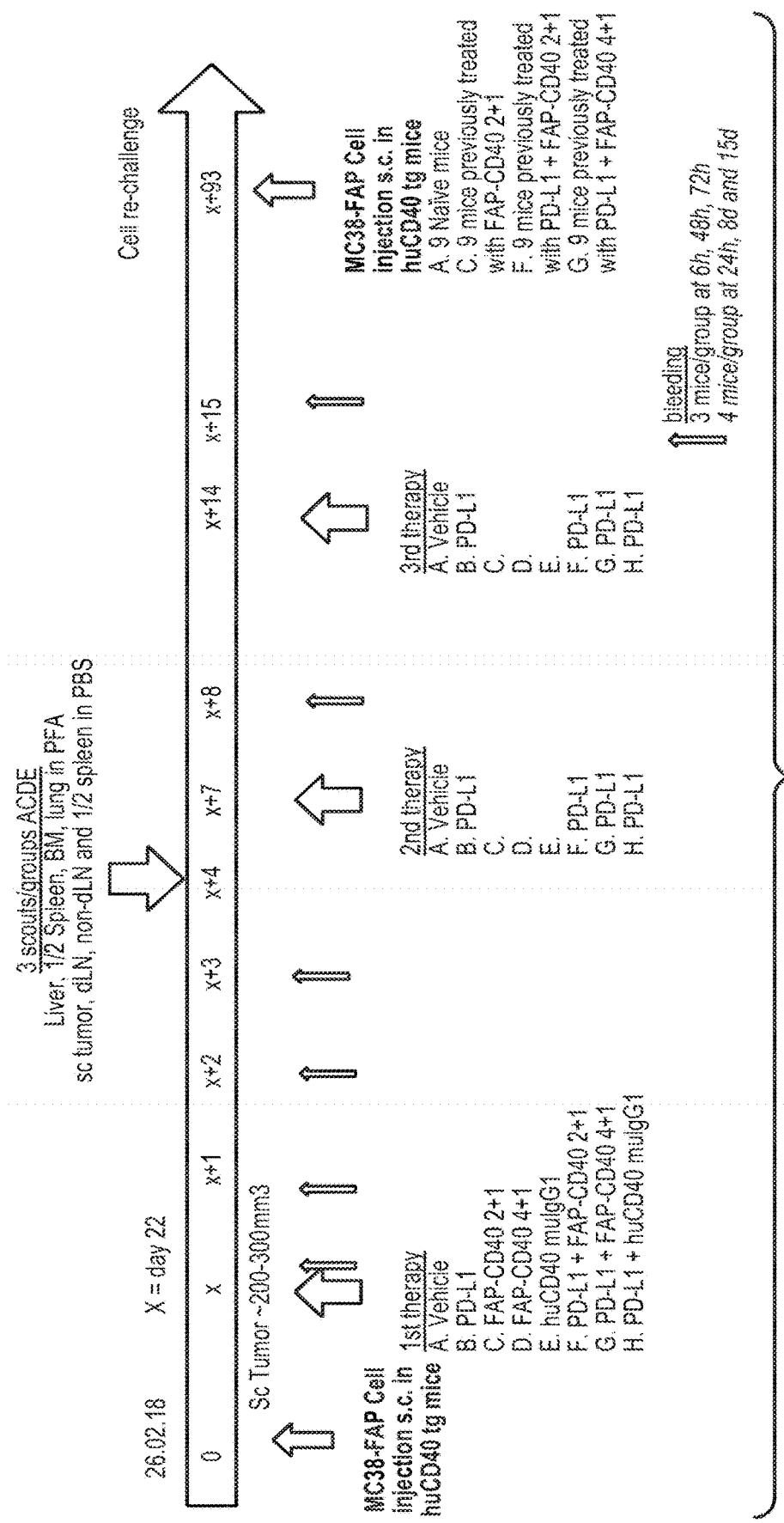
FIG. 11 shows the study design of an in vivo mouse study to evaluation the safety, pharmacokinetic and pharmacodynamic profile of FAP-targeted anti-CD40 binding molecules in comparison to a non-targeted anti-CD40 antibody in a subcutaneous MC38-FAP tumor model.

An in vivo study was designed (FIG. 11) in order to determine the effect of agonistic anti-FAP×CD40 antibodies on FAP-expressing tumor cells in immunocompetent mice. In particular, the difference between a bispecific FAP-CD40 antibody in a 4+1 format with a 28H1 FAP binding domain binding to murine FAP, a bispecific FAP-CD40 antibody in a 2+1 format with a 28H1 FAP binding domain and a FAP-independent CD40 control antibody with or without aPD-L1 treatment was evaluated.

A total of 97+9 (needed for the re-challenge experiments) huCD40 tg HO female mice, age 6-9 weeks at the start of experiment (purchased from Charles Rivers, France) and originally obtained from Taconic, were maintained under specific-pathogen-free condition with daily cycles of 12 h light/12 h darkness according to committed guidelines (GV-Solas; Felasa; TierschG). The experimental study protocol was reviewed and approved by the local government (ZH225-17). After arrival, animals were maintained for one week to get accustomed to the new environment and for observation. The mice were afterwards implanted with a transponder subcutaneously on the right side of the back for identification and maintained one more week for recovery. Continuous health monitoring was carried out on regular basis. Animals were controlled daily for clinical symptoms and detection of adverse effects.

MC38-muFAP invipa cells (CRC) were obtained from an in-vivo-passage performed at Roche Glycart AG and after expansion deposited in the Glycart internal cell bank. MC38-muFAP invipa cells were cultured in DMEM containing 10% FCS (PAA Laboratories, Austria), 1 mM Pyruvate, 1×NEAA and 6☐g/ml Puromycine. Cells were cultured at 37° C. in a water-saturated atmosphere at 5% $CO_2$. Cells were injected at an in vitro passage of 10 and a viability of 94.5%.

For tumor cell inoculation mice were anesthetized and injected subcutaneously, on the left flank, with a 29G needle (BD) with 100 µl of a solution containing $2\times10^6$ MC38-muFAP single cell suspension in 50% RPMI+50% Matrigel medium. For the re-challenge with the same tumor cell line 45 mice were injected on the right flank following the same procedure 93 days upon the 1st therapy.

At day 22, when the tumor mean reached 200 mm³, the mice were randomized into 8 different groups of 9 mice each with a similar mean of tumor size (Table 29). After randomization the mice were injected intra-peritoneal with a 29G needle with the different compounds (Table 30) according to the study groups (Table 31). 7 days and 14 days upon the 1st therapy, groups B, F, G and H were injected with a second and third dose of anti-PD-L1 intraperitoneal.

After randomization and therapy injection, the tumor size was followed 3 times a week by caliper measurement. Daily monitoring was performed to ensure the compliance with the welfare of the animals. Among the license criteria (ZH225-17), the mice were sacrificed in case of ulcerated tumors, tumors reaching a tumor volume above 3000 mm3 or mice which suffered a weight loss higher than 20% of their original body weight (at day 0). When termination was needed, the mice were anesthetized with isoflurane and a mechanical cervical dislocation was performed.

TABLE 30

Antigen binding molecules used

| Species | Molecule name | Substance Identifier |
|---|---|---|
| mouse | PD-L1 6E11 mIgG2a. PG LALA | P1AE0099 |
| human | FAP-CD40 4 + 1: 4+1_huIgG1_PGLALA_C-term_xFab_P1AE0817_28H1 | P1AE2024 |
| human | FAP-CD40 2 + 1: 2+1_huIgG1_PGLALA_C-term_xFab_P1AE0817_28H1 | P1AE2302 |
| human | CD40: muIgG1_wt_SGN40 | P1AE2301 |

TABLE 31

Study Groups for treatment

| Group | 1st therapy Day 22 | 2nd therapy Day 29 | 3rd therapy Day 36 |
|---|---|---|---|
| A | Vehicle | Vehicle | Vehicle |
| B | PD-L1 | PD-L1 | PD-L1 |
| C | FAP-CD40 2 + 1 | | |
| D | FAP-CD40 4 + 1 | | |
| E | huCD40 muIgG1 | | |
| F | PD-L1 + FAP-CD40 2 + 1 | PD-L1 | PD-L1 |
| G | PD-L1 + FAP-CD40 4 + 1 | PD-L1 | PD-L1 |
| H | PD-L1 + huCD40 muIgG1 | PD-L1 | PD-L1 |

From the excluded animals, 12 animals were selected and treated with the therapies from group A, C, D and E (3 animals per therapy) in order to be sacrificed as scouts to analyze the immunopharmacodynamic effects at day 4 upon the 1st therapy injection.

6.1 FAP-Targeted Anti-CD40 Binding Molecules Induce a Complete Tumor Remission and an Efficient Anti-Tumor Immune Memory Response The tumor size was monitored 3 times a week by caliper measurement. The JMP12 software was used for the statistical analysis of the tumor growth data. To test for significant differences in group means for multiple comparisons, the standard analysis of variance (ANOVA) using the Tukey-Kramer method was applied. Tukey-Kramer gives a test for all pairwise differences among the means; it is an exact alpha-level test if the samples sizes are the same.

93 days upon the 1st therapy, mice that showed a complete tumor regression were injected subcutaneously on the opposite flank with MC38-FAP tumor cells in order to determine the formation of an immune cell memory against this tumor cell line. As a control, 9 naïve C57bl/6-huCD40 tg mice were injected with the same MC38-FAP tumor cells

TABLE 29

Randomization of animals according to the tumor volume at day 22

| | Mean_ | Median_ | StDev_ | SEM_ | IQR (25%) | IQR (75%) | N (Animals) | N (Measurements) |
|---|---|---|---|---|---|---|---|---|
| TG1 | 205.87 | 183.09 | 117.82 | 39.27 | 83.77 | 118.89 | 9 | 9 |
| TG2 | 212.06 | 166.15 | 129.07 | 43.02 | 61.73 | 134.20 | 9 | 9 |
| TG3 | 203.06 | 195.36 | 109.90 | 36.63 | 86.46 | 71.22 | 9 | 9 |
| TG4 | 207.98 | 197.16 | 120.68 | 40.23 | 80.87 | 98.34 | 9 | 9 |
| TG5 | 222.03 | 193.11 | 160.66 | 53.55 | 84.25 | 69.29 | 9 | 9 |
| TG6 | 206.73 | 181.89 | 119.04 | 39.68 | 69.52 | 117.74 | 9 | 9 |
| TG7 | 207.83 | 195.20 | 132.17 | 44.06 | 84.94 | 62.45 | 9 | 9 |
| TG8 | 201.83 | 190.58 | 114.43 | 38.14 | 73.22 | 76.46 | 9 | 9 |
| excluded | | | | | | | 25 | | and the tumor growth was followed by caliper measurements 2 to 3 times a week, according to the vet license.

Figure 12:
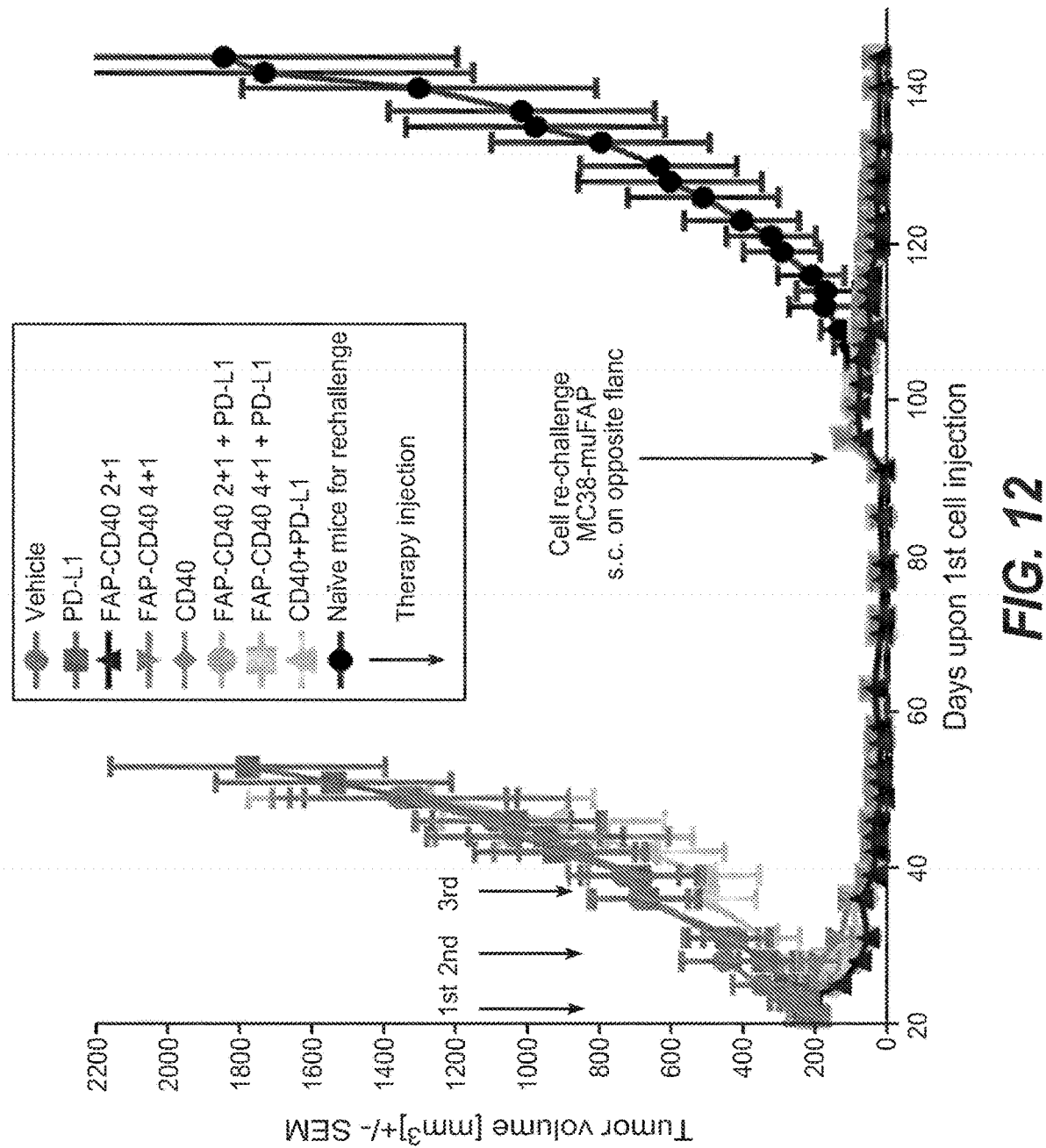
FIG. 12 shows the tumor growth upon the 1st and 2nd (re-challenge) MC38-FAP tumor cell injection of mice treated with the indicated single or combination antibody therapies. Arrows indicate the days of therapy injection and re-challenge. The y-axis represents the tumor volume in $mm^3$ and the x-axis the days upon the 1st MC38-FAP tumor cell injection. A complete tumor regression of MC38-FAP tumors upon FAP-CD40 antibody treatment, independently of the format and the co-injection of anti-PD-L1 antibody was observed. In contrast, in mice treated with anti-PD-L1 antibody alone, anti-CD40 antibody alone or anti-CD40 in combination with anti-PD-L1 antibody, tumor growth was comparable to mice treated with a vehicle control. Moreover, upon re-challenge, no MC38-FAP tumor grew in the groups previously treated with FAP-CD40 antibody whereas in naïve mice 100% of the tumors grew.

As shown in FIG. 12, both FAP-CD40 bispecific molecules (2+1 and 4+1) induced a complete tumor remission with and without PD-L1 treatment. In mice treated with non-targeted CD40, PD-L1 or both in combination tumor growth was not delayed compared to the vehicle group. In addition, upon re-challenge, no MC38-FAP tumor grew in the groups previously treated with FAP-CD40 antibody whereas in naïve mice 100% of the tumors grew. These results indicate a strong MC38-FAP anti-tumor efficacy and tumor growth regression of the targeted-CD40 therapy in contrast to the non-targeted CD40 therapy. Since all mice treated with an anti-FAP-CD40 antibody showed a 100% tumor remission there was no apparent anti-PD-L1 add-on effect in these mice. In addition, there was no demonstrated difference between the 2+1 and 4-1 format in terms of tumor growth inhibition. The re-challenge data indicate the formation of an efficient immune memory response against MC38-FAP tumor cells in all mice treated with a FAP-CD40 antibody.

The statistical analysis indicated that the data start to be significantly different as compared to the vehicle from day 28 on (6 days upon therapy) for the 2+1 FAP-CD40 antibody-treated group (FIG. 13A, Statistical analysis comparing all groups at day 28) and from day 31 on (9 days upon therapy) for the 4+1 FAP-CD40 antibody-treated group (FIG. 13B, Statistical analysis comparing all groups at day 31).

6.2 The 4+1 FAP-Targeted Anti-CD40 Binding Molecule has a Higher Serum Clearance Compared to the 2+1 FAP-Targeted Anti-CD40 Binding Molecule Blood from 3 to 4 mice per group were collected in order to follow the pharmacokinetic profile of the drugs upon intraperitoneal injection. Serum samples were collected 6 h, 24 h, 48 h, 72 h, 96 h, 8 days and 15 days following the first antibody therapy to analyze the blood anti-CD40 levels. A maximum of 100 µl of blood per time point was collected. The mice body temperature was slightly raised by a 39° C.-warmed box to ensure a good dilatation of the blood vessels. A puncture on the tail vein was performed with a 22G needle. The blood was collected in 1.1 ml Z-Gel micro tubes (SARSTEDT) and the serum was extracted by collecting the supernatant after centrifugation. Samples were stored at −20° C. and later analyzed for anti-CD40 levels using the respective antibody for calibration.

Anti-CD40 concentrations in the serum were tested using a CD40/Fc chimera (R&D, 1493-CD-050) ELISA for quantification of anti-CD40 huIgG, according to the protocol (Roche-Glycart, Switzerland). The reagents capture protein: human IgG-Fc biotin (Abcam, ab98561) and CD40/Fc chimera (R&D, 1493-CD-050), detection antibody: anti-mouse IgG (HRP) (Abcam, ab97040) or anti-huCH1-DIG (Roche-Penzberg, Germany) and anti-DIG-POD (Roche, 11633716001) were used. Serum samples were analyzed in serial dilutions depending on the injected dosage (mg/kg) and time of collection after anti-CD40 injection (6 h, 24 h, 48 h, 96 h). The absorption was measured using a measuring wavelength of 405 nm and a reference wavelength of 490 nm (SpectraMax i3 microplate reader, Molecular Devices).

For the PK analysis, the Phoenix 64, WinNonlin 6.4 software was used to calculate the area under the curve as well as the Cmax. Since the pharmacokinetics was only monitored up to 96 hours the PK parameters such as clearance and half-life are not depicted.

Figure 14:
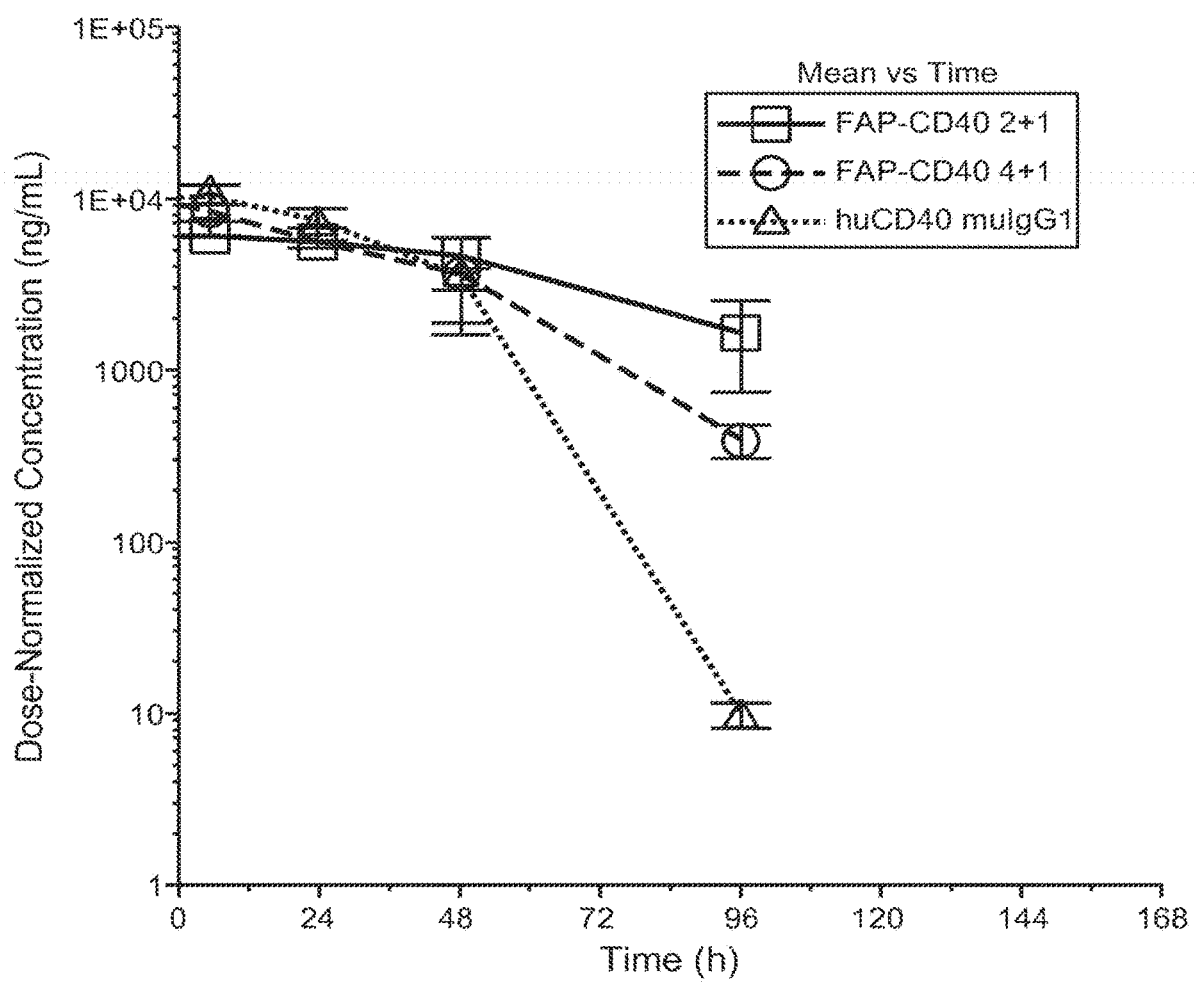
FIG. 14 shows the pharmacokinetic profile of a 4+1 and 2+1 FAP-targeted anti-CD40 binding molecule as well as a non-targeted parental anti-CD40 antibody in mice injected with a FAP-expressing murine colon adenocarcinoma tumor cell line (MC38-FAP). The y-axis represents the dose normalized concentration in the serum and the x-axis the time upon antibody injection. The highest clearance rate was observed for the non-targeted anti-CD40 antibody. The clearance rate of the FAP-targeted anti-CD40 binding molecule in a 4+1 format was lower compared to the non-target anti-CD40 molecule and the lowest clearance rate was observed for the FAP-targeted anti-CD40 binding molecule in a 2+1 format.
Figure 15A:
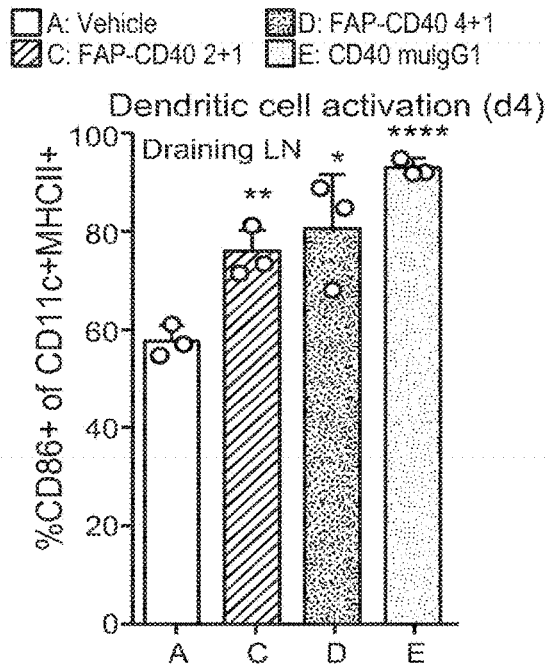
FIG. 15A, FIG. 15B, FIG. 15C, FIG. 15D, FIG. 16A, FIG. 16B, FIG. 16C, FIG. 16D, and FIG. 17A, FIG. 17B, FIG. 17C, FIG. 17D show the DC, T cell and B cell activation in draining lymph nodes (LN, FIG. 15A, FIG. 16A and FIG. 17A), non-draining lymph nodes (FIG. 15B, FIG. 16B and FIG. 17B), spleen (FIG. 15C, FIG. 16C and FIG. 17C) and tumor (FIG. 15D, FIG. 16D and FIG. 17D) of mice injected with a FAP-expressing murine colon adenocarcinoma tumor cell line (MC38-FAP) and treated with either non-targeted anti-CD40 (P1AE2301), anti-CD40-FAP 4+1 (P1AE2024), anti-CD40-FAP 2+1 (P1AE2302) or vehicle alone. DC and T cell activation in the tumor four days after therapy injection (FIG. 15D and FIG. 16D) was significantly increased in animals treated with anti-CD40-FAP 2+1 (P1AE2302) compared to vehicle-treated animals. In all other analyzed tissues (draining LN, non-draining LN and spleen) non-targeted anti-CD40, anti-CD40-FAP 4+1 and anti-CD40-FAP 2+1 induced a significant DC and T cell activation compared to vehicle group. In contrast, only the non-targeted anti-CD40 mediated a significant B cell activation in all analyzed tissues compared to the vehicle control group (FIG. 17A, FIG. 17B, FIG. 17C, and FIG. 17D, *$p<0.05$, $p<0.01$, *$p<0.001$, ****$p<0.0001$, unpaired, two-tailed Student's test).
Figure 15B:
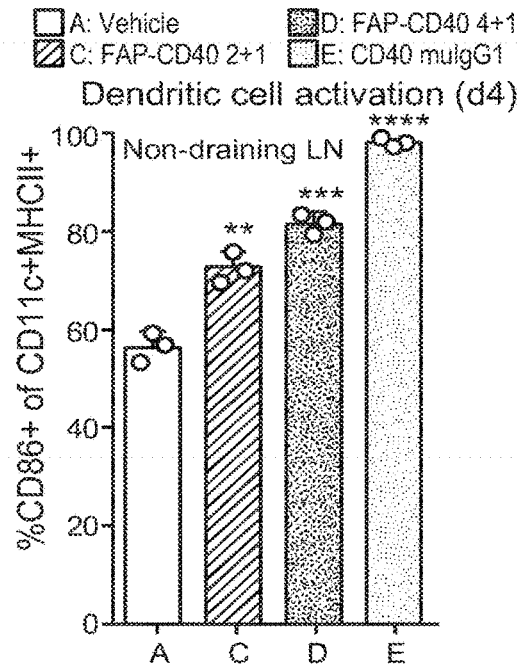
Figure 15C:
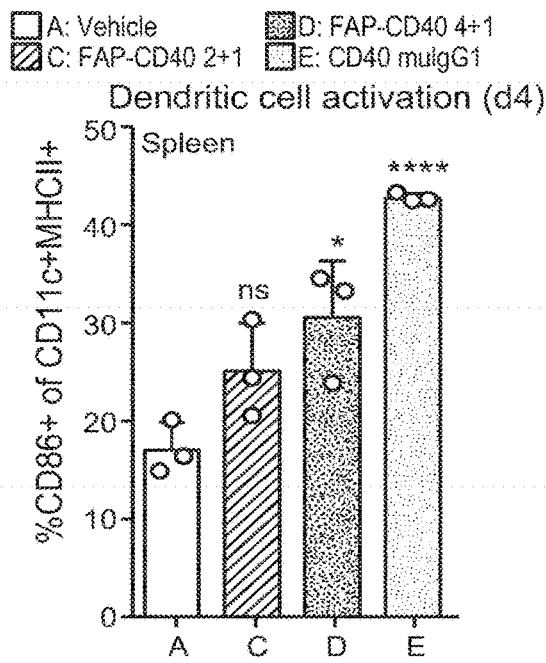
Figure 15D:
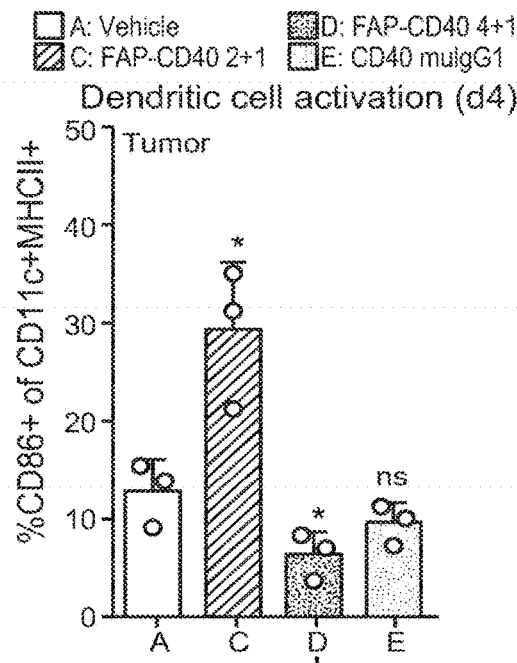
Figure 16A:
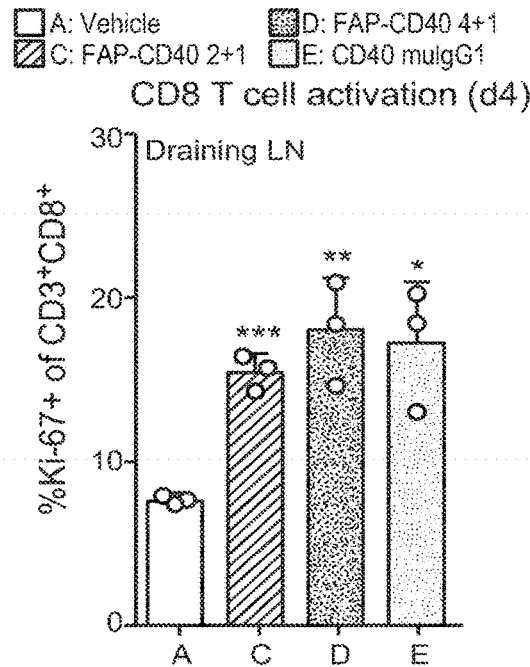
Figure 16B:
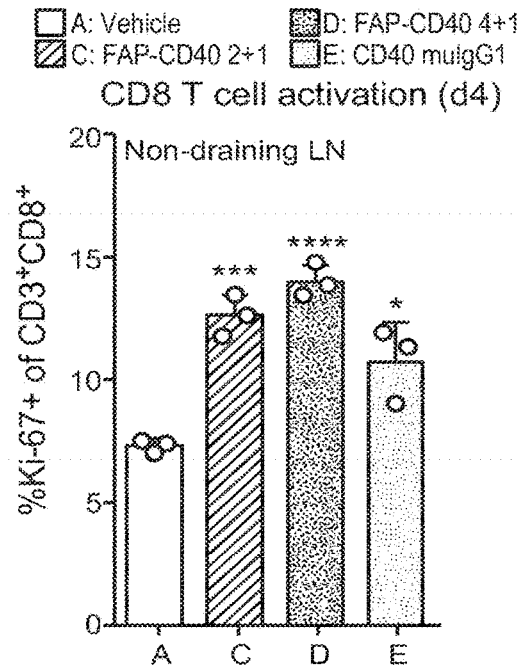
Figure 16C:
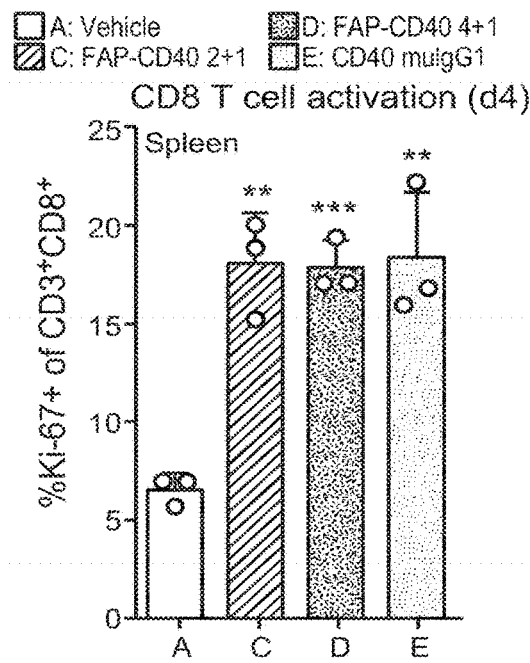
Figure 16D:
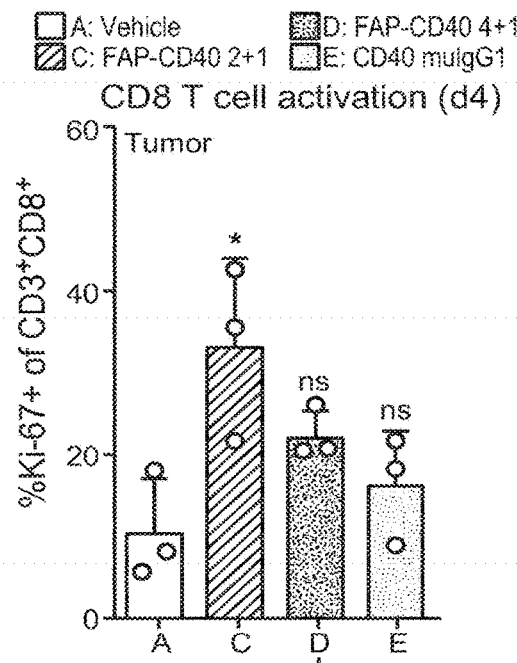
Figure 17A:
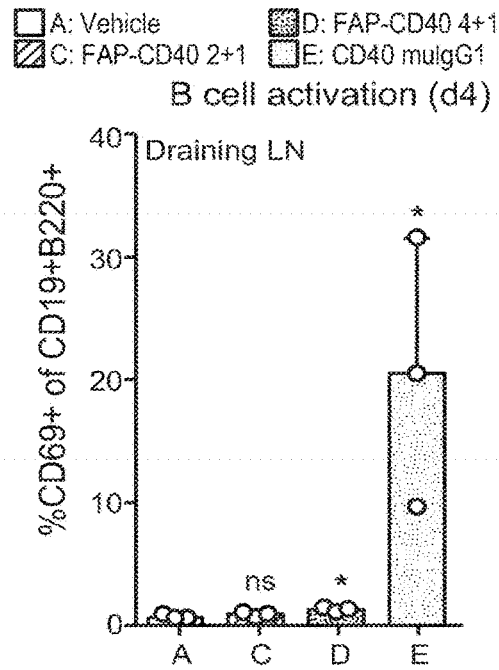
Figure 17B:
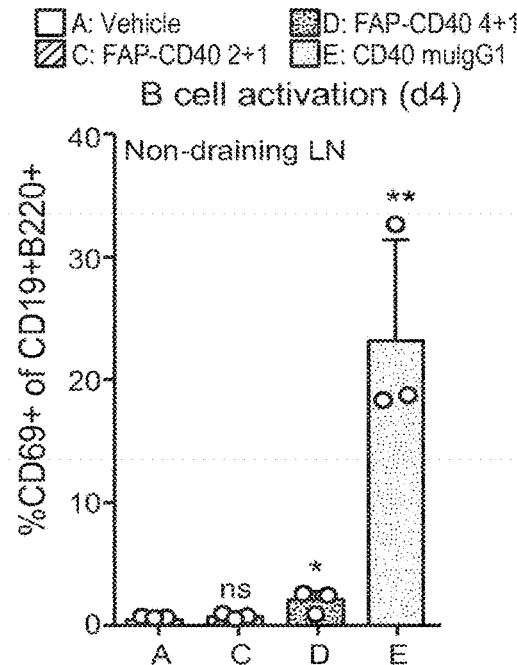
Figure 17C:
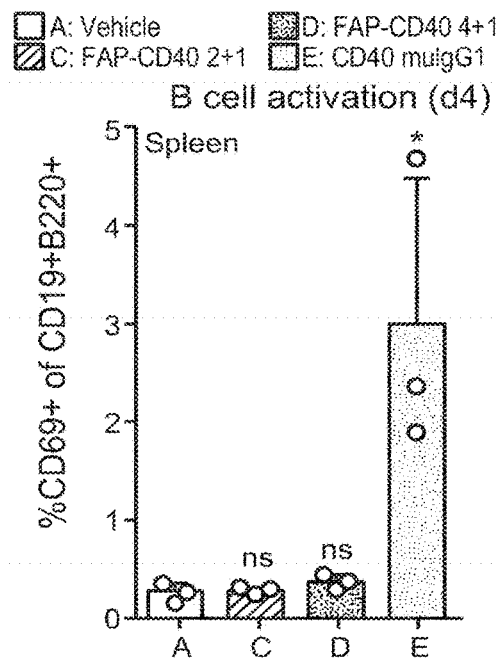
Figure 17D:
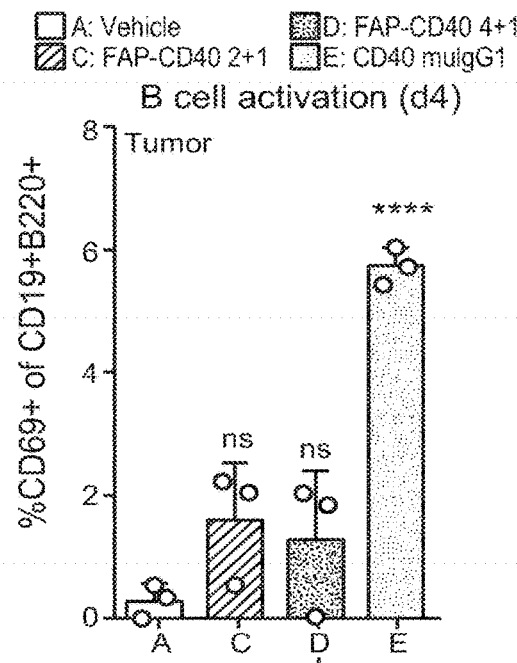

As shown in FIG. 14 and Table 32, a higher clearance was observed for the 4+1 format compared to the 2+1 format. This higher clearance can be explained by the CD40-specific Target-Mediated-Drug-Disposition (TMDD) that is more prominent for a tetravalent CD40 binder (4+1 format) than for a bivalent CD40 binder (2+1 format).

Also, the non-targeted CD40 showed a higher clearance as compared to both FAP-CD40 molecules. This clearance can't be explained by the TMDD hypothesis but could be due to Anti-Drug Antibodies (ADAs) formation upon CD40 therapy.

TABLE 32

| | PK parameters | | |
|---|---|---|---|
| | Dose (mg/kg) | Cmax (ng/mL) | AUClast (day*ng/mL) |
| FAP-CD40 2 + 1 | 13 | 78914 | 229808 |
| FAP-CD40 4 + 1 | 20 | 168667 | 334143 |
| huCD40 muIgG1 | 10 | 109762 | 193079 |

6.3 CD40-Mediated Activation of DCs, B Cells and T Cells by FAP-Targeted Anti-CD40 Binding Molecules 96 Hours after Treatment 96 h after the 1st therapy, 3 mice per group were sacrificed and the following organs were collected in PBS for flow cytometry analysis: tumor, spleen, inguinal draining lymph nodes and inguinal, axial and brachial non-draining lymph nodes.

For flow cytometer analysis, single cell suspensions of all collected organs were prepared as described in Example 5.2.1 and stained with fluorescently labelled antibodies. For this purpose, the prepared single cell suspensions were transferred into 96-well flat-bottom plates, washed with PBS and incubated with 50 µl of 3 µg/ml of Fc receptor blocking Mouse IgG Isotype Control (ThermoFisher Scientific, Cat. No. 10400C) in PBS. After 15 minutes of incubation at 4° C., cells were washed with PBS and 50 µl of a mixture of fluorescently labelled antibodies in PBS was added to the cells. The following antibodies were used: anti-mouse CD3 Pacific Blue™ (BD Bioscience, clone 500A2, Cat. No. 558214), anti-mouse CD86 BV605 (Biolegend, clone GL-1, Cat. No. 105037), CD45 Alexa Fluor 700 (eBioscience, clone 30-F11, Cat. No. 56-0451-82), anti-mouse CD19 BUV395 (BD Biosciences, clone 1D3, Cat. No. 563557), anti-mouse CD11c BV785 (Biolegend, clone N418, Cat. No. 117336), anti-mouse B220 APC-Cy7 (Biolegend, clone RA3-6B2, Cat. No. 103224), anti-mouse CD69 BUV737 (BD Biosciences, clone H1.2F3, Cat. No. 612793), anti-I-A/I-E PerCp-Cy5.5 (Biolegend, clone M5/114.15.2, Cat. No. 107626). In order to distinguish between live and dead cells, the viability dye Zombie Aqua™ or Fixable blue (both Life technologies) were added to the antibody mixture. Cells were incubated for 30 minutes at 4° C. with the extracellular staining antibody solution. Afterwards, cells were washed two times with PBS, permeabilized and intracellularly stained for Ki-67 using anti-mouse Ki-67 PE-Cy7 (eBioscience, clone SolA15, Cat. No. 25-5698-82) with the Foxp3/Transcription Factor Staining Buffer Set (eBioscience, Cat. No. 00-5523-00) according to the manufacturer's protocol. Cells were resuspended in 200 µl of PBS and analyzed the same day using a 5-laser LSR-Fortessa. Data analysis was performed using the FlowJo version 10 software. Viable CD45+, CD3+ and CD8+ T cells were analyzed for Ki-67 expression. Viable dendritic cells (CD45+, MHCII+, CD11c+) were analyzed for expression of the DC activation marker CD86 and viable B cells (CD45+, CD19+, B220+) were analyzed for expression of the B cell activation marker CD69.

As shown in FIG. 15A to FIG. 15D, both FAP-targeted anti-CD40 antibodies formats (2+1 and 4+1) induced a significant increase in DC activation (CD86 expression) in tumor-draining lymph nodes, non-draining lymph nodes and the spleen four days after treatment although to a lesser extent than the non-targeted anti-CD40 antibody. In contrast, only the FAP-targeted anti-CD40 antibody in a 2+1 format induced a significant DC activation in tumors compared to the vehicle group. As shown in FIG. 16A to FIG. 16D, the same pattern was observed for the activation of T cells (Ki-67 expression). A significant B cell activation (CD69 expression) in all analyzed tissue samples compared to the vehicle group was only observed in mice treated with the non-targeted anti-CD40 antibody (FIG. 17A to FIG. 17D).

6.4 FAP-Targeted Anti-CD40 Binding Molecules Induce Less Side Effects Compared to Non-Targeted CD40 Antibody in Mice 6.4.1 Mice Treated with FAP-Targeted Anti-CD40 Antibody Show No Weight Reduction in Contrast to Mice Treated with Non-Targeted Anti-CD40 Antibody After therapy injection, the weight of each mouse was measured daily for 15 days. Mice with a weight loss higher than 20% of their original body weight (at day 0) were sacrificed (here, no mice needed to be sacrificed).

Figure 18:
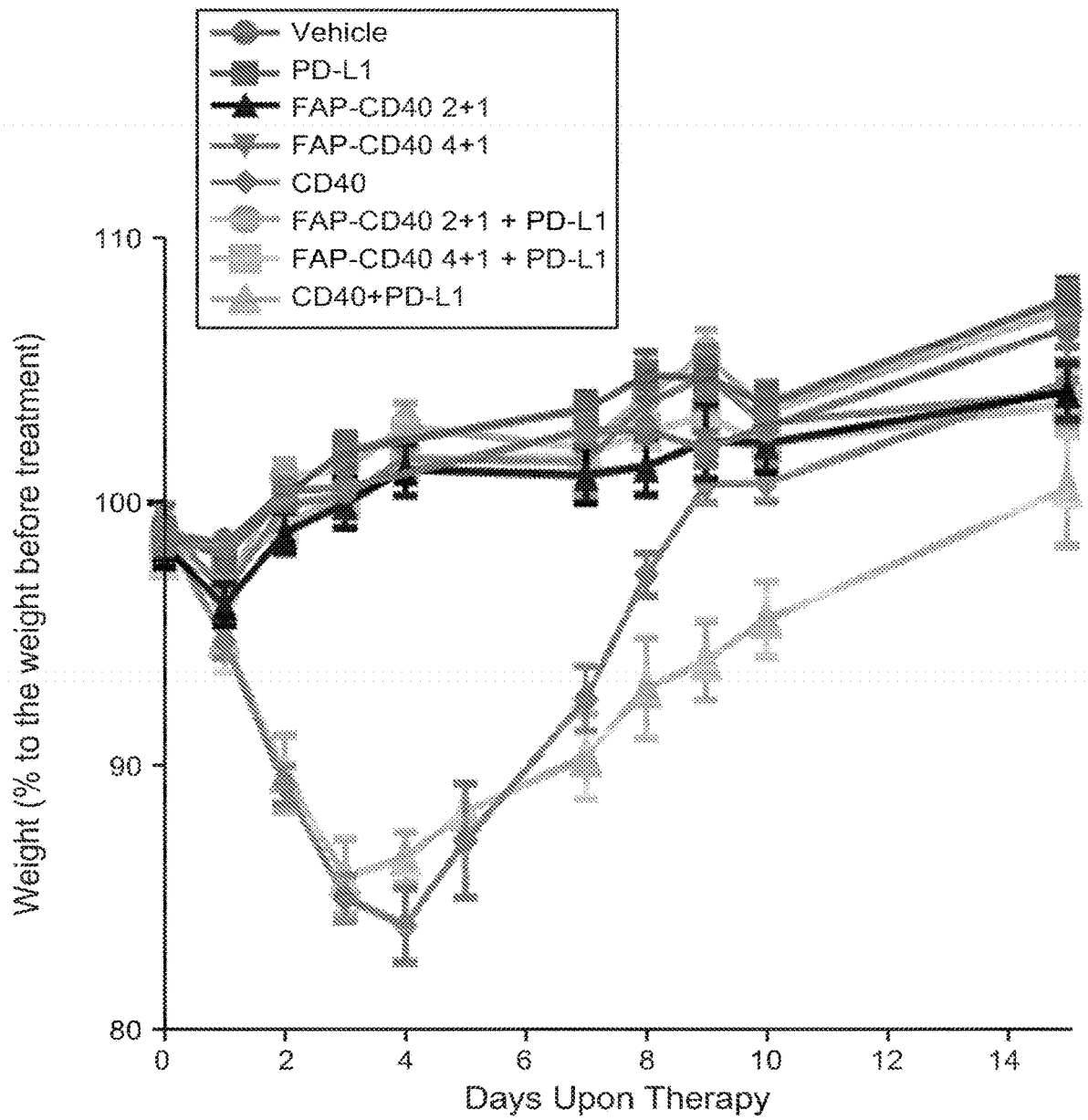
FIG. 18 shows the body weight of mice injected with a FAP-expressing murine colon adenocarcinoma tumor cell line (MC38-FAP) and treated with either non-targeted anti-CD40 (P1AE2301), anti-CD40-FAP 4+1 (P1AE2024), anti-CD40-FAP 2+1 (P1AE2302) or vehicle with or without co-injection of anti-PD-L1 antibody (P1AE0099). The y-axis shows the body weight in percent of the body weight prior to treatment and the x-axis shows the days after therapy injection. Only in mice treated with the non-targeted anti-CD40 antibody alone or in combination with anti-PD-L1 a clear body weight reduction was observed.

As FIG. 18 illustrates mice treated with non-targeted anti-CD40 antibody showed a clear weight loss upon antibody injection and this weight loss lasted longer in the case of a concomitant injection of anti-CD40 with anti-PD-L1 antibody. No weight loss was observed in the groups injected with 4+1 or 2+1 FAP-CD40 single agents, PD-L1 single agent and in the combination groups FAP-CD40 (4+1 or 2+1)+PD-L1. This result indicates a safe profile of the FAP-targeted anti-CD40 binding molecules as compared to the non-targeted anti-CD40 antibody.

6.4.1 Mice Treated with FAP-Targeted Anti-CD40 Antibody Show Less Anti-PD-L1-Mediated Adverse Events Compared to Mice Treated with Non-Targeted Anti-CD40 Antibody Some adverse events were observed upon the 3rd injection of the anti-PD-L1 antibody. No mice needed to be sacrificed but the symptoms were described as decreased activity of the mouse within 5 minutes after therapy injection, arched back and scruffy fur. Table 33 indicates the percent of mice showing those symptoms upon the 3rd therapy.

TABLE 33

Percentage of animals showing adverse events upon 3rd anti-PD-L1 therapy.

| Group | % of mice showing adverse events upon 3rd injection of PD-L1 | Recovery Time (minutes) |
| --- | --- | --- |
| PD-L1 | 33% | 30-40 |
| FAP-CD40 2 + 1 + PD-L1 | 44% | 10-20 |
| FAP-CD40 4 + 1 + PD-L1 | 55% | 10-20 |
| CD40 + PD-L1 | 100% | 30-40 |

The results show a clear increase of adverse events in the combination group PD-L1+CD40 whereas the percent of adverse events observed in the anti-PD-L1+FAP-CD40 groups (4+1 and 2+1) were only slightly increased compared to the anti-PD-L1 single agent-treated group.

The observed adverse events could be the result of a strong immune reaction (cytokine storm) due to a ADAs formation against anti-PD-L1, which is further increased in the presents of a non-targeted anti-CD40 antibody. This observation indicates a better safety profile of the targeted FAP-CD40 molecule compared to the non-targeted anti-CD40 antibody when both molecules are combined with an anti-PD-L1 antibody therapy.

In summary, the FAP-targeted anti-CD40 molecules with FAP-dependent activation of CD40 in a 4+1 and 2+1 format induce a potent anti-tumor immune response in tumor-bearing mice with reduced systemic toxicity compared to the untargeted anti-CD40 parental antibody.

The invention claimed is:

1. A method of treating an individual having a Fibroblast Activation Protein (FAP)-expressing cancer comprising administering to the individual an effective amount of a bispecific antigen binding molecule, comprising
   (a) at least one antigen binding domain capable of specific binding to CD40, and
   (b) at least one antigen binding domain capable of specific binding to FAP comprising a heavy chain variable region (VHFAP) comprising (i) CDR-H1 comprising the amino acid sequence of SEQ ID NO:3, (ii) CDR-H2 comprising the amino acid sequence selected from the group consisting of SEQ ID NO:4, SEQ ID NO: 11 and SEQ ID NO:12, and (iii) CDR-H3 comprising the amino acid sequence of SEQ ID NO:5, and a light chain variable region (VLFAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8.

2. The method of claim 1, wherein said antigen binding molecule additionally comprises (c) a Fc region composed of a first and a second subunit capable of stable association.

3. The method of claim 2, wherein the Fc region is an IgG Fc region, and wherein the IgG Fc region comprises one or more amino acid substitutions that reduce the binding affinity of the antibody to an Fc receptor and/or effector function.

4. The method of claim 3, wherein the IgG Fc region is an IgG1 Fc region or an IgG4 Fc region.

5. The method of claim 2, wherein the Fc region is of human IgG1 subclass with the amino acid mutations L234A, L235A and P329G as numbered according to the Kabat EU index.

6. The method of claim 1, wherein the antigen binding domain capable of specific binding to FAP comprises a heavy chain variable region (VHFAP) comprising an amino acid sequence that is at least about 90% identical to the amino acid sequence of SEQ ID NO: 9, and a light chain variable region ($V_L$FAP) comprising an amino acid sequence that is at least about 90% identical to the amino acid sequence of SEQ ID NO: 10.

7. The method of claim 1, wherein the antigen binding domain capable of specific binding to FAP comprises
a heavy chain variable region ($V_H$FAP) comprising the amino acid sequence selected from the group consisting of SEQ ID NO:15, SEQ ID NO:16, SEQ ID NO:17, SEQ ID NO: 18, SEQ ID NO:19 and SEQ ID NO:20, and
a light chain variable region ($V_L$FAP) comprising the amino acid sequence selected from the group consisting of SEQ ID NO:21, SEQ ID NO:22, SEQ ID NO:23, SEQ ID NO:24, SEQ ID NO:25 and SEQ ID NO:26.

8. The method of claim 1, wherein the antigen binding domain capable of specific binding to FAP comprises
(a) a heavy chain variable region ($V_H$FAP) comprising the amino acid sequence of SEQ ID NO: 15 and a light chain variable region ($V_L$FAP) comprising the amino acid sequence of SEQ ID NO:21, or
(b) a heavy chain variable region ($V_H$FAP) comprising the amino acid sequence of SEQ ID NO: 16 and a light chain variable region ($V_L$FAP) comprising the amino acid sequence of SEQ ID NO:21, or
(c) a heavy chain variable region ($V_H$FAP) comprising the amino acid sequence of SEQ ID NO: 16 and a light chain variable region ($V_L$FAP) comprising the amino acid sequence of SEQ ID NO:22, or
(d) a heavy chain variable region ($V_H$FAP) comprising the amino acid sequence of SEQ ID NO: 19 and a light chain variable region ($V_L$FAP) comprising the amino acid sequence of SEQ ID NO:25.

9. The method of claim 1, wherein the antigen binding domain capable of specific binding to CD40 comprises a heavy chain variable region ($V_H$CD40) comprising (i) CDR-H1 comprising the amino acid sequence of SEQ ID NO:27, (ii) CDR-H2 comprising the amino acid sequence of SEQ ID NO:28, and (iii) CDR-H3 comprising the amino acid sequence of SEQ ID NO:29, and a light chain variable region ($V_L$CD40) comprising (iv) CDR-L1 comprising the amino acid sequence of SEQ ID NO:30, (v) CDR-L2 comprising the amino acid sequence of SEQ ID NO:31, and (vi) CDR-L3 comprising the amino acid sequence of SEQ ID NO:32.

10. The method of claim 1, wherein the antigen binding domain capable of specific binding to CD40 comprises
(i) a heavy chain variable region ($V_H$CD40) comprising the amino acid sequence selected from the group consisting of SEQ ID NO:37, SEQ ID NO:38, SEQ ID NO:39 and SEQ ID NO: 40, and
(ii) a light chain variable region ($V_L$CD40) comprising the amino acid sequence selected from the group consisting of SEQ ID NO:41, SEQ ID NO:42, SEQ ID NO:43, and SEQ ID NO: 44.

11. The method of claim 1, wherein the antigen binding domain capable of specific binding to CD40 comprises
(i) a heavy chain variable region ($V_H$CD40) comprising the amino acid sequence selected from the group consisting of SEQ ID NO:45, SEQ ID NO:46, SEQ ID NO:47, SEQ ID NO: 48, SEQ ID NO:49 and SEQ ID NO:50, and
(ii) a light chain variable region ($V_L$CD40) comprising the amino acid sequence selected from the group consisting of SEQ ID NO:51, SEQ ID NO:52, SEQ ID NO:53, and SEQ ID NO: 54.

12. The method of claim 1, wherein the antigen binding domain capable of specific binding to CD40 comprises
(a) a VH comprising the amino acid sequence of SEQ ID NO:37 and a VL comprising the amino acid sequence of SEQ ID NO:41, or
(b) a VH comprising the amino acid sequence of SEQ ID NO:37 and a VL comprising the amino acid sequence of SEQ ID NO:42, or
(c) a VH comprising the amino acid sequence of SEQ ID NO:37 and a VL comprising the amino acid sequence of SEQ ID NO:43, or
(d) a VH comprising the amino acid sequence of SEQ ID NO:37 and a VL comprising the amino acid sequence of SEQ ID NO:44, or
(e) a VH comprising the amino acid sequence of SEQ ID NO:38 and a VL comprising the amino acid sequence of SEQ ID NO:41, or
(f) a VH comprising the amino acid sequence of SEQ ID NO:38 and a VL comprising the amino acid sequence of SEQ ID NO:42, or
(g) a VH comprising the amino acid sequence of SEQ ID NO:38 and a VL comprising the amino acid sequence of SEQ ID NO:43, or
(h) a VH comprising the amino acid sequence of SEQ ID NO:38 and a VL comprising the amino acid sequence of SEQ ID NO:44, or
(i) a VH comprising the amino acid sequence of SEQ ID NO:39 and a VL comprising the amino acid sequence of SEQ ID NO:41, or
(j) a VH comprising the amino acid sequence of SEQ ID NO:39 and a VL comprising the amino acid sequence of SEQ ID NO:42, or
(k) a VH comprising the amino acid sequence of SEQ ID NO:39 and a VL comprising the amino acid sequence of SEQ ID NO:43, or
(l) a VH comprising the amino acid sequence of SEQ ID NO:39 and a VL comprising the amino acid sequence of SEQ ID NO:44, or
(m) a VH comprising the amino acid sequence of SEQ ID NO:40 and a VL comprising the amino acid sequence of SEQ ID NO:41, or
(n) a VH comprising the amino acid sequence of SEQ ID NO:40 and a VL comprising the amino acid sequence of SEQ ID NO:42, or
(o) a VH comprising the amino acid sequence of SEQ ID NO:40 and a VL comprising the amino acid sequence of SEQ ID NO:43, or
(p) a VH comprising the amino acid sequence of SEQ ID NO:40 and a VL comprising the amino acid sequence of SEQ ID NO:44.

13. The method of claim 1, wherein the antigen binding domain capable of specific binding to CD40 comprises a VH comprising the amino acid sequence of SEQ ID NO: 37 and a VL comprising the amino acid sequence of SEQ ID NO:41.

14. The method of claim 1, wherein the antigen binding domain capable of specific binding to CD40 comprises
   (a) a VH comprising the amino acid sequence of SEQ ID NO:45 and a VL comprising the amino acid sequence of SEQ ID NO:51, or
   (b) a VH comprising the amino acid sequence of SEQ ID NO:46 and a VL comprising the amino acid sequence of SEQ ID NO:51, or
   (c) a VH comprising the amino acid sequence of SEQ ID NO:47 and a VL comprising the amino acid sequence of SEQ ID NO:51, or
   (d) a VH comprising the amino acid sequence of SEQ ID NO:48 and a VL comprising the amino acid sequence of SEQ ID NO:51, or
   (e) a VH comprising the amino acid sequence of SEQ ID NO:45 and a VL comprising the amino acid sequence of SEQ ID NO:52, or
   (f) a VH comprising the amino acid sequence of SEQ ID NO:46 and a VL comprising the amino acid sequence of SEQ ID NO:52, or
   (g) a VH comprising the amino acid sequence of SEQ ID NO:47 and a VL comprising the amino acid sequence of SEQ ID NO:52, or
   (h) a VH comprising the amino acid sequence of SEQ ID NO:48 and a VL comprising the amino acid sequence of SEQ ID NO:52, or
   (i) a VH comprising the amino acid sequence of SEQ ID NO:49 and a VL comprising the amino acid sequence of SEQ ID NO:53, or
   (j) a VH comprising the amino acid sequence of SEQ ID NO:50 and a VL comprising the amino acid sequence of SEQ ID NO:53, or
   (k) a VH comprising the amino acid sequence of SEQ ID NO:49 and a VL comprising the amino acid sequence of SEQ ID NO:54, or
   (l) a VH comprising the amino acid sequence of SEQ ID NO:50 and a VL comprising the amino acid sequence of SEQ ID NO:54.

15. The method of claim 1, wherein the antigen binding domain capable of specific binding to CD40 comprises a VH comprising the amino acid sequence of SEQ ID NO: 45 and a VL comprising the amino acid sequence of SEQ ID NO:51 or wherein the antigen binding domain capable of specific binding to CD40 comprises a VH comprising the amino acid sequence of SEQ ID NO:48 and a VL comprising the amino acid sequence of SEQ ID NO:51.

16. The method of claim 1, comprising
   (i) at least one antigen binding domain capable of specific binding to CD40, comprising a heavy chain variable region ($V_H$CD40) comprising the amino acid sequence of SEQ ID NO: 37 and a light chain variable region ($V_L$CD40) comprising the amino acid sequence of SEQ ID NO:41, and
   (ii) at least one antigen binding domain capable of specific binding to FAP, comprising a heavy chain variable region ($V_H$FAP) comprising the amino acid sequence of SEQ ID NO: 15 and a light chain variable region ($V_L$FAP) comprising the amino acid sequence of SEQ ID NO:21.

17. The method of claim 1, wherein the bispecific antigen binding molecule comprises
   (a) at least two Fab fragments capable of specific binding to CD40 connected to a Fc region, and
   (b) one antigen binding domain capable of specific binding to FAP connected to the C-terminus of the Fc region.

18. The method of claim 1, wherein the bispecific antigen binding molecule comprises
   (a) at least two Fab fragments capable of specific binding to CD40 fused to a Fc region, and
   (b) a cross-fab fragment capable of specific binding to FAP fused to the C-terminus of the Fc region.

19. The method of claim 18, wherein the cross-fab fragment capable of specific binding to FAP comprises a VH-Ckappa chain, and the VH-Ckappa chain of the cross-fab fragment is fused to the C-terminus of the Fc region.

20. The method of claim 1, wherein the bispecific antigen binding molecule comprises four Fab fragments capable of specific binding to CD40.

21. The method of claim 1, further comprising administering an additional therapeutic agent.

22. The method of claim 1, wherein the bispecific antigen binding molecule delays progression of said FAP-expressing cancer in the individual, or prolongs the survival of the individual suffering from said FAP-expressing cancer.

23. The method of claim 1, wherein the bispecific antigen binding molecule comprises two light chains, each comprising the amino acid sequence of SEQ ID NO: 66, one light chain comprising the amino acid sequence of SEQ ID NO:65, a first heavy chain comprising the amino acid sequence of SEQ ID NO:67, and a second heavy chain comprising the amino acid sequence of SEQ ID NO:68.

24. The method of claim 1, wherein the bispecific antigen binding molecule comprises two light chains, each comprising the amino acid sequence of SEQ ID NO: 62, one light chain comprising the amino acid sequence of SEQ ID NO:61, a first heavy chain comprising the amino acid sequence of SEQ ID NO:63, and a second heavy chain comprising the amino acid sequence of SEQ ID NO:64.

25. The method of claim 1, wherein said FAP-expressing cancer is colorectal carcinoma, gastric cancer, skin cancer, breast cancer, lung cancer, bladder cancer, or ovarian cancer.

26. A method of treating an individual having a FAP-expressing cancer comprising administering to the individual an effective amount of an antibody that specifically binds to FAP, wherein said antibody comprises a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO: 4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO: 14, (v) CDR-L2 comprising the amino acid sequence of SEQ ID NO:7, and (vi) CDR-L3 comprising the amino acid sequence of SEQ ID NO:8.

27. The method of claim 26, wherein said antibody comprises
   (a) a heavy chain variable region ($V_H$FAP) comprising the amino acid sequence of SEQ ID NO 15 and a light chain variable region ($V_L$FAP) comprising the amino acid sequence of SEQ ID NO:21, or
   (b) a heavy chain variable region ($V_H$FAP) comprising the amino acid sequence of SEQ ID NO: 16 and a light chain variable region ($V_L$FAP) comprising the amino acid sequence of SEQ ID NO:21, or
(c) a heavy chain variable region ($V_H$FAP) comprising the amino acid sequence of SEQ ID NO: 16 and a light chain variable region ($V_L$FAP) comprising the amino acid sequence of SEQ ID NO:22, or
(d) a heavy chain variable region ($V_H$FAP) comprising the amino acid sequence of SEQ ID NO: 19 and a light chain variable region ($V_L$FAP) comprising the amino acid sequence of SEQ ID NO:25.

* * * * *